United States Patent
Buschmann et al.

(10) Patent No.: US 8,044,053 B2
(45) Date of Patent: Oct. 25, 2011

(54) SULFONAMIDE SUBSTITUTED PYRAZOLINE COMPOUNDS, THEIR PREPARATION AND USE AS CB1 MODULATORS

(75) Inventors: Helmut Buschmann, Aachen (DE); Antonio Torrens-Jover, Terrassa (ES); Josef Mas-Prio, Rubi (ES); Susana Yenes-Minguez, Molins de Rei (ES)

(73) Assignee: Laboratories del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 12/445,260

(22) PCT Filed: Oct. 10, 2007

(86) PCT No.: PCT/EP2007/008812
§ 371 (c)(1),
(2), (4) Date: Mar. 4, 2010

(87) PCT Pub. No.: WO2008/043544
PCT Pub. Date: Apr. 17, 2008

(65) Prior Publication Data
US 2010/0184772 A1 Jul. 22, 2010

(30) Foreign Application Priority Data
Oct. 11, 2006 (EP) ..................... 06384015

(51) Int. Cl.
| | |
|---|---|
| A61K 31/501 | (2006.01) |
| A61K 31/496 | (2006.01) |
| A61K 31/497 | (2006.01) |
| A61K 31/437 | (2006.01) |
| A61K 31/4523 | (2006.01) |
| A61K 31/415 | (2006.01) |
| A61K 31/4178 | (2006.01) |
| A61K 31/4245 | (2006.01) |
| A61K 31/426 | (2006.01) |
| A61K 31/433 | (2006.01) |
| C07D 237/02 | (2006.01) |
| C07D 239/02 | (2006.01) |
| C07D 241/02 | (2006.01) |
| C07D 221/02 | (2006.01) |
| C07D 221/00 | (2006.01) |
| C07D 401/02 | (2006.01) |
| C07D 277/20 | (2006.01) |
| C07D 263/30 | (2006.01) |
| C07D 271/08 | (2006.01) |
| C07D 285/10 | (2006.01) |
| C07D 233/54 | (2006.01) |
| C07D 231/10 | (2006.01) |

(52) U.S. Cl. ................ 514/252.05; 514/252.1; 514/256; 514/299; 514/326; 514/362; 514/364; 514/365; 514/374; 514/385; 514/406; 544/235; 544/253; 544/338; 546/112; 546/275.4; 548/125; 548/134; 548/202; 548/235; 548/335.1; 548/377.1

(58) Field of Classification Search ............ 514/252.05, 514/252.1, 256, 299, 326, 362, 364, 365, 514/374, 385, 406; 544/235, 253, 338; 546/112, 546/275.4; 548/125, 134, 202, 235, 335.1
See application file for complete search history.

(56) References Cited

U.S. PATENT DOCUMENTS
2007/0021486 A1  1/2007 Barth et al.

FOREIGN PATENT DOCUMENTS
WO  WO 2005/074920 A1  8/2005
WO  WO 2005/077911 A1  8/2005

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Golub et al. Science (1999), vol. 286 531-537.*
Lala et al. Cancer and Metastasis Reviews (1998), 17(1), 91-106.*
Muccioli, G.G. and Lambert, D.M.: "Latest Advances in Cannabinoid Receptor Antagonists and Inverse Agonists". Expert Opin. Ther. Patents, vol. 16, No. 10, Oct. 2006, pp. 1405-1423, XP00242410.
Lange, Jos H.M. et al: "Synthesis, Biological Properties, and Molecular Modeling Investigations of Novel 3,4-Diarylpyrazolines as Potent and Selective CB1 Cannabinoid Receptor Antagonists" Journal of Medicinal Chemistry, American Chemical Society, US, vol. 47, No. 3, 2004, pp. 627-643, XP001188902 ISSN: 0022-2623.

* cited by examiner

Primary Examiner — Rebecca Anderson
Assistant Examiner — Samantha Shterengarts
(74) Attorney, Agent, or Firm — Banner & Witcoff, Ltd.

(57) ABSTRACT

The present invention relates to substituted pyrazoline compounds of general formula (I), methods for their preparation, medicaments comprising these compounds as well as their use for the preparation of a medicament for the treatment of humans and animals.

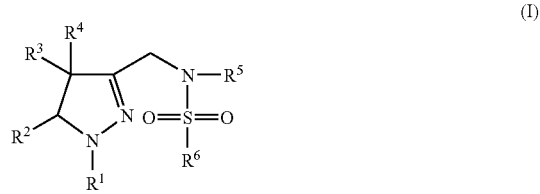

18 Claims, 2 Drawing Sheets

Figure 1:
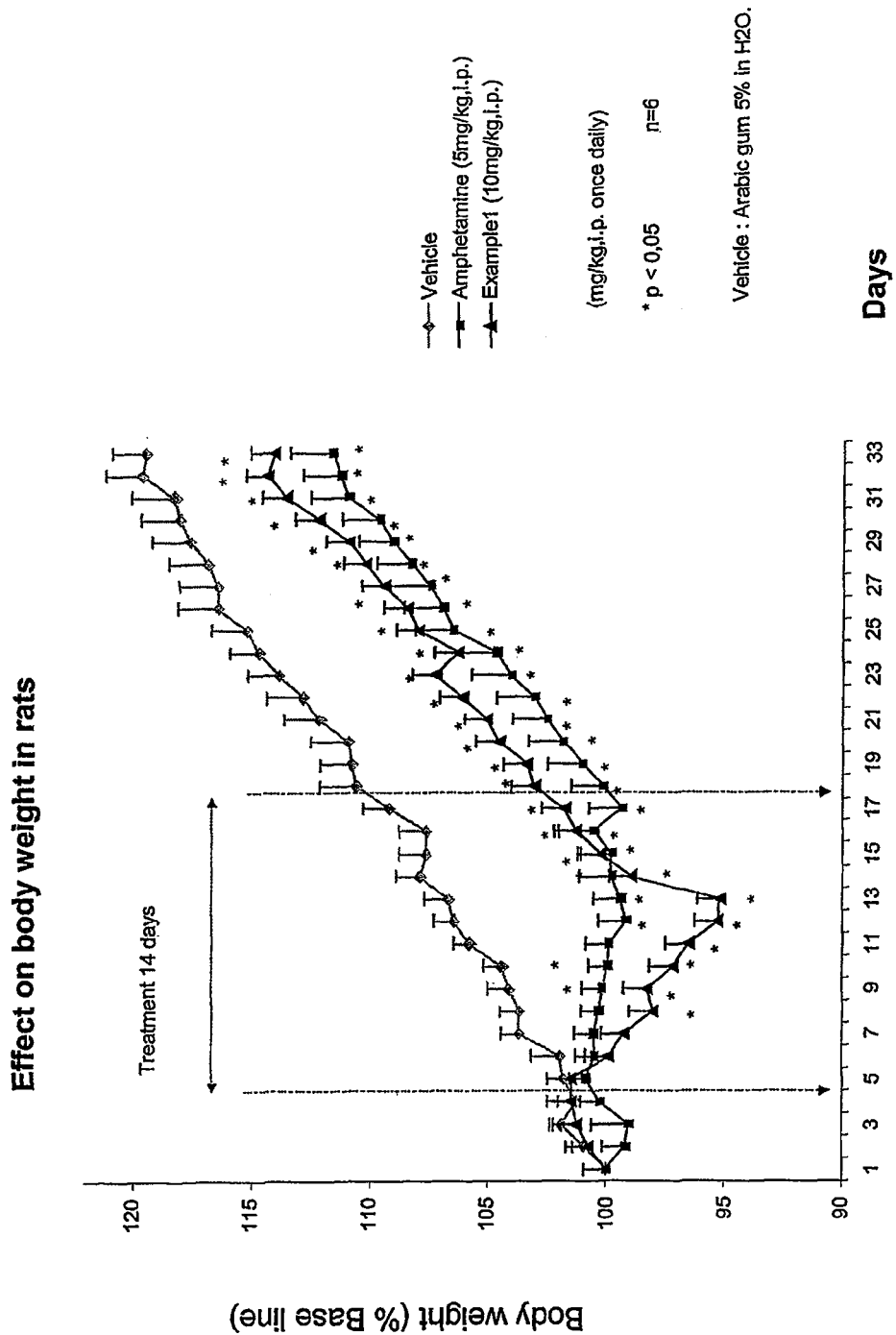
Figure 2:
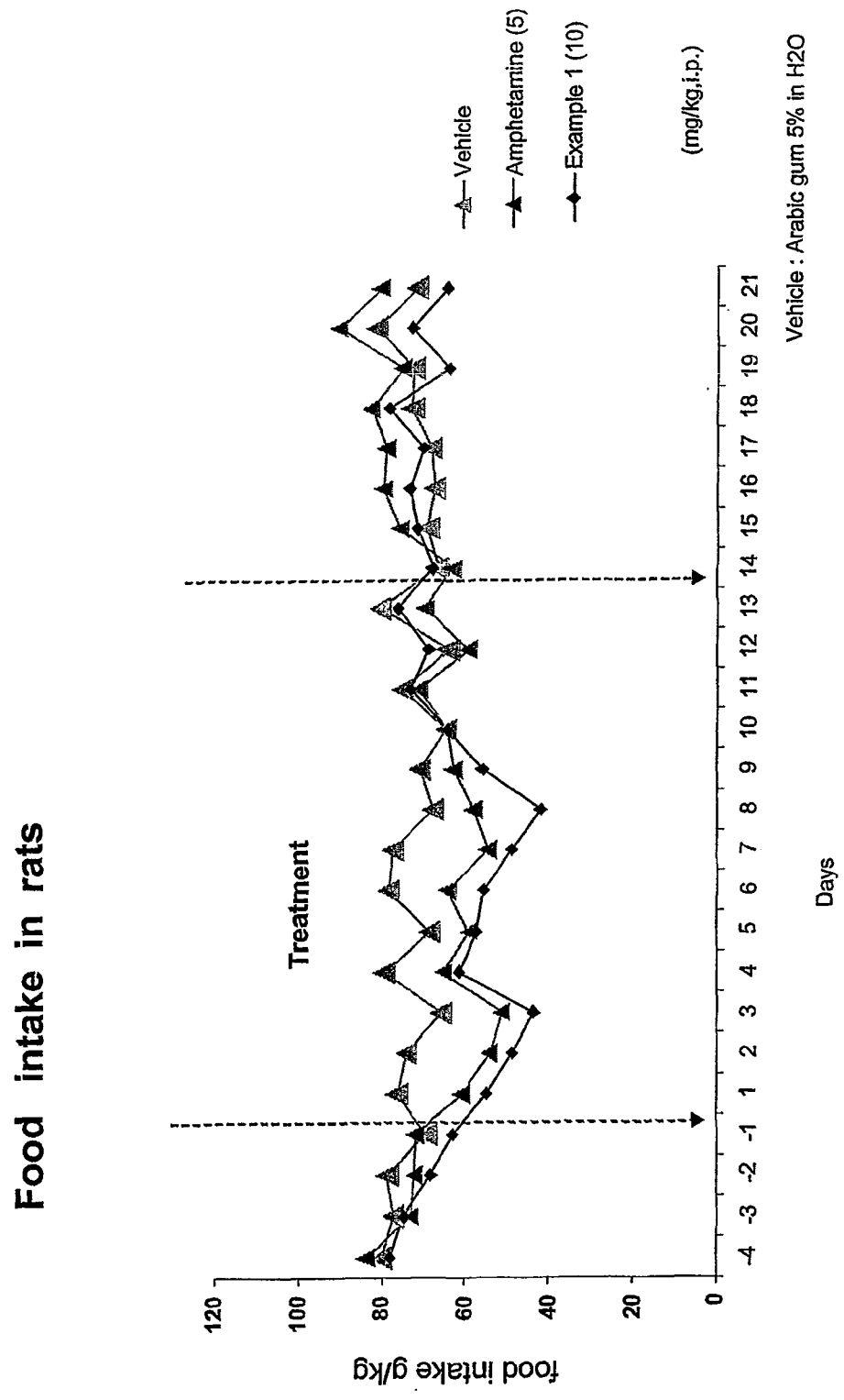

SULFONAMIDE SUBSTITUTED PYRAZOLINE COMPOUNDS, THEIR PREPARATION AND USE AS CB1 MODULATORS

CROSS-REFERENCE TO RELATED APPLICATIONS

This application is a U.S. National Stage application under 35 U.S.C. §371 of International Application No. PCT/EP2007/008812 (published as WO 2008/043544 A1), filed Oct. 10, 2007, which claims priority to EP Application No. 06384015.1, filed Oct. 11, 2006. Benefit of the filing date of each of these prior applications is hereby claimed. Each of these prior applications is hereby incorporated by reference in its entirety.

The present invention relates to substituted pyrazoline compounds, methods for their preparation, medicaments comprising these compounds as well as their use for the preparation of a medicament for the treatment of humans and animals.

Cannabinoids are compounds, which are derived from the cannabis sativa plant which is commonly known as marijuana. The most active chemical compound of the naturally occurring cannabinoids is tetrahydrocannabinol (THC), particularly $\Delta^9$-THC.

These naturally occurring cannabinoids as well as their synthetic analogues promote their physiological effects via binding to specific G-coupled receptors, the so-called cannabinoid-receptors.

At present, two distinct types of receptors that bind both the naturally occurring and synthetic cannabinoids have been identified and cloned. These receptors, which are designated $CB_1$ and $CB_2$ are involved in a variety of physiological or pathophysiological processes in humans and animals, e. g. processes related to the central nervous system, immune system, cardiovascular system, endocrinous system, respiratory system, the gastrointestinal tract or to reproduction, as described for example, in Hollister, Pharm. Rev. 38, 1986, 1-20; Reny and Singha, Prog. Drug. Res., 36, 71-114, 1991; Consroe and Sandyk, in Marijuana/Cannabinoids, Neurobiology and Neurophysiology, 459, Murphy L. and Barthe A. Eds., CRC Press, 1992.

Therefore, compounds, which have a high binding affinity for these cannabinoid receptors and which are suitable for modulating these receptors are useful in the prevention and/or treatment of cannabinoid-receptor related disorders.

In particular, the $CB_1$-receptor is involved in many different food-intake related disorders such as bulimia or obesity, including obesity associated with type II diabetes (non-insulin-dependent diabetes) and thus, compounds suitable for regulating this receptor may be used in the prophylaxis and/or treatment of these disorders.

Thus, it was an object of the present invention to provide novel compounds for use as active substances in medicaments. In particular, these active substances should be suitable for the modulation of cannabinoid receptors, more particularly for the modulation of cannabinoid 1 ($CB_1$) receptors.

Said object was achieved by providing the substituted pyrazoline compounds of general formula I given below, their stereoisomers, corresponding salts and corresponding solvates thereof. It has been found that these compounds have a high affinity for cannabinoid receptors, particularly for the $CB_1$-receptor, and that they act as modulators e. g. antagonists, inverse agonists or agonists on these receptors. They are therefore suitable for the prophylaxis and/or treatment of various disorders related to the central nervous system, the immune system, the cardiovascular system, the endocrinous system, the respiratory system, the gastrointestinal tract or reproduction in humans and/or animals, preferably humans including infants, children and grown-ups.

Thus, in one of its aspects the present invention relates to substituted pyrazoline compounds of general formula I,

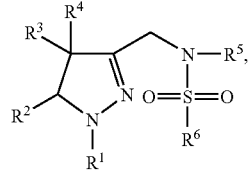

wherein $R^1$ represents unsubstituted or at least mono-substituted aryl which may be condensed with an unsubstituted or at least mono-substituted saturated or unsaturated, but not aromatic, mono- or bicyclic ring system; or
unsubstituted or at least mono-substituted heteroaryl which may be condensed with an unsubstituted or at least mono-substituted saturated or unsaturated, but not aromatic, mono- or bicyclic ring system;

$R^2$ represents unsubstituted or at least mono-substituted aryl which may be condensed with an unsubstituted or at least mono-substituted saturated or unsaturated, but not aromatic, mono- or bicyclic ring system; or
unsubstituted or at least mono-substituted heteroaryl which may be condensed with an unsubstituted or at least mono-substituted saturated or unsaturated, but not aromatic, mono- or bicyclic ring system;

$R^3$ and $R^4$, independent of one another, each represent H; F; Cl; Br; I; —CN;
—$NO_2$; —NC; —OH; —$NH_2$; —SH; —C(=O)—H; —C(=O)—OH; —O—$R^7$; —S—$R^8$; —C(=O)—$OR^9$; —C(=O)—$R^{10}$; unsubstituted or at least mono-substituted alkyl, alkenyl or alkinyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^5$ represents H or unsubstituted or at least mono-substituted alkyl, alkenyl or alkinyl; or —S(=O)$_2$—$R^6$;

$R^6$ represents —$NR^{6a}R^{6b}$; unsubstituted or at least mono-substituted alkyl, alkenyl or alkinyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^{6a}$ and $R^{6b}$, independent of one another, each represent H; unsubstituted or at least mono-substituted alkyl, alkenyl or alkinyl; or unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system;

$R^7$, $R^8$, $R^9$ and $R^{10}$, independent of one another, each represent unsubstituted or at least mono-substituted alkyl, alkenyl or alkinyl; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

Preferably heterocyloalkyl groups and heterocycloalkenyl groups in position of the substituent $R^6$ are bonded to the core structure via a nitrogen atom of their ring.

"Alkyl" according to the present invention is a monovalent saturated hydrocarbon chain having 1 to 16 carbon atoms, preferably 1 to 12 carbon atoms, more preferably 1 to 6 carbon atoms. Alkyl groups may be straight or branched. Preferred branched alkyl groups have one or two branches, preferably one branch.

"Alkenyl" according to the present invention is a monovalent hydrocarbon chain having 2 to 16 carbon atoms, preferably 2 to 12 carbon atoms, more preferably 2 to 6 carbon atoms and at least one carbon-carbon double bond. Preferably alkenyl groups have only one carbon-carbon double bond. Alkenyl groups may be straight or branched. Preferred branched alkenyl groups have one or two branches, preferably one branch.

"Alkinyl" according to the present invention is a monovalent hydrocarbon chain having 2 to 16 carbon atoms, preferably 2 to 12 carbon atoms, more preferably 2 to 6 carbon atoms and at least one carbon-carbon triple bond. Preferably alkinyl groups have only one carbon-carbon triple bond. Alkinyl groups may be straight or branched. Preferred branched alkinyl groups have one or two branches, preferably one branch.

Preferably alkyl groups including $C_{1-16}$alkyl, $C_{1-12}$alkyl and $C_{1-6}$alkyl, alkenyl groups including $C_{2-16}$alkenyl, $C_{2-12}$alkenyl and $C_{2-6}$alkenyl and alkinyl groups including $C_{2-16}$alkinyl, $C_{2-12}$alkinyl and $C_{2-6}$alkinyl may be unsubstituted or substituted with 1, 2, 3, 4 or 5 substituent(s) independently selected from the group consisting of —OH, F, Cl, Br, I, —O—$C_{1-6}$-alkyl, —OCF$_3$, —O—$C_2F_5$, —O—$C_3F_7$, —O—$C_4F_9$, —CF$_3$, —$C_2F_5$, —$C_3F_7$, —$C_4F_9$, —NH$_2$, —NH—$C_{1-6}$-alkyl, —N($C_{1-6}$-alkyl)$_2$, —C(=O)—OH, —C(=O)—O—$C_{1-6}$-alkyl, —C(=O)—NH$_2$, —C(=O)—NH—$C_{1-6}$-alkyl, —C(=O)—N($C_{1-6}$-alkyl)$_2$, —CN, —NO$_2$, —S(=O)—NH$_2$, —CHO, —C(=O)—$C_{1-6}$-alkyl, —S(=O)—$C_{1-6}$-alkyl, —S(=O)$_2$—$C_{1-6}$-alkyl, —NH—S(=O)—$C_{1-6}$-alkyl, —NH—C(=O)—O—$C_{1-6}$-alkyl and —NH—C(=O)—$C_{1-6}$-alkyl.

More preferably alkyl groups including $C_{1-16}$alkyl, $C_{1-12}$alkyl and $C_{1-6}$alkyl, alkenyl groups including $C_{2-16}$alkenyl, $C_{2-12}$alkenyl and $C_{2-6}$alkenyl and alkinyl groups including $C_{2-16}$alkinyl, $C_{2-12}$alkinyl and $C_{2-6}$alkinyl may be unsubstituted or substituted with 1, 2, 3, 4 or 5 substituent(s) independently selected from the group consisting of —OH, F, Cl, Br, I, —O—CH$_3$, —O—$C_2H_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —NH$_2$, —NH—CH$_3$, —NH—$C_2H_5$, —N(CH$_3$)$_2$, —N($C_2H_5$)$_2$, —CN, —NO$_2$, —NH—C(=O)—CH$_3$, —NH—(=O)—$C_2H_5$, —NH—C(=O)—C(CH$_3$)$_3$, —NH—C(=O)—O—CH$_3$, —NH—C(=O)—O—$C_2H_5$, —NH—C(=O)—O—C(CH$_3$)$_3$, —C(=O)—NH—CH$_3$, —C(=O)—NH—$C_2H_5$, —C(=O)—NH—C(CH$_3$)$_3$, —C(=O)—N(CH$_3$)$_2$, —C(=O)—N($C_2H_5$)$_2$, —C(=O)—OH, —C(=O)—O—CH$_3$, —C(=O)—O—$C_2H_5$, —C(=O)—O—C(CH$_3$)$_3$, —C(=O)—CH$_3$, —C(=O)—$C_2H_5$ and —C(=O)—C(CH$_3$)$_3$.

Suitable unsubstituted alkyl groups, preferably $C_{1-16}$alkyl groups, are selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl and n-hexadecyl.

Suitable at least mono-substituted alkyl groups, preferably $C_{1-6}$alkyl groups, are selected from the group consisting of —CF$_3$, —CH$_2$F, —CF$_2$H, —CH$_2$—O—CH$_3$, —$C_2F_5$, —CH$_2$—CH$_2$—F, —CH$_2$—CN, —CH$_2$—OH, —CH$_2$—CH$_2$—CN, —CH$_2$—CH$_2$—OH, —CH$_2$—CH$_2$—OCH$_3$, —CH$_2$—CH$_2$—CH$_2$—CN, —CH$_2$—CH$_2$—CH$_2$—OH, —CH$_2$—CH$_2$—CH$_2$—O—CH$_3$, —CH$_2$—CH$_2$—CH$_2$—CH$_2$—O—CH$_3$, —CH$_2$—NH$_2$, —CH$_2$—N(CH$_3$)$_2$, —CH$_2$—N($C_2H_5$)$_2$, —CH$_2$—CH—NH$_2$, —CH$_2$—CH$_2$—N(CH$_3$)$_2$, —CH$_2$—CH$_2$—N($C_2H_5$)$_2$, —CH$_2$—CH$_2$—CH$_2$—NH$_2$, —CH$_2$—CH$_2$—CH$_2$—N(CH$_3$)$_2$ and —CH$_2$—CH$_2$—CH$_2$—N($C_2H_5$)$_2$.

Suitable unsubstituted alkenyl groups, preferably $C_{2-16}$alkenyl groups, are selected from the group consisting of vinyl, n-propenyl, n-butenyl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl and n-hexadecenyl.

Suitable unsubstituted alkinyl groups, preferably $C_{2-16}$alkinyl groups, are selected from the group consisting of ethinyl, propinyl, n-butinyl, n-pentinyl, n-hexinyl, n-octinyl, n-noninyl, n-decinyl, n-undecinyl, n-dodecinyl, n-tridecinyl, n-tetradecinyl, n-pentadecinyl and n-hexadecinyl.

"Aryl" according to the present invention is an aromatic hydrocarbon ring system. Aryl rings are either monocyclic or fused bicyclic ring systems. Monocyclic aryl rings contain 6 carbon atoms in the ring. Monocyclic aryl rings are also referred to as phenyl rings. Bicyclic aryl rings contain 10 carbon atoms in the ring. Bicyclic aryl rings are also referred to as naphthyl.

"Heteroaryl" according to the present invention is a mono-, bi- or tricyclic ring system containing carbon atoms in the ring and 1, 2, 3, 4, 5 or 6 heteroatom(s) in the ring. Preferably the heteroatoms which are present as ring members in the heteroaryl group may, unless defined otherwise, independently be selected from the group consisting of nitrogen, oxygen and sulfur. More preferably a heteroaryl group is 5- to 14-membered, i. e. 5-, 6-, 7-, 8-, 9-, 10-, 11-, 12-, 13- or 14-membered, and may comprise 1, 2, 3 or 4 heteroatom(s) independently selected from the group consisting of nitrogen, oxygen and sulfur.

Aryl groups or heteroaryl groups may be unsubstituted or at least mono-substituted. Preferably said aryl groups and heteroaryl groups may be substituted with 1, 2, 3, 4 or 5 substituent(s) independently selected from the group consisting of —$C_{1-6}$-perfluoralkyl, —$C_{1-6}$-alkyl substituted with one or more —C(=O)—O—$CH_3$ groups, —$C_{1-6}$-alkyl substituted with one or more methoxy and/or ethoxy groups, —$C_{1-6}$-alkyl, —$C_{1-6}$-alkyl substituted with one or more hydroxy groups, —$C_{1-6}$-alkyl substituted with one or more chlorine atoms, —O—$C_{1-6}$-alkyl, —O—$C_{1-6}$-alkyl substituted with one or more methoxy and/or ethoxy groups, —S—$C_{1-6}$-alkyl, —C(=O)—OH, —C(=O)—O—$C_{1-6}$-alkyl, —O—C(=O)—$C_{1-6}$-alkyl, F, Cl, Br, I, —CN, —$OCF_3$, —O—$C_2F_5$, —O—$C_3F_7$, —O—$C_4F_9$, —$SCF_3$, —$SCF_3$, —$SCF_2H$, —$SCFH_2$, —OH, —SH, —$SO_3H$, —NH—C(=O)—$C_{1-6}$-alkyl, —N($C_{1-6}$-alkyl)-C(=O)—$C_{1-6}$-alkyl, —$NO_2$, —CHO, —C(=O)—$C_{1-6}$-alkyl, —C(=O)—$C_{1-6}$-perfluoroalkyl, —C(=S)—NH—$C_{1-6}$-alkyl, —$CF_2H$, —$CFH_2$, —C(=O)—$NR^AR^B$, —C(=O)—NH—$NR^CR^D$, —S(=O)—$C_{1-6}$-alkyl, —S(=O)$_2$—$C_{1-6}$-alkyl, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —$NR^ER^F$, —($C_{1-5}$-alkylene)-$NR^ER^F$, —S(=O)—$NH_2$, —S(=O)$_2$—NH—$C_{1-6}$-alkyl, —S(=O)$_2$—NH-phenyl, —NH—S(=O)$_2$—$C_{1-6}$-alkyl, cyclopropyl, cyclobutyl, cyclopentyl, cyclohexyl, pyrrolidinyl, piperidinyl, phenyl, thiophenyl, —O-phenyl and benzyl;

whereby in each case the cyclic moieties cyclopropyl, cyclobutyl, cyclopentyl, cyclohexyl, pyrrolidinyl, piperidinyl, phenyl, thiophenyl, —O-phenyl and benzyl can optionally be substituted with 1, 2, 3, 4 or 5 substituent(s) independently selected from the group consisting of F, Cl, Br, I, —OH, —$CF_3$, —CN, —$NO_2$, —$C_{1-6}$-alkyl, —O—$C_{1-6}$-alkyl, —O—$CF_3$ and —S—$CF_3$ and whereby $R^A$, $R^B$, $R^E$ and $R^F$, independent of one another, each represent hydrogen or —$C_{1-6}$-alkyl or $R^A$ and $R^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different $C_{1-6}$alkyl radicals and whereby $R^C$ and $R^D$, independent of one another, each represent hydrogen, —$C_{1-6}$-alkyl, —C(=O)—O—$C_{1-6}$-alkyl, $C_{3-8}$-cycloalkyl, —($C_{1-5}$-alkylene)-$C_{3-8}$-cycloalkyl, —($C_{1-6}$-alkylene)-O—$C_{1-6}$-alkyl or —$C_{1-6}$-alkyl substituted with one or more hydroxy groups or $R^C$ and $R^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(=O)—$C_{1-6}$-alkyl, —C(=O)—O—$C_{1-6}$-alkyl, —C(=O)—NH—$C_{1-6}$-alkyl, —C(=S)—NH—$C_{1-6}$-alkyl, oxo (=O), —$C_{1-6}$-alkyl substituted with one or more hydroxy groups, —($C_{1-6}$-alkylene)-O—$C_{1-6}$-alkyl and —C(=O)—$NH_2$.

More preferably said aryl groups and heteroaryl groups may be substituted with 1, 2, 3, 4 or 5 substituent(s) independently selected from the group consisting of —$CH_2$—$CH_2$—C(=O)—$OCH_3$, —$CH_2$—C(=O)—$OCH_3$, —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —C($OCH_3$)($C_2H_5$)$_2$, —C($OCH_3$)($CH_3$)$_2$, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —S—$CH_3$, —S—$C_2H_5$, —S—$CH_2$—$CH_2$—$CH_3$, —S—CH($CH_3$)$_2$, —S—$CH_2$—$CH_2$—$CH_2$—$CH_3$, —S—C($CH_3$)$_3$, —C(=O)—OH, —C(=O)—O—$CH_3$, —C(=O)—O—$C_2H_5$, —C(=O)—O—$C_3H_7$, —C(=O)—O—C($CH_3$)$_3$, —O—C(=O)—$CH_3$, —O—C(=O)—$C_2H_5$, —O—C(=O)—CH($CH_3$)$_2$, —O—C(=O)—$CH_2$—$CH_2$—$CH_3$, —O—C(=O)—$CH_2$—$CH_2$—$CH_3$, —O—C(=O)—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—C($CH_3$)$_3$, —$NO_2$, —CHO, —C(=O)—$CH_3$, —C(=O)—$C_2H_5$, —C(=O)—C($CH_3$)$_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —S(=O)$_2$-phenyl, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)-morpholinyl, —($CH_2$)-piperidinyl, —($CH_2$)-piperazinyl, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —S(=O)—$NH_2$, —S(=O)$_2$—NH—$CH_3$, —S(=O)$_2$—NH-phenyl, —NH—S(=O)$_2$—$CH_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl.

Preferred heteroaryl groups which are unsubstituted or at least mono-substituted are pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]-benzothiadiazolyl, [2.1.3]-benzoxadiazolyl, [1.2.3]-benzoxadiazolyl, benzoxazolyl, benzthiazolyl, benzisoxazolyl, benzisothiazolyl, imidazo[2,1-b]thiazolyl, 2H-chromenyl, pyranyl, indazolyl, quinazolinyl, benzotriazolyl, [1.2.4]-triazolyl, tetrazolyl, [1.2.3.4]-oxatriazolyl, [1.2.3.4]-thiatriazolyl, [1.2.3.5]-thiatriazolyl, [1.2.3.5]-oxatriazolyl, [1.2.3]-triazinyl, [1.2.4]-triazinyl, [1.2.4.5]-tetrazinyl, dibenzofuranyl, [1.3.5]-triazinyl, indolizinyl, purinyl, benzimidazolyl, pteridinyl, carbazolyl, cinnolinyl, phthalazinyl, quinoxalinyl, [1.8]-naphthypyridinyl, acridinyl, benzo[1,4]-dioxine, quinoxaline, or 2,3-dihydro-benzo[1,4]-dioxine, 1,2,3,4-tetrahydro-quinoxaline, 2,3-dioxo-1,2,3,4-tetrahydro-quinoxaline, and phenazinyl.

"Cycloalkyl" according to the present invention is a saturated hydrocarbon ring which can either be a monocyclic ring system or a spiro or bridged bicyclic ring system. Cycloalkyl rings contain from 3 to 16 carbon atoms, i. e. 3, 4, 5, 6, 7, 8, 9, 10, 11, 12, 13, 14, 15 or 16 carbon atoms, preferably from 3 to 10 carbon atoms, more preferably from 3 to 7 carbon atoms.

"Cycloalkenyl" according to the present invention is an unsaturated hydrocarbon ring which can either be a monocyclic ring system or a spiro or bridged bicyclic ring system. Cycloalkenyl rings are not aromatic and contain at least one carbon-carbon double bond. Preferably cycloalkenyl rings contain one carbon-carbon double bond. Cycloalkenyl rings contain from 5 to 16 carbon atoms, i. e. 5, 6, 7, 8, 9, 10, 11, 12, 13, 14, 15 or 16 carbon atoms, preferably from 5 to 10 carbon atoms, more preferably from 5 to 7 carbon atoms.

"Heterocycloalkyl" according to the present invention is a saturated hydrocarbon ring which can either be a monocyclic ring system or a spiro or bridged bicyclic ring system wherein 1, 2, 3 or 4, preferably 1 or 2, carbon atoms have been replaced by heteroatoms. Preferably the heteroatoms which are present as ring members in the heterocycloalkyl group may, unless defined otherwise, independently be selected from the group consisting of nitrogen, oxygen and sulfur. Preferably the heterocycloalkyl rings are 3- to 16-membered, i. e. 3-, 4-, 5-, 6-, 7-, 8-, 9-, 10-, 11-, 12-, 13-, 14-, 15- or 16-membered, more preferably 3- to 10-membered, and even more preferably 3- to 7-membered.

"Heterocycloalkenyl" according to the present invention is an unsaturated hydrocarbon ring which can either be a monocyclic ring system or a Spiro or bridged bicyclic ring system wherein 1, 2, 3 or 4, preferably 1 or 2, carbon atoms have been replaced by heteroatoms. Preferably the heteroatoms which are present as ring members in the heterocycloalkyl group may, unless defined otherwise, independently be selected from the group consisting of nitrogen, oxygen and sulfur. Preferably the heterocycloalkyl rings are 5- to 16-membered, i.e. 5-, 6-, 7-, 8-, 9-, 10-, 11-, 12-, 13-, 14-, 15- or 16-membered, more preferably 5- to 10-membered, even more preferably 5- to 7-membered. Heterocycloalkenyl rings are not aromatic and contain at least one carbon-carbon double bond. Preferably heterocycloalkenyl rings contain one carbon-carbon double bond.

Cycloalkyl groups including $C_{3-16}$cycloalkyl, $C_{3-10}$cycloalkyl and $C_{3-7}$cycloalkyl, cycloalkenyl rings including $C_{5-16}$cycloalkenyl, $C_{5-10}$cycloalkenyl and $C_{5-7}$cycloalkenyl, heterocycloalkyl including 3- to 16-membered heterocycloalkyl, 3- to 10-membered heterocycloalkyl and 3- to 7-membered heterocycloalkyl and heterocycloalkenyl including 5- to 16-membered heterocycloalkenyl, 5- to 10-membered heterocycloalkenyl and 5- to 7-membered heterocycloalkenyl can be unsubstituted or at least mono-substituted.

Preferably said cycloalkyl groups including $C_{3-16}$cycloalkyl, $C_{3-10}$cycloalkyl and $C_{3-7}$cycloalkyl, cycloalkenyl groups including $C_{5-16}$cycloalkenyl, $C_{5-10}$cycloalkenyl and $C_{5-7}$cycloalkenyl, heterocycloalkyl groups including 3- to 16-membered heterocycloalkyl, 3- to 10-membered heterocycloalkyl and 3- to 7-membered heterocycloalkyl and heterocycloalkenyl groups including 5- to 16-membered heterocycloalkenyl, 5- to 10-membered heterocycloalkenyl and 5- to 7-membered heterocycloalkenyl may in each case be substituted with 1, 2, 3, 4 or 5 substituent(s) independently selected from the group consisting of oxo (═O), thioxo (═S), —$C_{1-6}$-perfluoralkyl, —$C_{1-6}$alkyl, —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl, —O—$C_{1-6}$-alkyl substituted with one or more methoxy and/or ethoxy groups, —S—$C_{1-6}$-alkyl, —C(═O)—OH, —C(═O)—O—$C_{1-6}$-alkyl, —O—C(═O)—$C_{1-6}$-alkyl, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(═O)—$C_{1-6}$-alkyl, —N($C_{1-6}$-alkyl)-C(═O)—$C_{1-6}$-alkyl, —NO$_2$, —CHO, —C(═O)—$C_{1-6}$-alkyl, —C(═O)—$C_{1-6}$-perfluoroalkyl, —C(═S)—NH—$C_{1-6}$-alkyl, —CF$_2$H, —CFH$_2$, —C(═O)—NR$^A$R$^B$, —C(═O)—NH—NR$^C$R$^D$, —S(═O)—$C_{1-6}$-alkyl, —S(═O)$_2$—$C_{1-6}$-alkyl, —S(═O)$_2$-phenyl, —($C_{1-5}$-alkylene)-S—$C_{1-6}$-alkyl, —($C_{1-5}$-alkylene)-S(═O)—$C_{1-6}$-alkyl, —($C_{1-5}$-alkylene)-S(═O)$_2$—$C_{1-6}$-alkyl, —NR$^E$R$^F$, —($C_{1-5}$-alkylene)-NR$^E$R$^F$, —S(═O)—NH$_2$, —S(═O)$_2$—NH—$C_{1-6}$-alkyl, —S(═O)$_2$—NH-phenyl, —NH—S(═O)$_2$—$C_{1-6}$-alkyl, —O-benzyl, cyclopropyl, cyclobutyl, cyclopentyl, cyclohexyl, pyrrolidinyl, piperidinyl, phenyl, thiophenyl, —O-phenyl and benzyl;

whereby in each case the cyclic moieties cyclopropyl, cyclobutyl, cyclopentyl, cyclohexyl, pyrrolidinyl, piperidinyl, phenyl, thiophenyl, —O-Benzyl, —O-phenyl and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$ and whereby R$^A$, R$^B$, R$^E$ and R$^F$, independent of one another, each represent hydrogen or —$C_{1-6}$-alkyl or R$^A$ and R$^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different $C_{1-6}$alkyl radicals and whereby R$^C$ and R$^D$, independent of one another, each represent hydrogen, —$C_{1-6}$-alkyl, —C(═O)—O—$C_{1-6}$-alkyl, $C_{3-8}$-cycloalkyl, —($C_{1-5}$-alkylene)-$C_{3-8}$-cycloalkyl, —($C_{1-6}$-alkylene)-O—$C_{1-6}$-alkyl or —$C_{1-6}$-alkyl substituted with one or more hydroxy groups or R$^C$ and R$^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(═O)—$C_{1-6}$-alkyl, —C(═O)—O—$C_{1-6}$-alkyl, —C(═O)—NH—$C_{1-6}$-alkyl, —C(═S)—NH—$C_{1-6}$-alkyl, oxo (═O), —$C_{1-6}$-alkyl substituted with one or more hydroxy groups, —($C_{1-6}$-alkylene)-O—$C_{1-6}$-alkyl and —C(═O)—NH$_2$.

More preferably said cycloalkyl groups including $C_{3-16}$cycloalkyl, $C_{3-10}$cycloalkyl and $C_{3-7}$cycloalkyl, cycloalkenyl groups including $C_{5-16}$cycloalkenyl, $C_{5-10}$cycloalkenyl and $C_{5-7}$cycloalkenyl, heterocycloalkyl groups including 3- to 16-membered heterocycloalkyl, 3- to 10-membered heterocycloalkyl and 3- to 7-membered heterocycloalkyl and heterocycloalkenyl groups including 5- to 16-membered heterocycloalkenyl, 5- to 10-membered heterocycloalkenyl and 5- to 7-membered heterocycloalkenyl may each be substituted with 1, 2, 3, 4 or 5 substituent(s) independently selected from the group consisting of oxo (═O), thioxo (═S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$) (CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C (CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C (CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl.

Suitable cycloalkyl groups may preferably be selected from the group consisting of cyclopropyl, cyclobutyl, cyclopentyl, cyclohexyl, cycloheptyl, cyclooctyl and cyclononyl.

Suitable cycloalkenyl groups may preferably be selected from the group consisting of cyclopentenyl, cyclohexenyl, cycloheptenyl, cyclononenyl and cyclooctenyl.

Suitable heterocycloalkyl groups may preferably be selected from the group consisting of imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1.3)-dioxolan-2-yl, isoxazolidinyl, isothioazolidinyl, pyrazolidinyl, oxazolidinyl, (1.2.4)-oxadiazolidinyl, (1.2.4)-thiadiazolidinyl, (1.2.4)-triazolidin-3-yl, (1.3.4)-thiadiazolidin-2-yl, (1.3.4)-triazolidin-1-yl, (1.3.4)-triazoldidin-2-yl, tetrahydropyridazinyl, tetrahydropyrimidinyl, tetrahydropyrazinyl, (1.3.5)-tetrahydrotriazinyl, (1.2.4)-tetrahydrotriazin-1-yl, (1.3)-dithian-2-yl and (1.3)-thiazolidinyl.

Suitable heterocycloalkenyl groups may preferably be selected from the group consisting of (2.3)-dihydrofuranyl, (2.5)-dihydrofuranyl, (2.3)-dihydrothienyl, (2.5)-dihydrothienyl, (2.3)-dihydropyrrolyl, (2.5)-dihydropyrrolyl, (2.3)-dihydroisoxazolyl, (4.5)-dihydroisoxazolyl, (2.5)-dihydroisothiazolyl, (2.3)-dihydropyrazolyl, (4.5)-dihydropyrazolyl, (2.5)-dihydropyrazolyl, (2.3)-dihydrooxazolyl, (4.5)-dihydrooxazolyl, (2.5)-dihydrooxazolyl, (2.3)-dihydrothiazolyl, (4.5)-dihydrothiazolyl, (2.5)-dihydrothiazolyl, (2.3)-dihydroimidazolyl, (4.5)-dihydroimidazolyl, (2.5)-dihydroimidazolyl, (3.4.5.6)-tetrahydropyridin-2-yl, (1.2.5.6)-tetrahydropyridin-1-yl, (1.2)-dihydropyridin-1-yl, (1.4)-dihydropyridin-1-yl, dihydropyranyl, (1.2.3.4)-tetrahydropyrimidinyl and (1.2.3.4)-tetrahydropyridin-1-yl.

Suitable cycloalkyl groups, cycloalkenyl groups and heterocycloalkyl groups which form a bridged bicyclic ring system may preferably be selected from the group consisting of bicyclo[2.2.1]heptyl, bicyclo[3.1.1]heptyl, norbornenyl and 8-aza-bicyclo[3.2.1]octyl.

A suitable spirocyclic cycloalkyl and spirocyclic heterocycloalkyl group is 8-aza-spiro[4.5]decanyl.

A mono- or bicyclic ring system according to the present invention means a mono- or bicyclic hydrocarbon ring system that may be saturated, unsaturated or aromatic. Each of its different rings may show a different degree of saturation, i.e. they may be saturated, unsaturated or aromatic. Optionally each of the rings of the mono- or bicyclic ring system may contain one or more, preferably 1, 2 or 3, heteroatom(s) as ring member(s), which may be identical or different and which can preferably be selected from the group consisting of nitrogen, oxygen and sulfur. The rings of the mono- or bicyclic ring system are, independent of one another, preferably 5-, 6- or 7-membered.

The term "condensed" according to the present invention means that a ring or ring system is attached to another ring or ring system, whereby the terms "fused", "annulated" or "annelated" are also used by those skilled in the art to designate this kind of attachment.

A mono- or bicyclic ring system can be unsubstituted or at least mono-substituted. Preferably said mono- or bicyclic ring system may be substituted with 1, 2, 3, 4 or 5 substituent(s) independently selected from the group consisting of oxo (=O), thioxo (=S), —C$_{1-6}$-perfluoralkyl, —C$_{1-6}$-alkyl, —C$_{1-6}$-alkyl substituted with one or more hydroxy groups, —C$_{1-6}$-alkyl substituted with one or more chlorine atoms, —C$_{1-6}$-alkyl substituted with one or more methoxy and/or ethoxy groups, —O—C$_{1-6}$-alkyl, —O—C$_{1-6}$-alkyl substituted with one or more methoxy and/or ethoxy groups, —S—C$_{1-6}$-alkyl, —C(=O)—OH, —C(=O)—O—C$_{1-6}$-alkyl, —O—C(=O)—C$_{1-6}$-alkyl, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—C$_{1-6}$-alkyl, —N(C$_{1-6}$-alkyl)-C(=O)—C$_{1-6}$-alkyl, —NO$_2$, —CHO, —C(=O)—C$_{1-6}$-alkyl, —C(=O)—C$_{1-6}$-perfluoroalkyl, —C(=S)—NH—C$_{1-6}$-alkyl, —CF$_2$H, —CFH$_2$, —C(=O)—NR$^A$R$^B$, —C(=O)—NH—NR$^C$R$^D$, —S(=O)—C$_{1-6}$-alkyl, —S(=O)$_2$—C$_{1-6}$-alkyl, —S(=O)$_2$-phenyl, —(C$_{1-5}$-alkylene)-S—C$_{1-6}$-alkyl, —(C$_{1-5}$-alkylene)-S(=O)—C$_{1-6}$-alkyl, —(C$_{1-5}$-alkylene)-S(=O)$_2$—C$_{1-6}$-alkyl, —NR$^E$R$^F$, —(C$_{1-5}$-alkylene)-NR$^E$R$^F$, —S(=O)—NH$_2$, —S(=O)$_2$—NH—C$_{1-6}$-alkyl, —S(=O)$_2$—NH-phenyl, —NH—S(=O)$_2$—C$_{1-6}$-alkyl, cyclopropyl, cyclobutyl, cyclopentyl, cyclohexyl, pyrrolidinyl, piperidinyl, phenyl, thiophenyl, —O-phenyl and benzyl;

whereby in each case the cyclic moieties cyclopropyl, cyclobutyl, cyclopentyl, cyclohexyl, pyrrolidinyl, piperidinyl, phenyl, thiophenyl, —O-phenyl and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$ and whereby R$^A$, R$^B$, R$^E$ and R$^F$, independent of one another, each represent hydrogen or —C$_{1-6}$-alkyl or R$^A$ and R$^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different C$_{1-6}$alkyl radicals and whereby R$^C$ and R$^D$, independent of one another, each represent hydrogen, —C$_{1-6}$-alkyl, —C(=O)—O—C$_{1-6}$-alkyl, C$_{3-8}$-cycloalkyl, —(C$_{1-5}$-alkylene)-C$_{3-8}$-cycloalkyl, —(C$_{1-6}$-alkylene)-O—C$_{1-6}$-alkyl or —C$_{1-6}$-alkyl substituted with one or more hydroxy groups or $R^C$ and $R^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(=O)—O—$C_{1-6}$-alkyl, —C(=O)—NH—$C_{1-6}$-alkyl, —C(=S)—NH—$C_{1-6}$-alkyl, oxo (=O), —$C_{1-6}$-alkyl substituted with one or more hydroxy groups, —($C_{1-6}$-alkylene)-O—$C_{1-6}$-alkyl and —C(=O)—$NH_2$.

More preferably said mono- or bicyclic ring system may be substituted with 1, 2, 3, 4 or 5 substituent(s) independently selected from the group consisting of oxo (=O), thioxo (=S), —$CF_3$, —$C_2F_5$, —$C_3F_7$, —$C_4F_9$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —C($OCH_3$)($C_2H_5$)$_2$, —C($OCH_3$)($CH_3$)$_2$, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —S—$CH_3$, —S—$C_2H_5$, —S—$CH_2$—$CH_2$—$CH_3$, —S—CH($CH_3$)$_2$, —S—$CH_2$—$CH_2$—$CH_2$—$CH_3$, —S—C($CH_3$)$_3$, —C(=O)—OH, —C(=O)—O—$CH_3$, —C(=O)—O—$C_2H_5$, —C(=O)—O—$C_3H_7$, —C(=O)—O—C($CH_3$)$_3$, —O—C(=O)—$CH_3$, —O—C(=O)—$C_2H_5$, —O—C(=O)—CH($CH_3$)$_2$, —O—C(=O)—$CH_2$—$CH_2$—$CH_3$, —O—C(=O)—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—C($CH_3$)$_3$, —$NO_2$, —CHO, —C(=O)—$CH_3$, —C(=O)—$C_2H_5$, —C(=O)—C($CH_3$)$_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)—$C_3H_7$, —S(=O)$_2$-phenyl, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)-morpholinyl, —($CH_2$)-piperidinyl, —($CH_2$)-piperazinyl, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —S(=O)—$NH_2$, —S(=O)$_2$—NH—$CH_3$, —S(=O)$_2$—NH-phenyl, —NH—S(=O)$_2$—$CH_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl.

Aryl groups which are condensed with an unsubstituted or at least mono-substituted mono- or bicyclic ring system can be selected from the group consisting of [1.2.3.4]-tetrahydroquinolinyl, 2-oxo-[1.2.3.4]-tetrahydroquinolinyl, [1.2.3.4]-tetrahydroisoquinolinyl, [1.2.3.4]-tetrahydroquinazolinyl, (2.3)-dihydro-1H-cyclopenta[b]indolyl, 3H-benzothiazol-2-onyl, (2.3)-dihydrobenzothiazolyl, dihydrobenzofuranyl, [1.3]-benzodioxolyl, [1.4]-benzodioxanyl, [1.2.3.4]-tetrahydronaphthyl and [3.4]-dihydro-2H-benzo[1.4]oxazinyl.

Heteroaryl groups which are condensed with an unsubstituted or at least mono-substituted mono- or bicyclic ring system can be selected from the group consisting of 7,7a-dihydro-imidazo[2,1-b]thiazolyl and (2.3)-dihydro-1H-cyclopenta[b]indolyl.

Suitable heterocycloalkyl groups and heterocycloalkenyl groups which are each condensed with an unsubstituted or at least mono-substituted mono- or bicyclic ring system may preferably be selected from the group consisting of 7,7a-dihydro-imidazo[2,1-b]thiazolyl, indolinyl, isoindolinyl, (1.2.3.4)-tetrahydroquinolinyl, (1.2.3.4)-tetrahydroisoquinolinyl, octahydro-cyclopenta[c]pyrrolyl, (1.3.4.7.9a)-hexahydro-2H-quinolizinyl, (1.2.3.5.6.8a)-hexahydro-indolizinyl, decahydroquinolinyl, dodecahydro-carbazolyl, 9H-carbazolyl, decahydroisoquinolinyl, (6.7)-dihydro-4H-thieno[3.2-c]pyridinyl and (2.3)-dihydro-1H-benzo[de]isoquinolinyl.

Suitable cycloalkyl groups and cycloalkenyl groups which are each condensed with an unsubstituted or at least mono-substituted mono- or bicyclic ring system may preferably be selected from the group consisting of decahydronaphthyl and (1.2.3.4)-tetrahydronaphthyl.

"Alkylene" according to the present invention is a divalent saturated hydrocarbon chain having 1 to 16 carbon atoms, preferably 1 to 12 carbon atoms, more preferably 1 to 6 carbon atoms. Alkylene groups may be straight or branched. Preferred branched alkylene groups have one or two branches, preferably one branch.

"Alkenylene" according to the present invention is a divalent hydrocarbon chain having 2 to 16 carbon atoms, preferably 2 to 12 carbon atoms, more preferably 2 to 6 carbon atoms and at least one carbon-carbon double bond. Preferably alkenylene groups have only one carbon-carbon double bond. Alkenylene groups may be straight or branched. Preferred branched alkenyl groups have one or two branches, preferably one branch.

Preferably alkylene groups including $C_{1-16}$alkylene, $C_{1-12}$alkylene and $C_{1-6}$alkylene and alkenylene groups including $C_{2-16}$alkenylene, $C_{2-12}$alkenylene and $C_{2-6}$alkenylene may each be unsubstituted or substituted with 1, 2, 3, 4 or 5 substituent(s) selected from the group consisting of —O—$C_{1-6}$-alkyl, —S—$C_{1-6}$-alkyl, —F, Cl, Br, I, —CN, —$CF_3$, —$OCF_3$, —$SCF_3$, —OH, —SH, —$SO_3H$, —$NH_2$, —NH($C_{1-6}$-alkyl), —N($C_{1-6}$-alkyl)$_2$ and phenyl.

More preferably alkylene groups including $C_{1-16}$alkylene, $C_{1-12}$alkylene and $C_{1-6}$alkylene and alkenylene groups including $C_{2-16}$alkenylene, $C_{2-12}$alkenylene and $C_{2-6}$alkenylene may be unsubstituted or substituted with 1, 2, 3, 4 or 5 substituent(s) selected from the group consisting of —F, Cl, Br, I, —CN, —$CF_3$, —$OCF_3$, —$SCF_3$, —OH, —SH, —$SO_3H$, —$NH_2$, —NH—$CH_3$, —N($CH_3$)$_2$, —O—$CH_3$ and —O—$C_2H_5$.

Suitable alkylene groups, preferably $C_{1-6}$-alkylene groups, include —($CH_2$)—, —CH($CH_3$)—, —CH(phenyl), —($CH_2$)$_2$—, —($CH_2$)$_3$—, —($CH_2$)$_4$—, —($CH_2$)$_5$— and —($CH_2$)$_6$— and suitable alkenylene groups, preferably $C_{2-6}$-alkenylene groups, include —CH=CH—, —$CH_2$—CH=CH— and —CH=CH—$CH_2$—.

The substituted pyrazoline compounds of general formula I may be in form of a mixture of stereoisomers, particularly enantiomers or diastereomers, or pure stereoisomers, particularly enantiomers or diastereomers. Accordingly the general formula I may be in any of the following forms A to D, or—if both $R^3$ and $R^4$ are the same substituent, especially H—in forms E or F.

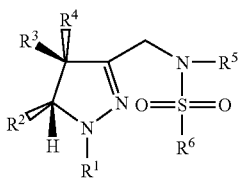
A

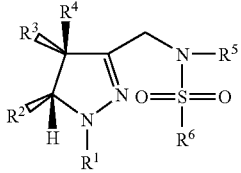
B

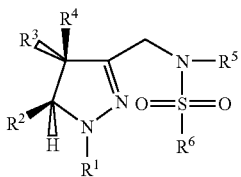
C

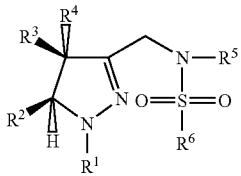
D

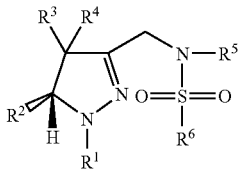
E

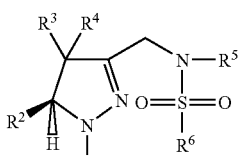
F

Thus it is a preferred embodiment of the current invention, if the general formula I is in Form A

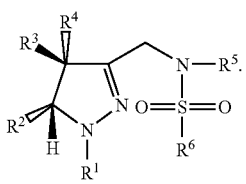
A

It is also a preferred embodiment of the current invention, if the general formula I is in Form B

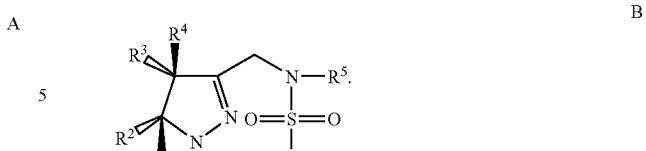
B

It is also a preferred embodiment of the current invention, if the general formula I is in Form C

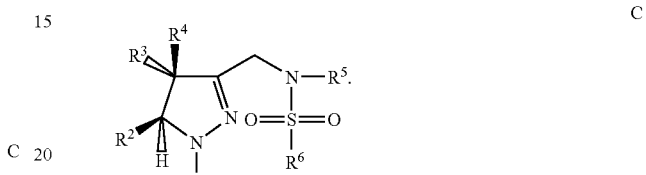
C

It is also a preferred embodiment of the current invention, if the general formula I is in Form D

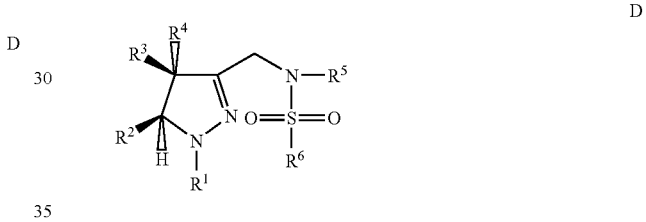
D

It is also a preferred embodiment of the current invention, if the general formula I is in Form E

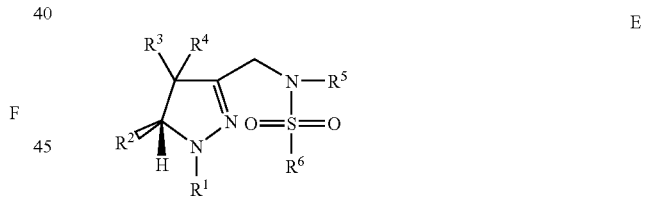
E

It is also a preferred embodiment of the current invention, if the general formula I is in Form F

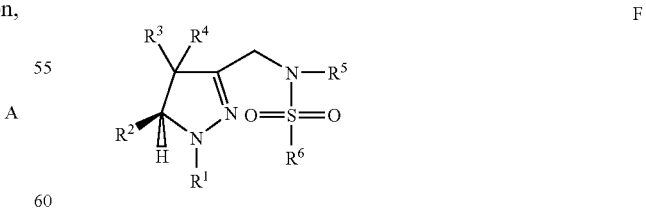
F

Preferred are substituted pyrazoline compounds of general formula I given above, wherein $R^1$ represents unsubstituted or at least mono-substituted aryl which may be condensed with an unsubstituted or at least mono-substituted saturated or unsaturated, but not aromatic, mono- or bicyclic ring system; or unsubstituted or at least mono-substituted heteroaryl which may be condensed with an unsubstituted or at least mono-substituted saturated or unsaturated, but not aromatic, mono- or bicyclic ring system;

$R^2$ represents unsubstituted or at least mono-substituted aryl which may be condensed with an unsubstituted or at least mono-substituted saturated or unsaturated, but not aromatic, mono- or bicyclic ring system; or unsubstituted or at least mono-substituted heteroaryl which may be condensed with an unsubstituted or at least mono-substituted saturated or unsaturated, but not aromatic, mono- or bicyclic ring system;

$R^3$ and $R^4$, independent of one another, each represent H; F; Cl; Br; I; —CN;

—NO$_2$; —NC; —OH; —NH$_2$; —SH; —C(=O)—H; —C(=O)—OH; —O—R$^7$; —S—R$^8$; —C(=O)—OR$^9$; —C(=O)—R$^{10}$; unsubstituted or at least mono-substituted alkyl, alkenyl or alkinyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^5$ represents H or unsubstituted or at least mono-substituted alkyl, alkenyl or alkinyl; or —S(=O)$_2$—R$^6$;

$R^6$ represents —NR$^{6a}$R$^{6b}$; unsubstituted or at least mono-substituted alkyl, alkenyl or alkinyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^{6a}$ and $R^{6b}$, independent of one another, each represent H; unsubstituted or at least mono-substituted alkyl, alkenyl or alkinyl; or unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system;

$R^7$, $R^8$, $R^9$ and $R^{10}$, independent of one another, each represent unsubstituted or at least mono-substituted alkyl, alkenyl or alkinyl; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof;

whereby the aforementioned aryl groups are 6- or 10-membered;

the aforementioned heteroaryl groups are 5-, 6-, 7-, 8-, 9-, 10-, 11-, 12-, 13- or 14-membered and contain 1, 2, 3 or 4 heteroatom(s) independently selected from the group consisting of nitrogen, oxygen and sulfur as ring member(s);

the aforementioned mono- or bicyclic ring systems may contain 1, 2 or 3 heteroatom(s) as ring member(s), which may be identical or different and which can independently be selected from the group consisting of nitrogen, oxygen and sulfur and whereby the rings of the aforementioned mono- or bicyclic ring systems are, independent of one another, 5-, 6- or 7-membered;

the aforementioned alkyl groups are linear or branched and have 1, 2, 3, 4, 5, 6, 7, 8, 9, 10, 11, 12, 13, 14, 15 or 16 carbon atoms in the chain;

the aforementioned alkylene groups are linear or branched and have 1, 2, 3, 4, 5, 6, 7, 8, 9, 10, 11, 12, 13, 14, 15 or 16 carbon atoms in the chain;

the aforementioned alkenyl groups are linear or branched and have 2, 3, 4, 5, 6, 7, 8, 9, 10, 11, 12, 13, 14, 15 or 16 carbon atoms in the chain;

the aforementioned alkenylene groups are linear or branched and have 2, 3, 4, 5, 6, 7, 8, 9, 10, 11, 12, 13, 14, 15 or 16 carbon atoms in the chain;

the aforementioned alkinyl groups are linear or branched and have 2, 3, 4, 5, 6, 7, 8, 9, 10, 11, 12, 13, 14, 15 or 16 carbon atoms in the chain;

the aforementioned cycloalkyl groups have 3, 4, 5, 6, 7, 8, 9, 10, 11, 12, 13, 14, 15 or 16 carbon atoms in the ring;

the aforementioned cycloalkenyl groups have 5, 6, 7, 8, 9, 10, 11, 12, 13, 14, 15 or 16 carbon atoms in the ring;

the aforementioned heterocycloalkyl groups are 3-, 4-, 5-, 6-, 7-, 8-, 9-, 10-, 11-, 12-, 13-, 14-, 15- or 16-membered;

the aforementioned heterocycloalkenyl groups are 5-, 6-, 7-, 8-, 9-, 10-, 11-, 12-, 13-, 14-, 15- or 16-membered;

the aforementioned heterocycloalkyl groups and heterocycloalkenyl groups each contain 1, 2, 3 or 4 heteroatom(s) independently selected from the group consisting of nitrogen, oxygen and sulfur;

the aforementioned alkyl groups, alkenyl groups and alkinyl groups each may be substituted with 1, 2, 3, 4 or 5 substituent(s) independently selected from the group consisting of —OH, F, Cl, Br, I, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —NH$_2$, —NH—CH$_3$, —NH—C$_2$H$_5$, —N(CH$_3$)$_2$, —N(C$_2$H$_5$)$_2$, —CN, —NO$_2$, —NH—C(=O)—CH$_3$, —NH—C(=O)—C$_2$H$_5$, —NH—C(=O)—C(CH$_3$)$_3$, —NH—C(=O)—O—CH$_3$, —NH—C(=O)—O—C$_2$H$_5$, —NH—C(=O)—O—C(CH$_3$)$_3$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —C(=O)—OH, —C(=O)—O—

CH₃, —C(=O)—O—C₂H₅, —C(=O)—O—C(CH₃)₃, —C(=O)—CH₃, —C(=O)—C₂H₅ and —C(=O)—C(CH₃)₃;

the aforementioned aryl groups and heteroaryl groups may be substituted with 1, 2, 3, 4 or 5 substituent(s) independently selected from the group consisting of —CH₂—CH₂—C(=O)—OCH₃, —CH₂—C(=O)—OCH₃, —CF₃, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, —C—(CH₃)₂(C₂H₅), n-pentyl, 2-pentyl, n-hexyl, —CH₂—OH, —CH₂—CH₂—OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), —O—S(=O)₂—CH₃, —O—S(=O)₂—C₂H₅, —O—S(=O)₂—CH₂—CH₂—CH₃, —O—S(=O)₂—CH(CH₃)₂, —O—S(=O)₂—CF₃, —O—S(=O)₂—CH₂CF₃, —O—S(=O)₂—CH₂—CH₂—CF₃, —S(=O)₂—NH₂, —S(=O)₂—NH—CH₃, —S(=O)₂—NH-phenyl, —NH—S(=O)₂—CH₃, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

the aforementioned cycloalkyl groups, cycloalkenyl groups, heterocycloalkyl groups and heterocycloalkenyl groups may each be substituted with 1, 2, 3, 4 or 5 substituent(s) independently selected from the group consisting of oxo (=O), thioxo (=S), —CF₃, —C₂F₅, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, n-pentyl, 2-pentyl, n-hexyl, —CH₂—OH, —CH₂—CH₂—OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

the aforementioned mono- or bicyclic ring systems may be substituted with 1, 2, 3, 4 or 5 substituent(s) independently selected from the group consisting of oxo (=O), thioxo (=S), —CF₃, —C₂F₅, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, n-pentyl, 2-pentyl, n-hexyl, —CH₂—OH, —CH₂—CH₂—OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

and the aforementioned alkylene groups and alkenylene groups may each be unsubstituted or substituted with 1, 2, 3, 4 or 5 substituent(s) selected from the group consisting of —O—$C_{1-6}$-alkyl, —S—$C_{1-6}$-alkyl, —F, Cl, Br, I, —CN, —CF₃, —OCF₃, —SCF₃, —OH, —SH, —SO₃H, —NH₂, —NH($C_{1-6}$-alkyl), —N($C_{1-6}$-alkyl)₂ and phenyl;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

More preferred are substituted pyrazoline compounds of general formula I given above, wherein $R^1$ and $R^2$, independent of one another, each represent a radical selected from the group consisting of phenyl, naphthyl, pyridinyl, furyl (furanyl), thienyl (thiophenyl), [1.3]-benzodioxolyl and [1.4]-benzodioxanyl, which in each case is bonded to the pyrazoline compound of general formula I via the aromatic or heteroaromatic part of the aforementioned radicals and which is in each case unsubstituted or which is in each case substituted with 1, 2, 3, 4 or 5 substituent(s) independently selected from the group consisting of —CF₃, —C₂F₅, —C₃F₇, —C₄F₉, —CH₂Cl, —CHCl₂, —C₂H₄Cl, methyl, ethyl, n-propyl, isopropyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —NH₂, —NH—CH₃, —NH—C₂H₅, —N(CH₃)₂, —N(C₂H₅)₂, —CH₂—N(CH₃)₂, —(CH₂)—N(C₂H₅)₂, —CH₂—N(C₃H₇)₂, —CH₂—N(C₄H₉)₂, —CH₂—N(CH₃)(C₂H₅), —O—S(=O)₂—CH₃, —O—S(=O)₂—C₂H₅, —O—S(=O)₂—CH₂—CH₃, —O—S(=O)₂—CH(CH₃)₂, —O—S(=O)₂—CF₃, —O—S(=O)₂—CH₂CF₃, —O—S(=O)₂—CH₂—CH₂—CF₃, —S(=O)—NH₂, —S(=O)₂—NH—CH₃ and —NH—S(=O)₂—CH₃;

$R^3$ represents H;

$R^4$ represents H; F; Cl; Br; —C(=O)—OH; —C(=O)—OR⁹; or a radical selected from the group consisting of methyl, ethyl, n-propyl, isopropyl, tert.-butyl and n-butyl, which is in each case unsubstituted;

$R^5$ represents H;

$R^6$ represents —NR^{6a}R^{6b}; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

a radical selected from the group consisting of 2.4-dioxo-1.2.3.4-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —(CH₂)-group and which is in each case unsubstituted or which is in each case substituted 1, 2 or 3 substituents selected from the group consisting of methyl, ethyl, n-propyl, isopropyl, n-butyl, 2-butyl, tert-butyl, F, Cl and Br and whereby pyrrolidinyl, piperidinyl, morpholinyl, piperazinyl and thiomorpholinyl are preferably bonded to the core structure via a nitrogen atom of their ring;

or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, thiazolyl, pyrazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —(CH₂)— or a —(CH₂)₂-group and which is in each case unsubstituted or which is in each case substituted with 1, 2, 3, 4 or 5 substituent(s) independently selected from the group consisting of —CH₂—CH₂—C(=O)—OCH₃, —CH₂—C(=O)—OCH₃, —CF₃, —C₂F₅, —C₃F₇, —C₄F₉, methyl, ethyl, n-propyl, isopropyl, n-butyl, isobutyl, 2-butyl, tert-butyl, —C—(CH₃)₂(C₂H₅), n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —C(=O)—O—CH₃, —C(=O)—O—C₂H₅, —C(=O)—O—CH₂—CH₂—CH₃, —C(=O)—O—CH(CH₃)₂, —C(=O)—O—CH₂—CH₂—CH₂—CH₃, —C(=O)—O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —NH—C(=O)—CH₃, —NH—C(=O)—C₂H₅, —NH—C(=O)—C(CH₃)₃, —S(=O)—CH₃, —S(=O)—C₂H₅, —S(=O)—C₃H₇, —S(=O)₂—CH₃, —S(=O)₂—C₂H₅, —S(=O)₂—C₃H₇, —NO₂, —NH₂, —NH—CH₃, —N(CH₃)₂, —NH—C₂H₅, —N(C₂H₅)₂, cyclopropyl, cyclobutyl, cyclopentyl, cyclohexyl, phenyl, —O-phenyl and benzyl;

$R^{6a}$ and $R^{6b}$, independent of one another, each represent H a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

$R^9$ represents a radical selected from the group consisting of methyl, ethyl, n-propyl, isopropyl, n-butyl, isobutyl, sec-butyl, tert-butyl and n-pentyl, which is in each case unsubstituted;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

Also more preferred are substituted pyrazoline compounds of general formula Ia,

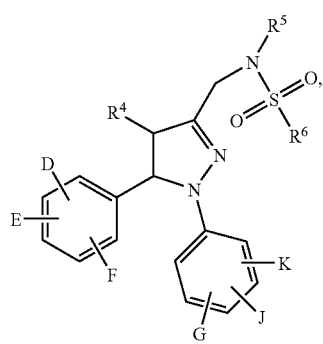

Ia wherein

D, E, F, G, J and K, independent of one another, each represent hydrogen, methyl, ethyl, n-propyl, isopropyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, F, Cl, Br, I, —CN, —OCF$_3$, —O—C$_2$F$_5$, —O—C$_3$F$_7$, —O—C$_4$F$_9$ and —OH;

R$^4$ represents H; F; Cl; Br; I; —CN; —NO$_2$; —NC; —OH; —NH$_2$; —SH; —C(=O)—H; —C(=O)—OH; —O—R$^7$; —S—R$^8$; —C(=O)—OR$^9$; —C(=O)—R$^{19}$; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

R$^5$ represents H or a radical selected from the group consisting of methyl, ethyl, n-propyl, isopropyl, n-butyl, isobutyl, sec-butyl, tert-butyl, n-pentyl, and n-hexyl, which is in each case unsubstituted;

R$^6$ represents —NR$^{6a}$R$^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —NH$_2$, —NH—CH$_3$, —NH—C$_2$H$_5$, —N(CH$_3$)$_2$, —N(C$_2$H$_5$)$_2$, —CN and —NO$_2$;

a radical selected from the group consisting of (1.2.3.4)-tetrahydropyrimidinyl, 7,7a-dihydro-imidazo[2,1-b]thiazolyl, cyclopropyl, cyclobutyl, cyclopentyl, cyclohexyl, cycloheptyl, cyclooctyl, cyclononyl, cyclopentenyl, cyclohexenyl, cycloheptenyl, cyclononenyl, cyclooctenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1.3)-dioxolan-2-yl, isoxazolidinyl, isothioazolidinyl, pyrazolidinyl, oxazolidinyl, (1.2.4)-oxadiazolidinyl, (1.2.4)-thiadiazolidinyl, (1.2.4)-triazolidin-3-yl, (1.3.4)-thiadiazolidin-2-yl, (1.3.4)-triazolidin-1-yl, (1.3.4)-triazoldidin-2-yl, tetrahydropyridazinyl, tetrahydropyrimidinyl, tetrahydropyrazinyl, (1.3.5)-tetrahydrotriazinyl, (1.2.4)-tetrahydrotriazin-1-yl, (1.3)-dithian-2-yl, (1.3)-thiazolidinyl, (2.3)-dihydroimidazolyl, (4.5)-dihydroimidazolyl, (2.5)-dihydroimidazolyl, (3.4.5.6)-tetrahydropyridin-2-yl, (1.2.5.6)-tetrahydropyridin-1-yl, (1.2)-dihydropyridin-1-yl, (1.4)-dihydropyridin-1-yl, dihydropyranyl, (1.2.3.4)-tetrahydropyridin-1-yl, bicyclo[2.2.1]heptyl, bicyclo[3.1.1]heptyl, norbornenyl, 8-aza-bicyclo[3.2.1]octyl and 8-aza-spiro[4.5]decanyl, which in each case may be bonded via a C$_{1-3}$-alkylene group or a C$_{2-3}$-alkenylene group and which is in each case unsubstituted or which is in each case substituted with 1, 2, 3, 4 or 5 substituent(s) independently selected from the group consisting of oxo (=O), thioxo (=S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—CH$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

or a radical selected from the group consisting of 2-oxo-(1.2.3.4)-tetrahydroquinolinyl, phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]- benzothiadiazolyl, [2.1.3]-benzoxadiazolyl, [1.2.3]-benzoxadiazolyl, benzoxazolyl, benzthiazolyl, benzisoxazolyl, benzisothiazolyl, imidazo[2,1-b]thiazolyl, 2,3-dihydro-benzo[1,4]-dioxine, 1,2,3,4-tetrahydro-quinoxaline, 2,3-dioxo-1,2,3,4-tetrahydro-quinoxaline, 2H-chromenyl, pyranyl, indazolyl, quinazolinyl, benzotriazolyl, (2.3)-dihydrobenzothiazolyl, dihydrobenzofuranyl, 3H-benzothiazol-2-onyl, [1.3]-benzodioxolyl, [1.4]-benzodioxanyl, [1.2.3.4]-tetrahydronaphthyl, [3.4]-dihydro-2H-benzo[1.4]oxazinyl, (2.3)-dihydro-1H-cyclopenta[b]indolyl, [1.2.3.4]-tetrahydroquinolinyl, [1.2.3.4]-tetrahydroisoquinolinyl and [1.2.3.4]-tetrahydroquinazolinyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of —$CH_2$—$CH_2$—C(=O)—$OCH_3$, —$CH_2$—C(=O)—$OCH_3$, —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, —C—$(CH_3)_2(C_2H_5)$, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)—$CH_3$, —S(=O)—$C_2H_5$, —S(=O)—$C_3H_7$, —$S(=O)_2$—$CH_3$, —$S(=O)_2$—$C_2H_5$, —$S(=O)_2$—$C_3H_7$, —$S(=O)_2$-phenyl, —$NH_2$, —NH—$CH_3$, —NH—$C_2H_5$, —$N(CH_3)_2$, —$N(C_2H_5)_2$, —$CH_2$—$N(CH_3)_2$, —$(CH_2)$-morpholinyl, —$(CH_2)$-piperidinyl, —$(CH_2)$-piperazinyl, —$(CH_2)$—$N(C_2H_5)_2$, —$CH_2$—$N(C_3H_7)_2$, —$CH_2$—$N(C_4H_9)_2$, —$CH_2$—$N(CH_3)(C_2H_5)$, —S(=O)—$NH_2$, —$S(=O)_2$—NH—$CH_3$, —$S(=O)_2$—NH-phenyl, —NH—$S(=O)_2$—$CH_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

$R^{6a}$ and $R^{6b}$, independent of one another, each represent H or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—$CH_3$ and —O—$C_2H_5$;

$R^7$, $R^8$, $R^9$ and $R^{10}$, independent of one another, each represent a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

or a radical selected from the group consisting of phenyl, naphthyl, pyridinyl, furyl(furanyl), thienyl(thiophenyl), pyrrolyl, oxazolyl, isoxazolyl, thiazolyl, isothiazolyl, imidazolyl, pyrazolyl, pyridazinyl, indolyl, isoindolyl, pyrimidinyl, pyrazinyl, quinolinyl, isoquinolinyl, benzo[b]furanyl, benzo[b]thiophenyl, benzoxazolyl, benzthiazolyl, benzisoxazolyl, benzisothiazolyl, imidazo[2,1-b]thiazolyl, 2H-chromenyl, pyranyl, indazolyl, quinazolinyl and benzotriazolyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)—$CH_3$, —S(=O)—$C_2H_5$, —S(=O)—$C_3H_7$, —$S(=O)_2$—$CH_3$, —$S(=O)_2$—$C_2H_5$, —$S(=O)_2$—$C_3H_7$, —$NH_2$, —NH—$CH_3$, —NH—$C_2H_5$, —$N(CH_3)_2$, —$N(C_2H_5)_2$, —$CH_2$—$N(CH_3)_2$, —$(CH_2)$—$N(CH_2)$—$N(C_2H_5)_2$, —$CH_2$—$N(C_3H_7)_2$, —$CH_2$—$N(C_4H_9)_2$, —$CH_2$—$N(CH_3)(C_2H_5)$, —$S(=O)_2$—NH—$CH_3$ and —NH—$S(=O)_2$—$CH_3$;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

The substituted pyrazoline compounds of general formula Ia may be in form of a mixture of stereoisomers, particularly enantiomers or diastereomers, or pure stereoisomers, particularly enantiomers or diastereomers. Accordingly the general formula Ia may be in any of the following forms A to D, or—if $R^4$ is H—in forms E or F.

A
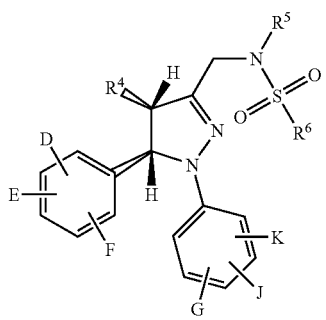
B
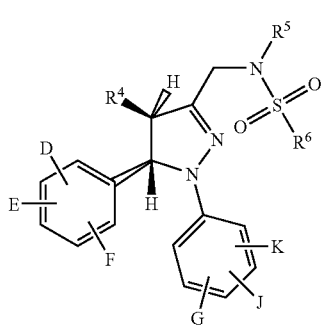
C
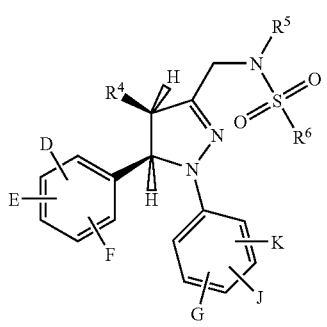
D
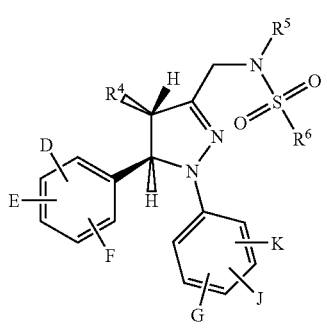
E
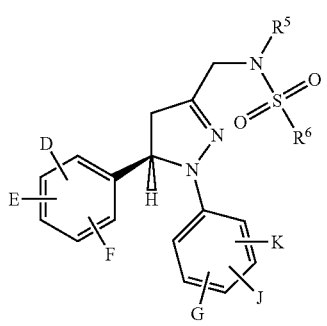
F
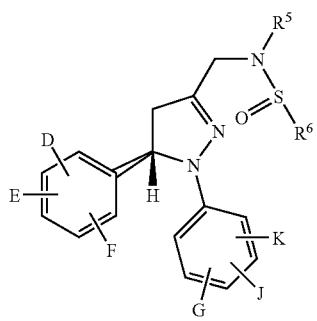
Thus it is a preferred embodiment of the current invention, if the general formula Ia is in Form A
A
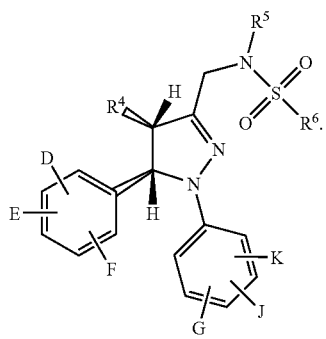
It is also a preferred embodiment of the current invention, if the general formula Ia is in Form B
B
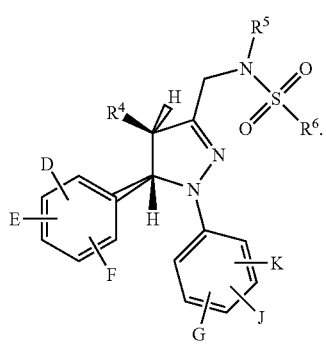
It is also a preferred embodiment of the current invention, if the general formula Ia is in Form C

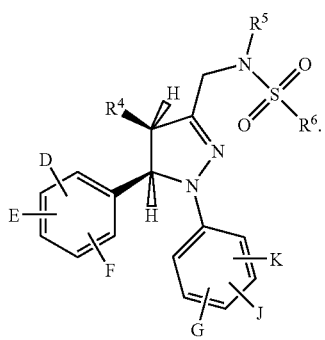

It is also a preferred embodiment of the current invention, if the general formula Ia is in Form D

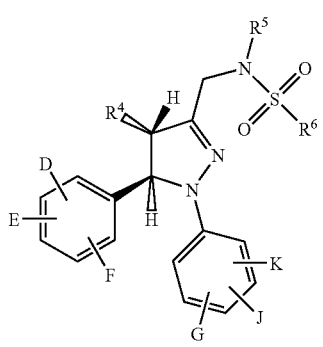

It is also a preferred embodiment of the current invention, if the general formula Ia is in Form E

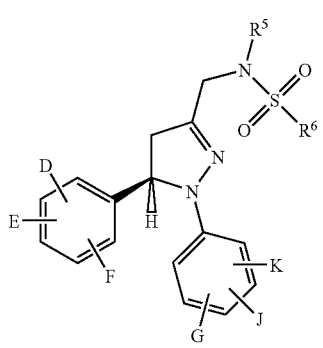

It is also a preferred embodiment of the current invention, if the general formula Ia is in Form F

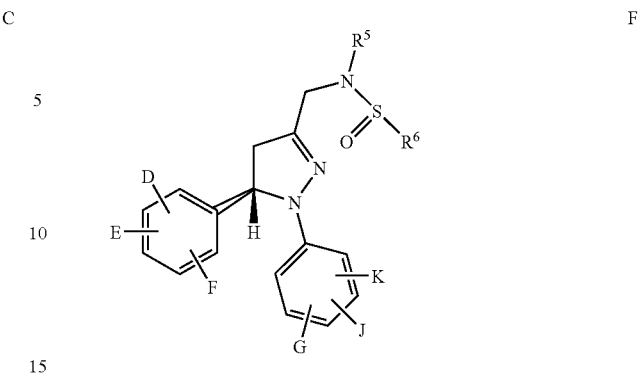

Even more preferred are substituted pyrazoline compounds of general formula Ia, wherein D, E, F, G, J and K, independent of one another, each represent hydrogen,
methyl, ethyl, n-propyl, isopropyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, F, Cl, Br, I, —CN, —OCF$_3$, —O—C$_2$F$_5$, —O—C$_3$F$_7$, —O—C$_4$F$_9$ and —OH;

R$^4$ represents H; F; Cl; Br; —C(=O)—OH; —C(=O)—OR$^9$; or a radical selected from the group consisting of methyl, ethyl, n-propyl, isopropyl, tert.-butyl and n-butyl, which is in each case unsubstituted;

R$^5$ represents H;

R$^6$ represents —NR$^{6a}$R$^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

a radical selected from the group consisting of 2.4-dioxo-1.2.3.4-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —(CH$_2$)-group and which is in each case unsubstituted or which is in each case substituted with 1, 2 or 3 substituent(s) selected from the group consisting of methyl, ethyl, n-propyl, isopropyl, n-butyl, 2-butyl, tert-butyl, F, Cl and Br and whereby pyrrolidinyl, piperidinyl, morpholinyl, piperazinyl and thiomorpholinyl are preferably bonded to the core structure via a nitrogen atom of their ring;

or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —(CH$_2$)— or a —(CH$_2$)$_2$— group and which is in each case unsubstituted or which is in each case substituted with 1, 2, 3, 4 or 5 substituent(s) independently selected from the group consisting of —$CH_2$—$CH_2$—C(=O)—$OCH_3$, —$CH_2$—C(=O)—$OCH_3$, —$CF_3$, —$C_2F_5$, —$C_3F_7$, —$C_4F_9$, methyl, ethyl, n-propyl, isopropyl, n-butyl, isobutyl, 2-butyl, tert-butyl, —C—$(CH_3)_2(C_2H_5)$, n-pentyl, 2-pentyl, n-hexyl, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—C$(CH_3)_3$, —C(=O)—O—$CH_3$, —C(=O)—O—$C_2H_5$, —C(=O)—O—$CH_2$—$CH_2$—$CH_3$, —C(=O)—O—CH$(CH_3)_2$, —C(=O)—O—$CH_2$—$CH_2$—$CH_2$—$CH_3$, —C(=O)—O—C$(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—C$(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —NH—C(=O)—$CH_3$, —NH—C(=O)—$C_2H_5$, —NH—C(=O)—C$(CH_3)_3$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —$NO_2$, —$NH_2$, —NH—$CH_3$, —N$(CH_3)_2$, —NH—$C_2H_5$, —N$(C_2H_5)_2$, cyclopropyl, cyclobutyl, cyclopentyl, cyclohexyl, phenyl, —O-phenyl and benzyl;

and $R^9$ represents a radical selected from the group consisting of methyl, ethyl, n-propyl, isopropyl, n-butyl, isobutyl, sec-butyl, tert-butyl and n-pentyl, which is in each case unsubstituted;

$R^{6a}$ and $R^{6b}$, independent of one another, each represent H a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

Also more preferred are substituted pyrazoline compounds of general formula Ib,

wherein

D, G and J, independent of one another, each represent hydrogen, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—C$(CH_3)_3$, —O—S(=O)$_2$—$CH_3$, —O—S(=O)$_2$—$C_2H_5$, —O—S(=O)$_2$—$CH_2$—$CH_2$—$CH_3$, —O—S(=O)$_2$—CH$(CH_3)_2$, —O—S(=O)$_2$—$CF_3$, —O—S(=O)$_2$—$CH_2CF_3$, —O—S(=O)$_2$—$CH_2$—$CH_2$—$CF_3$, F, Cl, Br, I, and —OH;

$R^4$ represents H; F; Cl; Br; I; —CN; —$NO_2$; —NC; —OH; —$NH_2$; —SH; —C(=O)—H; —C(=O)—OH; —O—$R^7$; —S—$R^8$; —C(=O)—O$R^9$; —C(=O)—$R^{10}$; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

$R^5$ represents H or a radical selected from the group consisting of methyl, ethyl, n-propyl, isopropyl, n-butyl, isobutyl, sec-butyl, tert-butyl, n-pentyl, and n-hexyl, which is in each case unsubstituted;

$R^6$ represents —$NR^{6a}R^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—C$(CH_3)_3$, —$NH_2$, —NH—$CH_3$, —NH—$C_2H_5$, —N$(CH_3)_2$, —N$(C_2H_5)_2$, —CN and —$NO_2$;

a radical selected from the group consisting of (1.2.3.4)-tetrahydropyrimidinyl, 7,7a-dihydro-imidazo[2,1-b]thiazolyl, cyclopropyl, cyclobutyl, cyclopentyl, cyclohexyl, cycloheptyl, cyclooctyl, cyclononyl, cyclopentenyl, cyclohexenyl, cycloheptenyl, cyclononenyl, cyclooctenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1.3)-dioxolan-2-yl, isoxazolidinyl, isothioazolidinyl, pyrazolidinyl, oxazolidinyl, (1.2.4)-oxadiazolidinyl, (1.2.4)-thiadiazolidinyl, (1.2.4)-triazolidin-3-yl, (1.3.4)-thiadiazolidin-2-yl, (1.3.4)-triazolidin-1-yl, (1.3.4)-triazoldidin-2-yl, tetrahydropyridazinyl, tetrahydropyrimidinyl, tetrahydropyrazinyl, (1.3.5)-tetrahydrotriazinyl, (1.2.4)-tetrahydrotriazin-1-yl, (1.3)-dithian-2-yl, (1.3)-thiazolidinyl, (2.3)-dihydroimidazolyl, (4.5)-dihydroimidazolyl, (2.5)-dihydroimidazolyl, (3.4.5.6)-tetrahydropyridin-2-yl, (1.2.5.6)-tetrahydropyridin-1-yl, (1.2)-dihydropyridin-1-yl, (1.4)-dihydropyridin-1-yl, dihydropyranyl, (1.2.3.4)-tetrahydropyridin-1-yl, bicyclo[2.2.1]heptyl, bicyclo[3.1.1]heptyl, norbornenyl, 8-aza-bicyclo[3.2.1]octyl and 8-aza-spiro[4.5]decanyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of oxo (=O), thioxo (=S), —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —C$(OCH_3)(C_2H_5)_2$, —C$(OCH_3)(CH_3)_2$, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—C$(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—C$(CH_3)_3$, —C(=O)—OH, —C(=O)—O—$CH_3$, —C(=O)—O—$C_2H_5$, —C(=O)—O—$C_3H_7$, —C(=O)—O—C$(CH_3)_3$, —O—C(=O)—$CH_3$, —O—C(=O)—$C_2H_5$, —O—C(=O)—CH$(CH_3)_2$, —O—C(=O)—$CH_3$, —O—C(=O)—$CH_2$—$CH_3$, —O—C(=O)—C$(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

or a radical selected from the group consisting of 2-oxo-(1.2.3.4)-tetrahydroquinolinyl, phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]-benzothiadiazolyl, [2.1.3]-benzoxadiazolyl, [1.2.3]-benzoxadiazolyl, benzoxazolyl, benzthiazolyl, benzisoxazolyl, benzisothiazolyl, imidazo[2,1-b]thiazolyl, 2,3-dihydro-benzo[1,4]-dioxine, 1,2,3,4-tetrahydro-quinoxaline, 2,3-dioxo-1,2,3,4-tetrahydro-quinoxaline, 2H-chromenyl, pyranyl, indazolyl, quinazolinyl, benzotriazolyl, (2.3)-dihydrobenzothiazolyl, dihydrobenzofuranyl, 3H-benzothiazol-2-onyl, [1.3]-benzodioxolyl, [1.4]-benzodioxanyl, [1.2.3.4]-tetrahydronaphthyl, [3.4]-dihydro-2H-benzo[1.4]oxazinyl, (2.3)-dihydro-1H-cyclopenta[b]indolyl, [1.2.3.4]-tetrahydroquinolinyl, [1.2.3.4]-tetrahydroisoquinolinyl and [1.2.3.4]-tetrahydroquinazolinyl, which in each case may be bonded via a C$_{1-3}$-alkylene group or a C$_{2-3}$-alkenylene group and which is in each case unsubstituted or which is in each case substituted with 1, 2, 3, 4 or 5 substituent(s) independently selected from the group consisting of —CH$_2$—CH$_2$—C(=O)—OCH$_3$, —CH$_2$—C(=O)—OCH$_3$, —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, —C—(CH$_3$)$_2$(C$_2$H$_5$), n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

$R^{6a}$ and $R^{6b}$, independent of one another, each represent H or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—CH$_3$ and —O—C$_2$H$_5$;

$R^7$, $R^8$, $R^9$ and $R^{10}$, independent of one another, each represent a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

or a radical selected from the group consisting of phenyl, naphthyl, pyridinyl, furyl(furanyl), thienyl(thiophenyl), pyrrolyl, oxazolyl, isoxazolyl, thiazolyl, isothiazolyl, imidazolyl, pyrazolyl, pyridazinyl, indolyl, isoindolyl, pyrimidinyl, pyrazinyl, quinolinyl, isoquinolinyl, benzo[b]furanyl, benzo[b]thiophenyl, benzoxazolyl, benzthiazolyl, benzisoxazolyl, benzisothiazolyl, imidazo[2,1-b]thiazolyl, 2H-chromenyl, pyranyl, indazolyl, quinazolinyl and benzotriazolyl, which in each case may be bonded via a C$_{1-3}$-alkylene group or a C$_{2-3}$-alkenylene group and which is in each case unsubstituted or which is in each case substituted with 1, 2, 3, 4 or 5 substituent(s) independently selected from the group consisting of —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$ and —NH—S(=O)$_2$—CH$_3$;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

The substituted pyrazoline compounds of general formula Ib may be in form of a mixture of stereoisomers, particularly enantiomers or diastereomers, or pure stereoisomers, particularly enantiomers or diastereomers. Accordingly the general formula Ib may be in any of the following forms A to D, or—if R$^4$ is H—in forms E or F.

A
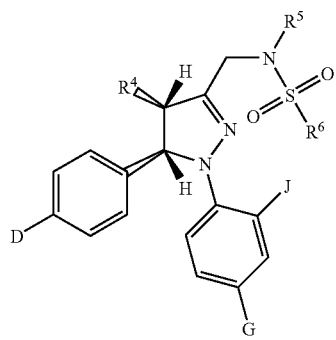

B
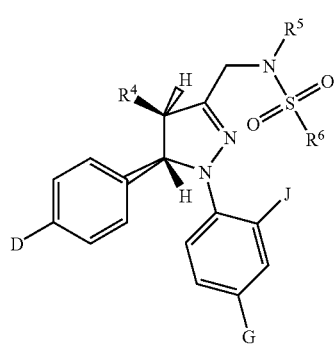

C
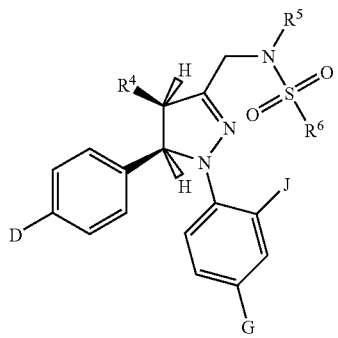

D
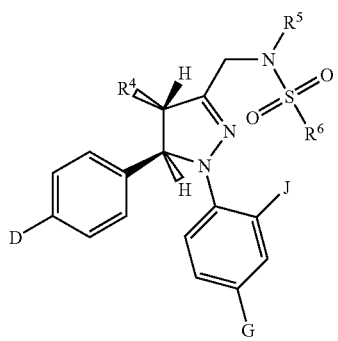

E
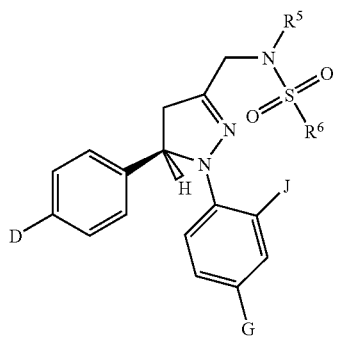

F
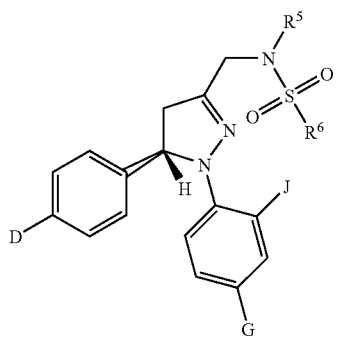

Thus it is a preferred embodiment of the current invention, if the general formula Ib is in Form A

A

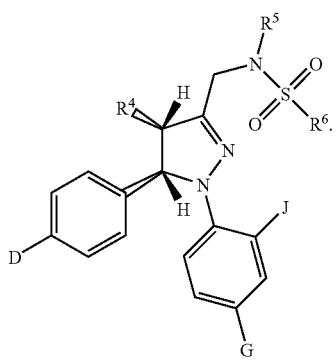

It is also a preferred embodiment of the current invention, if the general formula Ib is in Form B

B

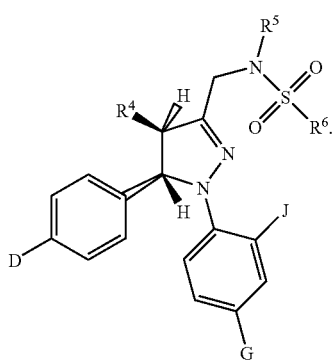

It is also a preferred embodiment of the current invention, if the general formula Ia is in Form C

C

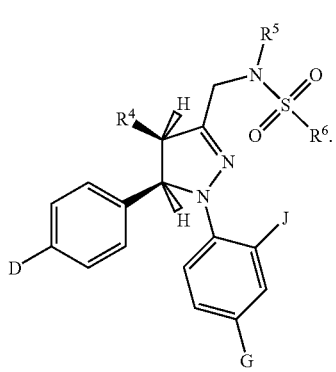

It is also a preferred embodiment of the current invention, if the general formula Ib is in Form D

D

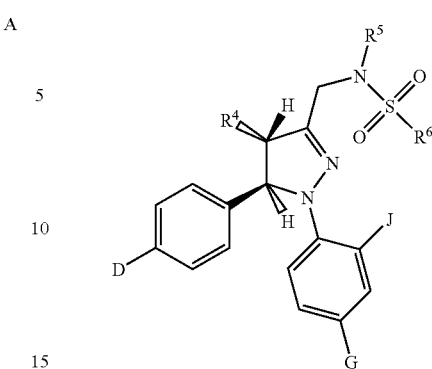

It is also a preferred embodiment of the current invention, if the general formula Ib is in Form E

E

It is also a preferred embodiment of the current invention, if the general formula Ib is in Form F

F

Even more preferred are substituted pyrazoline compounds of general formula Ib, wherein D, G and J, independent of one another, each represent hydrogen, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —O—$S(=O)_2$—$CH_3$, —O—$S(=O)_2$—$C_2H_5$, —O—$S(=O)_2$—$CH_2$—$CH_2$—$CH_3$, —O—$S(=O)_2$—$CH(CH_3)_2$, —O—$S(=O)_2$—$CF_3$, —O—$S(=O)_2$—$CH_2CF_3$, —O—$S(=O)_2$—$CH_2$—$CH_2$—$CF_3$, F, Cl, Br, I, and —OH;

$R^4$ represents H; F; Cl; Br; —C(=O)—OH; —C(=O)—$OR^9$; or a radical selected from the group consisting of methyl, ethyl, n-propyl, isopropyl, tert.-butyl and n-butyl, which is in each case unsubstituted;

$R^5$ represents H;

$R^6$ represents —$NR^{6a}R^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

a radical selected from the group consisting of 2.4-dioxo-1.2.3.4-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —($CH_2$)-group and which is in each case unsubstituted or which is substituted with 1, 2 or 3 substituent(s) selected from the group consisting of methyl, ethyl, n-propyl, isopropyl, n-butyl, 2-butyl, tert-butyl, F, Cl and Br and whereby pyrrolidinyl, piperidinyl, morpholinyl, piperazinyl and thiomorpholinyl are preferably bonded to the core structure via a nitrogen atom of their ring;

or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —($CH_2$)— or a —($CH_2$)$_2$-group and which is in each case unsubstituted or which is in each case substituted with 1, 2, 3, 4 or 5 substituent(s) independently selected from the group consisting of —$CH_2$—$CH_2$—$C(=O)$—$OCH_3$, —$CH_2$—$C(=O)$—$OCH_3$, —$CF_3$, —$C_2F_5$, —$C_3F_7$, —$C_4F_9$, methyl, ethyl, n-propyl, isopropyl, n-butyl, isobutyl, 2-butyl, tert-butyl, —C—($CH_3$)$_2$($C_2H_5$), n-pentyl, 2-pentyl, n-hexyl, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—C($CH_3$)$_3$, —$C(=O)$—O—$CH_3$, —$C(=O)$—O—$C_2H_5$, —$C(=O)$—O—$CH_2$—$CH_2$—$CH_3$, —$C(=O)$—O—CH($CH_3$)$_2$, —$C(=O)$—O—$CH_2$—$CH_2$—$CH_2$—$CH_3$, —$C(=O)$—O—C($CH_3$)$_3$, —S—$CH_3$, —S—$C_2H_5$, —S—$CH_2$—$CH_2$—$CH_3$, —S—CH($CH_3$)$_2$, —S—$CH_2$—$CH_2$—$CH_2$—$CH_3$, —S—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —NH—$C(=O)$—$CH_3$, —NH—$C(=O)$—$C_2H_5$, —NH—$C(=O)$—C($CH_3$)$_3$, —$S(=O)$—$CH_3$, —$S(=O)$—$C_2H_5$, —$S(=O)$—$C_3H_7$, —$S(=O)_2$—$CH_3$, —$S(=O)_2$—$C_3H_7$, —$NO_2$, —$NH_2$, —NH—$CH_3$, —N($CH_3$)$_2$, —NH—$C_2H_5$, —N($C_2H_5$)$_2$, cyclopropyl, cyclobutyl, cyclopentyl, cyclohexyl, phenyl, —O-phenyl and benzyl;

$R^{6a}$ and $R^{6b}$, independent of one another, each represent H a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

and $R^9$ represents a radical selected from the group consisting of methyl, ethyl, n-propyl, isopropyl, n-butyl, isobutyl, sec-butyl, tert-butyl and n-pentyl, which is in each case unsubstituted;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

Still even more preferred are substituted pyrazoline compounds of general formula Ib, wherein D, G and J, each represent Cl;

$R^4$ represents H;

$R^5$ represents H;

$R^6$ represents —$NR^{6a}R^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

a radical selected from the group consisting of 2.4-dioxo-1.2.3.4-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —($CH_2$)-group and which is in each case unsubstituted or which is substituted with 1, 2 or 3 substituent(s) selected from the group consisting of methyl, ethyl, n-propyl, isopropyl, n-butyl, 2-butyl, tert-butyl, F, Cl and Br and whereby pyrrolidinyl, piperidinyl, morpholinyl, piperazinyl and thiomorpholinyl are preferably bonded to the core structure via a nitrogen atom of their ring;

or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —($CH_2$)— or a —($CH_2$)$_2$-group and which is in each case unsubstituted or which is in each case substituted with 1, 2, 3, 4 or 5 substituent(s) independently selected from the group consisting of —$CH_2$—$CH_2$—$C(=O)$—$OCH_3$, —$CH_2$—$C(=O)$—$OCH_3$, —$CF_3$, —$C_2F_5$, —$C_3F_7$, —$C_4F_9$, methyl, ethyl, n-propyl, isopropyl, n-butyl, isobutyl, 2-butyl, tert-butyl, —C—($CH_3$)$_2$($C_2H_5$), n-pentyl, 2-pentyl, n-hexyl, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—C($CH_3$)$_3$, —$C(=O)$—O—$CH_3$, —$C(=O)$—O—$C_2H_5$, —$C(=O)$—O—$CH_2$—$CH_2$—$CH_3$, —$C(=O)$—O—CH($CH_3$)$_2$, —$C(=O)$—O—$CH_2$—$CH_2$—$CH_2$—$CH_3$, —$C(=O)$—O—C($CH_3$)$_3$, —S—$CH_3$, —S—$C_2H_5$, —S—$CH_2CH_2$—$CH_3$, —S—CH($CH_3$)$_2$, —S—$CH_2$—$CH_2$—$CH_2$—$CH_3$, —S—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —NH—$C(=O)$—$CH_3$, —NH—$C(=O)$—$C_2H_5$, —NH—$C(=O)$—C($CH_3$)$_3$, —$S(=O)$—$CH_3$, —$S(=O)$—$C_2H_5$, —$S(=O)$—$C_3H_7$, —$S(=O)_2$—$CH_3$, —$S(=O)_2$—$C_2H_5$, —$S(=O)_2$—$C_3H_7$, —NO$_2$, —NH$_2$, —NH—CH$_3$, —N(CH$_3$)$_2$, —NH—C$_2$H$_5$, —N(C$_2$H$_5$)$_2$, cyclopropyl, cyclobutyl, cyclopentyl, cyclohexyl, phenyl, —O-phenyl and benzyl;

R$^{6a}$ and R$^{6b}$, independent of one another, each represent H a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

Also very preferred is a compound of general formula Ic according to the invention

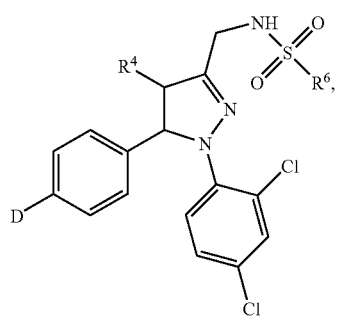

wherein

D represents —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, F, Cl, Br, I, or —OH;

R$^4$ represents hydrogen, —CH$_3$, —C$_2$H$_5$, —CH$_2$—CH$_2$—CH$_3$, —CH(CH$_3$)$_2$, —CH$_2$—CH$_2$—CH$_2$—CH$_3$, —CH$_2$—CH(CH$_3$)$_2$, or —CH(CH$_3$)$_3$;

and R$^6$ is defined above.

The substituted pyrazoline compounds of general formula Ic may be in form of a mixture of stereoisomers, particularly enantiomers or diastereomers, or pure stereoisomers, particularly enantiomers or diastereomers. Accordingly Formula Ic may be in any appropriate stereochemical form as described above for Formulas I, Ia or Ib.

Very preferred is also a compound of general formula Ic, according to the invention, wherein D represents —O—CH$_3$, —O—C$_2$H$_5$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CH$_2$—CH$_2$—CF$_3$, F, Cl, Br or —OH; and/or R$^4$ represents hydrogen, —CH$_3$, or —C$_2$H$_5$; and/or R$^6$ as defined in any embodiment above.

Highly preferred is a compound of general formula Id

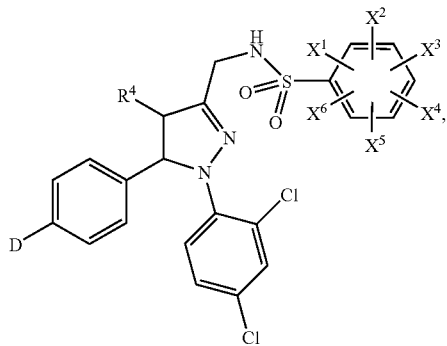

wherein

D represents —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, F, Cl, Br, I, or —OH;

R$^4$ represents hydrogen, —CH$_3$, —C$_2$H$_5$, —CH$_2$—CH$_2$—CH$_3$, —CH(CH$_3$)$_2$, —CH$_2$—CH$_2$—CH$_2$—CH$_3$, —CH$_2$—CH(CH$_3$)$_2$, or —CH(CH$_3$)$_3$;

and X$^1$, X$^2$, X$^3$, X$^4$ and X$^5$ independently from one another represent hydrogen, —CH$_2$—CH$_2$—C(=O)—OCH$_3$, —CH$_2$—C(=O)—OCH$_3$, —CF$_3$, methyl, ethyl, n-propyl, isopropyl, n-butyl, isobutyl, 2-butyl, tert-butyl, —C—(CH$_3$)$_2$(C$_2$H$_5$), —O—CH$_3$, —O—C$_2$H$_5$, —O—CH$_2$—CH$_2$—CH$_3$, —O—CH(CH$_3$)$_2$, C(=O)—O—CH$_3$, C(=O)—O—C$_2$H$_5$, F, Cl, Br, I, —CN, —OCF$_3$, —OH, —NH—C(=O)—CH$_3$, —NH—C(=O)—C$_2$H$_5$, —S(=O)$_2$—CH$_3$, —S(=O)$_2$—C$_2$H$_5$, NO$_2$, —NH$_2$, —NH—CH$_3$, —NH—C$_2$H$_5$, —N(CH$_3$)$_2$, —N(C$_2$H$_5$)$_2$, cyclopropyl, cyclobutyl, cyclopentyl, cyclohexyl, phenyl, —O-phenyl and benzyl.

The substituted pyrazoline compounds of general formula Id may be in form of a mixture of stereoisomers, particularly enantiomers or diastereomers, or pure stereoisomers, particularly enantiomers or diastereomers. Accordingly Formula Id may be in any appropriate stereochemical form as described above for Formulas I, Ia or Ib.

Highly preferred are substituted pyrazoline compounds of the invention selected from the group consisting of N-[1-(2,4-Dichloro-phenyl)-5-(4-ethoxy-phenyl)-4,5-dihydro-1H-pyrazol-3-ylmethyl]-2,5-difluoro-benzenesulfonamide, N-[5-(4-Chloro-phenyl)-1-(2,4-dichloro-phenyl)-4,5-dihydro-1H-pyrazol-3-ylmethyl]-2-methyl-5-nitro-benzenesulfonamide, or N-[5-(4-Chloro-phenyl)-1-(2,4-dichloro-phenyl)-4,5-dihydro-1H-pyrazol-3-ylmethyl]-3-nitro-benzenesulfonamide; L optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

In another aspect the present invention relates to a process for the preparation of at least one compound of general formula I, wherein at least one compound of general formula II,

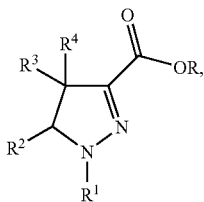

wherein $R^1$, $R^2$, $R^3$ and $R^4$ have the above defined meaning, and R denotes hydrogen or a $C_{1-6}$alkyl group, is reacted in a reaction medium, in the presence of a reducing agent, preferably in the presence of a reducing agent selected from the group consisting of sodium borohydride, lithium aluminium hydride and lithium borohydride, to yield at least one compound of general formula III,

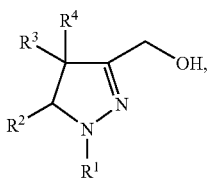

wherein $R^1$, $R^2$, $R^3$ and $R^4$ have the above defined meaning, which is optionally isolated and/or purified;
and at least one compound of general formula III is reacted in a reaction medium, preferably in a reaction medium selected from the group consisting of dichloromethane and toluene, with at least one halogenation agent, preferably with at least one halogenation agent selected from the group consisting of $S(=O)Cl_2$, $PCl_5$, HBr, $BBr_3$ and $PBr_3$, or with at least one compound of general formula $X-S(=O)_2-Cl$, wherein X denotes methyl, phenyl, p-methylphenyl or trifluoromethyl, preferably at a temperature between 0° C. and 100° C., preferably for 1 to 15 hours, to yield at least one compound of general formula IV,

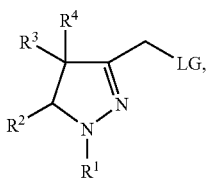

wherein $R^1$, $R^2$, $R^3$ and $R^4$ have the above defined meaning, and LG denotes Cl, Br, methansulfonate, benzenesulfonate, toluenesulfonate or trifluoromethansulfonate, which is optionally isolated and/or purified;
and at least one compound of general formula IV is reacted in a reaction medium, preferably in a reaction medium selected from the group consisting of acetone, tetrahydrofuran, water, ethyl acetate, chloroform, acetonitrile, toluene, 2-propanol, dichloromethane, dimethylformamide and mixtures thereof, with at least one compound of general formula $H_2NR^5$, wherein $R^5$ has the above defined meaning, optionally in the presence of at least one base, preferably in the presence of at least one organic base selected from the group consisting of pyridine, triethylamine, diisopropylethylamine, N-methylmorpholine and dimethylaminopyridine, preferably at a temperature between 0° C. and 120° C., preferably for 4 to 24 hours, and optionally treatment with a solution of hydrogen chloride, to yield at least one compound of general formula V, optionally in form of the respective hydrogen chloride,

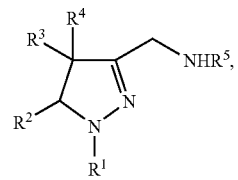

wherein $R^1$, $R^2$, $R^3$, $R^4$ and $R^5$ have the above defined meaning, which is optionally isolated and/or purified;
or at least one compound of general formula II, wherein R denotes hydrogen, is reacted in a reaction medium with thionyl chloride or thionyl bromide to yield at least one compound of general formula VI,

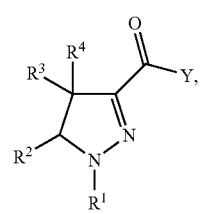

wherein $R^1$, $R^2$, $R^3$ and $R^4$ have the above defined meaning, and Y denotes chlorine or bromine, which is optionally purified and/or isolated;
and at least one compound of general formula VI is reacted in a reaction medium, preferably in a reaction medium selected from the group consisting of acetone, tetrahydrofuran, water, ethyl acetate, chloroform, acetonitrile, toluene, 2-propanol, dichloromethane, dimethylformamide and mixtures thereof, with at least one compound of general formula $H_2NR^5$, wherein $R^5$ has the above defined meaning, optionally in the presence of at least one base, preferably in the presence of at least one organic base selected from the group consisting of pyridine, triethylamine, diisopropylethylamine, N-methylmorpholine and

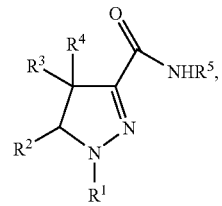

dimethylaminopyridine, to yield at least one compound of general formula VII,
wherein $R^1$, $R^2$, $R^3$, $R^4$ and $R^5$ have the above defined meaning, which is optionally purified and/or isolated;
and at least one compound of general formula VII is reacted in a reaction medium with at least one reducing agent, preferably with at least one reducing agent selected from the group consisting of lithiumaluminiumhydride, borane and sodium, or is reacted in a reaction medium via catalytic hydrogenation, to yield at least one compound of general formula V, which is optionally purified and/or isolated;

and at least one compound of general formula V is reacted in a reaction medium, optionally in an inert atmosphere, optionally in the presence of at least one base, preferably at least one base selected from the group consisting of diisopropylethylamine, triethylamine, pyridine, dimethylaminopyridine and N-methylmorpholine, with at least one compound of general formula $R^6$—$S(=O)_2$-Hal, wherein $R^6$ has the above defined meaning and Hal denotes a halogen atom, preferably a chlorine atom, to yield at least one compound of general formula I,

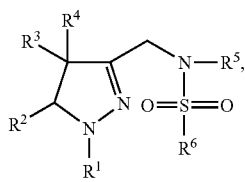

wherein $R^1$, $R^2$, $R^3$, $R^4$, $R^5$ and $R^6$ have the above defined meaning, which is optionally isolated and/or purified.

Compounds of general formula II, wherein $R^3$ denotes hydrogen, can be prepared according to the disclosure of WO 88/5046, WO 2005/74920, US 2005/171179 and WO 2005/77911. The respective parts of the literature are hereby incorporated by reference.

In case $R^3$ is unlike hydrogen, the compounds of general formula II can be prepared as outlined in general scheme 1.

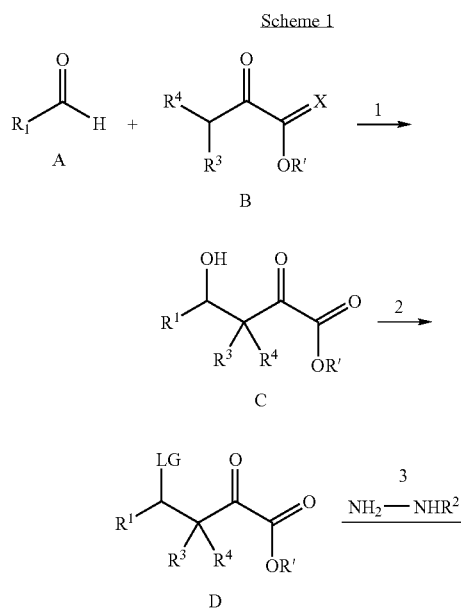

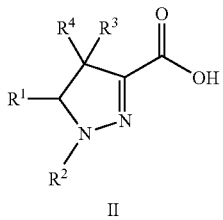

In step 1 a compound of general formula B or a corresponding enolate of said compound is reacted with a compound of general formula A in a reaction medium, preferably in a protic reaction medium, more preferably in a reaction medium selected from the group consisting of methanol, ethanol, isopropanol, n-butanol, water and mixtures thereof, in the presence of at least one base, preferably in the presence of an alkali metal hydroxide such as sodium hydroxide or potassium hydroxide or an alkali metal methoxide such as sodium methoxide or in the presence of lithium diisopropylamide in an aprotic solvent, preferably in tetrahydrofuran.

In step 2 a compound of general formula C is transformed into a compound of general formula D which contains a good living group LG, preferably a leaving group selected from the group consisting of mesyl and tosyl, using conventional methods known to those skilled in the art.

In step 3 a compound of general formula D is reacted with a compound of general formula $NH_2$—$NHR^2$ in a reaction medium, preferably in a reaction medium selected from the group consisting of methanol, ethanol, isopropanol, n-butanol, dieethylether, tert-butyl-methylether, dioxane, tetrahydrofuran or mixtures of at least two of these afore mentioned reaction media. Also preferably, said reaction may be carried out in the presence of an acid, whereby the acid may be organic such as acetic acid and/or inorganic such as hydrochloric acid. Alternatively the reaction may also be carried out in the presence of a base such as piperidine, piperazine, sodium hydroxide, potassium hydroxide, sodium methoxide or sodium ethoxide or mixtures of at least two of these bases. Reaction temperature as well as the duration of the reaction may vary over a broad range. Suitable reaction temperatures range from room temperature, i.e. approximately 25° C. to the boiling point of the reaction medium. Suitable reaction times may vary for example from several minutes to several hours.

The compounds of general formula II, wherein $R^3$ is unlike hydrogen, can also be obtained by the reaction sequence described in scheme 2.

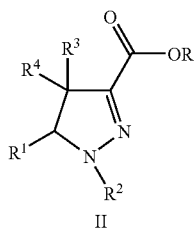

A compound of general formula E, wherein $R^1$, $R^3$ and $R^4$ have the meaning given above, is reacted with a compound of general formula F, wherein $R^2$ has the meaning given above, R represents a $C_{1-6}$-alkyl radical and Y represents a chlorine or bromine atom, in a reaction medium, preferably in an aprotic or protic reaction medium, more preferably in toluene and/or chloroform and/or ethanol, in the presence of a base, preferably an organic base, more preferably an organic base selected from the group consisting of triethylamine, pyridine, diisopropylethylamine, dimethylaminopyridine, 1,4-diazabicyclo[2.2.2]octane and N-methylmorpholine, at a temperature between 0° C. and 150° C. to yield a compound of general formula II. If a mixture of regioisomers is obtained, said regioisomers can be separated by standard methods known to those skilled in the art, e. g. chromatographic methods or crystallisation. The process is disclosed in Bull. Chem. Soc. Japan 1984, 57 (3), 787-790. The respective description is hereby incorporated by reference and forms part of the disclosure.

The aforementioned reactions involving the synthesis of the 4,5-dihydro-pyrazole ring or the reaction of a compound comprising said ring are preferably carried out under an inert atmosphere, preferably under a nitrogen or argon atmosphere, to avoid oxidation of the ring-system.

During some synthetic reactions described above the protection of sensitive or reactive groups may be necessary and/or desirable. This can be performed by using conventional protective groups like those described in Protective groups in Organic Chemistry, ed. J. F. W. McOmie, Plenum Press, 1973; T. W. Greene & P. G. M. Wuts and Protective Groups in Organic Chemistry, John Wiley & sons, 1991. The respective parts of the description is hereby incorporated by reference and form part of the disclosure. The protective groups may be eliminated when convenient by means well-known to those skilled in the art.

If the substituted pyrazoline compounds of general formulae I, Ia and Ib are obtained in form of a mixture of stereoisomers, particularly enantiomers or diastereomers, said mixtures may be separated by standard procedures known to those skilled in the art, e.g. chromatographic methods or crystallisation with chiral reagents. It is also possible to obtain pure stereoisomers via stereoselective synthesis.

In a further aspect the present invention also provides a process for the preparation of salts of substituted pyrazoline compounds of general formulae I, Ia and Ib and stereoisomers thereof, wherein at least one compound of general formulae I, Ia or Ib having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of substituted pyrazoline compounds of general formulae I, Ia and Ib or stereoisomers thereof, wherein at least one compound of general formulae I, Ia or Ib having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e. g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

In the presence of several acidic or basic groups, mono- or poly-salts may be formed. Compounds of the formulae I, Ia or Ib having an acidic group, for example a free carboxyl group, and a basic group, for example an amino group, may also be present in the form of inner salts, i.e., in zwitterionic form, or a part of the molecule may be present in the form of an inner salt and another part in the form of a normal salt.

Solvates, preferably hydrates, of the substituted pyrazoline compounds of general formulae I, Ia or Ib, of corresponding stereoisomers, of corresponding N-oxides or of corresponding salts thereof may also be obtained by standard procedures known to those skilled in the art.

The purification and isolation of the inventive substituted pyrazoline compounds of general formulae I, Ia or Ib, of a corresponding stereoisomer, or salt, or solvate or any intermediate thereof may, if required, be carried out by conventional methods known to those skilled in the art, e.g. chromatographic methods or recrystallisation.

The substituted pyrazoline compounds of general formulae I, Ia and Ib given above, their stereoisomers, corresponding salts thereof and corresponding solvates are toxicologically acceptable and are therefore suitable as pharmaceutical active substances for the preparation of medicaments.

It has been found that the substituted pyrazoline compounds of general formulae I, Ia and Ib given above, stereoisomers thereof, corresponding salts and corresponding solvates have a high affinity to cannabinoid receptors, particularly to cannabinoid 1 ($CB_1$)-receptors, i.e. they are selective ligands for the $CB_1$-receptor and act as modulators, e.g. antagonists, inverse agonists or agonists, on these receptors. In particular, these pyrazoline compounds show little or no development of tolerance during treatment, particularly with respect to food intake, i.e. if the treatment is interrupted for a given period of time and then continued afterwards, the inventively used pyrazoline compounds will again show the desired effect. After ending the treatment with the pyrazoline compounds, the positive influence on the body weight is found to continue.

Furthermore, these substituted pyrazoline compounds show relatively weak Herg channel affinity, thus a low risk of prolongation of the QT-interval is to be expected for these compounds.

In summary, the inventively used substituted pyrazoline compounds are distinguished by a broad spectrum of beneficial effects, while at the same time showing relatively little undesired effects, i.e. effects which do not positively contribute to or even interfere with the well being of the patient.

Thus, an other aspect of the present invention relates to a medicament comprising at least one substituted pyrazoline compound of general formula I, optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof, and optionally at least one physiologically acceptable auxiliary agent.

Preferably said medicament is suitable for the modulation (regulation) of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferably said medicament is suitable for the prophylaxis and/or treatment of psychosis.

Also particularly preferably said medicament is suitable for the prophylaxis and/or treatment of food intake disorders, preferably bulimia, anorexia, cachexia, obesity and/or type II diabetus mellitus (non-insulin dependent diabetes mellitus), more preferably obesity, or metabolic syndrome. The inventive medicament also seems to be active in the prophylaxis and/or treatment of appetence disorders, e.g. the pyrazoline compounds of general formula I also reduce the desire for sweets.

The metabolic syndrome and definitions thereof are described in detail by Eckel et al., The Lancet, Vol. 365 (2005), 1415-1428, included herewith by reference. One of the respective definitions was established by the WHO in 1998 (as described in Alberti et al., Diabet. Med. 1998, 15, pages 539-53, the respective description thereof is herewith incorporated by reference and forms part of the present disclosure). The other, more widely accepted, definition of the metabolic syndrome was established by the Adult Treatment Panel (ATP III) of the US National Cholesterol Education Program (NCEP) in 2001, as described in JAMA 2001; 285; 2486-97, the respective description thereof is herewith incorporated by reference and forms part of the present disclosure.

The metabolic syndrome is characterised by an interaction of several physiological parameters such as triglycerides, lipids, blood pressure, glucose levels and insuline levels.

Even though obesity may play a critical role in the development of metabolic syndrome, many of its aspects are weight independent, especially some lipid parameters. Especially the positive influence on the weight independent aspects of the metabolic syndrome (see e.g. Pagotto and Pasquali, The Lancet, Vol. 365 (2005), 1363, 1364, included herewith by reference) like some blood parameters, especially lipid parameters is one of the major and surprising advantages of the inventively used substituted pyrazoline compounds.

In another aspect, said medicament is suitable for the treatment of weight independent aspects of metabolic syndrome.

Also particular preferably said medicament is suitable for improving cardiovascular and/or metabolic risk factors, such as one or more of the following factors:

Elevated triglycerides, whereby elevated levels of triglycerides are preferably understood as being >150 mg/dl, Low HDL cholesterol, whereby low levels of HDL cholesterol are preferably understood as being <40 mg/dl in men and <50 mg/dl in women, Hypertension, whereby hypertension is preferably understood as being >130/85 mmHg, Impaired fasting glucose, whereby impaired fasting glucose levels are preferably understood as being >110 mg/dl, Insulin resistance, Dyslipidemia, in a subject, preferably a human.

Also particularly preferably said medicament is suitable for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Particularly preferably said medicament is suitable for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Thus the inventive medicament is active in the treatment of abstinence, craving reduction and relapse prevention of alcohol intake. The inventive medicament can also be used in the prophylaxis and/or treatment of smoking addiction, cessation and/or dependence including treatment for craving reduction and relapse prevention of tobacco smoking.

Medicaments and/or drugs, which are frequently the subject of misuse include opioids, barbiturates, cannabis, cocaine, amphetamines, phencyclidine, hallucinogens and benzodiazepines.

The medicament is also suitable for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebellar disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhoea, asthma, memory disorders, pruritus, pain, or for potentiation of the analgesic effect of narcotic and non-narcotic analgesics, or for influencing intestinal transit.

The medicament is also suitable for the prophylaxis and/or treatment of one or more disorders selected from the group consisting of dementia and related disorders, preferably for the prophylaxis and/or treatment of one or more types of dementia selected from the group consisting of memory loss, vascular dementia, mild cognitive impairment, frontotemporal dementia and Pick's disease; binge eating disorders; juvenile obesity; drug induced obesity; atypical depression; behavioural addictions; attention deficit disorders; Tourette's syndrome; suppression of reward-related behaviours; e. g. conditioned place avoidance such as suppression of cocaine- and morphine induced conditioned place preference; impulsivity; sexual dysfunction; preferably for the prophylaxis and/or treatment of one or more types of sexual dysfunction selected from the group consisting of erectile difficulty and female sexual dysfunction; seizure disorders; nausea; emesis; neuroinflammatory disease, preferably for the prophylaxis and/or treatment of one or more types of neuroinflammatory diseases selected from the group consisting of multiple sclerosis, demyelinisation related disorders, Guillan-Barré syndrome, viral encephalitis and cerebrovascular accidents; neurological disorders; muscle spasticity; traumatic brain injury; spinal cord injury; inflammation and immunomodulatory disorders, preferably for the treatment and/or prophylaxis of one or more types of inflammation and immunomodulatory disorders selected from the group consisting of cutaneous T-cell lymphoma, rheumatoid arthritis, systemic lupus erythematosus, sepsis, sarcoidosis, idiopathic pulmonary fibrosis, bronchopulmonary dysplasia, retinal disease, scleroderma, renal ischemia, mycocardial infarction, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, chronic obstructive pulmonary disease and bronchitis; cerebral apoplexy; craniocerebral trauma; neuropathic pain disorders; gastric ulcers; atheriosclerosis and liver cirrhosis.

Another aspect of the present invention is the use of at least one substituted pyrazoline compound of general formula I given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, and optionally one or more pharmaceutically acceptable excipients, for the preparation of a medicament for the modulation of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of psychosis.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of food intake disorders, preferably bulimia, anorexia, cachexia, obesity and/or type II diabetus mellitus (non-insuline dependent diabetes mellitus), more preferably obesity.

Also particularly preferred is the use of at least one of the pyrazoline compounds as defined herein and optionally one or more pharmaceutically acceptable excipients, for the preparation of a medicament for the treatment of metabolic syndrome.

Another aspect of the invention is the use of one or more pyrazoline compounds as defined herein for the manufacture of a medicament for improvement of cardiovascular and/or metabolic risk factors, such as one or more of the following factors:

Elevated triglycerides, whereby elevated levels of triglycerides are preferably understood as being >150 mg/dl, Low HDL cholesterol, whereby low levels of HDL cholesterol are preferably understood as being <40 mg/dl in men and <50 mg/dl in women, Hypertension, whereby Hypertension is preferably understood as being >130/85 mmHg, Impaired fasting glucose, whereby impaired fasting glucose levels are preferably understood as being >110 mg/dl, Insulin resistance, Dyslipidemia.

Another aspect of the invention is the use of one or more pyrazoline compounds as defined herein for the manufacture of a medicament for the treatment of the weight independent aspects of metabolic syndrome.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Also particularly preferred is the use of at least one of the of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding solvate thereof, and optionally one or more pharmaceutically acceptable excipients, for the preparation of a medicament for the prophylaxis and/or treatment of one or more disorders selected from the group consisting of dementia and related disorders, preferably for the prophylaxis and/or treatment of one or more types of dementia selected from the group consisting of memory loss, vascular dementia, mild cognitive impairment, frontotemporal dementia and Pick's disease; binge eating disorders; juvenile obesity; drug induced obesity; atypical depression; behavioural addictions; attention deficit disorders; Tourette's syndrome; suppression of reward-related behaviours; e. g. conditioned place avoidance such as suppression of cocaine- and morphine induced conditioned place preference; impulsivity; sexual dysfunction;

preferably for the prophylaxis and/or treatment of one or more types of sexual dysfunction selected from the group consisting of erectile difficulty and female sexual dysfunction;

seizure disorders; nausea; emesis; neuroinflammatory disease, preferably for the prophylaxis and/or treatment of one or more types of neuroinflammatory diseases selected from the group consisting of multiple sclerosis, demyelinisation related disorders, Guillan-Barré syndrome, viral encephalitis and cerebrovascular accidents;

neurological disorders; muscle spasticity; traumatic brain injury; spinal cord injury; inflammation and immunomodulatory disorders, preferably for the treatment and/or prophylaxis of one or more types of inflammation and immunomodulatory disorders selected from the group consisting of cutaneous T-cell lymphoma, rheumatoid arthritis, systemic lupus erythematosus, sepsis, sarcoidosis, idiopathic pulmonary fibrosis, bronchopulmonary dysplasia, retinal disease, scleroderma, renal ischemia, myocardial infarction, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, chronic obstructive pulmonary disease and bronchitis; cerebral apoplexy; craniocerebral trauma; neuropathic pain disorders; gastric ulcers; atheriosclerosis and liver cirrhosis.

Medicaments/drugs, which are frequently the subject of misuse include opioids, barbiturates, cannabis, cocaine, amphetamines, phencyclidine, hallucinogens and benzodiazepines.

Also preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebella disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhoea, asthma, memory disorders, pruritus, pain, or for potentiation of the analgesic effect of narcotic and non-narcotic analgesics, or for influencing intestinal transit.

Dementia is a disease characterised by the progressive deterioration in cognitive and social adaptive functions that can eventually interfere with the patient's ability to live independently. Dementia also constitutes of impairment in short- and long-term memory plus additional symptoms, such as problems with abstract thinking, judgement, or personality. An estimated 18 million patients suffer from dementia worldwide. The most common forms of dementia include Alzheimer's disease and vascular dementia. Other forms are frontotemporal dementia and Pick's disease.

Dementia can also be of vascular origin. Vascular dementia (atherosclerotic cerebrovascular disease) is considered to be the second most common dementia of late life, affecting approximately 10-15% of all cases. AD and vascular dementia can exist in isolation or together (mixed dementia). In vascular dementia, atherosclerotic changes in cerebral vessels can lead to reduced local blood flow that results in multiple small strokes (multi-infarct dementia). Vascular dementia is pharmacologically treated by stroke prophylaxis, and by treatment of the cognitive deficit.

Alzheimer's disease (AD), the most common and important form of dementia, is a neurodegenerative disorder that is characterised by progressive impairment of cognitive functions, such as abstract reasoning and memory. Currently, an estimated 2 million people in the United States and 12 million world-wide are afflicted by this disease. Due to increasing life expectancy, it is predicted that there will be over 100 million AD patients world-wide by the year 2050. AD is one of the most prevalent illnesses in the elderly. The majority of AD patients are in their sixties or older. More than 5% of all persons over the age of 70 have significant memory loss due to AD.

AD is mainly characterised through a gradual development of forgetfulness. In further advanced disease stages, other failures in cerebral function become increasingly apparent. This includes impairment of speech, writing, and arithmetic skills. Visiospacial orientation, such as parking the car, dressing properly, and giving and understanding directions to a location, can become defective or impaired. In late stage disease, patients forget how to use common objects and tools while retaining necessary motor power and co-ordination for these activities.

Schizophrenia is characterised by profound disruption in cognition and emotion, affecting the most fundamental human attributes: language, thought, perception, affect, and sense of self. Positive symptoms include psychotic manifestations, such as hearing internal voices or experiencing other sensations not connected to an obvious source (hallucinations) and assigning unusual significance or meaning to normal events or holding fixed false personal beliefs (delusions). Negative symptoms are characterised by affective flattening and lack of initiative or goals (avolition), loss of usual interests or pleasures (anhedonia), disturbances of sleep and eating, dysphoric mood (depressed, anxious, irritable, or angry mood) and difficulty concentrating or focusing attention.

Major depression is a multifaceted disorder characterised by primarily by dysphoric mood and loss of interest or pleasure in activities that were once enjoyable. Other physical and psychological symptoms include inability to concentrate, motor disturbances (psychomotor retardation or agitation), feelings of worthlessness, inappropriate guilt, thoughts of suicide, and disturbances in appetite and sleep.

Anxiety disorders are a group of syndromes that include generalised anxiety disorder, panic disorder, phobias, obsessive-compulsive disorder, and post traumatic stress disorder. Although each disorder has its own distinct features, all share common symptoms of excessive worrying, intense fears and dread, hypervigilance and/or somatic symptoms, in the absence of a dangerous situation.

Normal sexual function requires, among others, the ability to achieve and maintain penile erection. Major anatomic structures of the penis that are involved in erectile function include the corpus cavernosum, corpus spinosum, and the tunica albuginea (a collagenous sheath that surrounds each corpus). The corpora are composed of a mass of smooth muscle (trabecula) which contains a network of endothelial-lined vessels (lacunar spaces). Penile tumescence and erection is caused by relaxation of the arteries and corporal smooth muscles, while closing emissary veins, leading to increased blood flow into the lacunar network. Central and peripheral enervation contributes to regulation of the erectile response.

Erectile dysfunction (ED) may result from failure to initiate, fill, or store adequate blood volume within the lacunar network of the penis. Depending on the underlying dysfunction, ED may be vasculogenic, neurogenic, endocrinologic, diabetic, psychogenic, or medication-related.

ED affects 10-25% of middle-aged and elderly men, and has a profound impact on the well-being of affected men. It is currently treated using PDE5 inhibitors such as vardenafil, tadalifil, and sildenafil. Intraurethral alpostadil (prostaglandin El) may be used in patients that fail on oral agents. In addition, vacuum constriction devices (VCD) are a well-established, non-invasive therapy.

Female sexual dysfunction (FSD) is highly prevalent, age-related, and progressive. It affects 30 to 50% of women. FSD denotes a range of medical problems and is categorised according to disorders of (1) desire, (2) arousal, (3) orgasm and (4) sexual pain, and symptoms include diminished vaginal lubrication, pain and discomfort with intercourse, decreased arousal, and difficulty achieving orgasm. On a molecular level, vasoactive intestinal peptide (VIP), nitric oxide (NO), and sex hormones such as estrogens and androgens have been suggested to be important in female sexual function. Current treatment approaches include oestrogen replacement therapy, methyl testosterone, PDE5 inhibitors such as sildenafil, the NO-donor L-arginine, prostaglandin El, phentolamine, and the dopamine agonists apomorphine.

The medicament according to the present invention may be in any form suitable for the application to humans and/or animals, preferably humans including infants, children and adults and can be produced by standard procedures known to those skilled in the art. The medicament can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilising agents, solubilising agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or retarded release. The multiparticulate forms, such as pellets or granules, may e.g. be filled into a capsule, compressed into tablets or suspended in a suitable liquid.

Suitable controlled release formulations, materials and methods for their preparation are known from the prior art, e.g. from the table of contents of "Modified-Release Drug Delivery Technology", Rathbone, M. J. Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York, (2000); "Controlled Drug Delivery", Vol, I, Basic Concepts, Bruck, S. D. (Ed.), CRD Press Inc., Boca Raton (1983) y de Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective descriptions are hereby incorporated by reference and form part of the disclosure.

Medicaments according to the present invention may also comprise an enteric coating, so that their dissolution is dependent on pH-value. Due to said coating the medicament can pass the stomach undissolved and the respective substituted pyrazoline compound of general formula I is liberated in the intestinal tract. Preferably the enteric coating is soluble at a pH value of 5 to 7.5. Suitable materials and methods for the preparation are known from the prior art.

Typically, the medicaments according to the present invention may contain 1-60% by weight of one or more substituted pyrazoline compounds as defined herein and 40-99% by weight of one or more auxiliary substances (additives).

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000, even more preferably 1 to 150 milligrams of active substance to be administered during one or several intakes per day.

Pharmacological Methods

I. In-Vitro Determination of Affinity to CB1/CB2-Receptors a)

The in-vitro determination of the affinity of the inventive substituted pyrazoline compounds to $CB_1/CB_2$-Rezeptors is carried out as described in the publication of Ruth A. Ross, Heather C. Brockie et al., "Agonist-inverse agonist characterisation at $CB_1$ and $CB_2$ cannabinoid receptors of L-759633, L759656 and AM630", British Journal of Pharmacology, 126, 665-672, (1999), whereby the transfected human $CB_1$ and $CB_2$ receptors of Receptor Biology, Inc. are used. The radioligand used for both receptors is [$^3$H]-CP55940. The respective parts of the description is hereby incorporated by reference and forms part of the present disclosure.

b)
Rat Cerebellum CB1 Binding

Binding affinity to CB1 receptor was evaluated according to a modification of the method described by Govaerts et al., Eur J Pharmac Sci 23, 233-243 (2004). The respective parts of the description is hereby incorporated by reference and forms part of the present disclosure.

Briefly, cerebellum from male wistar rats (250-300 g) were carefully dissected on ice and homogenates were prepared with Potter-Helveheim in a cold 50 mM Tris-HCl solution containing 5 mM $MgCl_2$, 1 mM EDTA and 0.25 M sucrose, pH 7.4. The suspension was centrifuged at 1,000×g for 5 minutes. The supernatants were collected and centrifuged 50,000×g for 15 minutes. The resulting pellets were then resuspended in Tris-HCl buffer without sucrose, homogenised and incubated for 15 min at 37° C. in an orbital shaker bath and centrifuged again at 50,000×g for 15 min. Pellets were weighted, resuspended in Tris-HCl buffer without sucrose, homogenised with Ultraturrax at 13,500 rpm for 3×5 seconds and alicuoted in 0.9 ml volumes in Eppendorf tubes. Alicuotes were centrifuged at 20,800×g for 5 minutes, supernatants discarded and pellets were frozen at −80° C. until use. Total protein concentration was determined using the Bio-Rad Lowry method based kit. Competitive binding experiments were performed in presence of 1 nM [$^3$H]-CP 55,940 in siliconised glass tubes containing 100 μg protein/tube resuspended in 1 ml final volume of 50 mM Tris-HCl, 5 mM $MgCl_2$, 1 mM EDTA, 0.5% (w/v) bovine serum albumin, pH 7.4. Compounds were present at various concentrations and the non specific binding was determined in the presence of 10 μM HU-210. After 1 hour incubation at 30° C., the suspension was rapidly filtered through 0.5% PEI pre-treated GF/B fiber filters on a 96-well harvester and washed 3 times with 3 ml ice-cold binding buffer without bovine serum albumin. Radioactivity on filters was measured with Wallac Winspectral 1414 counter by liquid scintillation in 6 ml Ecoscint H (National Diagnostics, U.K.). Assays were made in triplicates.

Binding data were analysed by non-linear regression with the software GraphPad Prism Version 3.03.

II. In-Vivo Bioassay System for Determination of Cannabinoid Activity

Mouse Tetrad Model

Substances with affinity for cannabinoid receptors are known to produce a wide range of pharmacological effects. It is also known that intravenous administration of a substance with affinity for cannabinoid receptors in mice produces analgesia, hypothermia, sedation and catalepsy. Individually, none of these effects can be considered as proof that a tested substance has affinity for cannabinoid-receptors, since all of these effects are common for various classes of centrally active agents. However, substances, which show all of these effects, i.e. substances that are active in this so-called tetrad model are considered to have affinity for the cannabinoid receptors. It has further been shown that cannabinoid receptor antagonists are highly effective in blocking the effects of a cannabinoid agonist in the mouse tetrad model.

The tetrad model is described, for example, in the publication of A. C. Howlett et al, International Union of Pharmacology XXVII. Classification of Cannabinoid Receptors, Pharmacol Rev 54, 161-202, 2002 and David R. Compton et al., "In-vivo Characterization of a Specific Cannabinoid Receptor Antagonist (SR141716A): Inhibition of Tetrahydrocannbinol-induced Responses and Apparent Agonist Activity", J. Pharmacol. Exp. Ther. 277, 2, 586-594, 1996. The corresponding parts of the descriptions are hereby incorporated by reference.

Material and Methods

Male NMRI mice with a weight of 20-30 g (Harlan, Barcelona, Spain) are used in all of the following experiments.

Before testing in the behavioural procedures given below, mice are acclimatised to the experimental setting. Pre-treatment control values are determined for analgesia hot plate latency (in seconds), rectal temperature, sedation and catalepsy.

In order to determine the agonistic activity of the substance to be tested, the mice are injected intravenously with the substance to be tested or the vehicle alone. 15 minutes after injection, latency in hot plate analgesia is measured.

Rectal temperature, sedation and catalepsy are measured 20 minutes after injection.

In order to determine the antagonistic activity the identical procedure is used as for the determination of the agonistic effects, but with the difference that the substance to be evaluated for its antagonistic activity is injected 5 minutes before the intravenous injection of 1.25 mg/kg Win-55,212 a known cannabinoid-receptor agonist.

Hot Plate Analgesia

The hot plate analgesia is determined according to the method described in Woolfe D. et al. "The evaluation of analgesic action of pethidine hydrochloride (Demerol)", J. Pharmacol. Exp. Ther. 80, 300-307,1944. The respective description is hereby incorporated by reference and forms part of the present disclosure.

The mice are placed on a hot plate (Harvard Analgesimeter) at 55±0.5° C. until they show a painful sensation by licking their paws or jumping and the time for these sensations to occur is recorded. This reading is considered the basal value (B). The maximum time limit the mice are allowed to remain on the hot plate in absence of any painful response is 40 seconds in order to prevent skin damage. This period is called the cut-off time (PC).

Fifteen minutes after the administration of the substance to be tested, the mice are again placed on the hot plate and the afore described procedure is repeated. This period is called the post-treatment reading (PT).

The degree of analgesia is calculated from the formula:

$$\% \text{ MPE of Analgesia} = (PT-B)/(PC-B) \times 100$$

MPE=Maximum possible effect.

Determination of Sedation and Ataxia

Sedation and ataxia is determined according to the method described in Desmet L. K. C. et al. "Anticonvulsive properties of Cinarizine and Flunarizine in Rats and Mice", Arzneim.-Forsch. (Frug Res) 25, 9, 1975. The respective description is hereby incorporated by reference and forms part of the present disclosure.

The chosen scoring system is

0: no ataxia;
1: doubtful;
2: obvious calmness and quiet;
3 pronounced ataxia;
prior to as well as after treatment.

The percentage of sedation is determined according to the formula:

$$\% \text{ of sedation} = \text{arithmetic mean}/3 \times 100$$

Hypothermia:

Hypothermia is determined according to the method described in David R. Compton et al. "In-vivo Characterization of a Specific Cannabinoid Receptor Antagonist (SR141716A) Inhibition of Tetrahydrocannbinol-induced Responses and Apparent Agonist Activity", J. Pharmacol Exp Ther. 277, 2, 586-594, 1996. The respective description is hereby incorporated by reference and forms part of the present disclosure.

The base-line rectal temperatures are determined with a thermometer (Yello Springs Instruments Co., Panlabs) and a thermistor probe inserted to 25 mm before the administration of the substance to be tested. Rectal temperature is again measured 20 minutes after the administration of the substances to be tested. The temperature difference is calculated for each animal, whereby differences of $\leq -2°$ C. are considered to represent activity.

Catalepsy:

Catalepsy is determined according to the method described in Alpermann H. G. et al. "Pharmacological effects of Hoe 249: A new potential antidepressant", Drugs Dev. Res. 25, 267-282. 1992. The respective description is hereby incorporated by reference and forms part of the present disclosure.

The cataleptic effect of the substance to be tested is evaluated according to the duration of catalepsy, whereby the animals are placed head downwards with their kinlegs upon the top of the wooden block.

The chosen scoring system is:

Catalepsy for:

more than 60 seconds=6; 50-60 seconds=5, 40-50 seconds=4, 30-40 seconds=3, 20-30 seconds=2, 5-10 seconds=1, and less than 5 seconds=0.

The percentage of catalepsy is determined according to the following formula:

% Catalepsy=arithmetic mean/6×100

III. In Vivo Testing for Antiobesic Activity a) Acute Treatment

Normally handled rats were habituated to a reversed cycle 12/12 h, and the tested compound as well as saline was acutely orally administered. After administration the cumulated food intake (g) was measured at 6 h and 24 h. Following that the difference in body weight between control and compound treated animals was measured. This is a variation of the test according to Colombo et al. as described below.

b) Long-Term Treatment

The in-vivo testing for antiobesic activity of the inventive pyrazoline compounds is carried out as described in the publication of G. Colombo et al., "Appetite Suppression and Weight Loss after the Cannabinoid Antagonist SR 141716"; Life Sciences, 63 (8), 113-117, (1998). The respective part of the description is hereby incorporated by reference and forms part of the present disclosure.

IV. In Vivo Testing for Antidepressant Activity

The in-vivo testing for antidepressant activity of the inventive pyrazoline compounds in the water despair test is carried out as described in the publication of E. T. Tzavara et al., "The CB1 receptor antagonist SR141716A selectively increases monoaminergic neurotransmission in the medial prefrontal cortex: implications for therapeutic actions"; Br. J. Pharmacol. 2003, 138(4):544:53. The respective part of the description is hereby incorporated by reference and forms part of the present disclosure.

The present invention is illustrated below with the aid of examples. These illustrations are given solely by way of example and do not limit the general spirit of the present invention.

V. In Vitro Determination of Antagonism to CB1-Receptor

Membrane Preparation:

Chinese hamster ovary (CHO) cells stable expressing recombinant human cannabinoid 1 receptor (CB1) were cultured in nutrient mixture Ham's F 12 supplemented with 10% heat-inactivated fetal bovine serum, 2 mM L-glutamine, 50 U/ml penicillin, 50 U/ml streptomycin and 0.5 mg/ml geneticin. In order to obtain cells, culture flasks were washed twice with phosphate buffered saline and scraped. Then, cells were collected by centrifugation (200×g, 10 min) and stored dry at −80° C. Cells were homogenised in ice-cold 20 mM HEPES, 10 mM EDTA (pH 7.5) and centrifuged at 40,000×g for 15 min at 4° C. The pellet was resuspended in 20 mM HEPES, 0.1 mM EDTA (pH 7.5) and centrifuged for 15 min at 4° C. The final pellet was resuspended in 20 mM HEPES, 0.1 mM EDTA (pH 7.5), and divided in aliquots and stored at −80° C. until use.

[$^{35}$S]GTPγS Binding Assay:

The reaction was performed in 96-well plates. Membranes (15 µg protein/well) were incubated for 60 min at 30° C. in buffer (50 mM HEPES, 100 mM KCl, 5 mM $MgCl_2$, 1 mM EDTA, 0.1% wt/vol bovine serum albumin, 5 µM GDP, saponin (10 µg/ml), 0.5 nM [$^{35}$S]GTPγS, pH 7.4) with compound at 1 µM final concentration in either the absence or presence of dose response curve of agonist WIN 55,212-2 between 3 nM and 3 µM. The incubation was terminated by rapid filtration through Millipore Multiscreen glass fiber FB, and rinsed two-times with ice-cold assay buffer. Filter plates were dried and 30 µl of scintillation liquid was added. Radioactivity was determined using Wallac Microbeta Trilux. Each experiment was performed at least in duplicate. A WIN 55,212-2 dose-response either alone or in the presence of Rimonabant (1 µM) was systematically performed.

Calculations:

The average of basal [$^{35}$S]GTPγS binding was subtracted from all binding data. In order to compare the antagonism results from one screening campaign to another one, the difference between the maximal agonist effect of WIN 55,212-2 alone, and the maximal antagonism effect due to WIN 55,212-2 plus Rimonabant (1 µM) was defined as 100%.

Further Methods:

Alcohol Intake

The following protocol may be used to evaluate the effects of alcohol intake in alcohol preferring (P) female rats (e.g. bred at Indiana University) with an extensive drinking history. The following reference provides detailed a description of P rats: Lumeng, L, et al., "Different sensitivities to ethanol in alcohol-preferring and- nonpreferring rats," Pharmacol, Biochem Behav., 16, 125-130 (1982).

Female rats are given 2 hours of access to alcohol (10% v/v and water, 2-bottle choice) daily at the onset of the dark cycle. The rats are maintained on a reverse cycle to facilitate experimenter interactions. The animals are initially assigned to four groups equated for alcohol intakes: Group 1-vehicle; Group 2-positive control (e. g. 5.6 mg/kg AM251; Group3-low dose test compound; and Group 4-high dose of test compound. Test compounds are generally mixed into a vehicle of 30% (w/v)-cyclodextrin in distilled water at a volume of 1-2 ml/kg. Vehicle injections are given to all groups for the first two days of the experiment. This is followed by 2 days of drug injections (to the appropriate groups) and a final day of vehicle injections. On the drug injection days, drugs are given sc 30 minutes prior to a 2-hour alcohol access period. Alcohol intake for all animals is measured during the test period and a comparison is made between drug and vehicle-treated animals to determine effects of the compounds on alcohol drinking behaviour.

Additional drinking studies can be done utilising female C57Bl/6 mice (Charles River). Several studies have shown that this strain of mice will readily consume alcohol with little to no manipulation required (Middaugh et al., "Ethanol Consumption by C57BU6 Mice: Influence of Gender and Procedural Variables" Alcohol, 17 (3), 175-183, 1999; Le et al., "Alcohol Consumption by C57BL/6, BALA/c, and DBA/2 Mice in a Limited Access Paradigm" Pharmacology Biochemistry and Behavior, 47, 375-378, 1994).

For example, upon arrival mice are individually housed and given unlimited access to powdered rat chow, water and a 10% (w/v) alcohol solution. After 2-3 weeks of unlimited access, water is restricted for 20 hours and alcohol is restricted to only 2 hours access daily. This is done in a manner that the access period was the last 2 hours of the dark part of the light cycle.

Once drinking behaviour is stabilised, testing can commence. Mice are considered stable when the average alcohol consumption for 3 days is 20% of the average for all 3 days. Day 1 of test consists of all mice receiving vehicle injection (sc or ip). Thirty to 120 minutes post injection access is given to alcohol and water. Alcohol consumption for that day is calculated (g/kg) and groups are assigned so that all groups have equivocal alcohol intake. On day 2 and 3, mice are injected with vehicle or drug and the same protocol as the previous day is followed. Day 4 iss wash out and no injections are given. Data is analysed using repeated measures ANOVA. Change in water or alcohol consumption is compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (e.g. 300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i. e., sc, ip, iv). Drugs are prepared in methylcellulose, water or other specified vehicle (examples include PEG400, 30% beta-cyclo dextran and propylene glycol). Oxygen consumption and ambulatory activity are measured every 10 minutes for an additional 1-6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-minO2 consumption values, excluding periods of high ambulatory activity (ambulatory activity count >100) and excluding the first 5 values of the pre-dose period and the first value from the post-dose period. Change in oxygen consumption is reported as percent and is calculated by dividing the post-dosing resting oxygen consumption by the pre-dose oxygen consumption*100. Experiments will typically be done with n=4-6 rats and results reported are mean+/−SEM.

Interpretation:

An increase in oxygen consumption of >10% is considered a positive result. Historically, vehicle-treated rats have no change in oxygen consumption from pre-dose basal.

Nicotine Dependence

An intravenous nicotine self-administration model or place preference model may be used to assess the effects of a test compound on nicotine dependence (see, e.g., Vastola, et al. Physiol. Behav. 77:107-114, 2002; Brower, et al., Brain Res. 930:12-20, 2002).

Place Preference

Sprague-Dawley rats are used in this study (Vastola, et al., 2002). Animals are housed in a temperature-controlled, 12 h/12 h illumination cycle with ad libitum access to food and water. Conditioning and testing are conducted in a chamber divided into two compartments with a door separating the two compartments. Behavior of the animals is recorded by video camera.

Animals are habituated to the injection procedure for several days. The animals are then placed into the test chamber and given free access to both compartments. The initial preference for a particular compartment is determined. For the conditioning trials, animals are injected with nicotine and restricted to the nonpreferred compartment, or the animals are injected with saline and restricted to the preferred compartment. On test day, the door separating the compartments is removed, the animal is placed in the centre of the chamber and allowed to move freely between compartments. Time spent in each compartment is scored. Preferential occupancy of the nicotine compartment follows from the conditioned reinforcing effects of nicotine.

Self-Administration

Self-administration in animals is a predictor of a compound's abuse potential in humans. Modifications to this procedure may also be used to identify compounds that prevent or block the reinforcing properties of drags that have abuse potential. A compound that extinguishes the self-administration of a drag may prevent that drag's abuse or its dependence.

Sprague-Dawley rats are used in this study. Initially, animals are housed in a temperature-controlled, 12 h/12 h illumination cycle with ad libitum access to food and water. The animals are then implanted with jugular catheters which exit through the animal's back, and each animal is placed in an individual operant chamber (Brower, et al., 2002). The catheters are connected to a computer-driven syringe pump which is located outside of the chamber. The chamber contains two levers with a green light located above each lever. The light is illuminated when nicotine is available.

In a self-administration test, animals are placed in the operant chambers and the levers are randomly designated as an active and inactive lever. Each response on the active lever produces an infusion of nicotine. Presses on the inactive lever have no effect, but are also recorded. Animals are then trained to self-administer nicotine over a set period of time by having drag access during each daily session. Illumination of the chamber house light signals the beginning of the session and the availability of nicotine. When the session ends, the house light is turned off. Initially, a nicotine infusion occurs with every press of the active lever. Once lever-pressing behavior has been established, the number of presses to produce a nicotine infusion is increased. After stable nicotine self-administration is obtained, the effect of a test compound on the nicotine-reinforced behavior may be evaluated. Administration of this test compound prior to the session can either potentiate, extinguish, or produce no change to the self-administrating behavior. Tests are conducted every two days, and the order of the administration of the test compound doses is controlled.

Alzheimer/Dementia Experiments

Morris Water Maze Task

The Morris water maze is a behavioural in vivo test to measure spatial orientation learning and memory through a complex learning task. It is highly suitable for testing compounds that enhance learning and memory. A circular water tank or pool (diameter 2 m, height 0.7 m) is filled with water, and a 10 cm 2 platform is placed 1-1.5 cm below the water surface at a defined location within the pool. The escape platform is not visible for an animal swimming in the water tank. For the experiment, a rat or mouse is placed into the pool to swim freely.

The animals have the task to localise the submerged platform, and the time and distance required for successful retrieval is measured. Multiple extra-maze cues are provided by the furniture in the room, including desks, computer equipment, a second water tank, the presence of the experimenter, and by a radio on a shelf that is playing softly.

Before administration of the test compound, animals are usually trained in the task 4 times a day for 5 days. Test compounds are administered orally or intraperitoneally on the day of the experiment at a defined time (e.g., 30 minutes before the first swim test). Control animals are dosed with the corresponding vehicle not containing test compound. Active compounds yield shorter times and distances to localise the platform (i.e., the better the animal remembers the location of the platform, the shorter the distance covered and the faster the platform is reached).

The test can also be carried out using transgenic or cognitively impaired animals. Cognitive impairment is induced either by old age or experimentally through brain lesions, such as bilateral lesions of the entorhinal cortex in rats. Such lesions can be induced by intracerebral injections of the excitotoxin ibotenic acid.

Object Recognition Task

The object recognition task is used to assess the effects of compounds on the cognitive performance of rodents. A rat is placed in an open field, in which two identical objects are located. The rats inspects both objects during the initial trial of the test. After a certain retention interval (e.g., 24 hours), a second trial is carried out. Here, one of the two objects used in the first trial (the 'familiar' object) and a novel object are placed in the open field, and the inspection time at each of the objects is measured. Good retention is reflected by higher exploration times towards the novel compared with the 'familiar' object.

Administration of the putative cognition enhancer prior to the first trial predominantly allows assessment of the effects on acquisition, and on the consolidation processes. Administration of the test compound after the first trial allows to assess the effects on consolidation processes, whereas administration before the second trial allows to measure effects on retrieval processes.

Passive Avoidance Task

The passive avoidance task assesses memory performance in rats and mice. The inhibitory avoidance uses an apparatus consisting of a box with two compartments separated by a guillotine door that can be operated by the experimenter. One compartment is illuminated with bright light, and the other compartment is dark. A threshold of 2 cm separates the two compartments when the guillotine door is 15 raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. During the habituation sessions and the retention session, the rat is allowed to explore the apparatus for 300 seconds. The rat is placed in the light compartment, facing the wall opposite to the guillotine door. After an accommodation period of 15 seconds, the guillotine door is opened so that all parts of the apparatus can be visited freely. Rats normally avoid brightly lit areas and will enter the dark compartment within a few seconds.

In the shock session, the guillotine door between the compartments is lowered as soon as the rat has entered the dark compartment with all paws, and a scrambled 1 mA footshock is administered for 2 seconds. Then the rat is removed from the apparatus and returned into its home cage. The procedure during the retention session is identical to that of the habituation sessions.

The step-through latency, that is, the first latency of entering the dark compartment (in seconds) during the retention session is an index of the memory performance of the animal: a better retention is assumed if the latency to enter the dark compartment is longer. A test compound is given 30 minutes before the shock session, together with 1 mg/kg scopolamine. Scopolamine impairs the memory performance during the retention session 24 hours later. If the test compound increases the enter latency compared with the scopolamine-treated controls, it is considered to possess cognition enhancing activity. T-maze Spontaneous Alternation Task The T-maze spontaneous alternation task (TeMCAT) assesses the spatial memory performance in mice. The start arm and the two goal arms of the T-maze are provided with guillotine doors that can be operated manually by the experimenter. A mouse is put into the start arm at the beginning of training. In the first trial, either the left or right goal arm is blocked by lowering the respective guillotine door (forced trial).

After the mouse has been released from the start arm, it will explore the maze, eventually entering the open goal arm, and return to the start position, where it will be confined for 5 seconds, by lowering the guillotine door. Then, the animal can choose freely between the left and right goal arm (all guillotine-doors opened) during 14 additional trials (free choice trials). As soon as a mouse has entered one goal arm, the other arm is closed. The mouse eventually returns to the start arm and is free to visit whichever arm it wants after having been confined to the start arm for 5 seconds. After completion of 14 free choice trials in one session, the animal is removed from the maze.

Out of the 14 trials the alternations in percent are calculated. This percentage and the total time needed to complete the first forced trial and the subsequent 14 free choice trials (in seconds) is analysed. In addition, cognitive deficits can be induced by injection of scopolamine 30 minutes before the start of the training session. A cognition enhancer, administered before the training session, will at least partially, antagonise the scopolamine-induced reduction in the spontaneous alternation rate.

Depression Model

A forced swim or tail suspension model may be used to assess the efficacy of antidepressant compounds (see, e.g., Porsolt, et al., Nature 266:730-732, 1977; Stem, et al., Psychopharmacology 85:367-370, 1985).

Forced Swim Test

Rats or mice are placed in a cylinder filled with water 23-25° C. from which no escape is possible. Initially, animals struggle and try to escape, but eventually adopt a characteristic immobile posture and make no further attempts to escape except for small movements needed their head above water. Animals are dosed with a compound and the activity (swimming or climbing) or immobility is measured by an observer.

The immobility is considered by some to reflect a 'behavioral despair' in which animals cease to struggle to escape the aversive situation. A wide variety of clinically used antidepressants (TCAs, MAOIs, SSRIs, atypicals) decrease immobility in this test and has a good predictive validity in that it detects antidepressants with different mechanisms of action but its construct validity is weak. At least two distinct active behavioural patterns are produced by pharmacologically selective antidepressant drugs. Serotonin-selective reuptake inhibitors increase swimming behavior, whereas drugs acting primarily to increase extracellular levels of norepinephrine or dopamine increase climbing behavior. There are false positives (psychostimulants) but relatively few false negatives ([beta]-adrenergic agonists). The test is sensitive to muscle-relaxant (benzodiazepines) and sedative (neuroleptics) effects, leading to enhanced immobility. False positives and false negatives can often be screened by measuring if the compound produces locomotor stimulation or sedation.

Tail Suspension Test

When suspended by the tail, mice will initially struggle and try to escape and then alternate between active escape attempts and immobility. In this test, animals are dosed with a compound and the immobility is measured by an observer for 6 min. Porsolt describes the immobile behavior as 'behavioral despair' which animals cease to struggle to escape the aversive situation. A large variety of clinically antidepressants (tricyclics, MAOIs, SSRIs, and atypicals) reduce immobility in this model. The test has a good predictive validity for antidepressant activity and works for most antidepressant classes including but has some false positives (psychostimulants). The test is sensitive to muscle-relaxant (benzodiazepines) and sedative (neuroleptics) effects, which lead to enhanced immobility. False positives and false negatives can often be screened by measuring if the compound produces locomotor stimulation or sedation. Strain differences in the tail suspension test have been found in mice. The tail suspension test has some face validity but its construct validity is rather weak.

Schizophrenia Model

A prepulse inhibition model may be used to assess the efficacy of antipsychotic compounds (see Swerdlow and Geyer, Schizophrenia Bulletin 24: 285-301, 1998).

Prepulse Inhibition

Prepulse inhibition is the process whereby a relatively mild stimulus, the prepulse, suppresses the response to a strong, startle-eliciting stimulus when the prepulse precedes the startle stimulus by a brief duration (about 10 to 500 milliseconds). Prepulse inhibition is a cross-species phenomenon (ie, it is present in mammals ranging from mice to humans), yet it is relatively absent among schizophrenic patients. The deficit in PPI in schizophrenic patients is thought to reflect the loss of sensorimotor gating that may lead to sensory flooding and cognitive fragmentation. In this test, mice or rats are administered compounds and individually placed into a holder on a transducer platform to measure whole body startle. The holder is housed in a startle chamber with background white noise. Following a brief habituation period, animals are given multiple trials of a weak auditory prepulse stimulus, followed by a strong auditory startle stimulus. Four types of trials are given: prepulse plus startle, prepulse alone, startle alone, and no stimulation. PPI is measured as the amount of inhibition of startle following the prepulse and is expressed as the percentage of basic startle. As a control, measurements are taken in the no stimulation and prepulse alone trials. PPI is considered a test with good predictive, face and construct validity for schizophrenia. Putative antipsychotics can be tested alone to determine if they enhance PPI. Alternately, antipsychotics can be screened to determine if they block various agents that disrupt PPI (apomorphine, d-amphetamine, PCP, ketamine, DOI). Finally, mutant mice with or without drugs can be screened using the PPI procedure.

Anxiety Model

An elevated plus maze model may be used to assess the efficacy of anxiolytic compounds (see Pellow and File, Pharm. Biochem. Behav. 24, 525-529, 1986).

Elevated Plus Maze

The elevated plus maze is widely used as an anxiety paradigm that examines the conflict between the drive to explore and the aversiveness of heights and open spaces of rats or mice. The maze is a cross made up of two open and two closed arms that is raised above the ground. The combination of light, the open arms, and the height is thought to produce unconditioned fear or anxiety responses in mice or rats. The test apparatus is an open top maze constructed of opaque plastic with alternating open and enclosed arms. For rats, each arm is 45-55 cm long and 8-12 cm wide, with the sides of the enclosed arms 35-45 cm high, the juncture approximately 10×10 cm, and the maze is elevated 45-55 cm above the floor. The mouse elevated plus maze consists of two closed arms (15×6×30 cm) and two open arms (1×6×30 cm) forming a cross, with a quadrangular centre (6×6 cm). The maze is placed 50 cm above the floor. Testing is performed in a room free of noise and distraction. On test days animals are administered drug or vehicle. If a pre-treatment period is necessary, the animals are returned to the home cage for the duration of the pre-treatment time; otherwise, the animals are placed in a clear plastic holding chamber singly or with cage mates for 1-10 minutes prior to test time. Rats are then placed in the centre of the maze always oriented in the same direction, either consistently facing an open arm or an enclosed arm. For 5-10 minutes, entries into each arm and the time spent in each arm are recorded by the observer(s) or by videotape or a computer receiving input from a video camera mounted above the maze. To count as an entry, all four paws must be inside the arm. If necessary, additional measures of anxiety-related behaviours will be recorded, i.e., time spent motionless, time spent in the centre, time spent grooming, and the number of rears, stretching postures or feces produced. Following testing the animals are returned to the home cages. When animals are placed in the centre of the maze, they spend most of their time in the closed arms, avoiding the open arms. Anxiolytic drugs, such as benzodiazepines, will increase the amount of time animals spend in the open arms. The test is also sensitive to anxiogenic drugs, which lends strong support for its predictive validity.

Erectile Dysfunction

Drugs affecting erectile function may be tested by measuring the effect on apomorphine-evoked increases in intracavernous pressure in the awake rat as described by Andersson, et al., (J. Urol. 161: 1707-17] 2, 1999). One end of a polyethylene tubing is implanted into the cavernosal space of the penis of male Sprague-Dawley rats. After recovery from the surgery, intracavernous pressure is recorded using a pressure transducer connected to a multichannel pen-recorder. Erections are induced by administration of apomorphine (100-250 ug/kg s.c.) with or without test compound, and the results are compared for the treated group and the non-treated group.

Female Sexual Dysfunction

Systems to test compounds for the treatment of female sexual dysfunction include in vitro and in situ models using vaginal or clitoral smooth muscle preparations, histological evaluation, and vaginal blood flow assessments. In vivo studies of sexual responses focus on behavioural paradigms involving lordotic posturing and receptivity, as well as indices of motivation using a dual chamber pacing method (see, e.g., Hale, et al., Int. J. Impot. Res. 15 Suppl 5: S75-79, 2003).

The present invention is illustrated below with the aid of examples. These illustrations are given solely by way of example and do not limit the general spirit of the present invention.

PREPARATION OF EXAMPLE COMPOUNDS

Preparation of Intermediate Compound A: 5-(4-Chlorophenyl)-1-(2,4-dichlorophenyl)-4,5-dihydro-1H-pyrazole-3-carboxylic acid methyl ester

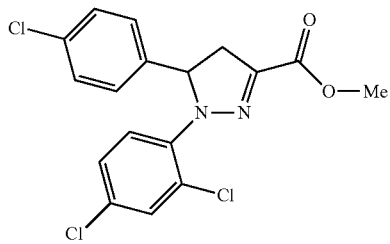

A mixture of 5-(4-chloro-phenyl)-1-(2,4-dichloro-phenyl)-4,5-dihydro-1H-pyrazole-3-carboxylic acid (78.0 g, 0.21 mol), methanol 150 mL, p-TsOH.H$_2$O (0.042 mol) in toluene (350 mL) was stirred for 24 hours at 80° C. The reaction mixture was cooled to room temperature and the solvent was concentrated in vacuo. The residue was taken up in EtOAc (300 mL) and subsequently washed with sat. aq. NH$_4$Cl and water and dried. The solvent was removed in vacuo to yield the title compound (80.27 g, 99%) white solid.

$^1$H-NMR (CDCl$_3$, 250 MHz, δ): 7.27-7.04 (m, 7H, ArH); 5.86 (dd, J=6.0, 12.6 Hz, 1H, CH); 3.89 (s, 3H, CH$_3$); 3.68 (dd, J=12.6, 18.1 Hz, 1H, CH); 3.25 (dd, J=6.0, 18.1 Hz, 1H, CH).

Preparation of Intermediate Compound B: 5-(4-Chloro-phenyl)-1-(2,4-dichloro-phenyl)-4,5-dihydro-1H-pyrazole-3-yl]methanol

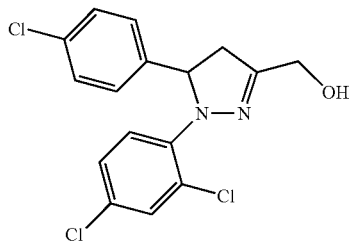

Sodium borohydride (5.93 g, 0.157 mol) was added to a solution of 5-(4-chlorophenyl)-1-(2,4-dichlorophenyl)-4,5-dihydro-1H-pyrazole-3-carboxylic acid methyl ester (40.13 g, 0.105 Mol) in methanol (500 mL) at −10° C. over a period of 30 min. The reaction mixture was stirred for 1 hour at room temperature and subsequently refluxed for 48 hours. After 17, 23 and 41 hours, an additional amount of sodium borohydride (3 times×5.93 g, 0.470 mol) was added at room temperature and the reaction mixture was further stirred at reflux. After cooling to 0° C., the reaction was quenched by addition of water (250 mL) and EtOAc (600 mL). The organic layer was washed with brine (2×500 mL) and water and dried and the solvent was removed in vacuo to yield the title compound (37.06 g, 99%) as a white solid which was used in the next step without further purification.

$^1$H-NMR (CDCl$_3$, 250 MHz, δ): 7.19-6.88 (m, 7H, ArH); 5.57 (dd, J=5.21, 11.25 Hz, 1H, CH); 4.44 (s, 2H, CH$_2$); 3.42 (m, 1H, CH); 2.94 (dd, J=5.2, 17.6 Hz, 1H, CH).

Preparation of Intermediate Compound C: [5-(4-Chloro-phenyl)-1-(2,4-dichloro-phenyl)-4,5-dihydro-1H-pyrazole-3-yl]methyl methanesulfonate

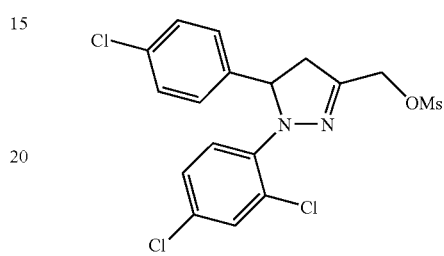

Methanesulfonyl chloride (12.50 mL, 0.160 mol) and triethylamine (28 mL, 0.200 mol) were added to a solution of 5-(4-chloro-phenyl)-1-(2,4-dichloro-phenyl)-4,5-dihydro-1H-pyrazole-3-yl]methanol (47.65 g, 0.134 mol) in dichloromethane (350 mL) at 0° C. temperature. After stirring for 6 hours at 0° C. the solvent was evaporated under reduced pressure. The residue was taken up in EtOAc (200 mL) and water (100 mL). The organic layer was washed with water (2×100 mL) and dried, and the solvent was evaporated in vacuo to yield the title compound (58.0 g, 100%) which was used in the next step without further purification.

Preparation of Compound A: [5-(4-Chloro-phenyl)-1-(2,4-dichloro-phenyl)-4,5-dihydro-1H-pyrazole-3-yl]methyl amine

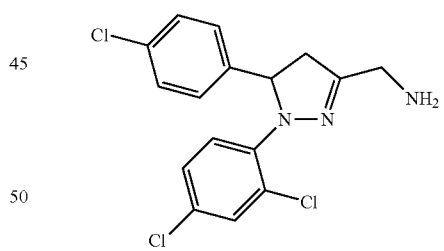

A solution of [5-(4-Chloro-phenyl)-1-(2,4-dichloro-phenyl)-4,5-dihydro-1H-pyrazole-3-yl]methyl methanesulfonate (58 g, 0.134 mol) in THF (200 mL) and NH$_4$OH aq. (25%, 412 mL, 2.68 mol) was stirred at room temperature for 15 hours. The excess ammonia was removed in vacuo and EtOAc (200 mL) and sat. aq. NaHCO$_3$ (150 mL) was added. The organic layer was separated and the aqueous phase was extracted with EtOAc, the combined organic layers were washed with sat. aq. NaHCO$_3$ (2×150 mL), brine (200 mL) and water (1×200 mL), dried over anhydrous sodium sulfate and the solvent was evaporated under reduced pressure to afford the crude material (89.85 g). This material was purified by column chromatography using dichloromethane, methanol and ammonium hydroxide (97:3:1) in silica gel to yield the [5-(4-chloro-phenyl)-1-(2,4-dichloro-phenyl)-4,5-dihydro-1H-pyrazole-3-yl]methyl amine (18.90 g, 40%, two steps) as a yellow solid.

$^1$H-NMR (CDCl$_3$, 250 MHz, δ): 7.27 (m, 1H, ArH); 7.22 (d, J=0.55 Hz, 1H, ArH); 7.17 (m, 2H, ArH); 7.13 (m, 1H, ArH); 7.07-7 (m, 2H, ArH); 5.58 (dd, J=5.2, 11.0 Hz, 1H, CH); 3.68 (s, 2H, CH$_2$); 3.45 (dd, J=11.0, 17.0 Hz, 1H, CH); 2.93 (dd, J=4.9, 16.7 Hz, 1H, CH).

Preparation of Compound B: [5-(4-Chloro-phenyl)-1-(2,4-dichloro-phenyl)-4,5-dihydro-1H-pyrazole-3-yl]methyl amine hydrochloride

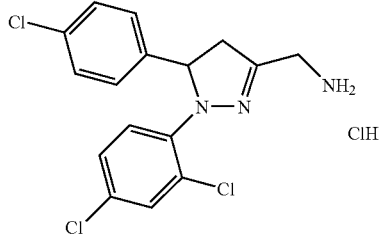

A solution of [5-(4-Chloro-phenyl)-1-(2,4-dichloro-phenyl)-4,5-dihydro-1H-pyrazole-3-yl]methyl amine (19.33 g, 0.0545 mol) in diethylether (100 mL) and hydrogen chloride [2.0 M in diethyl ether (100 mL)] was stirred for 24 hours at room temperature and the solid formed was filtered off, washed with diethylether and dried to yield the [5-(4-Chloro-phenyl)-1-(2,4-dichloro-phenyl)-4,5-dihydro-1H-pyrazole-3-yl]methyl amine hydrochloride (19.41 g, 91%) as a yellow solid.

$^1$H-NMR (DMSO-d$_6$, 300 MHz, δ): 8.49 (sa, 3H, NH$_3$); 7.48 (d, J=8.8 Hz, 1H, ArH); 7.39 (d, J=2.34 Hz, 1H, ArH); 7.29-7.18 (m, 5H, ArH); 5.7 (dd, J=4.7, 11.1 Hz, 1H, CH); 3.91 (c, J=16.7 Hz, 2H, CH$_2$); 3.57 (dd, J=17.6, 18.2 Hz, 1H, CH); 3.02 (dd, J=4.7, 18.2 Hz, 1H, CH).

General Procedure for the Synthesis of Compounds 1 to 77

The compound of general formula V in form of the respective hydrogen chloride (1 mmol) was suspended in dry dichloromethane (10 mL) and diisopropylethylamine (0.25 mmol) was added. The reaction mixture was stirred at room temperature for 15 min. The sulfonyl chloride of general formula Cl—S(═O)$_2$—R$^6$ (1 mmol) was added and the mixture was stirred at room temperature until the starting material disappeared (typically within 2-3 hours). If starting material was still detected, the mixture was stirred overnight. The reaction mixture was washed with water, dried over anhydrous sodium sulfate and the solvent was evaporated under reduced pressure and the residue was recrystallized or purified by conventional methods such as flash chromatography described in the art.

Example 34

2-Chloro-N-[5-(4-chloro-phenyl)-1-(2,4-dichloro-phenyl)-4,5-dihydro-1H-pyrazole-3-ylmethyl]-6-methyl-benzenesulfonamide A solution of [5-(4-chloro-phenyl)-1-(2,4-dichloro-phenyl)-4,5-dihydro-1H-pyrazole-3-yl]methyl amine hydrochloride (391 mg, 1 mmol) was suspended in dry dichloromethane (10 mL), and diisopropylethylamine (323 mg, 0.25 mmol) was added. The reaction mixture was stirred at room temperature for 15 min. 2-Chloro-6-methyl-benzenesulfonyl chloride (225 mg, 1 mmol) was added and the reaction mixture was stirred at room temperature overnight. The solution was then washed with water, dried over anhydrous sodium sulfate and the solvent evaporated under reduced pressure to yield 2-chloro-N-[5-(4-Chloro-phenyl)-1-(2,4-dichloro-phenyl)-4,5-dihydro-1H-pyrazole-3-ylmethyl]-6-methyl-benzenesulfonamide which was purified by column chromatography using dichloromethane/methanol (98:2) (440 mg, 81% as a cream solid).

1H NMR (300 MHz, METHANOL-d$_4$) δ ppm 2.70 (s, 3H) 2.86 (dd, J=17.58, 6.15 Hz, 1H) 3.37 (dd, J=17.58, 11.28 Hz, 1H) 4.00 (d, J=16.05 Hz, 1H) 4.06 (d, J=16.05 Hz, 1H) 5.38 (dd, J=11.28, 6.15 Hz, 1H) 7.08 (d, J=5.86 Hz, 2H) 7.05-7.10 (m, 2H) 7.14-7.23 (m, 3H) 7.29 (d, J=7.47 Hz, 1H) 7.38-7.49 (m, 1H) 7.41 (t, J=7.69 Hz, 1H)

Example 38

2-Chloro-N-[5-(4-chloro-phenyl)-1-(2,4-dichloro-phenyl)-4,5-dihydro-1H-pyrazole-3-ylmethyl]-5-fluoro-2-methyl-benzenesulfonamide

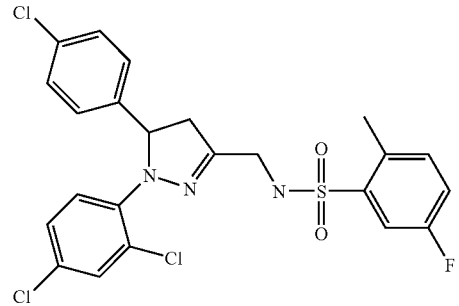

According to general sulfonamide coupling procedure, [5-(4-Chloro-phenyl)-1-(2,4-dichloro-phenyl)-4,5-dihydro-1H-pyrazole-3-yl]methyl amine hydrochloride was reacted with 5-fluoro-2-methylbenzenesulfonyl chloride. The reaction yield was 88% of 2-Chloro-N-[5-(4-Chloro-phenyl)-1-(2,4-dichloro-phenyl)-4,5-dihydro-1H-pyrazole-3-ylmethyl]-5-fluoro-2-methyl-benzenesulfonamide as a solid.

1H NMR (300 MHz, CHLOROFORM-d) □ ppm 2.63 (s, 3H) 2.87 (dd, J=17.43, 5.71 Hz, 1H) 3.37 (dd, J=17.36, 11.21 Hz, 1H) 3.93 (d, J=16.57 Hz, 1H) 4.03 (d, J=16.57 Hz, 1H) 5.30 (br. s., 1H) 5.53 (dd, J=11.21, 5.79 Hz, 1H) 6.98 (d, J=8.35 Hz, 2H) 7.03 (s, 2H) 7.12-7.22 (m, 4H) 7.29 (m, 1H) 7.74 (dd, J=8.57, 2.71 Hz, 1H)

Example 63

(R)-2-Chloro-N-[5-(4-chloro-phenyl)-1-(2,4-dichloro-phenyl)-4,5-dihydro-1H-pyrazole-3-ylmethyl]-5-fluoro-2-methyl-benzenesulfonamide

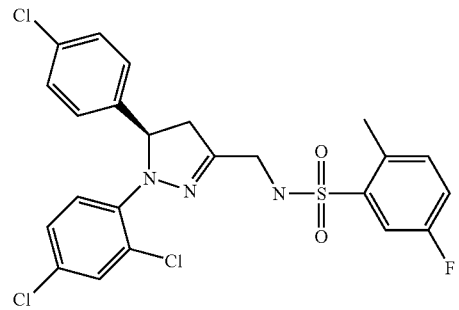

Example 64

(S)-2-Chloro-N-[5-(4-chloro-phenyl)-1-(2,4-dichloro-phenyl)-4,5-dihydro-1H-pyrazole-3-ylmethyl]-5-fluoro-2-methyl-benzenesulfonamide

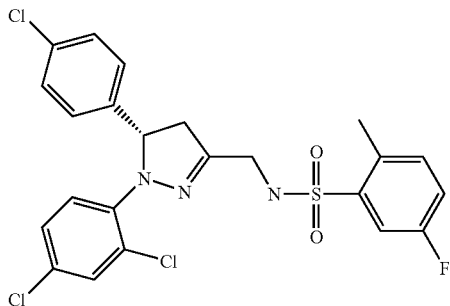

By chiral HPLC preparative in the Chiralpak AD-H with isocratic method n-Heptane/2-Propanol (95:5) are obtained this enantiomers examples 63 and 64

The appropriate chiral acid can be obtained by chiral methods (like chiral HPLC) and could provide the pure enantiomers and the pure diastereoisomers.

The following compounds were prepared according to the processes described for the preparation of compound (example 34) above. Those skilled in the art are familiar with the starting materials that are needed to obtain said compounds.

In the structures depicted below —N—S(=O)$_2$— means —NH—S(=O)$_2$—.

| | | | |
|---|---|---|---|
| A | 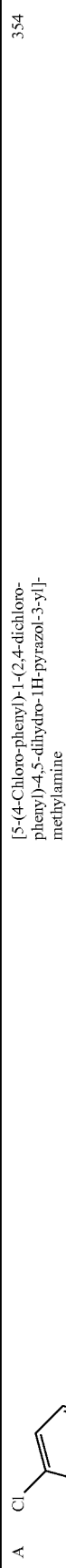 | [5-(4-Chloro-phenyl)-1-(2,4-dichloro-phenyl)-4,5-dihydro-1H-pyrazol-3-yl]-methylamine | 354 |
| B | 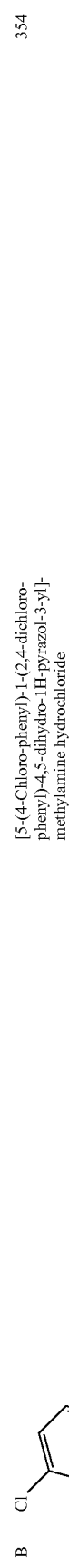 | [5-(4-Chloro-phenyl)-1-(2,4-dichloro-phenyl)-4,5-dihydro-1H-pyrazol-3-yl]-methylamine hydrochloride | 354 |
| C | 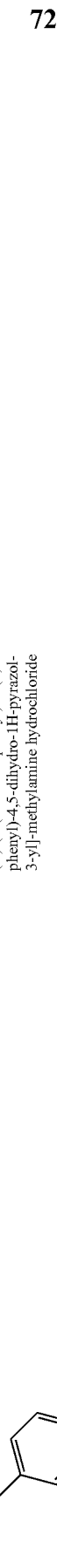 | (R)-(5-(4-Chloro-phenyl)-1-(2,4-dichloro-phenyl)-4,5-dihydro-1H-pyrazol-3-yl]-methylamine hydrochloride | 354 |

-continued
| | | |
|---|---|---|
| D | 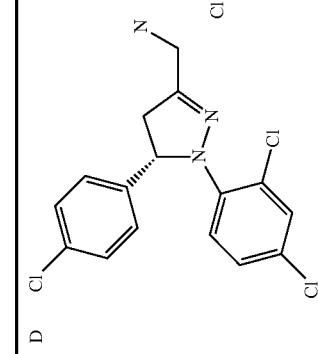 | (S)-[5-(4-Chloro-phenyl)-1-(2,4-dichloro-phenyl)-4,5-dihydro-1H-pyrazol-3-yl]-methylamine hydrochloride | 354 |
| E | 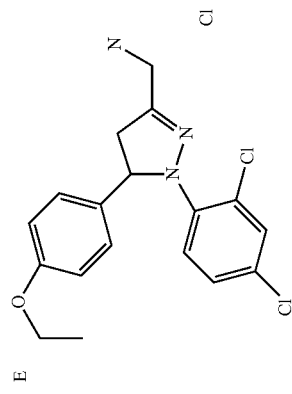 | [1-(2,4-Dichloro-phenyl)-5-(4-ethoxy-phenyl)-4,5-dihydro-1H-pyrazol-3-yl]-methylamine hydrochloride | 364 |
| F | 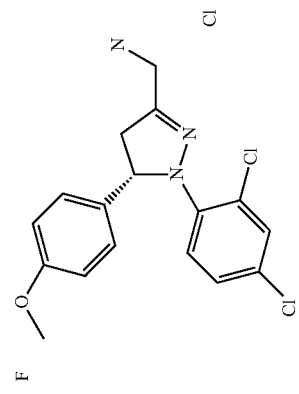 | [1-(2,4-Dichloro-phenyl)-5-(4-methoxy-phenyl)-4,5-dihydro-1H-pyrazol-3-yl]-methylamine hydrochloride | 350 |

-continued
| | | |
|---|---|---|
| G | [5-(4-Bromo-phenyl)-1-(2,4-dichloro-phenyl)-4,5-dihydro-1H-pyrazol-3-yl]-methylamine hydrochloride | 399 |
| H | (4R,5R)-[5-(4-Chloro-phenyl)-1-(2,4-dichloro-phenyl)-4-methyl-4,5-dihydro-1H-pyrazol-3-yl]-methylamine | 368 |
| I | (4S,5S)-[5-(4-Chloro-phenyl)-1-(2,4-dichloro-phenyl)-4-methyl-4,5-dihydro-1H-pyrazol-3-yl]-methylamine | 368 |
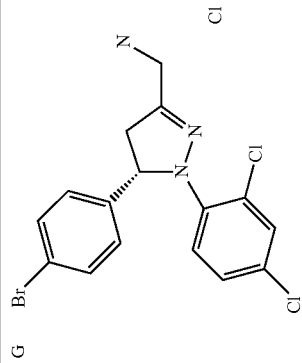
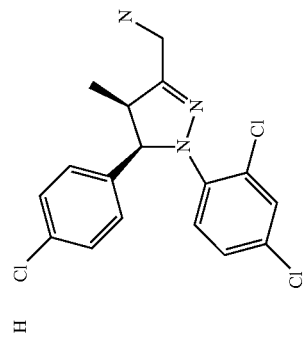
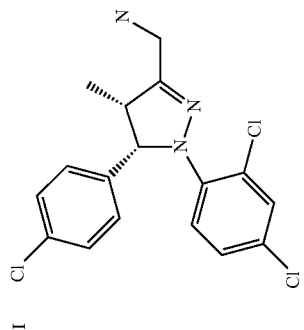

| | | |
|---|---|---|
| J | (4RS,5RS)-[5-(4-Chloro-phenyl)-1-(2,4-dichloro-phenyl)-4-methyl-4,5-dihydro-1H-pyrazol-3-yl]-methylamine 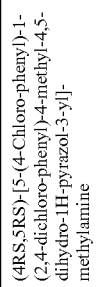 | 368 |
| 1 | 3-Chloro-N-[5-(4-chloro-phenyl)-1-(2,4-dichloro-phenyl)-4,5-dihydro-1H-pyrazol-3-ylmethyl]-benzenesulfonamide 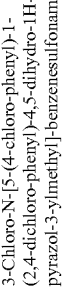 | 528 |
| 2 | N-((5-(4-chlorophenyl)-1-(2,4-dichlorophenyl)-4,5-dihydro-1H-pyrazol-3-yl)methyl)dimethylaminosulfonamide 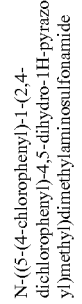 | 461 |
| 3 | N-[5-(4-Chloro-phenyl)-1-(2,4-dichloro-phenyl)-4,5-dihydro-1H-pyrazol-3-ylmethyl]-3-methoxy-benzene sulfonamide 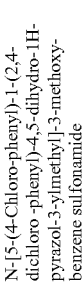 | 524 |

| | | -continued | |
|---|---|---|---|
| 4 | 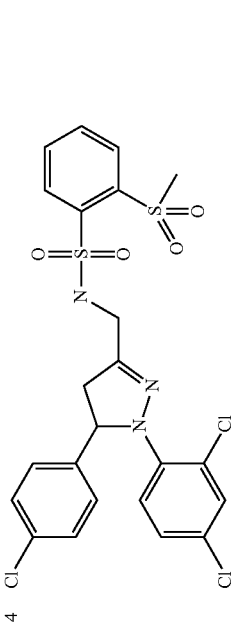 | N-[5-(4-Chloro-phenyl)-1-(2,4-dichloro-phenyl)-4,5-dihydro-1H-pyrazol-3-ylmethyl]-2-methanesulfonyl-benzenesulfonamide | 572 |
| 5 | 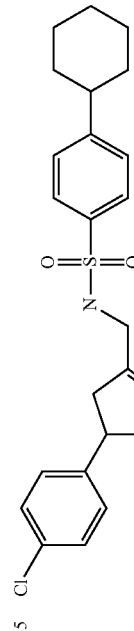 | N-[5-(4-Chloro-phenyl)-1-(2,4-dichloro-phenyl)-4,5-dihydro-1H-pyrazol-3-yl methyl]-4-cyclohexyl-benzenesulfonamide | 576 |
| 6 | 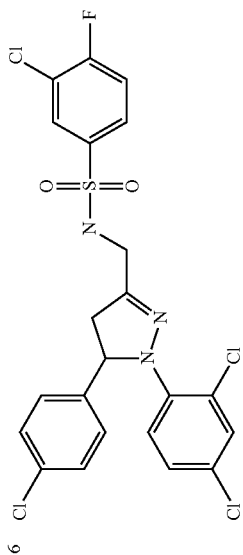 | 3-Chloro-N-[5-(4-chloro-phenyl)-1-(2,4-dichloro-phenyl)-4,5-dihydro-1H-pyrazol-3-ylmethyl]-4-fluoro-benzenesulfonamide | 546 |
| 7 | 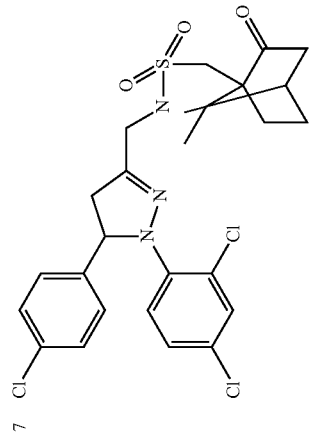 | N-[5-(4-Chloro-phenyl)-1-(2,4-dichloro-phenyl)-4,5-dihydro-1H-pyrazol-3-ylmethyl]-C-(7,7-dimethyl-2-oxo-bicyclo[2.2.1]hept-1-yl)-methanesulfonamide | 568 |

| | | | |
|---|---|---|---|
| 8 | 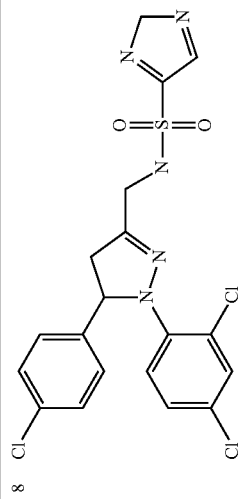 | 2H-Imidazole-4-sulfonic acid [5-(4-chloro-phenyl)-1-(2,4-dichloro-phenyl)-4,5-dihydro-1H-pyrazol-3-ylmethyl]-amide | 484 |
| 9 | 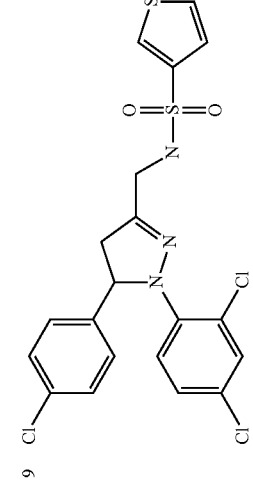 | Thiophene-3-sulfonic acid [5-(4-chloro-phenyl)-1-(2,4-dichloro-phenyl)-4,5-dihydro-1H-pyrazol-3-ylmethyl]-amide | 500 1H NMR (300 MHz, METHANOL-d4) ppm 2.94 (dd, J=17.58, 5.49 Hz, 1H) 3.39 (dd, J=17.58, 11.21 Hz, 1 H) 3.96 (s, 2 H) 5.55 (dd, J=11.21, 5.49 Hz, 1 H) 7.06–7.29 (m, 7 H) 7.42 (d, J=5.13 Hz, 1 H) 7.65 (dd, J=4.98, 3.08 Hz, 1 H) 8.14 (d, J=2.93 Hz, 1 H) |
| 10 | 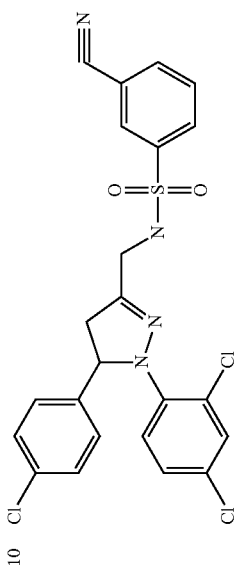 | N-((5-(4-chlorophenyl)-1-(2,4-dichlorophenyl)-4,5-dihydro-1H-pyrazol-3-yl)methyl)-3-cyanobenzenesulfonamid | 519 |
| 11 | 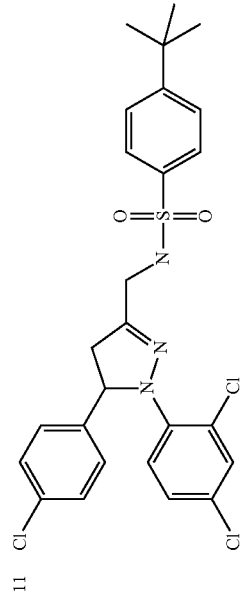 | 4-tert-Butyl-N-[5-(4-chloro-phenyl)-1-(2,4-dichloro-phenyl)-4,5-dihydro-1H-pyrazol-3-ylmethyl]-benzenesulfonamide | 550 |

| | | | |
|---|---|---|---|
| 12 | 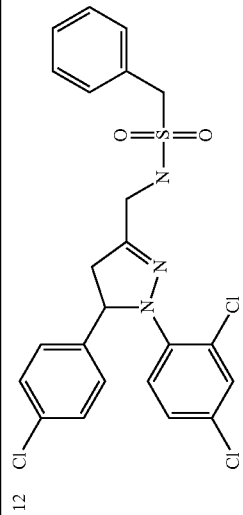 | N-[5-(4-Chloro-phenyl)-1-(2,4-dichloro-phenyl)-4,5-dihydro-1H-pyrazol-3-ylmethyl]-C-phenyl-methanesulfonamide | 508 |
| 13 | 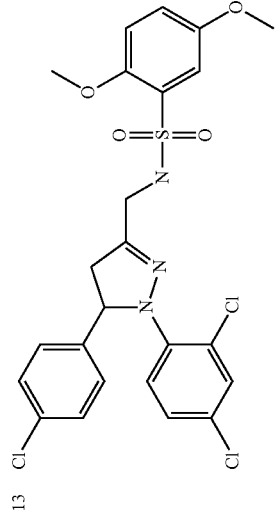 | N-[5-(4-Chloro-phenyl)-1-(2,4-dichloro-phenyl)-4,5-dihydro-1H-pyrazol-3-ylmethyl]-2,5-dimethoxy-benzenesulfonamide | 554 |
| 14 | 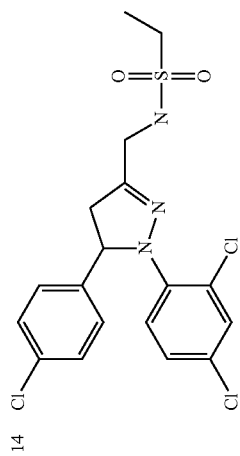 | Ethanesulfonic acid [5-(4-chloro-phenyl)-1-(2,4-dichloro-phenyl)-4,5-dihydro-1H-pyrazol-3-ylmethyl]-amide | 446 |
| 15 | 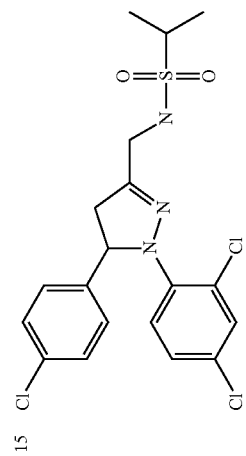 | Propane-2-sulfonic acid [5-(4-chloro-phenyl)-1-(2,4-dichloro-phenyl)-4,5-dihydro-1H-pyrazol-3-ylmethyl]-amide | 460 |

| | | | |
|---|---|---|---|
| 16 | 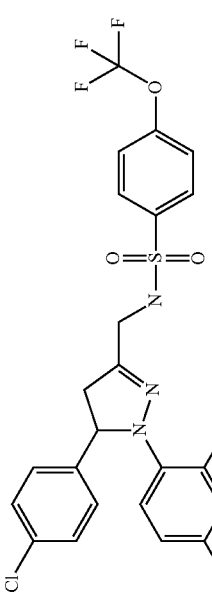 | N-[5-(4-Chloro-phenyl)-1-(2,4-dichloro-phenyl)-4,5-dihydro-1H-pyrazol-3-ylmethyl]-4-trifluoromethoxy-benzenesulfonamide | 578 |
| 17 | 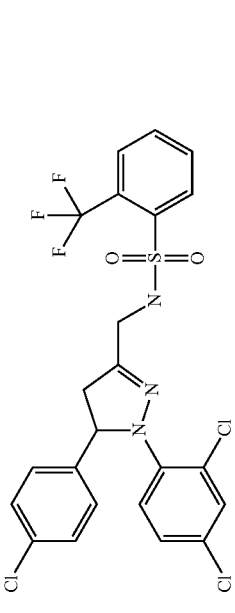 | N-[5-(4-Chloro-phenyl)-1-(2,4-dichloro-phenyl)-4,5-dihydro-1H-pyrazol-3-ylmethyl]-2-trifluoromethyl-benzenesulfonamide | 562 |
| 18 | 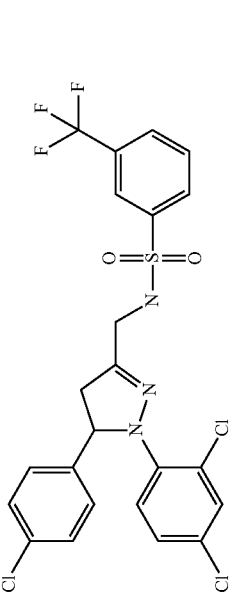 | N-[5-(4-Chloro-phenyl)-1-(2,4-dichloro-phenyl)-4,5-dihydro-1H-pyrazol-3-ylmethyl]-3-trifluoromethyl-benzenesulfonamide | 562 |
| 19 | 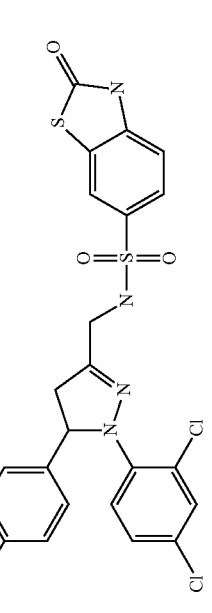 | 2-Oxo-2,3-dihydro-benzothiazole-6-sulfonic acid [5-(4-chloro-phenyl)-1-(2,4-dichloro-phenyl)-4,5-dihydro-1H-pyrazol-3-ylmethyl]-amide | 567 |

| | | | |
|---|---|---|---|
| 20 | 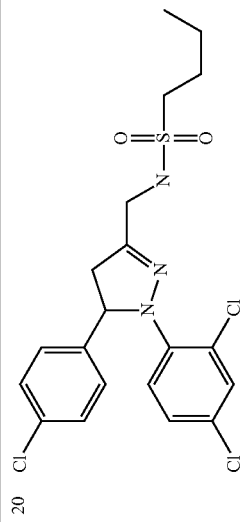 | Butane-1-sulfonic acid [5-(4-chloro-phenyl)-1-(2,4-dichloro-phenyl)-4,5-dihydro-1H-pyrazol-3-ylmethyl]-amide | 474 |
| 21 | 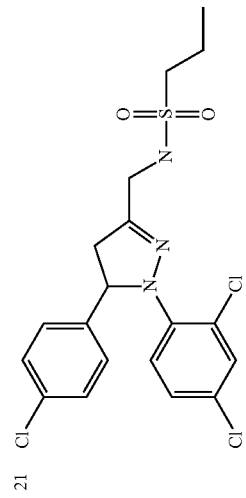 | Propane-1-sulfonic acid [5-(4-chloro-phenyl)-1-(2,4-dichloro-phenyl)-4,5-dihydro-1H-pyrazol-3-ylmethyl]-amide | 460 |
| 22 | 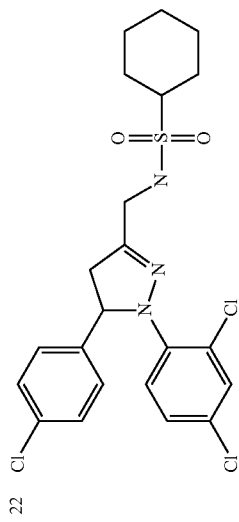 | Cyclohexanesulfonic acid [5-(4-chloro-phenyl)-1-(2,4-dichloro-phenyl)-4,5-dihydro-1H-pyrazol-3-ylmethyl]-amide | 500 |
| 23 | 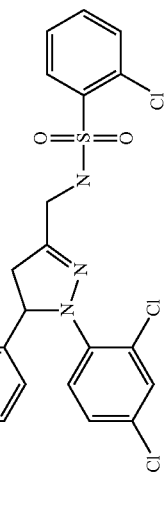 | 2-Chloro-N-[5-(4-chloro-phenyl)-1-(2,4-dichloro-phenyl)-4,5-dihydro-1H-pyrazol-3-ylmethyl]-benzenesulfonamide | 528 |

| | | |
|---|---|---|
| 24 | N-[5-(4-Chloro-phenyl)-1-(2,4-dichloro-phenyl)-4,5-dihydro-1H-pyrazol-3-ylmethyl]-3-methyl-benzenesulfonamide 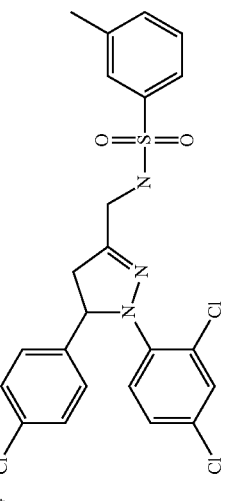 | 508 |
| 25 | N-[5-(4-Chloro-phenyl)-1-(2,4-dichloro-phenyl)-4,5-dihydro-1H-pyrazol-3-ylmethyl]-4-phenoxy-benzenesulfonamide 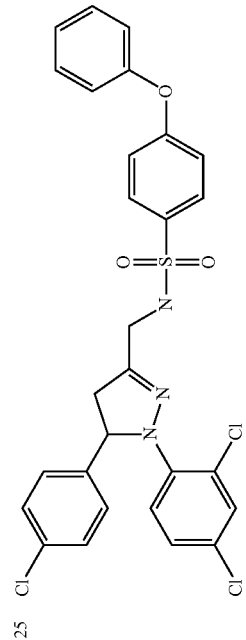 | 586 |
| 26 | Biphenyl-2-sulfonic acid [5-(4-chloro-phenyl)-1-(2,4-dichloro-phenyl)-4,5-dihydro-1H-pyrazol-3-ylmethyl]-amide 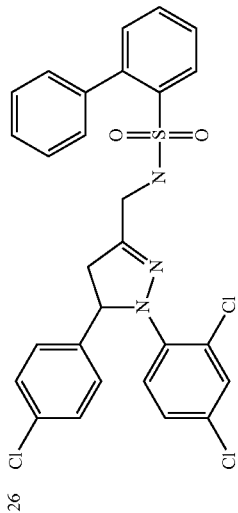 | 570 |
| 27 | 3-Chloro-N-[5-(4-chloro-phenyl)-1-(2,4-dichloro-phenyl)-4,5-dihydro-1H-pyrazol-3-ylmethyl]-2-fluoro-benzenesulfonamide 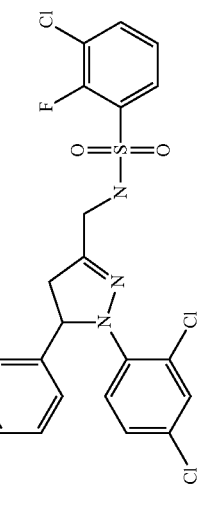 | 546 |

| | -continued | | |
|---|---|---|---|
| 28 | [structure] | N-[5-(4-Chloro-phenyl)-1-(2,4-dichloro-phenyl)-4,5-dihydro-1H-pyrazol-3-ylmethyl]-3-fluoro-benzenesulfonaamide | 512 |
| 29 | [structure] | N-[5-(4-Chloro-phenyl)-1-(2,4-dichloro-phenyl)-4,5-dihydro-1H-pyrazol-3-ylmethyl]-4-methoxy-benzenesulfonamide | 524 |
| 30 | [structure] | 4-Bromo-N-[5-(4-chloro-phenyl)-1-(2,4-dichloro-phenyl)-4,5-dihydro-1H-pyrazol-3-ylmethyl]-benzenesulfonamide | 573 |
| 31 | [structure] | N-[5-(4-Chloro-phenyl)-1-(2,4-dichloro-phenyl)-4,5-dihydro-1H-pyrazol-3-ylmethyl]-C-cyclohexyl-methanesulfonamide | 514 |

| | | | |
|---|---|---|---|
| 32 | 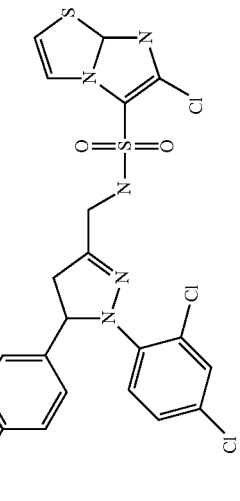 | 6-Chloro-7,7a-dihydro-imidazo[2,1-b]thiazole-5-sulfonic acid [5-(4-chloro-phenyl)-1-(2,4-dichloro-phenyl)-4,5-dihydro-1H-pyrazol-3-ylmethyl]-amide | 576 |
| 33 | 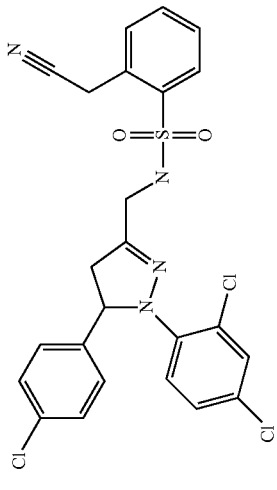 | N-((5-(4-chlorophenyl)-1-(2,4-dichlorophenyl)-4,5-dihydro-1H-pyrazol-3-yl)methyl)-2-cyanobenzenesulfonamide | 519 |
| 34 | 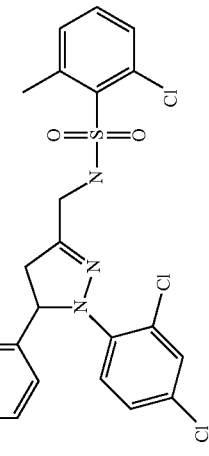 | 2-Chloro-N-[5-(4-chloro-phenyl)-1-(2,4-dichloro-phenyl)-4,5-dihydro-1H-pyrazol-3-ylmethyl]-6-methyl-benzenesulfonamide | 542 1H NMR (300 MHz, METHANOL-$d_4$) δ ppm 2.70 (s, 3 H) 2.86 (dd, J=17.58, 6.15 Hz, 1 H) 3.37 (dd, J=17.58, 11.28 Hz, 1 H) 4.00 (d, J=16.05 Hz, 1 H) 4.06 (d, J=16.05 Hz, 1 H) 5.38 (dd, J=11.28, 6.15 Hz, 1 H) 7.08 (d, J=5.86 Hz, 2 H) 7.05-7.10 (m, 2 H) 7.14-7.23 (m, 3 H) 7.29 (d, J=7.47 Hz, 1 H) 7.38-7.49 |

| | | | |
|---|---|---|---|
| 35 | ![structure] | 3-(4-{[5-(4-Chloro-phenyl)-1-(2,4-dichloro-phenyl)-4,5-dihydro-1H-pyrazol-3-ylmethyl]-sulfamoyl}-phenyl)-propionic acid methyl ester | 580 |
| 36 | ![structure] | N-[5-(4-Chloro-phenyl)-1-(2,4-dichloro-phenyl)-4,5-dihydro-1H-pyrazol-3-ylmethyl]-2-methoxy-4-methyl-benzenesulfonamide | 538 |
| 37 | ![structure] | Benzo[b]thiophene-3-sulfonic acid [5-(4-chloro-phenyl)-1-(2,4-dichloro-phenyl)-4,5-dihydro-1H-pyrazol-3-ylmethyl]-amide | 550 |
| 38 | ![structure] | N-[5-(4-Chloro-phenyl)-1-(2,4-dichloro-phenyl)-4,5-dihydro-1H-pyrazol-3-ylmethyl]-5-fluoro-2-methyl-benzenesulfonamide | 526 1H NMR (300 MHz, CHLOROFORM-d) ppm 2.63 (s, 3H) 2.87 (dd, J=17.43, 5.71 Hz, 1 H) 3.37 (dd, J=17.36, 11.21 Hz, 1 H) 3.93 (d, J=16.57 Hz, 1 H) 4.03 (d, J=16.57 Hz, 1 H) 5.3 (br. s., 1 H) 5.53 (dd, J=11.21, 5.79 Hz, 1 H) 6.98 (d, J=8.35 Hz, 2H0 7.03 (s, 2 H) 7.12-7.22 (m, 4 H) 7.29 (m, 1 H) 7.74 (dd, J=8.57, 2.71 Hz, 1 H) |

| # | Structure | Name | NMR | MW |
|---|---|---|---|---|
| 39 | 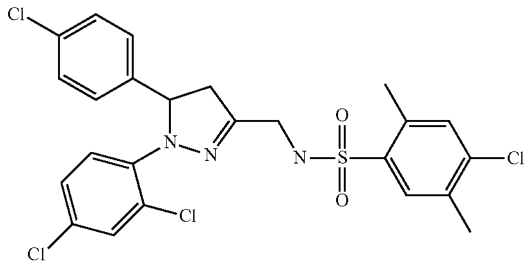 | 4-Chloro-N-[5-(4-chloro-phenyl)-1-(2,4-dichloro-phenyl)-4,5-dihydro-1H-pyrazol-3-ylmethyl]-2,5-dimethyl-benzenesulfonamide | 1H NMR (300 MHz, CHLOROFORM-d) δ ppm 2.39 (s, 3 H) 2.60 (s, 3 H) 2.85 (dd, J=17.43, 5.86 Hz, 1 H) 3.34 (dd, J=17.43, 11.28 Hz, 1 H) 3.88 (d, J=16.71 Hz, 1 H) 3.98 (d, J=16.71 Hz, 1 H) 5.22 (br. s., 1 H) 5.5 (dd, J=11.28, 5.86 Hz, 1 H) 6.98 (d, J=8.50 Hz, 2H) 7.04 (d, J=1.17 Hz, 2 H) 7.12-7.22 (m, 3 H) 7.30 (s, 1 H) 7.86 (s, 1 H) | 556 |
| 40 | 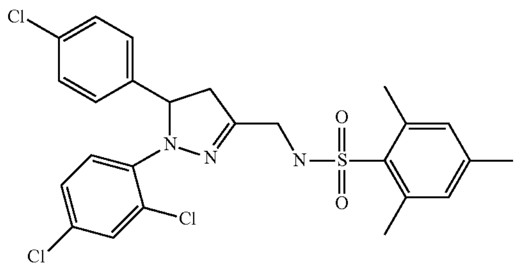 | N-[5-(4-Chloro-phenyl)-1-(2,4-dichloro-phenyl)-4,5-dihydro-1H-pyrazol-3-ylmethyl]-2,4,6-trimethyl-benzenesulfonamide | | 536 |
| 41 | 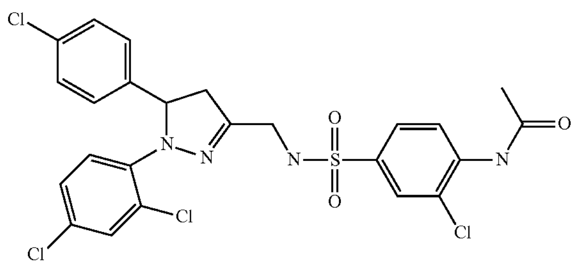 | N-(2-Chloro-4-{[5-(4-chloro-phenyl)-1-(2,4-dichloro-phenyl)-4,5-dihydro-1H-pyrazol-3-ylmethyl]-sulfamoyl}-phenyl)-acetamide | | 585 |
| 42 | 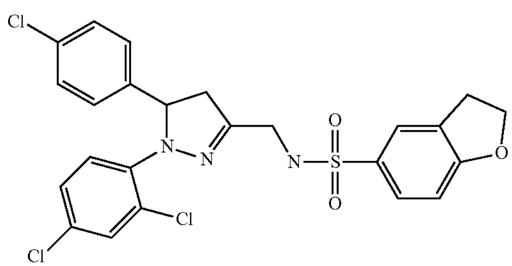 | 2,3-Dihydro-benzofuran-5-sulfonic acid [5-(4-chloro-phenyl)-1-(2,4-dichloro-phenyl)-4,5-dihydro-1H-pyrazol-3-ylmethyl]-amide | | 536 |

| | | | |
|---|---|---|---|
| 43 | 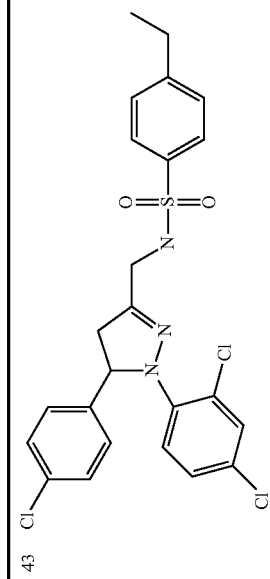 | N-[5-(4-Chloro-phenyl)-1-(2,4-dichloro-phenyl)-4,5-dihydro-1H-pyrazol-3-ylmethyl]-4-ethyl-benzenesulfonamide | 522 |
| 44 | 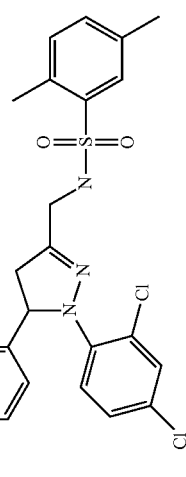 | N-[5-(4-Chloro-phenyl)-1-(2,4-dichloro-phenyl)-4,5-dihydro-1H-pyrazol-3-ylmethyl]-2,5-dimethyl-benzenesulfonamide | 522 |
| 45 | 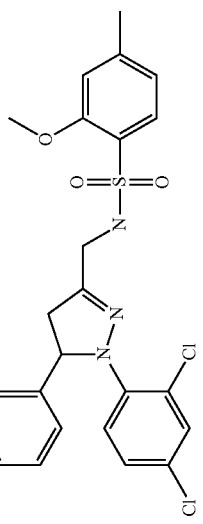 | N-[5-(4-Chloro-phenyl)-1-(2,4-dichloro-phenyl)-4,5-dihydro-1H-pyrazol-3-ylmethyl]-2-methoxy-4-methyl-benzenesulfonamide | 538 |
| 46 | 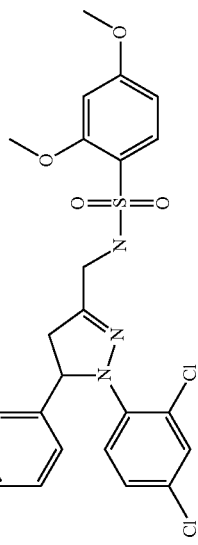 | N-[5-(4-Chloro-phenyl)-1-(2,4-dichloro-phenyl)-4,5-dihydro-1H-pyrazol-3-ylmethyl]-2,4-dimethoxy-benzenesulfonamide | 554 |

| | | | |
|---|---|---|---|
| 47 | 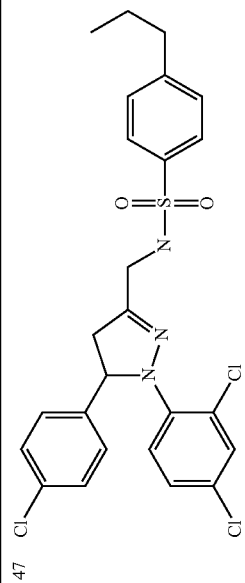 | N-[5-(4-Chloro-phenyl)-1-(2,4-dichloro-phenyl)-4,5-dihydro-1H-pyrazol-3-ylmethyl]-4-propyl-benzenesulfonamide | 536 |
| 48 | 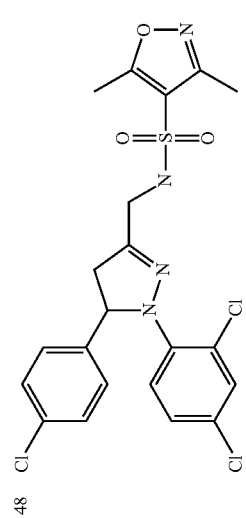 | 3,5-Dimethyl-isoxazole-4-sulfonic acid [5-(4-chloro-phenyl)-1-(2,4-dichloro-phenyl)-4,5-dihydro-1H-pyrazol-3-ylmethyl]-amide | 513 |
| 49 | 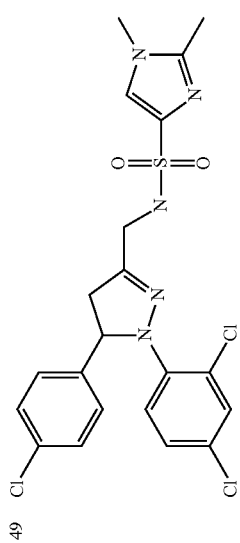 | 1,2-Dimethyl-1H-imidazole-4-sulfonic acid [5-(4-chloro-phenyl)-1-(2,4-dichloro-phenyl)-4,5-dihydro-1H-pyrazol-3-ylmethyl]-amide | 512 |
| 50 | 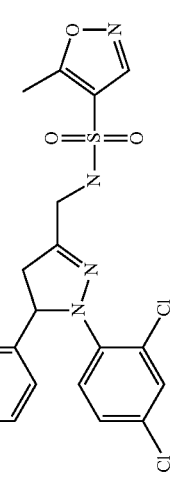 | 5-Methyl-isoxazole-4-sulfonic acid [5-(4-chloro-phenyl)-1-(2,4-dichloro-phenyl)-4,5-dihydro-1H-pyrazol-3-ylmethyl]-amide | 499 |

| | | | |
|---|---|---|---|
| 51 | 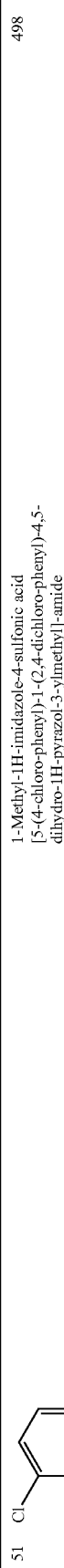 | 1-Methyl-1H-imidazole-4-sulfonic acid [5-(4-chloro-phenyl)-1-(2,4-dichloro-phenyl)-4,5-dihydro-1H-pyrazol-3-ylmethyl]-amide | 498 |
| 52 | 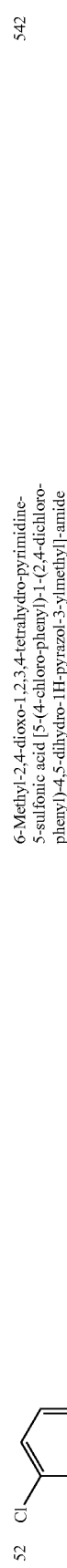 | 6-Methyl-2,4-dioxo-1,2,3,4-tetrahydro-pyrimidine-5-sulfonic acid [5-(4-chloro-phenyl)-1-(2,4-dichloro-phenyl)-4,5-dihydro-1H-pyrazol-3-ylmethyl]-amide | 542 |
| 53 | 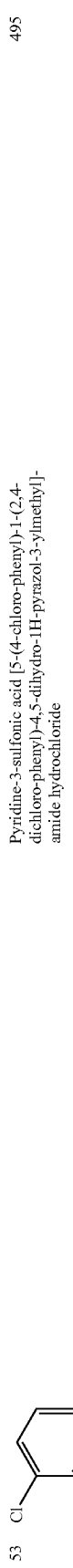 ClH | Pyridine-3-sulfonic acid [5-(4-chloro-phenyl)-1-(2,4-dichloro-phenyl)-4,5-dihydro-1H-pyrazol-3-ylmethyl]-amide hydrochloride | 495 |
| 54 | 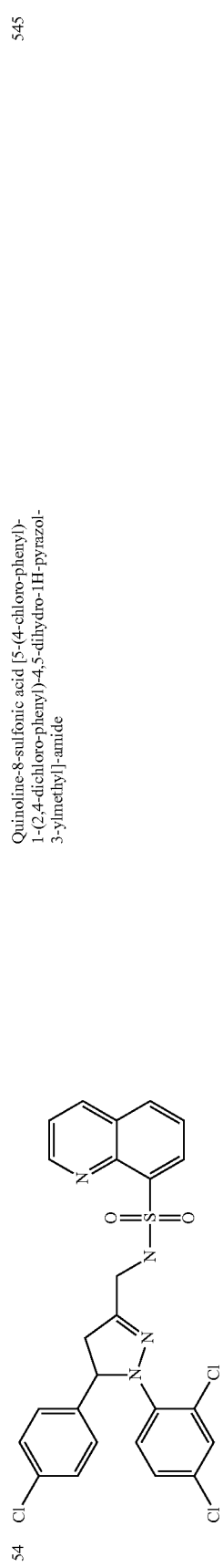 | Quinoline-8-sulfonic acid [5-(4-chloro-phenyl)-1-(2,4-dichloro-phenyl)-4,5-dihydro-1H-pyrazol-3-ylmethyl]-amide | 545 |

| | | |
|---|---|---|
| 55 | 5-Amino-naphthalene-1-sulfonic acid [5-(4-chloro-phenyl)-1-(2,4-dichloro-phenyl)-4,5-dihydro-1H-pyrazol-3-ylmethyl]-amide | 559 |
| 56 | 3-Methyl-quinoline-8-sulfonic acid [5-(4-chloro-phenyl)-1-(2,4-dichloro-phenyl)-4,5-dihydro-1H-pyrazol-3-ylmethyl]-amide | 559 |
| 57 | N-(5-{[5-(4-Chloro-phenyl)-1-(2,4-dichloro-phenyl)-4,5-dihydro-1H-pyrazol-3-ylmethyl]-sulfamoyl}-naphthalen-1-yl)-acetamide | 601 |
| 58 | 5-Dimethylamino-naphthalene-1-sulfonic acid [5-(4-chloro-phenyl)-1-(2,4-dichloro-phenyl)-4,5-dihydro-1H-pyrazol-3-ylmethyl]-amide | 587 |

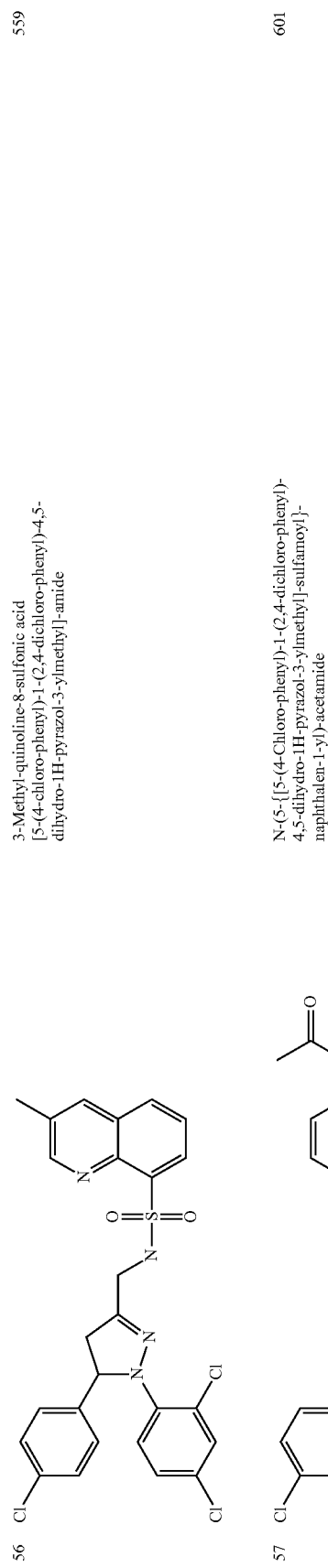

-continued

| | | | |
|---|---|---|---|
| 59 | 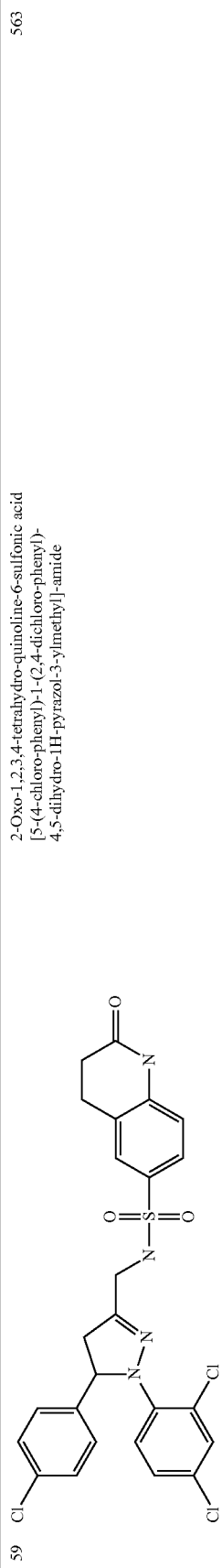 2-Oxo-1,2,3,4-tetrahydro-quinoline-6-sulfonic acid [5-(4-chloro-phenyl)-1-(2,4-dichloro-phenyl)-4,5-dihydro-1H-pyrazol-3-ylmethyl]-amide | | 563 |
| 60 | 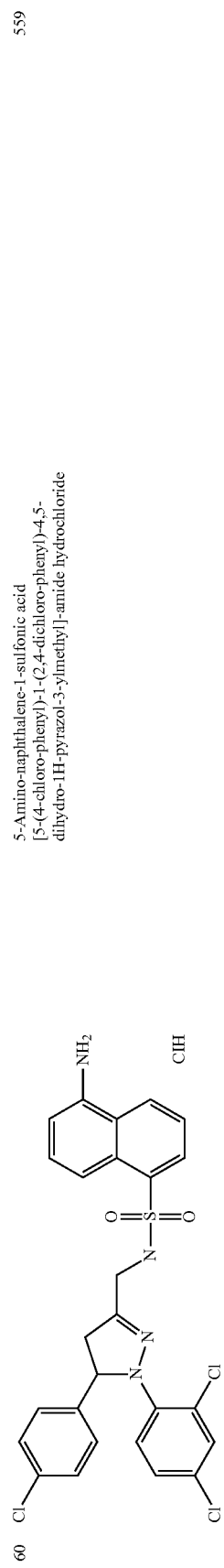 5-Amino-naphthalene-1-sulfonic acid [5-(4-chloro-phenyl)-1-(2,4-dichloro-phenyl)-4,5-dihydro-1H-pyrazol-3-ylmethyl]-amide hydrochloride | | 559 |
| 61 | 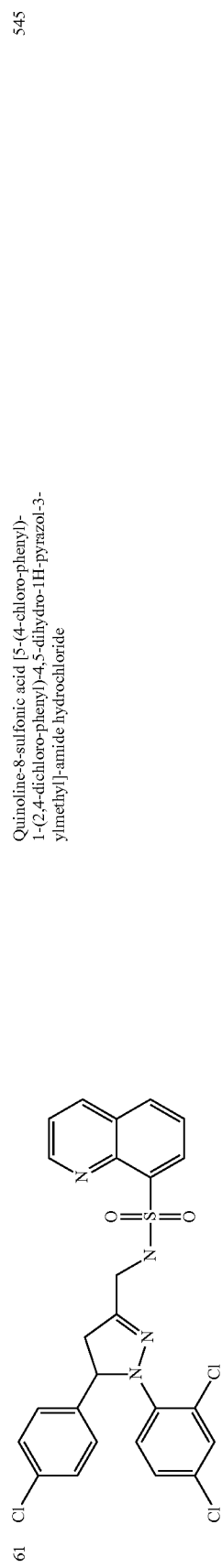 Quinoline-8-sulfonic acid [5-(4-chloro-phenyl)-1-(2,4-dichloro-phenyl)-4,5-dihydro-1H-pyrazol-3-ylmethyl]-amide hydrochloride | | 545 |
| 62 | 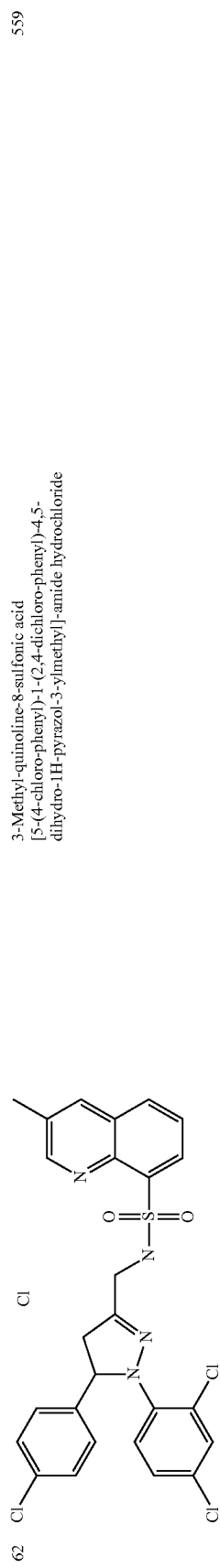 3-Methyl-quinoline-8-sulfonic acid [5-(4-chloro-phenyl)-1-(2,4-dichloro-phenyl)-4,5-dihydro-1H-pyrazol-3-ylmethyl]-amide hydrochloride | | 559 |

| | | | |
|---|---|---|---|
| 63 | 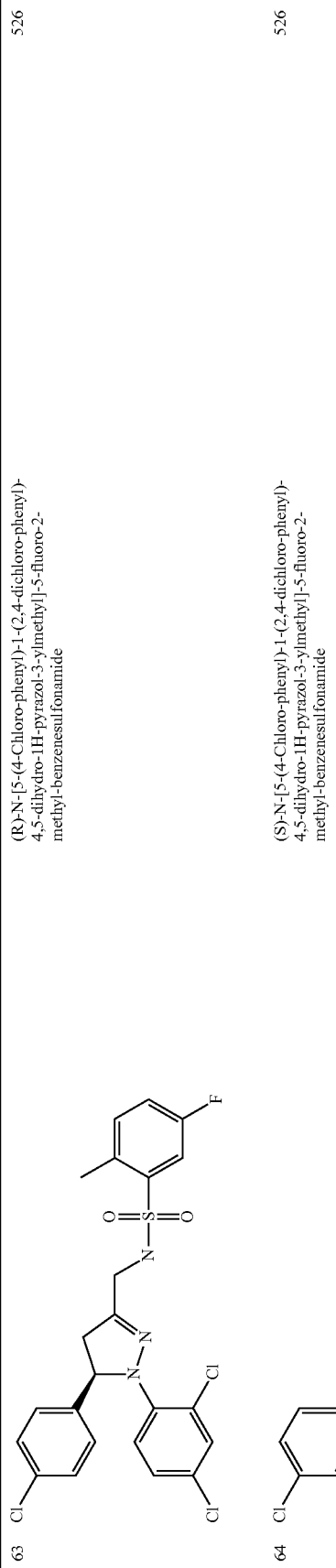 | (R)-N-[5-(4-Chloro-phenyl)-1-(2,4-dichloro-phenyl)-4,5-dihydro-1H-pyrazol-3-ylmethyl]-5-fluoro-2-methyl-benzenesulfonamide | 526 |
| 64 | | (S)-N-[5-(4-Chloro-phenyl)-1-(2,4-dichloro-phenyl)-4,5-dihydro-1H-pyrazol-3-ylmethyl]-5-fluoro-2-methyl-benzenesulfonamide | 526 |
| 65 | | (R)-2-Chloro-N-[5-(4-chloro-phenyl)-1-(2,4-dichloro-phenyl)-4,5-dihydro-1H-pyrazol-3-ylmethyl]-6-methyl-benzenesulfonamide | 542 |
| 66 | | (S)-2-Chloro-N-[5-(4-chloro-phenyl)-1-(2,4-dichloro-phenyl)-4,5-dihydro-1H-pyrazol-3-ylmethyl]-6-methyl-benzenesulfonamide | 542 |

| | -continued | | |
|---|---|---|---|
| 67 | (R)-4-Chloro-N-[5-(4-chloro-phenyl)-1-(2,4-dichloro-phenyl)-4,5-dihydro-1H-pyrazol-3-ylmethyl]-2,5-dimethyl-benzenesulfonamide | | 556 |
| 68 | (S)-4-Chloro-N-[5-(4-chloro-phenyl)-1-(2,4-dichloro-phenyl)-4,5-dihydro-1H-pyrazol-3-ylmethyl]-2,5-dimethyl-benzenesulfonamide | | 556 |
| 69 | (R)-N-[5-(4-Chloro-phenyl)-1-(2,4-dichloro-phenyl)-4,5-dihydro-1H-pyrazol-3-ylmethyl]-2,5-dimethyl-benzenesulfonamide | | 522 |
| 70 | (S)-N-[5-(4-Chloro-phenyl)-1-(2,4-dichloro-phenyl)-4,5-dihydro-1H-pyrazol-3-ylmethyl]-2,5-dimethyl-benzenesulfonamide | | 522 |

| | | | |
|---|---|---|---|
| 71 | 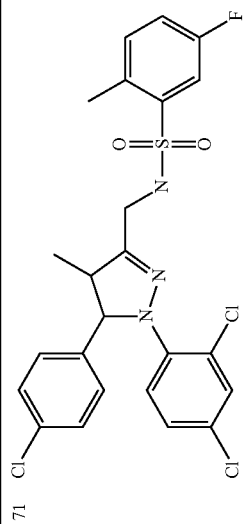 | N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 540 |
| 72 | 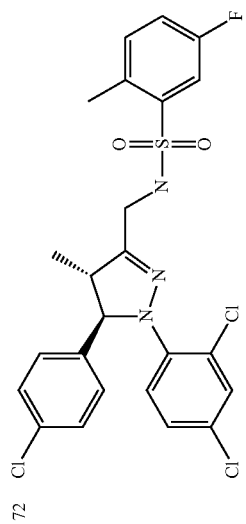 | trans(4SR,5RS)-N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 540 |
| 73 | 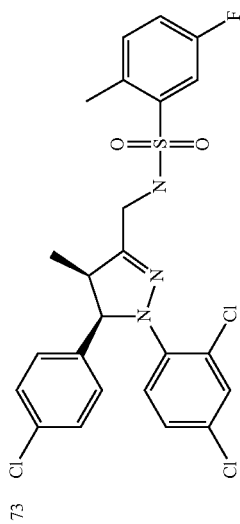 | cis-(4RS,5RS)-N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 1H NMR (400 MHz, DMSO-$d_6$) δ ppm 0.62 (d, J=7.42 Hz, 3 H) 2.57 (s, 3 H) 3.41 (dd, J=10.45, 7.51 Hz, 1 H) 3.86 (d, J=14.07 Hz, 2 H) 5.49 (d, J=10.55 Hz, 1 H) 6.94 (d, J=8.21 Hz, 2 H) 7.12 (d=8.99 Hz, 1 H) 7.19-7.29 | 540 |
| 74 | 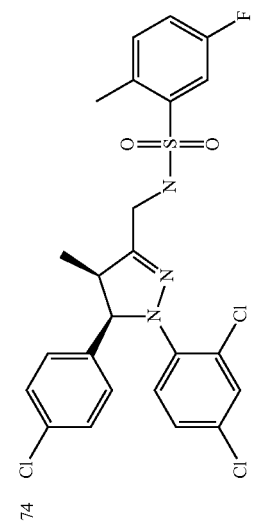 | (4R,5R)-N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 540 |

| | | -continued | |
|---|---|---|---|
| 75 | 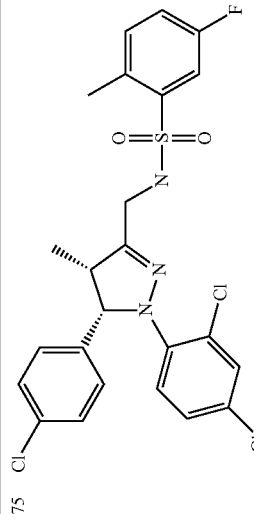 | (4S,5S)-N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 540 |
| 76 | 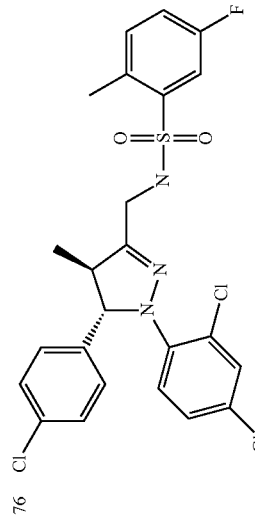 | (4R,5S)-N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 540 |
| 77 | 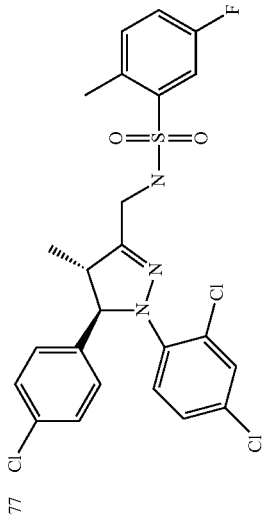 | (4S,5R)-N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide | 540 |
| 78 | 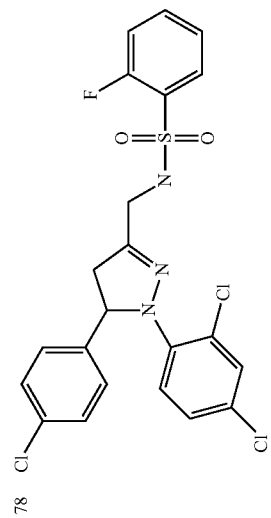 | N-[5-(4-Chloro-phenyl)-1-(2,4-dichloro-phenyl)-4,5-dihydro-1H-pyrazol-3-ylmethyl]-2-fluoro-benzenesulfonamide | 512 |

-continued

| | | | |
|---|---|---|---|
| 79 | 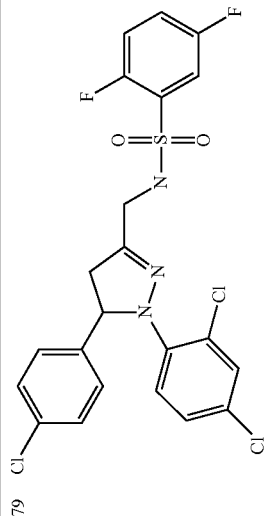 | N-[5-(4-Chloro-phenyl)-1-(2,4-dichloro-phenyl)-4,5-dihydro-1H-pyrazol-ylmethyl]-2,5-difluoro-benzenesulfonamide | 530 |
| 80 | 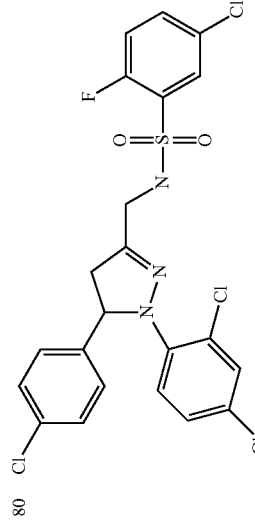 | 5-Chloro-N-[5-(4-chloro-phenyl)-1-(2,4-dichloro-phenyl)-4,5-dihydro-1H-pyrazol-3-ylmethyl]-2-fluoro-benzenesulfonamide | 546 |
| 81 | 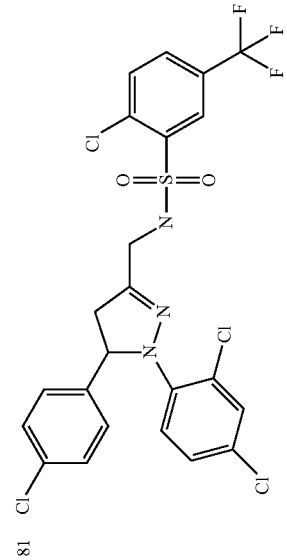 | 2-Chloro-N-[5-(4-chloro-phenyl)-1-(2,4-dichloro-phenyl)-4,5-dihydro-1H-pyrazol-3-ylmethyl]-5-trifluoromethyl-benzenesulfonamide | 596 |
| 82 | 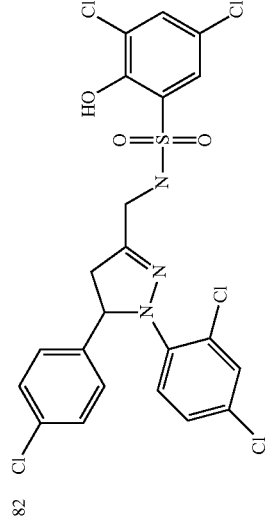 | 3,5-Dichloro-N-[5-(4-chloro-phenyl)-1-(2,4-dichloro-phenyl)-4,5-dihydro-1H-pyrazol-3-ylmethyl]-2-hydroxy-benzenesulfonamide | 578 |

| | | | |
|---|---|---|---|
| 83 | 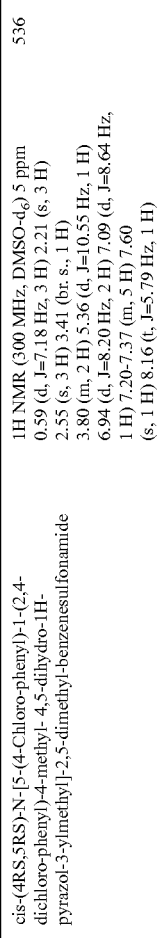 | cis-(4RS,5RS)-N-[5-(4-Chloro-phenyl)-1-(2,4-dichloro-phenyl)-4-methyl-4,5-dihydro-1H-pyrazol-3-ylmethyl]-2,5-dimethyl-benzenesulfonamide | 1H NMR (300 MHz, DMSO-$d_6$) δ ppm 0.59 (d, J=7.18 Hz, 3 H) 2.21 (s, 3 H) 2.55 (s, 3 H) 3.41 (br. s., 1 H) 3.80 (m, 2 H) 5.36 (d, J=10.55 Hz, 1 H) 6.94 (d, J=8.20 Hz, 2 H) 7.09 (d, J=8.64 Hz, 1 H) 7.20–7.37 (m, 5 H) 7.60 (s, 1 H) 8.16 (t, J=5.79 Hz, 1 H) | 536 |
| 84 |  | 3,5-dichloro-N-((5-(4-chlorophenyl)-1-(2,4-dichlorophenyl)-4,5-dihydro-1H-pyrazol-3-yl)methyl)-N-(3,5-dichloro-2-hydroxyphenylsulfonyl)-2-hydroxybenzenesulfonamide | | 802 |
| 85 |  | N-[5-(4-Chloro-phenyl)-1-(2,4-dichloro-phenyl)-4,5-dihydro-1H-pyrazol-3-ylmethyl]-4-fluoro-2-methyl-benzenesulfonamide | | 526 |

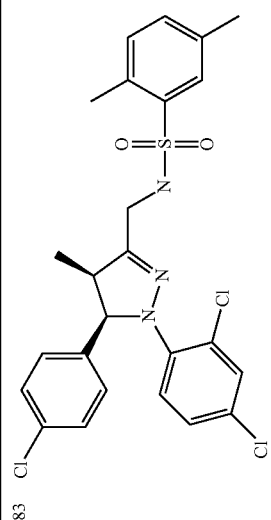
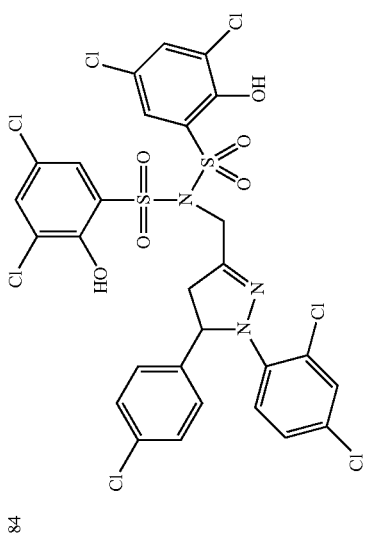
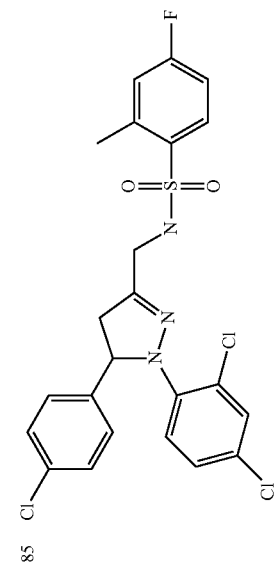

| | | | |
|---|---|---|---|
| 86 | N-[5-(4-Chloro-phenyl)-1-(2,4-dichloro-phenyl)-4,5-dihydro-1H-pyrazol-3-ylmethyl]-3-fluoro-4-methyl-benzenesulfonamide | 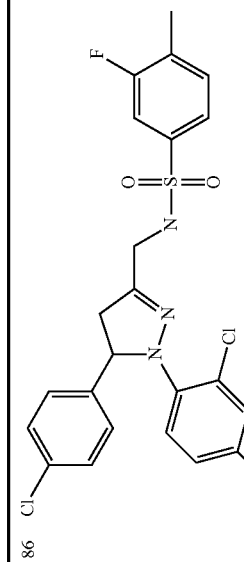 | 526 |
| 87 | 5-Bromo-6-chloro-pyridine-3-sulfonic acid [5-(4-chloro-phenyl)-1-(2,4-dichloro-phenyl)-4,5-dihydro-1H-pyrazol-3-ylmethyl]-amide | 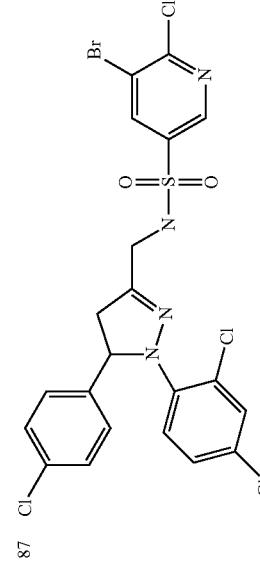 | 608 |
| 88 | 3,5-Dichloro-N-[5-(4-chloro-phenyl)-1-(2,4-dichloro-phenyl)-4,5-dihydro-1H-pyrazol-3-ylmethyl]-4-hydroxy-benzenesulfonamide | 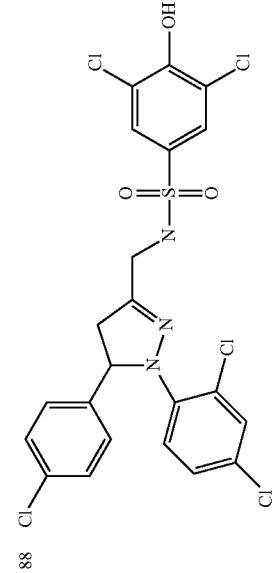 | 578 |
| 89 | N-[5-(4-Chloro-phenyl)-1-(2,4-dichloro-phenyl)-4,5-dihydro-1H-pyrazol-3-ylmethyl]-benzenesulfonamide | 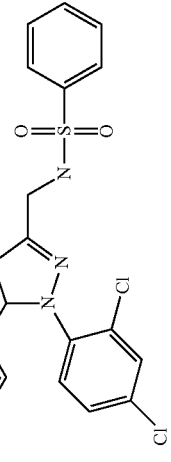 | 494 |

| | | | |
|---|---|---|---|
| 90 | 3-{[5-(4-Chloro-phenyl)-1-(2,4-dichloro-phenyl)-4,5-dihydro-1H-pyrazol-3-ylmethyl]-sulfamoyl}-thiophene-2-carboxylic acid methyl ester | 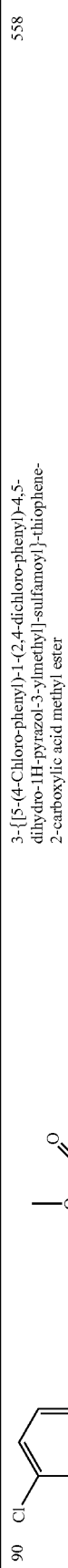 | 558 |
| 91 | 5-Bromo-6-chloro-pyridine-3-sulfonic acid [5-(4-chloro-phenyl)-1-(2,4-dichloro-phenyl)-4,5-dihydro-1H-pyrazol-3-ylmethyl]-amide hydrochloride | 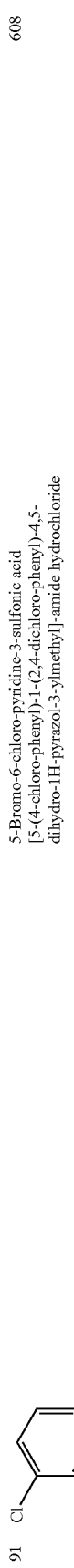 | 608 |
| 92 | N-[1-(2,4-Dichloro-phenyl)-5-(4-methoxy-phenyl)-4,5-dihydro-1H-pyrazol-3-ylmethyl]-2-fluoro-benzenesulfonamide | 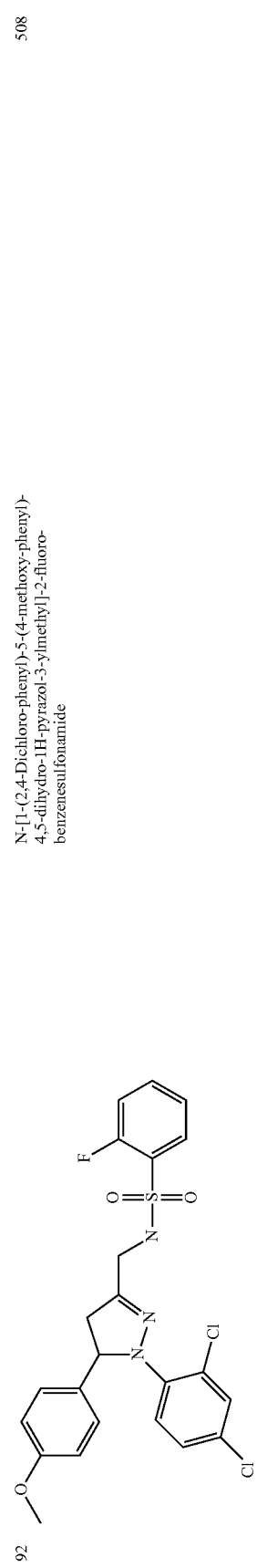 | 508 |

| | -continued | | |
|---|---|---|---|
| 93 | 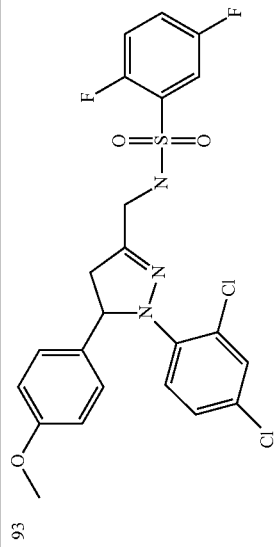 | N-[1-(2,4-Dichloro-phenyl)-5-(4-methoxy-phenyl)-4,5-dihydro-1H-pyrazol-3-ylmethyl]-2,5-difluoro-benzenesulfonamide | 526 |
| 94 | 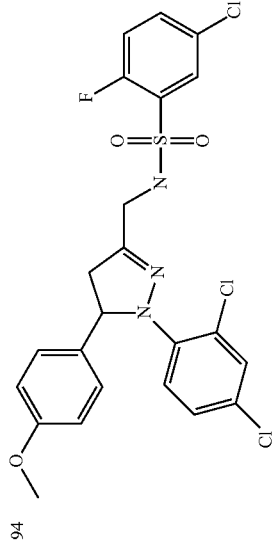 | 5-Chloro-N-[1-(2,4-dichloro-phenyl)-5-(4-methoxy-phenyl)-4,5-dihydro-1-pyrazol-3-ylmethyl]-2-fluoro-benzenesulfonamide | 542 |
| 95 | 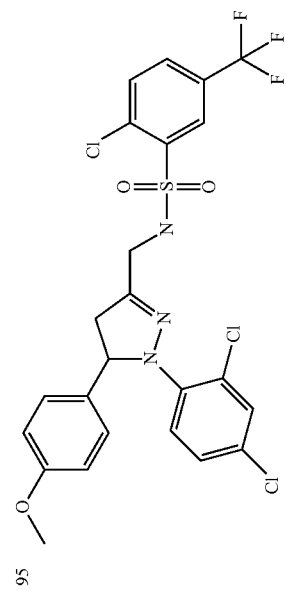 | 2-Chloro-N-[1-(2,4-dichloro-phenyl)-5-(4-methoxy-phenyl)-4,5-dihydro-1H-pyrazol-3-ylmethyl]-5-trifluoromethyl-benzenesulfonamide | 592 |

| | | | |
|---|---|---|---|
| 96 | 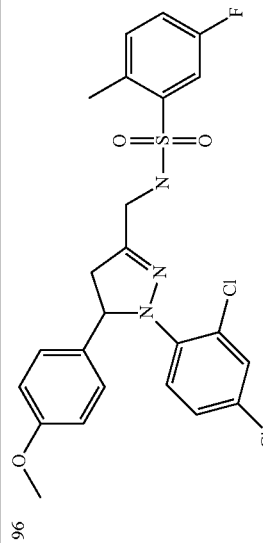 | N-[1-(2,4-Dichloro-phenyl)-5-(4-methoxy-phenyl)-4,5-dihydro-1H-pyrazol-3-ylmethyl]-5-fluoro-2-methyl-benzene sulfonamide | 522 |
| 97 | 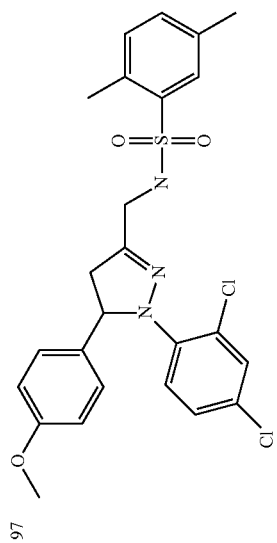 | N-[1-(2,4-Dichloro-phenyl)-5-(4-methoxy-phenyl)-4,5-dihydro-1H-pyrazol-3-ylmethyl]-2,5-dimethyl-benzenesulfonamide | 518 |
| 98 | 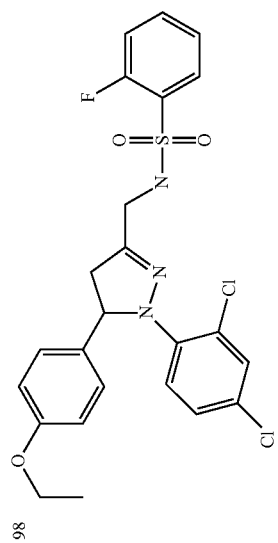 | N-[1-(2,4-Dichloro-phenyl)-5-(4-ethoxy-phenyl)-4,5-dihydro-1H-pyrazol-3-ylmethyl]-2-fluoro-benzenesulfonafonamide | 522 |
| 99 | 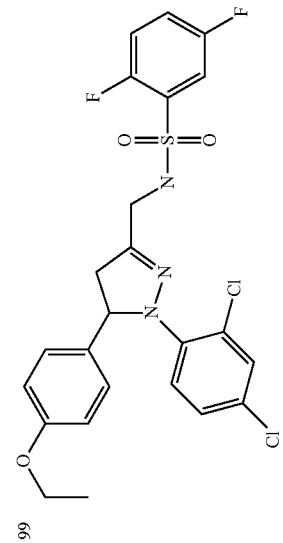 | N-[1-(2,4-Dichloro-phenyl)-5-(4-ethoxy-phenyl)-4,5-dihydro-1H-pyrazol-3-ylmethyl]-2,5-difluoro-benzenesulfonamide | 540 |

| | | |
|---|---|---|
| 100 | 5-Chloro-N-[1-(2,4-dichloro-phenyl)-5-(4-ethoxy-phenyl)-4,5-dihydro-1H-pyrazol-3-ylmethyl]-2-fluoro-benzenesulfonamide 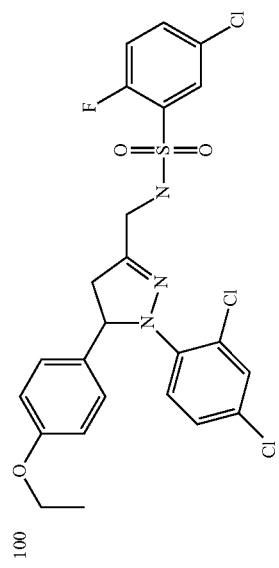 | 556 |
| 101 | 2-Chloro-N-[1-(2,4-dichloro-phenyl)-5-(4-ethoxy-phenyl)-4,5-dihydro-1H-pyrazol-3-ylmethyl]-5-trifluoromethyl-benzenesulfonamide 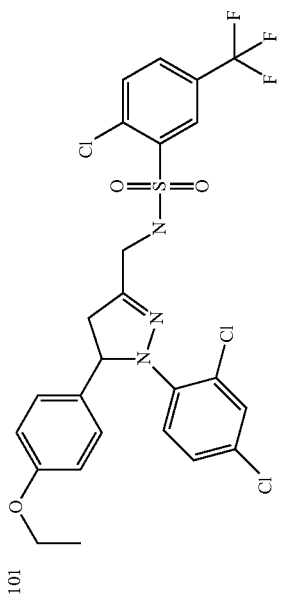 | 606 |
| 102 | N-[1-(2,4-Dichloro-phenyl)-5-(4-ethoxy-phenyl)-4,5-dihydro-1H-pyrazol-3-ylmethyl]-5-fluoro-2-methyl-benzenesulfonamide 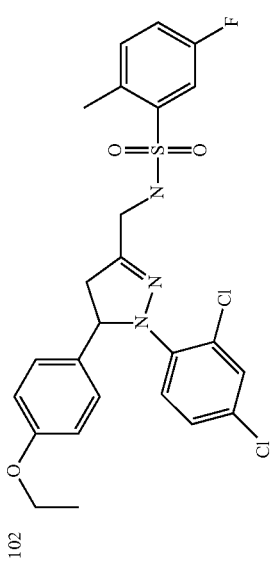 | 536 |

| | | |
|---|---|---|
| 103 | N-[1-(2,4-Dichloro-phenyl)-5-(4-ethoxy-phenyl)-4,5-dihydro-1H-pyrazol-3-ylmethyl]-2,5-dimethyl-benzenesulfonamide | 532 |
| | 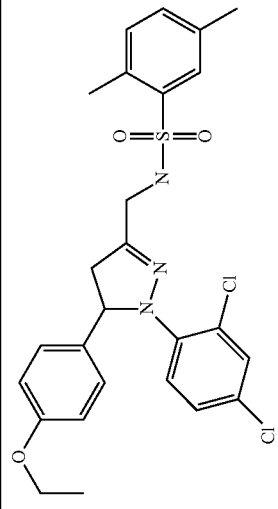 | |
| 104 | (R)-N-[5-(4-Chloro-phenyl)-1-(2,4-dichloro-phenyl)-4,5-dihydro-1H-pyrazol-3-ylmethyl]-2-fluoro-benzenesulfonamide | 512 |
| | 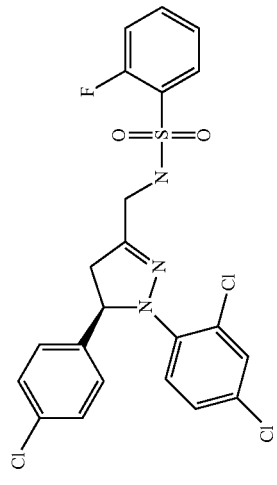 | |
| 105 | (R)-N-[5-(4-Chloro-phenyl)-1-(2,4-dichloro-phenyl)-4,5-dihydro-1H-pyrazol-3-ylmethyl]-2,5-difluoro-benzenesulfonamide | 530 |
| | 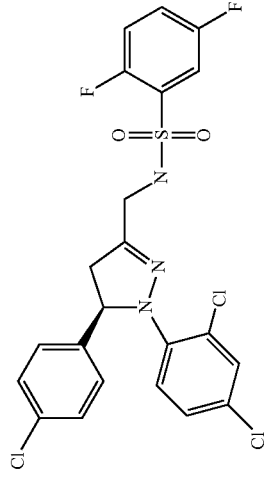 | |
| 106 | (R)-5-Chloro-N-[5-(4-chloro-phenyl)-1-(2,4-dichloro-phenyl)-4,5-dihydro-1H-pyrazol-3-ylmethyl]-2-fluoro-benzenesulfonamide | 546 |
| | 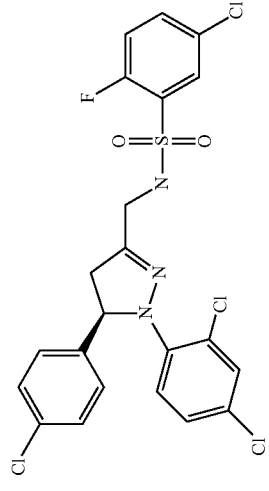 | |

-continued

| | | | |
|---|---|---|---|
| 107 | 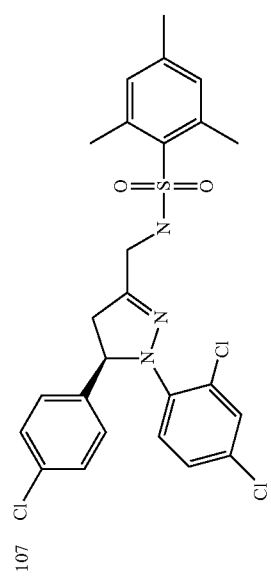 | (R)-N-[5-(4-Chloro-phenyl)-1-(2,4-dichloro-phenyl)-4,5-dihydro-1H-pyrazol-3-ylmethyl]-2,4,6-trimethyl-benzenesulfonamide | 536 |
| 108 | 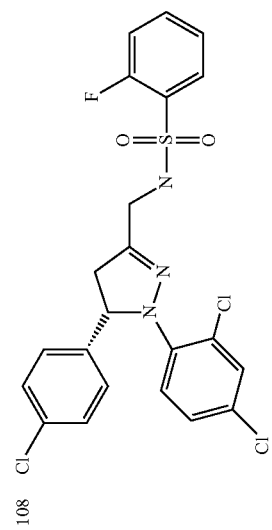 | (S)-N-[5-(4-Chloro-phenyl)-1-(2,4-dichloro-phenyl)-4,5-dihydro-1H-pyrazol-3-ylmethyl]-2-fluoro-benzenesulfonamide | 512 |
| 109 | 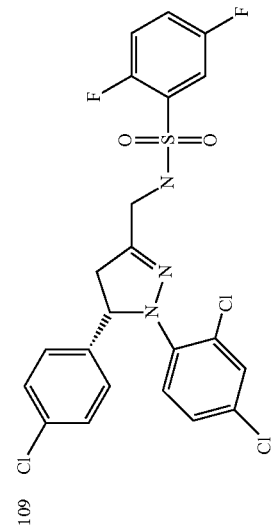 | (S)-N-[5-(4-Chloro-phenyl)-1-(2,4-dichloro-phenyl)-4,5-dihydro-1H-pyrazol-3-ylmethyl]-2,5-difluoro-benzenesulfonamide | 530 |
| 110 | 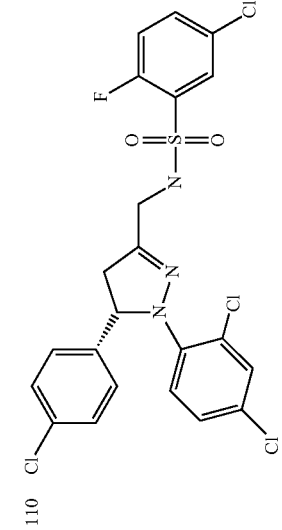 | (S)-5-Chloro-N-[5-(4-chloro-phenyl)-1-(2,4-dichloro-phenyl)-4,5-dihydro-1H-pyrazol-3-ylmethyl]-2-fluoro-benzenesulfonamide | 546 |

| | -continued | | |
|---|---|---|---|
| 111 | (S)-N-5-(4-Chloro-phenyl)-1-(2,4-dichloro-phenyl)-4,5-dihydro-1H-pyrazol-3-ylmethyl]-2,4,6-trimethyl-benzenesulfonamide | 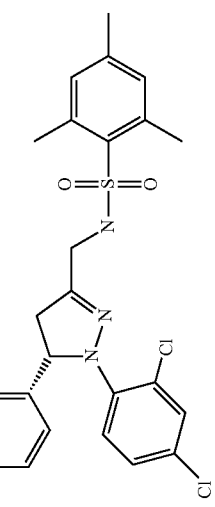 | 536 |
| 112 | 2-Oxo-2H-chromene-5-sulfonic acid [5-(4-chloro-phenyl)-1-(2,4-dichloro-phenyl)-4,5-dihydro-1H-pyrazol-3-ylmethyl]-amide | 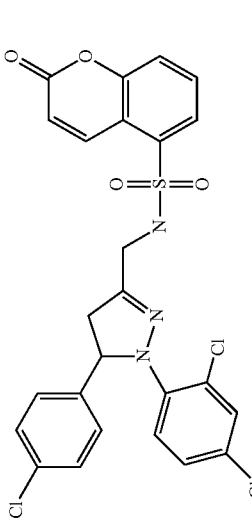 | 562 |
| 113 | N-[5-(4-Chloro-phenyl)-1-(2,4-dichloro-phenyl)-4,5-dihydro-1H-pyrazol-3-ylmethyl]-2,6-difluoro-benzenesulfonamide | 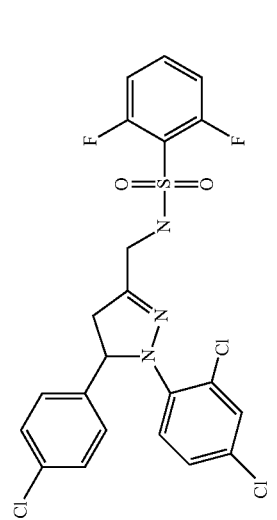 | 530 |
| 114 | Biphenyl-4-sulfonic acid [5-(4-chloro-phenyl)-1-(2,4-dichloro-phenyl)-4,5-dihydro-1H-pyrazol-3-ylmethyl]-amide | 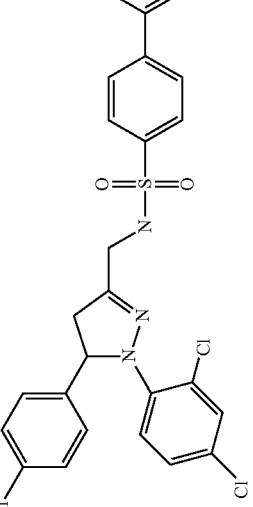 | 570 |

-continued

| | | | |
|---|---|---|---|
| 115 | 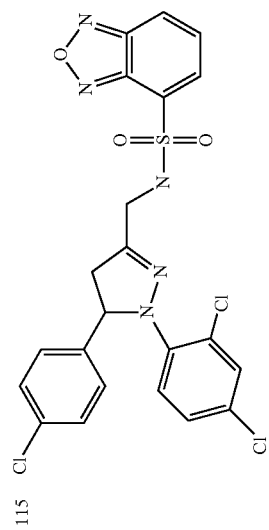 | Benzo[1,2,5]oxadiazole-4-sulfonic acid [5-(4-chloro-phenyl)-1-(2,4-didichloro-phenyl)-4,5-dihydro-1H-pyrazol-3-ylmethyl]-amide | 536 |
| 116 | 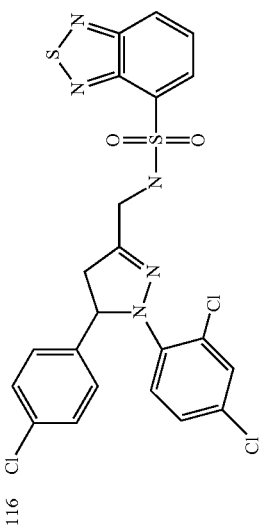 | Benzo[1,2,5]thiadiazole-4-sulfonic acid [5-(4-chloro-phenyl)-1-(2,4-dichloro-phenyl)-4,5-dihydro-1H-pyrazol-3-ylmethyl]-amide | 552 |
| 117 | 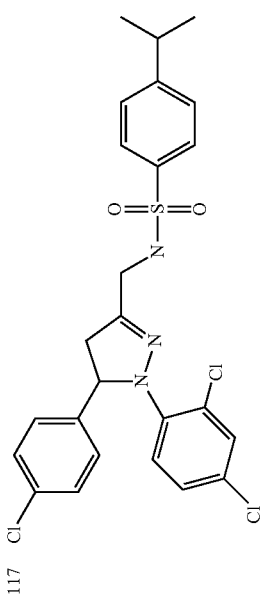 | N-[5-(4-Chloro-phenyl)-1-(2,4-dichloro-phenyl)-4,5-dihydro-1H-pyrazol-3-ylmethyl]-4-isopropyl-benzenesulfonamide | 536 |
| 118 | 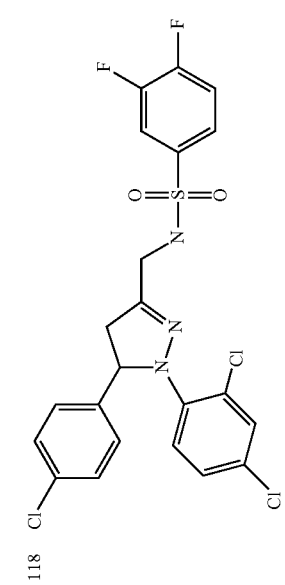 | N-[5-(4-Chloro-phenyl)-1-(2,4-dichloro-phenyl)-4,5-dihydro-1H-pyrazol-3-ylmethyl]-3,4-difluoro-benzenesulfonamide | 530 |

| | | |
|---|---|---|
| 119 | 3,4-Dichloro-N-[5-(4-chloro-phenyl)-1-(2,4-dichloro-phenyl)-4,5-dihydro-1H-pyrazol-3-ylmethyl]-benzenesulfonamide 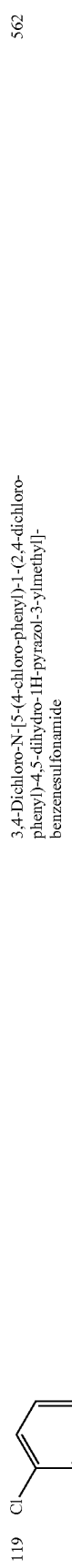 | 562 |
| 120 | 7-Chloro-benzo[1,2,5]oxadiazole-4-sulfonic acid [5-(4-chloro-phenyl)-1-(2,4-dichloro-phenyl)-4,5-dihydro-1H-pyrazol-3-ylmethyl]-amide 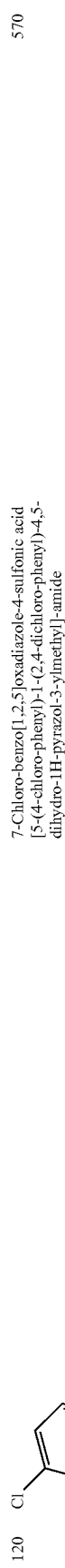 | 570 |
| 121 | N-[5-(4-Chloro-phenyl)-1-(2,4-dichloro-phenyl)-4,5-dihydro-1H-pyrazol-3-ylmethyl]-4-isopropoxy-benzenesulfonamide 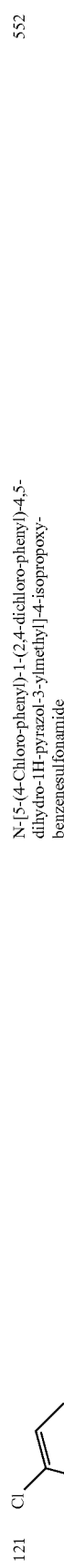 | 552 |

| | | |
|---|---|---|
| 122 | 3-Chloro-N-[5-(4-chloro-phenyl)-1-(2,4-dichloro-phenyl)-4,5-dihydro-1H-pyrazol-3-ylmethyl]-4-methoxy-benzenesulfonamide 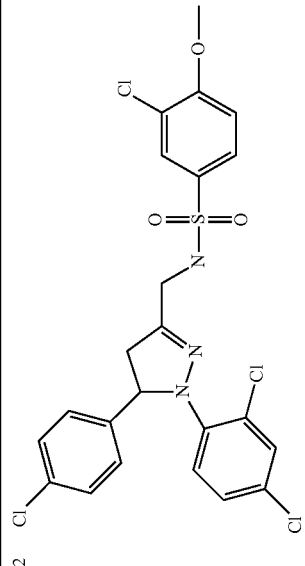 | 558 |
| 123 | 2,4-Dimethyl-thiazole-5-sulfonic acid [5-(4-chloro-phenyl)-1-(2,4-dichloro-phenyl)-4,5-dihydro-1H-pyrazol-3-ylmethyl]amide 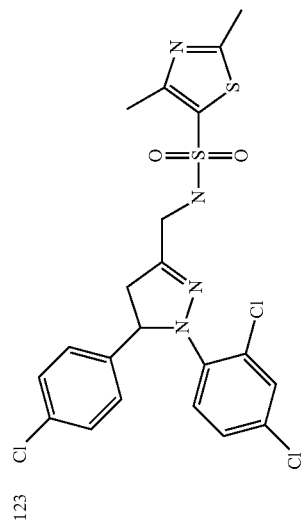 | 529 |
| 124 | N-[5-(4-Chloro-phenyl)-1-(2,4-dichloro-phenyl)-4,5-dihydro-1H-pyrazol-3-ylmethyl]-2,4-difluoro-benzenesulfonamide 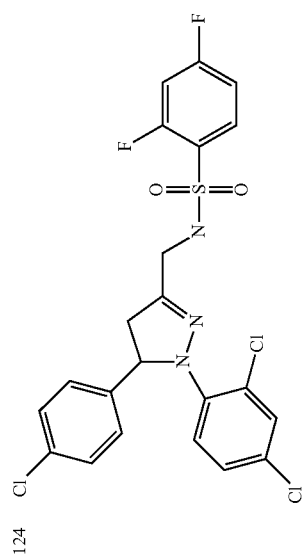 | 530 |

-continued
| | | | |
|---|---|---|---|
| 125 | Benzo[b]thiophene-2-sulfonic acid [5-(4-chloro-phenyl)-1-(2,4-dichloro-phenyl)-4,5-dihydro-1H-pyrazol-3-ylmethyl]-amide | 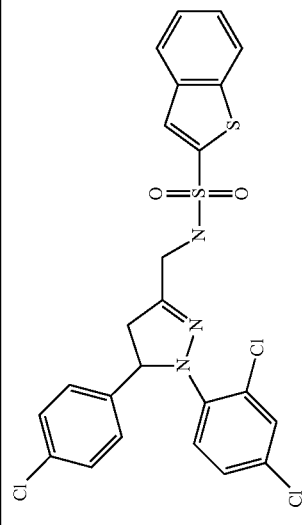 | 550 |
| 126 | 3-Bromo-N-[5-(4-chloro-phenyl)-1-(2,4-dichloro-phenyl)-4,5-dihydro-1H-pyrazol-3-ylmethyl]-benzenesulfonamide | 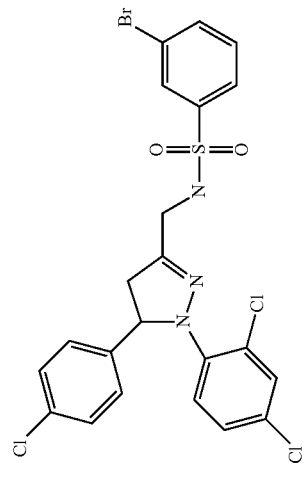 | 573 |
| 127 | N-[5-(4-Chloro-phenyl)-1-(2,4-dichloro-phenyl)-4,5-dihydro-1H-pyrazol-3-ylmethyl]-2,3,5,6-tetramethyl-benzenesulfonamide | 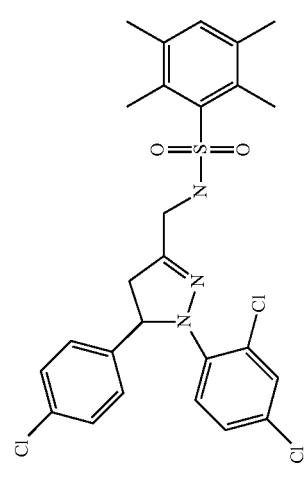 | 550 |

| | | |
|---|---|---|
| 128 | 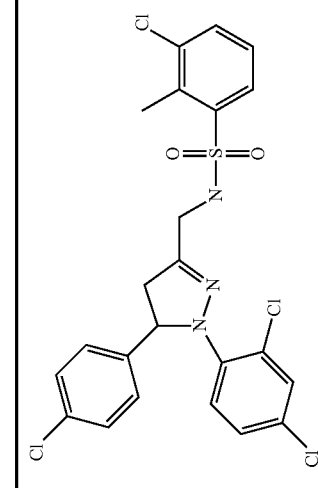 3-Chloro-N-[5-(4-chloro-phenyl)-1-(2,4-dichloro-phenyl)-4,5-dihydro-1H-pyrazol-3-ylmethyl]-2-methyl-benzenesulfonamide | 542 |
| 129 | 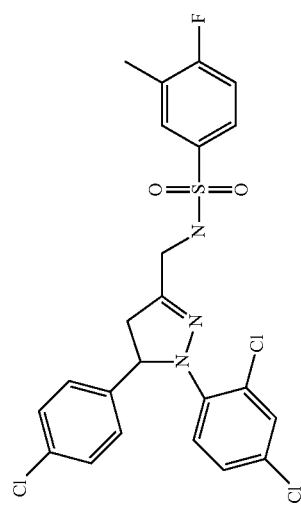 N-[5-(4-Chloro-phenyl)-1-(2,4-dichloro-phenyl)-4,5-dihydro-1H-pyrazol-3-ylmethyl]-4-fluoro-3-methyl-benzenesulfonamide | 526 |
| 130 | 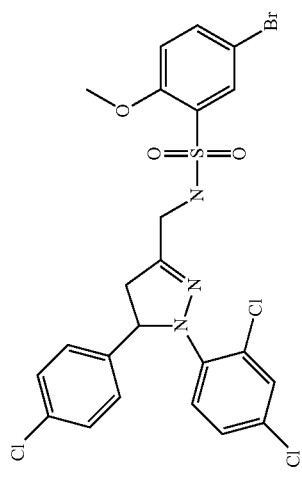 5-Bromo-N-[5-(4-chloro-phenyl)-1-(2,4-dichloro-phenyl)-4,5-dihydro-1H-pyrazol-3-ylmethyl]-2-methoxy-benzenesulfonamide | 603 |

-continued
| | | |
|---|---|---|
| 131 | 2-(2,2,2-Trifluoro-acetyl)-1,2,3,4-tetrahydro-isoquinoline-7-sulfonic acid [5-(4-chloro-phenyl)-1-(2,4-dichloro-phenyl)-4,5-dihydro-1H-pyrazol-3-ylmethyl]-amide | 645 |
| | 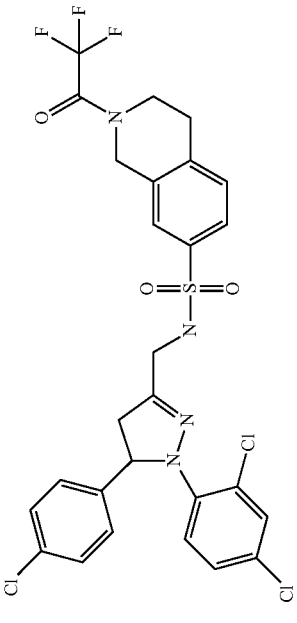 | |
| 132 | N-[5-(4-Chloro-phenyl)-1-(2,4-dichloro-phenyl)-4,5-dihydro-1H-pyrazol-3-ylmethyl]-2,3,4,5,6-pentamethyl-benzenesulfonamide | 564 |
| | 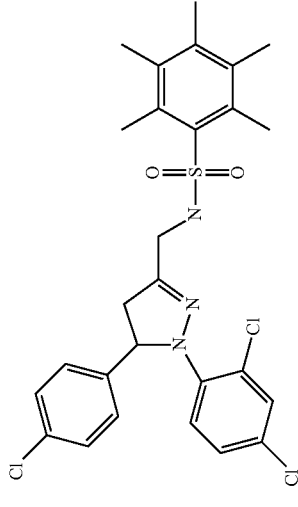 | |
| 133 | 2,4-Dichloro-N-[5-(4-chloro-phenyl)-1-(2,4-dichloro-phenyl)-4,5-dihydro-1H-pyrazol-3-ylmethyl]-benzenesulfonamide | 562 |
| | 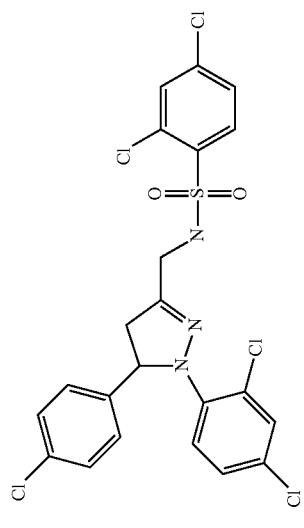 | |

-continued
| | | |
|---|---|---|
| 134 | 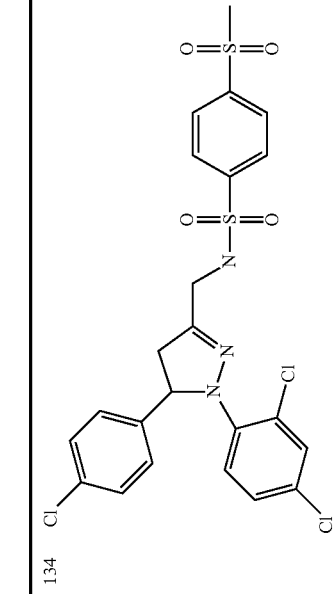 | N-[5-(4-Chloro-phenyl)-1-(2,4-dichloro-phenyl)-4,5-dihydro-1H-pyrazol-3-ylmethyl]-4-methanesulfonyl-benzenesulfonamide | 572 |
| 135 | 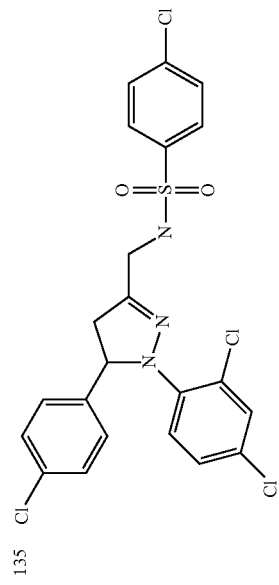 | 4-Chloro-N-[5-(4-chloro-phenyl)-1-(2,4-dichloro-phenyl)-4,5-dihydro-1H-pyrazol-3-ylmethyl]-benzenesulfonamide | 528 |
| 136 | 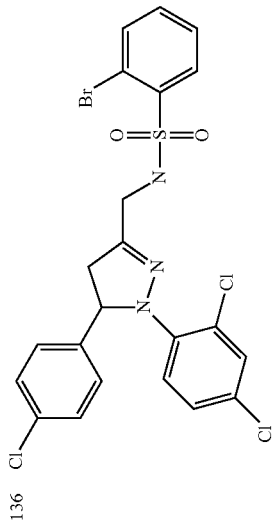 | 2-Bromo-N-[5-(4-chloro-phenyl)-1-(2,4-dichloro-phenyl)-4,5-dihydro-1H-pyrazol-3-ylmethyl]-benzenesulfonamide | 573 |

| | | | |
|---|---|---|---|
| 137 | 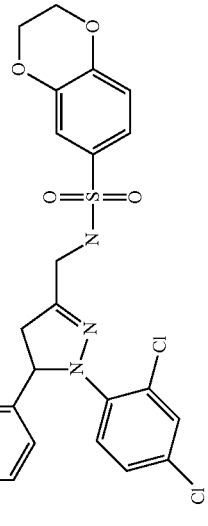 | 2,3-Dihydro-benzo[1,4]dioxine-6-sulfonic acid [5-(4-chloro-phenyl)-1-(2,4-dichloro-phenyl)-4,5-dihydro-1H-pyrazol-3-ylmethyl]-amide | 552 |
| 138 | 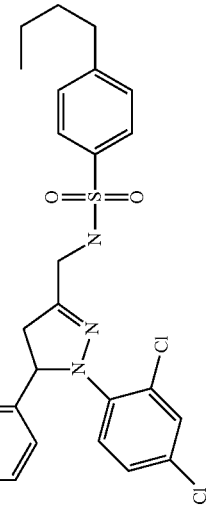 | 4-Butyl-N-[5-(4-chloro-phenyl)-1-(2,4-dichloro-phenyl)-4,5-dihydro-1H-pyrazol-3-ylmethyl]-benzenesulfonamide | 550 |
| 139 | 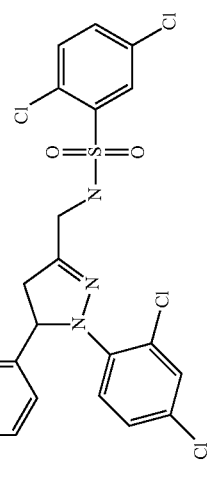 | 2,5-Dichloro-N-[5-(4-chloro-phenyl)-1-(2,4-dichloro-phenyl)-4,5-dihydro-1H-pyrazol-3-ylmethyl]-benzenesulfonamide | 562 |
| 140 | 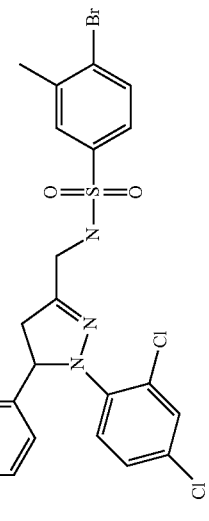 | 4-Bromo-N-[5-(4-chloro-phenyl)-1-(2,4-dichloro-phenyl)-4,5-dihydro-1H-pyrazol-3-ylmethyl]-3-methyl-benzenesulfonamide | 587 |

| | | -continued | |
|---|---|---|---|
| 141 | 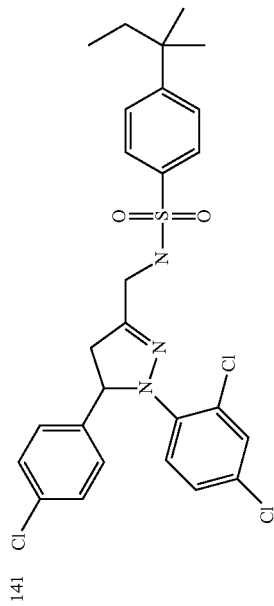 | N-[5-(4-Chloro-phenyl)-1-(2,4-dichloro-phenyl)-4,5-dihydro-1H-pyrazol-3-ylmethyl]-4-(1,1-dimethyl-propyl)-benzenesulfonamide | 564 |
| 142 | 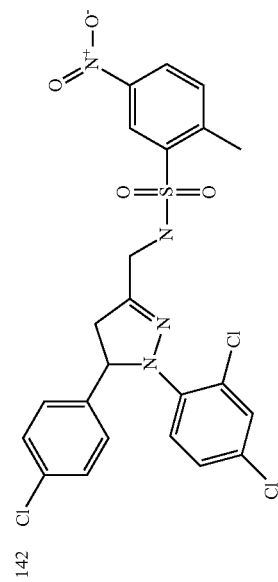 | N-[5-(4-Chloro-phenyl)-1-(2,4-dichloro-phenyl)-4,5-dihydro-1H-pyrazol-3-ylmethyl]-2-methyl-5-nitro-benzenesulfonamide | 553 |
| 143 | 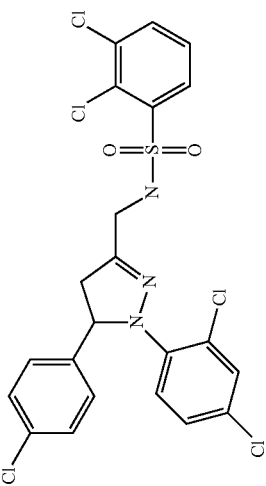 | 2,3-Dichloro-N-[5-(4-chloro-phenyl)-1-(2,4-dichloro-phenyl)-4,5-dihydro-1H-pyrazol-3-ylmethyl]-benzenesulfonamide | 562 |

| | -continued | | |
|---|---|---|---|
| 144 | N-[5-(4-Chloro-phenyl)-1-(2,4-dichloro-phenyl)-4,5-dihydro-1H-pyrazol-3-ylmethyl]-3-nitro-benzenesulfonamide | 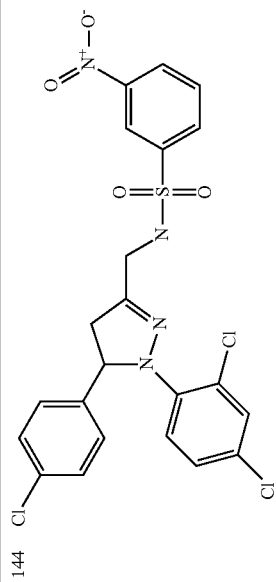 | 539 |
| 145 | 2-Bromo-N-[5-(4-chloro-phenyl)-1-(2,4-dichloro-phenyl)-4,5-dihydro-1H-pyrazol-3-ylmethyl]-4-fluoro-benzenesulfonamide | 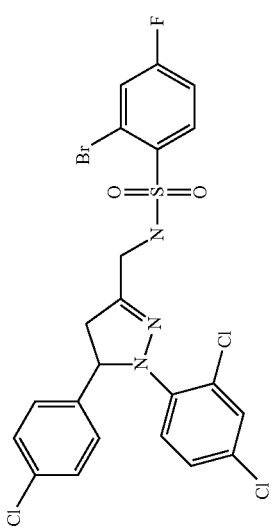 | 591 |
| 146 | 4-Bromo-N-[5-(4-chloro-chloro-1-(2,4-dichloro-phenyl)-4,5-dihydro-1H-pyrazol-3-ylmethyl]-3-trifluoromethyl-benzenesulfonamide | 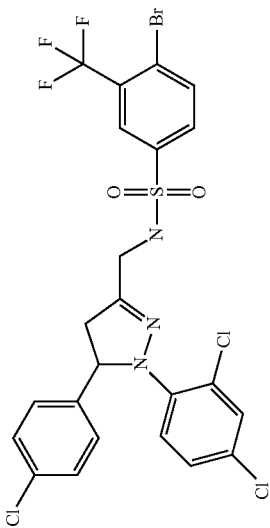 | 641 |

| | | |
|---|---|---|
| 147 | 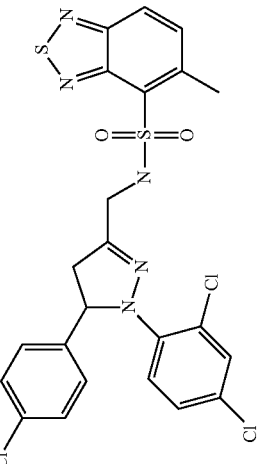 5-Methyl-benzo[1,2,5]thiadiazole-4-sulfonic acid [5-(4-chloro-phenyl)-1-(2,4-dichloro-phenyl)-4,5-dihydro-1H-pyrazol-3-ylmethyl]-amide | 566 |
| 148 | 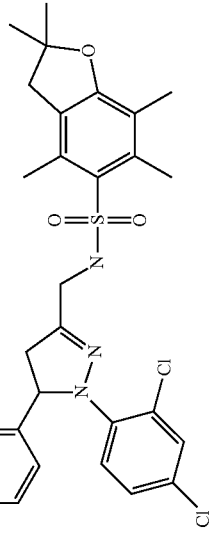 2,2,4,6,7-Pentamethyl-2,3-dihydro-benzofuran-5-sulfonic acid [5-(4-chloro-phenyl)-1-(2,4-dichloro-phenyl)-4,5-dihydro-1H-pyrazol-3-ylmethyl]-amide | 606 |
| 149 | 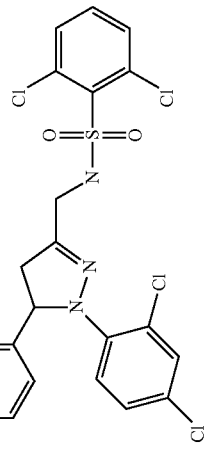 2,6-Dichloro-N-[5-(4-chloro-phenyl)-1-(2,4-dichloro-phenyl)-4,5-dihydro-1H-pyrazol-3-ylmethyl]-benzenesulfonamide | 562 |
| 150 | 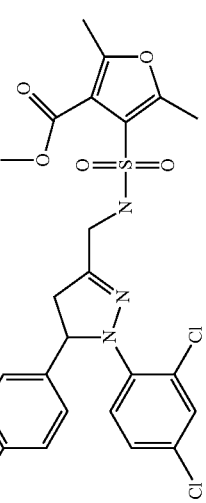 4-{[5-(4-Chloro-phenyl)-1-(2,4-dichloro-phenyl)-4,5-dihydro-1H-pyrazol-3-ylmethyl]-sulfamoyl}-2,5-dimethyl-furan-3-carboxylic acid methyl ester | 570 |

| | | | |
|---|---|---|---|
| 151 | 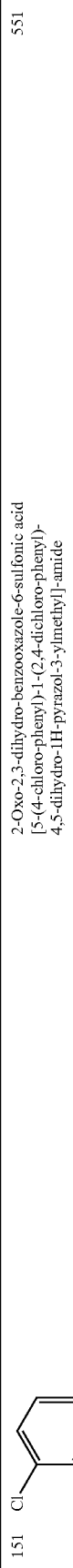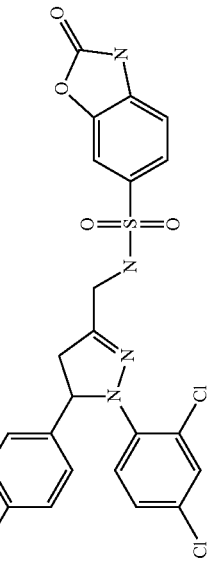 | 2-Oxo-2,3-dihydro-benzooxazole-6-sulfonic acid [5-(4-chloro-phenyl)-1-(2,4-dichloro-phenyl)-4,5-dihydro-1H-pyrazol-3-ylmethyl]-amide | 551 |
| 152 | 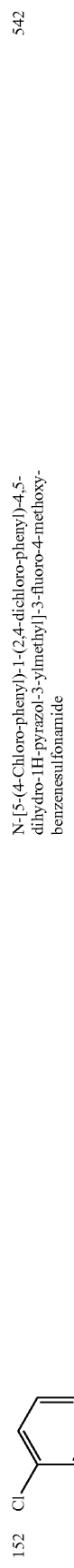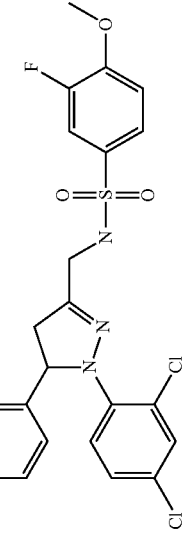 | N-[5-(4-Chloro-phenyl)-1-(2,4-dichloro-phenyl)-4,5-dihydro-1H-pyrazol-3-ylmethyl]-3-fluoro-4-methoxy-benzenesulfonamide | 542 |
| 153 | 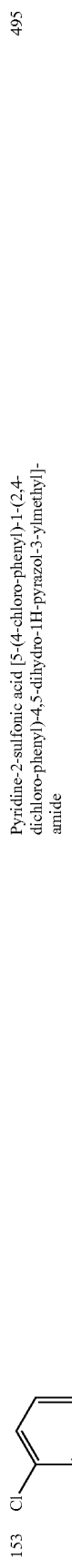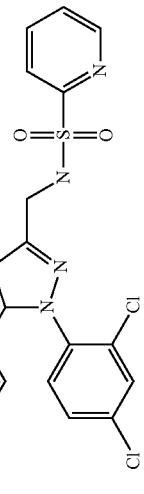 | Pyridine-2-sulfonic acid [5-(4-chloro-phenyl)-1-(2,4-dichloro-phenyl)-4,5-dihydro-1H-pyrazol-3-ylmethyl]-amide | 495 |
| 154 | 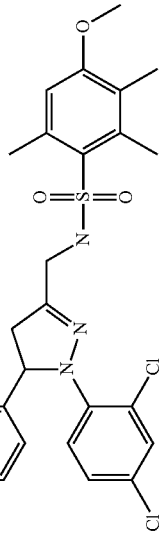 | N-[5-(4-Chloro-phenyl)-1-(2,4-dichloro-phenyl)-4,5-dihydro-1H-pyrazol-3-ylmethyl]-4-methoxy-2,3,6-trimethyl-benzenesulfonamide | 566 |

| | | | |
|---|---|---|---|
| 155 | 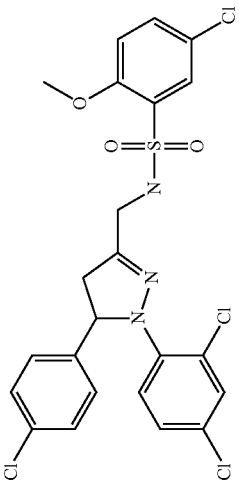 | 5-Chloro-N-[5-(4-chloro-phenyl)-1-(2,4-dichloro-phenyl)-4,5-dihydro-1H-pyrazol-3-ylmethyl]-2-methoxy-benzenesulfonamide | 558 |
| 156 | 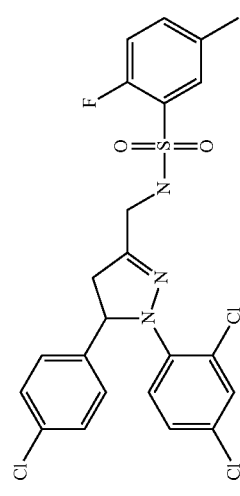 | N-[5-(4-Chloro-phenyl)-1-(2,4-dichloro-phenyl)-4,5-dihydro-1H-pyrazol-3-ylmethyl]-2-fluoro-5-methyl-benzenesulfonamide | 526 |
| 157 | 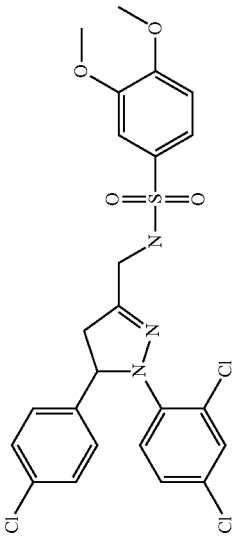 | N-[5-(4-Chloro-phenyl)-1-(2,4-dichloro-phenyl)-4,5-dihydro-1H-pyrazol-3-ylmethyl]-3,4-dimethoxy-benzenesulfonamide | 554 |
| 158 | 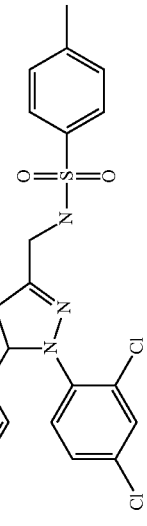 | N-[5-(4-Chloro-phenyl)-1-(2,4-dichloro-phenyl)-4,5-dihydro-1H-pyrazol-3-ylmethyl]-4-methyl-benzenesulfonamide | 508 |

| | | | |
|---|---|---|---|
| 159 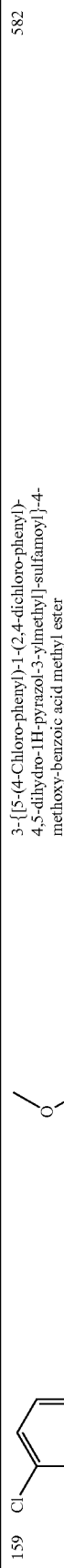 | 3-{[5-(4-Chloro-phenyl)-1-(2,4-dichloro-phenyl)-4,5-dihydro-1H-pyrazol-3-ylmethyl]-sulfamoyl}-4-methoxy-benzoic acid methyl ester | 582 |
| 160 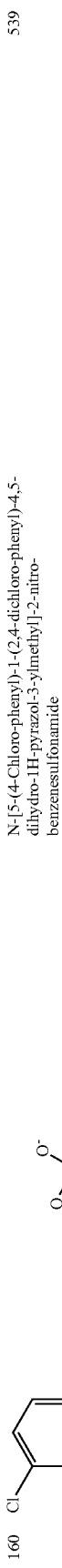 | N-[5-(4-Chloro-phenyl)-1-(2,4-dichloro-phenyl)-4,5-dihydro-1H-pyrazol-3-ylmethyl]-2-nitro-benzenesulfonamide | 539 |
| 161 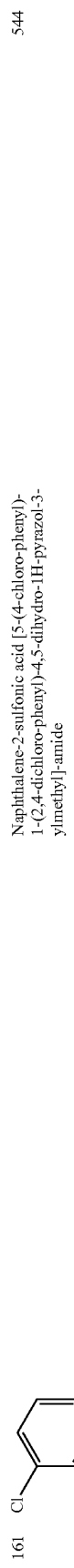 | Naphthalene-2-sulfonic acid [5-(4-chloro-phenyl)-1-(2,4-dichloro-phenyl)-4,5-dihydro-1H-pyrazol-3-ylmethyl]-amide | 544 |
| 162 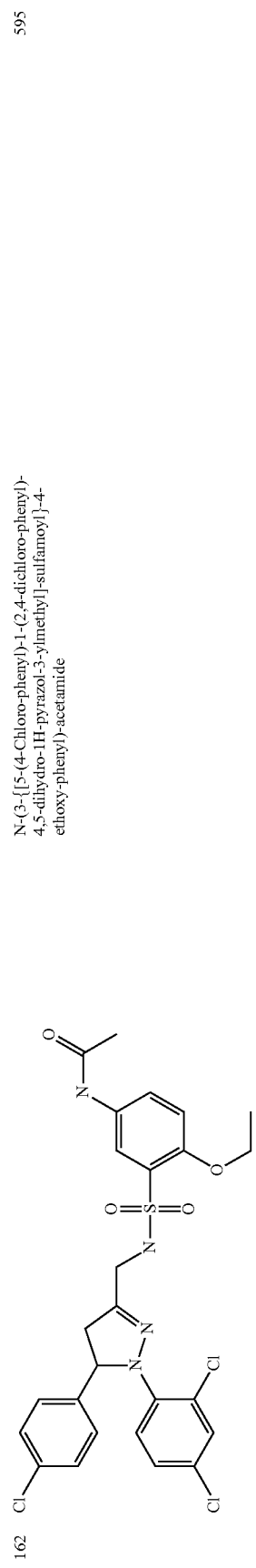 | N-(3-{[5-(4-Chloro-phenyl)-1-(2,4-dichloro-phenyl)-4,5-dihydro-1H-pyrazol-3-ylmethyl]-sulfamoyl}-4-ethoxy-phenyl)-acetamide | 595 |

-continued

| | | | |
|---|---|---|---|
| 163 | 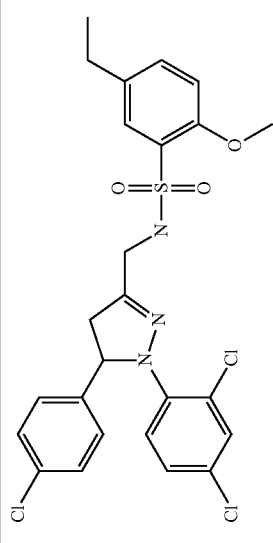 | N-[5-(4-Chloro-phenyl)-1-(2,4-dichloro-phenyl)-4,5-dihydro-1H-pyrazol-3-ylmethyl]-5-ethyl-2-methoxy-benzenesulfonamide | 552 |
| 164 | 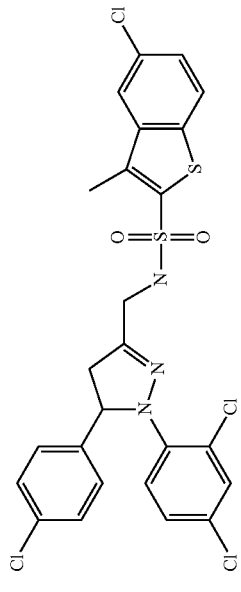 | 5-Chloro-3-methyl-benzo[b]thiophene-2-sulfonic acid [5-(4-chloro-phenyl)-1-(2,4-dichloro-phenyl)-4,5-dihydro-1H-pyrazol-3-ylmethyl]-amide | 598 |
| 165 | 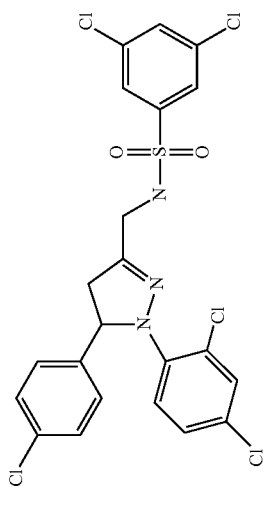 | 3,5-Dichloro-N-[5-(4-chloro-phenyl)-1-(2,4-dichloro-phenyl)-4,5-dihydro-1H-pyrazol-3-ylmethyl]-benzenesulfonamide | 562 |
| 166 | 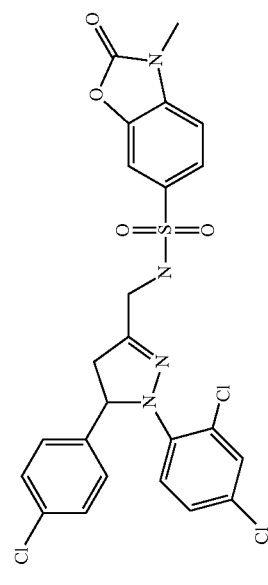 | 3-Methyl-2-oxo-2,3-dihydro-benzooxazole-6-sulfonic acid [5-(4-chloro-phenyl)-1-(2,4-dichloro-phenyl)-4,5-dihydro-1H-pyrazol-3-ylmethyl]-amide | 565 |

| | | |
|---|---|---|
| 167 | 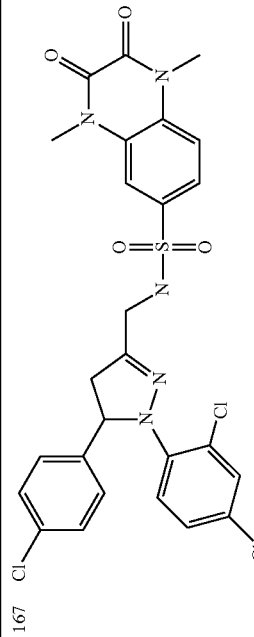 | 1,4-Dimethyl-2,3-dioxo-1,2,3,4-tetrahydro-quinoxaline-6-sulfonic acid [5-(4-chloro-phenyl)-1-(2,4-dichloro-phenyl)-4,5-dihydro-1H-pyrazol-3-ylmethyl]-amide | 606 |
| 168 | 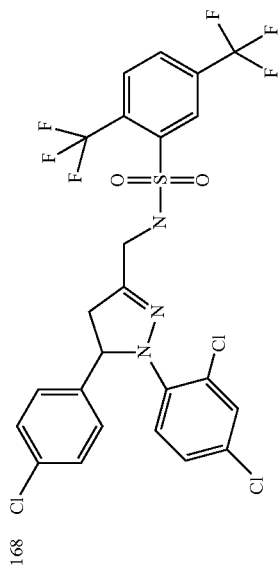 | 1,3,5-Trimethyl-1H-pyrazole-4-sulfonic acid [5-(4-chloro-phenyl)-1-(2,4-dichloro-phenyl)-4,5-dihydro-1H-pyrazol-3-ylmethyl]-amide | 526 |
| 169 | 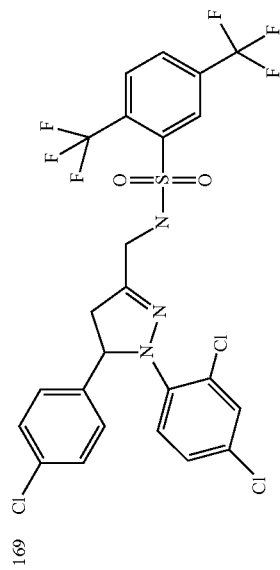 | N-[5-(4-Chloro-phenyl)-1-(2,4-dichloro-phenyl)-4,5-dihydro-1H-pyrazol-3-ylmethyl]-2,5-bis-trifluoromethyl-benzenesulfonamide | 630 |
| 170 | 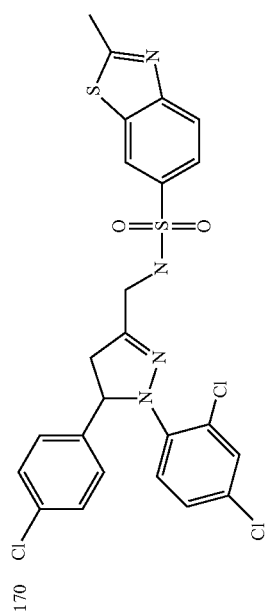 | 2-Methyl-benzothiazole-6-sulfonic acid [5-(4-chloro-phenyl)-1-(2,4-dichloro-phenyl)-4,5-dihydro-1H-pyrazol-3-ylmethyl]-amide | 565 |

| | | |
|---|---|---|
| 171 | 4-Chloro-N-[5-(4-chloro-phenyl)-1-(2,4-dichloro-phenyl)-4,5-dihydro-1H-pyrazol-3-ylmethyl]-2,5-difluoro-benzenesulfonamide | 564 |
| 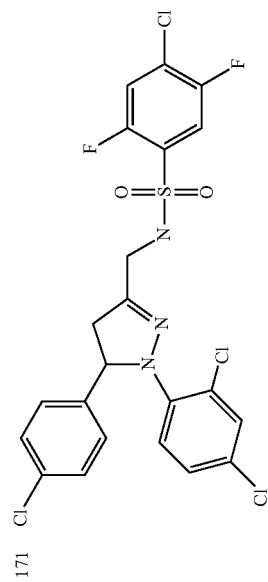 | | |
| 172 | N-[5-(4-Chloro-phenyl)-1-(2,4-dichloro-phenyl)-4,5-dihydro-1H-pyrazol-3-ylmethyl]-2,4,5-trifluoro-benzenesulfonamide | 548 |
| 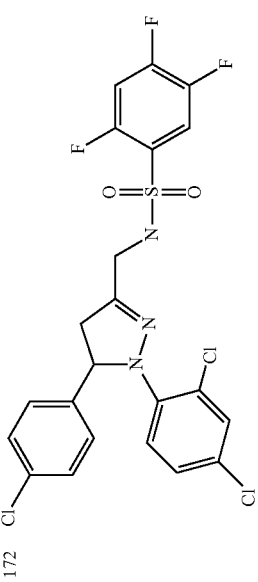 | | |
| 173 | 5-Bromo-N-[5-(4-chloro-phenyl)-1-(2,4-dichloro-phenyl)-4,5-dihydro-1H-pyrazol-3-ylmethyl]-2,4-difluoro-benzenesulfonamide | 609 |
| 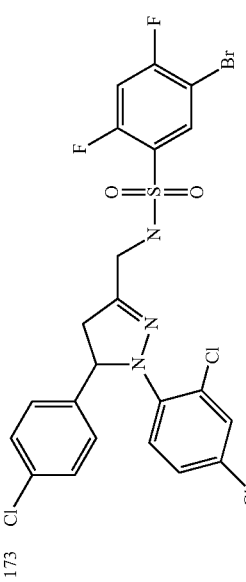 | | |
| 174 | N-[5-(4-Chloro-phenyl)-1-(2,4-dichloro-phenyl)-4,5-dihydro-1H-pyrazol-3-ylmethyl]-2-nitro-4-trifluoromethyl-benzenesulfonamide | 607 |
| 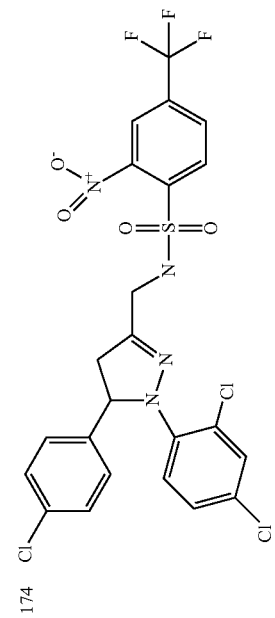 | | |

| | | | |
|---|---|---|---|
| 175 | [structure] | N-[5-(4-Chloro-phenyl)-1-(2,4-dichloro-phenyl)-4,5-dihydro-1H-pyrazol-3-ylmethyl]-2,3,4,5,6-pentafluoro-benzenesulfonamide | 584 |
| 176 | [structure] | 4-Bromo-N-[5-(4-chloro-phenyl)-1-(2,4-dichloro-phenyl)-4,5-dihydro-1H-pyrazol-3-ylmethyl]-2-trifluoromethoxy-benzenesulfonamide | 657 |
| 177 | [structure] | 5-Chloro-N-[5-(4-chloro-phenyl)-1-(2,4-dichloro-phenyl)-4,5-dihydro-1H-pyrazol-3-ylmethyl]-2,4-difluoro-benzenesulfonamide | 564 |
| 178 | [structure] | N-[5-(4-Chloro-phenyl)-1-(2,4-dichloro-phenyl)-4,5-dihydro-1H-pyrazol-3-ylmethyl]-2,3,4-trifluoro-benzenesulfonamide | 548 |

| | | |
|---|---|---|
| 179 | 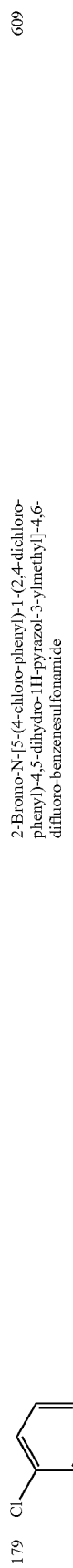 | 2-Bromo-N-[5-(4-chloro-phenyl)-1-(2,4-dichloro-phenyl)-4,5-dihydro-1H-pyrazol-3-ylmethyl]-4,6-difluoro-benzenesulfonamide | 609 |
| 180 | 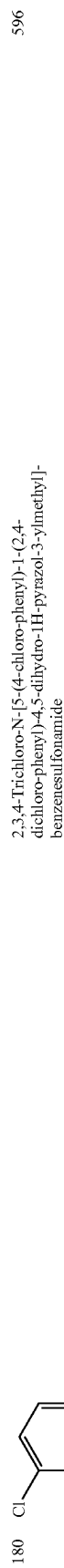 | 2,3,4-Trichloro-N-[5-(4-chloro-phenyl)-1-(2,4-dichloro-phenyl)-4,5-dihydro-1H-pyrazol-3-ylmethyl]-benzenesulfonamide | 596 |
| 181 | 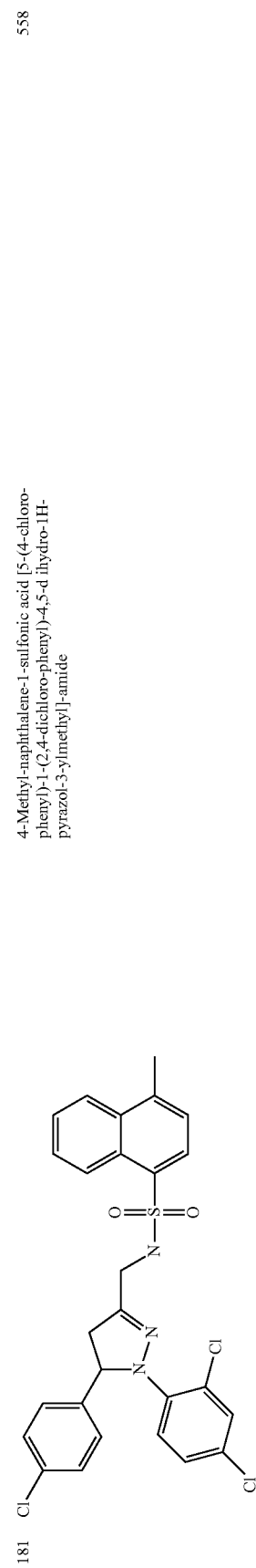 | 4-Methyl-naphthalene-1-sulfonic acid [5-(4-chloro-phenyl)-1-(2,4-dichloro-phenyl)-4,5-dihydro-1H-pyrazol-3-ylmethyl]-amide | 558 |

| | | | |
|---|---|---|---|
| 182 | 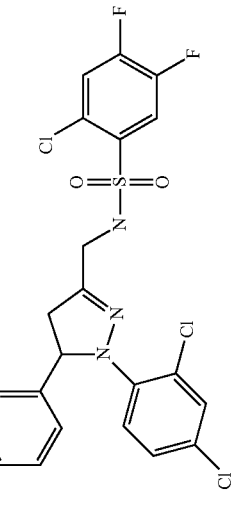 | 2-Chloro-N-[5-(4-chloro-phenyl)-1-(2,4-dichloro-phenyl)-4,5-dihydro-1H-pyrazol-3-ylmethyl]-4,5-difluoro-benzenesulfonamide | 564 |
| 183 | 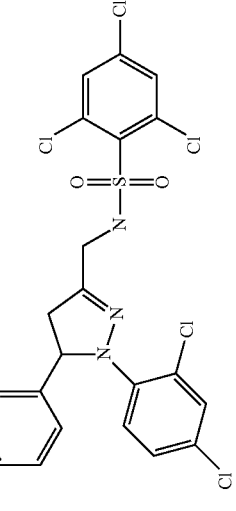 | 2,4,6-Trichloro-N-[5-(4-chloro-phenyl)-1-(2,4-dichloro-phenyl)-4,5-dihydro-1H-pyrazol-3-ylmethyl]-benzenesulfonamide | 596 |
| 184 | 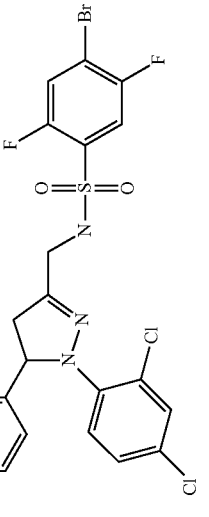 | 4-Bromo-N-[5-(4-chloro-phenyl)-1-(2,4-dichloro-phenyl)-4,5-dihydro-1H-pyrazol-3-ylmethyl]-2,5-difluoro-benzenesulfonamide | 609 |
| 185 | 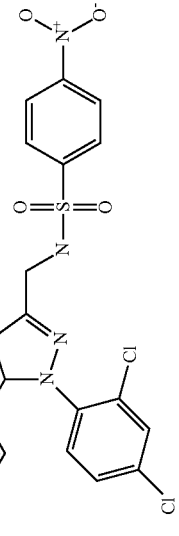 | N-[5-(4-Chloro-phenyl)-1-(2,4-dichloro-phenyl)-4,5-dihydro-1H-pyrazol-3-ylmethyl]-4-nitro-benzenesulfonamide | 539 |

| | | |
|---|---|---|
| 186 | 2,4-Dichloro-N-[5-(4-chloro-phenyl)-1-(2,4-dichloro-phenyl)-4,5-dihydro-1H-pyrazol-3-ylmethyl]-5-methyl-benzenesulfonamide 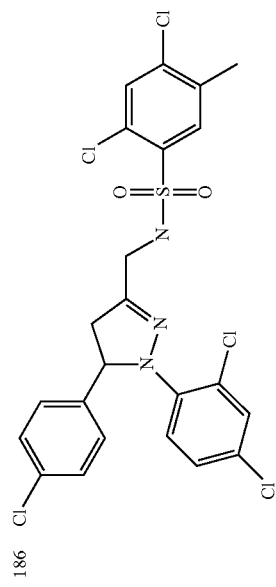 | 576 |
| 187 | Naphthalene-1-sulfonic acid [5-(4-chloro-phenyl)-1-(2,4-dichloro-phenyl)-4,5-dihydro-1H-pyrazol-3-ylmethyl]-amide 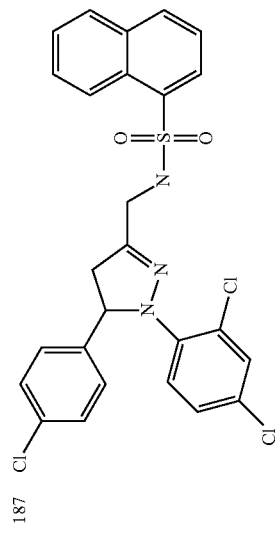 | 544 |
| 188 | N-[5-(4-Chloro-phenyl)-1-(2,4-dichloro-phenyl)-4,5-dihydro-1H-pyrazol-3-ylmethyl]-4-fluoro-2-methyl-benzenesulfonamide 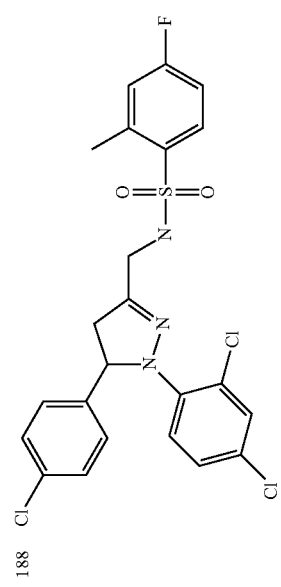 | 526 |

-continued
| | | |
|---|---|---|
| 189 | (S)-N-[5-(4-Chloro-phenyl)-1-(2,4-dichloro-phenyl)-4,5-dihydro-1H-pyrazol-3-ylmethyl]-benzenesulfonamide | 494 |
| 190 | (S)-Pyridine-3-sulfonic acid [5-(4-chloro-phenyl)-1-(2,4-dichloro-phenyl)4,5-dihydro-1H-pyrazol-3-ylmethyl]-amide hydrochloride | 495 |
| 191 | (S)-6-Chloro-imidazo[2,1-b]thiazole-5-sulfonic acid [5-(4-chloro-phenyl)-1-(2,4-dichloro-phenyl)-4,5-dihydro-1H-pyrazol-3-ylmethyl]-amide | 574 |
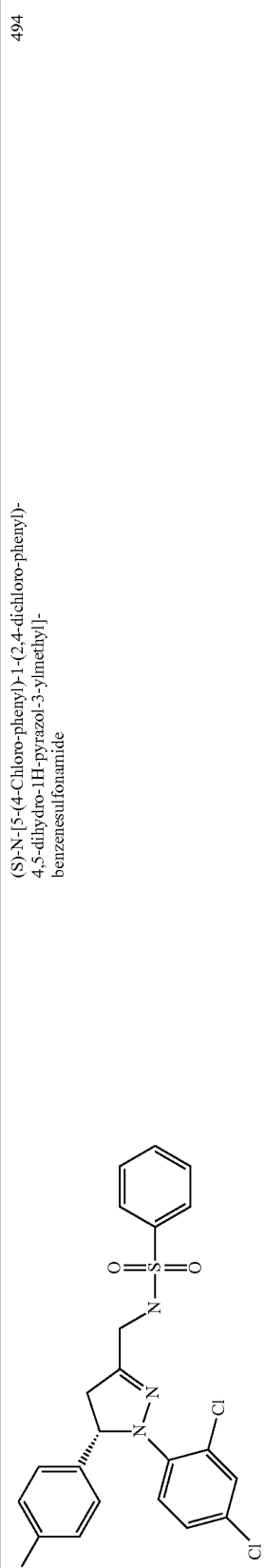
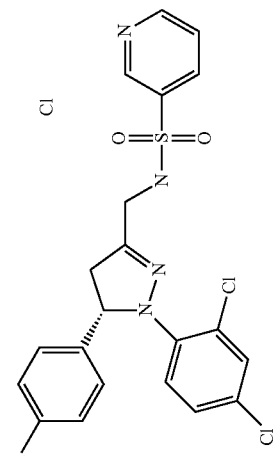
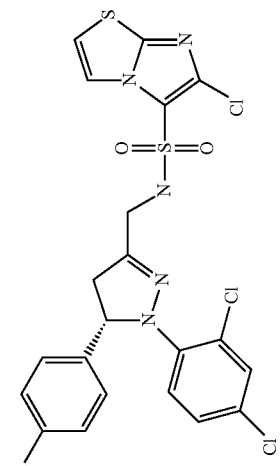

| | -continued | |
|---|---|---|
| 192 | (S)-2-Chloro-N-[5-(4-chloro-phenyl)-1-(2,4-dichloro-phenyl)-4,5-dihydro-1H-pyrazol-3-ylmethyl]-5-trifluoromethyl-benzenesulfonamide | 596 |
| 193 | (R)-N-[5-(4-Chloro-phenyl)-1-(2,4-dichloro-phenyl)-4,5-dihydro-1H-pyrazol-3-ylmethyl]-4-fluoro-2-methyl-benzenesulfonamide | 526 |
| 194 | (R)-N-[5-(4-Chloro-phenyl)-1-(2,4-dichloro-phenyl)-4,5-dihydro-1H-pyrazol-3-ylmethyl]-benzenesulfonamide | 494 |
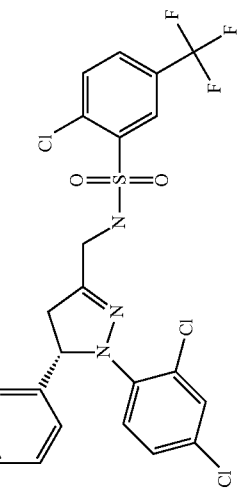
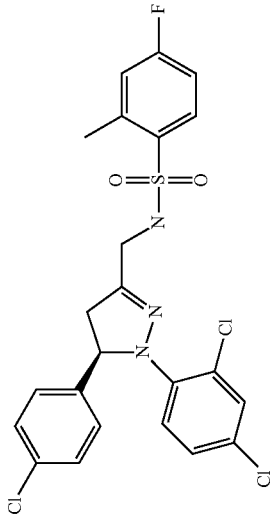
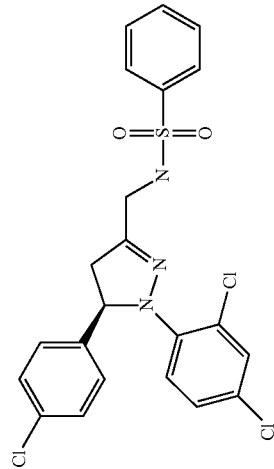

| | | |
|---|---|---|
| 195 | (R)-Pyridine-3-sulfonic acid [5-(4-chloro-phenyl)-1-(2,4-dichloro-phenyl)-4,5-dihydro-1H-pyrazol-3-ylmethyl]-amide 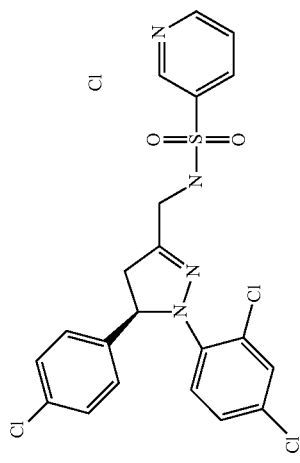 | 495 |
| 196 | (R)-6-Chloro-imidazo[2,1-b]thiazole-5-sulfonic acid [5-(4-chloro-phenyl)-1-(2,4-dichloro-phenyl)-4,5-dihydro-1H-pyrazol-3-ylmethyl]-amide 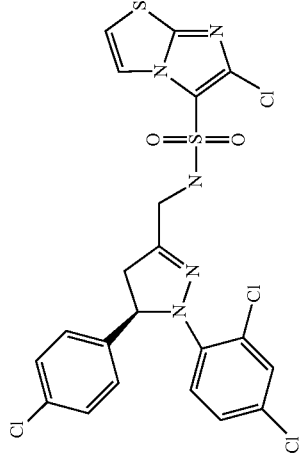 | 574 |
| 197 | (R)-2-Chloro-N-[5-(4-chloro-phenyl)-1-(2,4-dichloro-phenyl)-4,5-dihydro-1H-pyrazol-3-ylmethyl]-5-trifluoromethyl-benzenesulfonamide 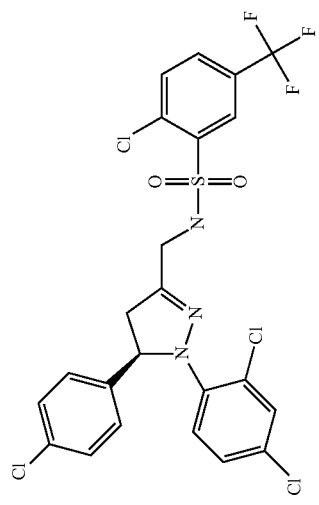 | 596 |

| | -continued | |
|---|---|---|
| 198 | N-[1-(2,4-Dichloro-phenyl)-5-(4-methoxy-phenyl)-4,5-dihydro-1H-pyrazol-3-ylmethyl]-2-fluoro-5-methyl-benzenesulfonamide 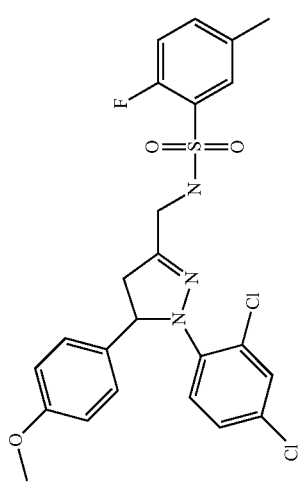 | 522 |
| 199 | N-[1-(2,4-Dichloro-phenyl)-5-(4-methoxy-phenyl)-4,5-dihydro-1H-pyrazol-3-ylmethyl]-4-fluoro-2-methyl-benzenesulfonamide 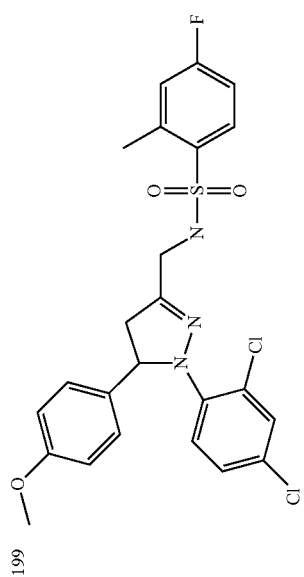 | 522 |
| 200 | N-[1-(2,4-Dichloro-phenyl)-5-(4-methoxy-phenyl)-4,5-dihydro-1H-pyrazolylmethyl]-benzenesulfonamide 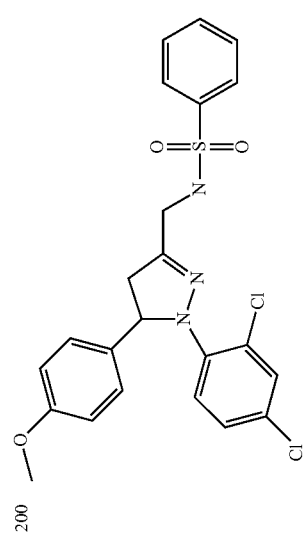 | 490 |

| | -continued | | |
|---|---|---|---|
| 201 | Pyridine-3-sulfonic acid [1-(2,4-dichloro-phenyl)-5-(4-methoxy-phenyl)-4,5-dihydro-1H-pyrazol-3-ylmethyl]-amide hydrochloride | 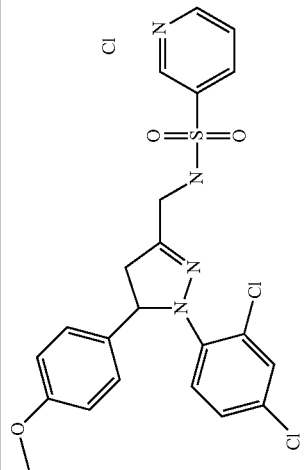 | 491 |
| 202 | 6-Chloro-imidazo[2,1-b]thiazole-5-sulfonic acid [1-(2,4-dichloro-phenyl)-5-(4-methoxy-phenyl)-4,5-dihydro-1H-pyrazol-3-ylmethyl]-amide | 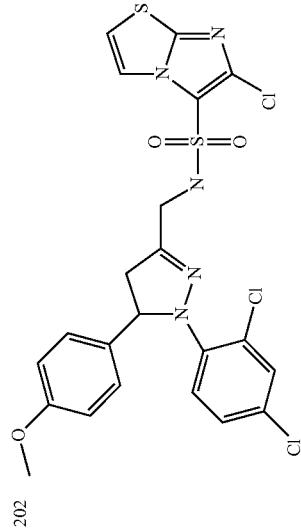 | 570 |
| 203 | N-[1-(2,4-Dichloro-phenyl)-5-(4-methoxy-phenyl)-4,5-dihydro-1H-pyrazol-3-ylmethyl]-2-methoxy-5-methyl-benzenesulfonamide | 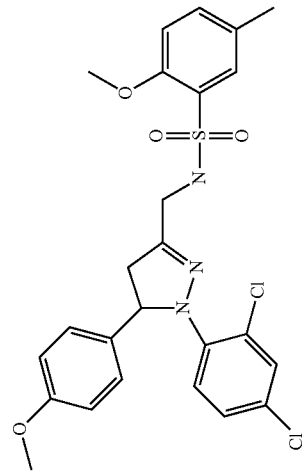 | 534 |

| | | |
|---|---|---|
| 204 | N-(1-(2,4-Dichloro-phenyl)-5-(4-ethoxy-phenyl)-4,5-dihydro-1H-pyrazol-3-ylmethyl]-2-fluoro-5-methyl-benzenesulfonamide 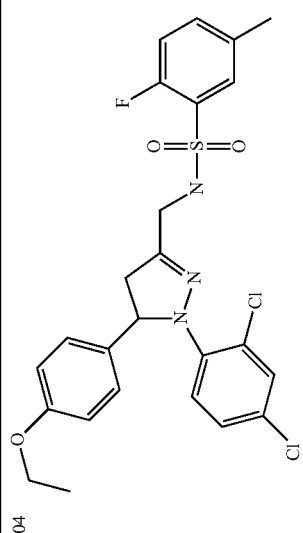 | 536 |
| 205 | N-[1-(2,4-Dichloro-phenyl)-5-(4-ethoxy-phenyl)-4,5-dihydro-1H-pyrazol-3-ylmethyl]-4-fluoro-2-methyl-benzenesulfonamide 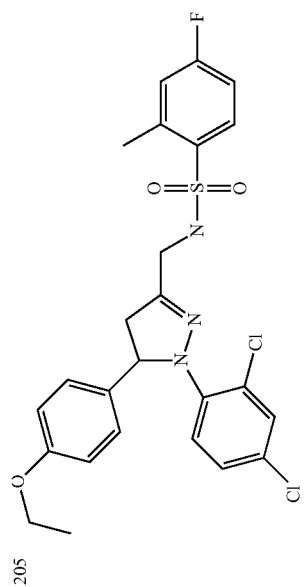 | 536 |
| 206 | N-(1-(2,4-Dichloro-phenyl)-5-(4-ethoxy-phenyl)-4,5-dihydro-1H-pyrazol-3-ylmethyl]-benzenesulfonamide 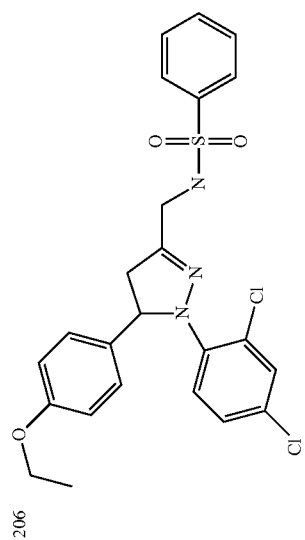 | 504 |

| | | |
|---|---|---|
| 207 | Pyridine-3-sulfonic acid [1-(2,4-dichloro-phenyl)-5-(4-ethoxy-phenyl)-4,5-dihydro-1H-pyrazol-3-ylmethyl]-amide 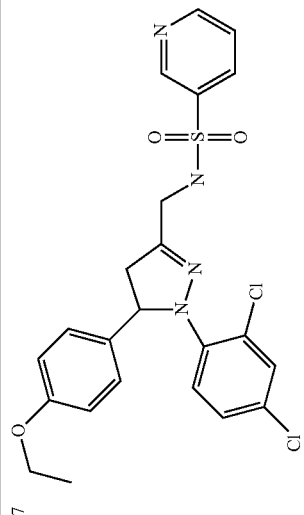 | 505 |
| 208 | 6-Chloro-imidazo[2,1-b]thiazole-5-sulfonic acid [1-(2,4-dichloro-phenyl)-5-(4-ethoxy-phenyl)-4,5-dihydro-1H-pyrazol-3-ylmethyl]-amide 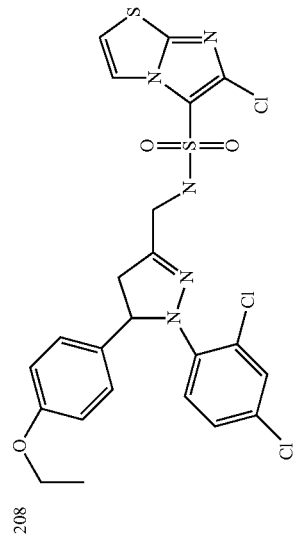 | 584 |
| 209 | N-[1-(2,4-Dichloro-phenyl)-5-(4-ethoxy-phenyl)-4,5-dihydro-1H-pyrazol-3-ylmethyl]-2-methoxy-5-methyl-benzenesulfonamide 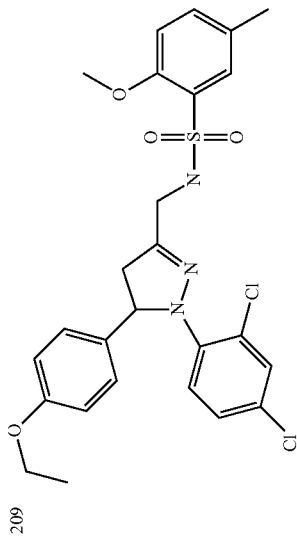 | 548 |

| | | |
|---|---|---|
| 210 | N-[1-(2,4-Dichloro-phenyl)-5-(4-ethoxy-phenyl)-4,5-dihydro-1H-pyrazol-3-ylmethyl]-2,6-difluoro-benzenesulfonamide | 540 |
| 211 | 2-Chloro-N-[1-(2,4-dichloro-phenyl)-5-(4-ethoxy-phenyl)-4,5-dihydro-1H-pyrazol-3-ylmethyl]-benzenesulfonamide | 538 |
| 212 | N-[1-(2,4-Dichloro-phenyl)-5-(4-ethoxy-phenyl)-4,5-dihydro-1H-pyrazol-3-ylmethyl]-2,4-difluoro-benzenesulfonamide | 540 |
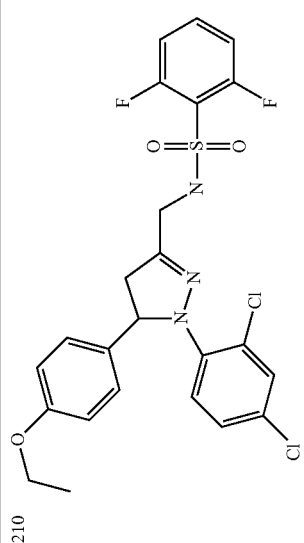
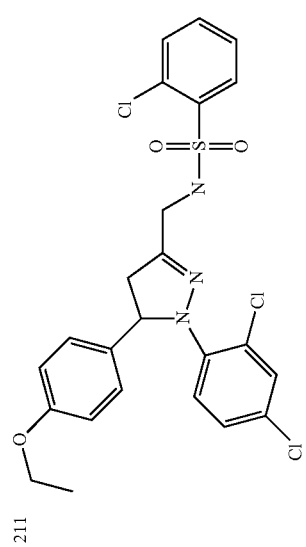
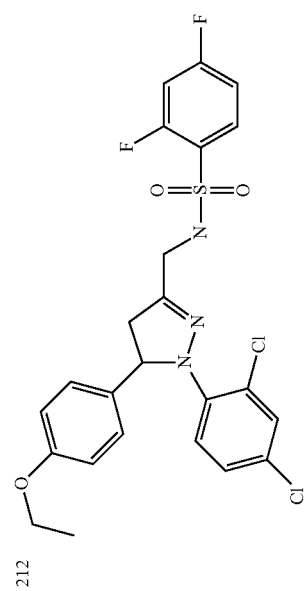

| | | |
|---|---|---|
| 213 | 2-Chloro-N-[1-(2,4-dichloro-phenyl)-5-(4-ethoxy-phenyl)-4,5-dihydro-1H-pyrazol-3-ylmethyl]-6-methyl-benzenesulfonamide 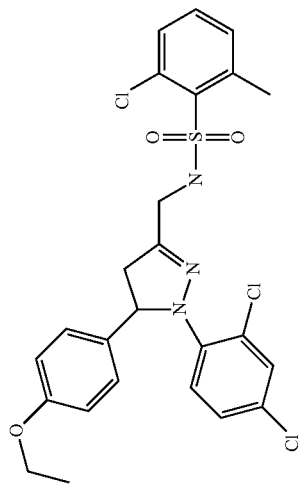 | 552 |
| 214 | N-[1-(2,4-Dichloro-phenyl)-5-(4-ethoxy-phenyl)-4,5-dihydro-1H-pyrazol-3-ylmethyl]-3-methyl-benzenesulfonamide 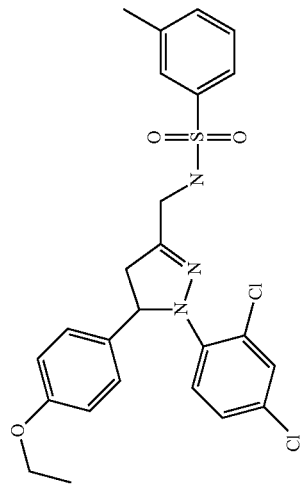 | 518 |
| 215 | N-[1-(2,4-Dichloro-phenyl)-5-(4-ethoxy-phenyl)-4,5-dihydro-1H-pyrazol-3-ylmethyl]-3-methoxy-benzenesulfonamide 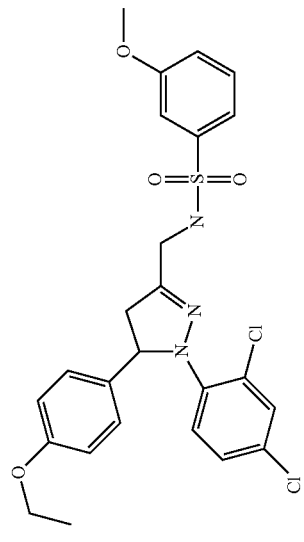 | 534 |

| | | |
|---|---|---|
| 216 | 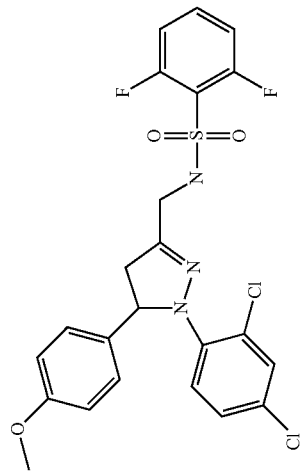 N-[1-(2,4-Dichloro-phenyl)-5-(4-methoxy-phenyl)-4,5-dihydro-1H-pyrazol-3-ylmethyl]-2,6-difluoro-benzenesulfonamide | 526 |
| 217 | 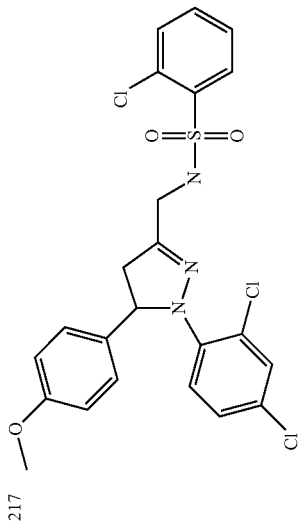 2-Chloro-N-[1-(2,4-dichloro-phenyl)-5-(4-methoxy-phenyl)-4,5-dihydro-1H-pyrazol-3-ylmethyl]-benzenesulfonamide | 524 |
| 218 | 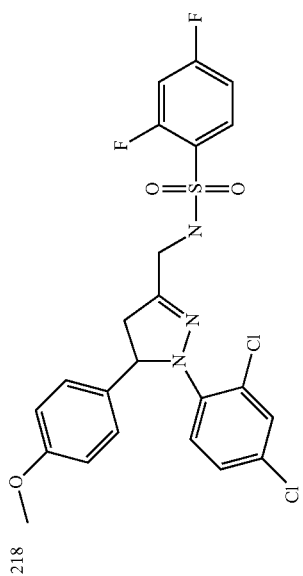 N-[1-(2,4-Dichloro-phenyl)-5-(4-methoxy-phenyl)-4,5-dihydro-1H-pyrazol-3-ylmethyl]-2,4-difluoro-benzenesulfonamide | 526 |

| | | |
|---|---|---|
| 219 | 2-Chloro-N-[1-(2,4-dichloro-phenyl)-5-(4-methoxy-phenyl)-4,5-dihydro-1H-pyrazol-3-ylmethyl]-6-methyl-benzenesulfonamide 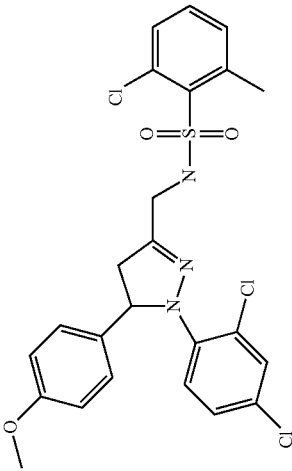 | 538 |
| 220 | N-[1-(2,4-Dichloro-phenyl)-5-(4-methoxy-phenyl)-4,5-dihydro-1H-pyrazol-3-ylmethyl]-3-methyl-benzenesulfonamide 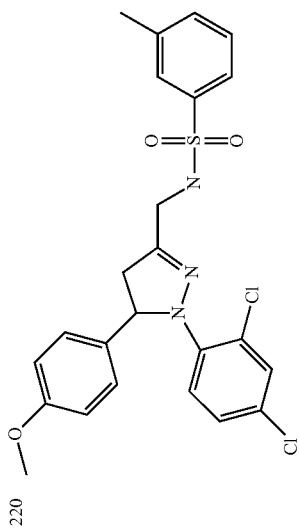 | 504 |
| 221 | N-[1-(2,4-Dichloro-phenyl)-5-(4-methoxy-phenyl)-4,5-dihydro-1H-pyrazol-3-ylmethyl]-3-methoxy-benzenesulfonamide 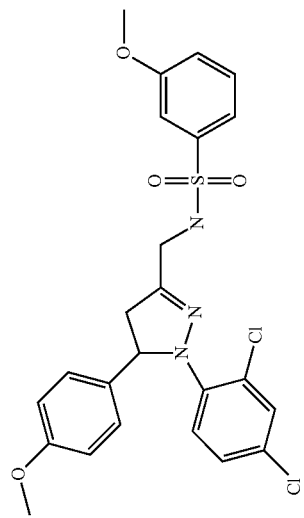 | 520 |

-continued
| | | |
|---|---|---|
| 222 | 1,2,3,4-Tetrahydro-isoquinoline-7-sulfonic acid [5-(4-chloro-phenyl)-1-(2,4-dichloro-phenyl)-4,5-dihydro-1H-pyrazol-3-ylmethyl]-amide | 549 |
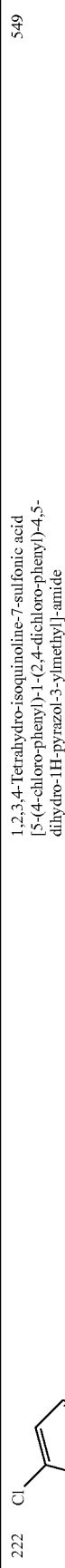
| | | |
|---|---|---|
| 223 | Benzo[1,2,5]oxadiazole-4-sulfonic acid [1-(2,4-dichloro-phenyl)-5-(4-methoxy-phenyl)-4,5-dihydro-1H-pyrazol-3-ylmethyl]-amide | 532 |
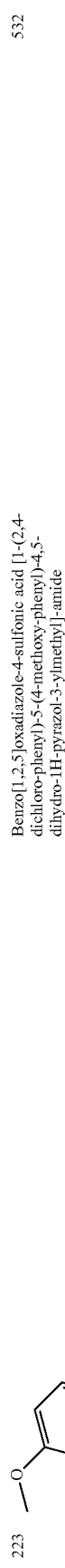
| | | |
|---|---|---|
| 224 | N-[1-(2,4-Dichloro-phenyl)-5-(4-methoxy-phenyl)-4,5-dihydro-1H-pyrazol-3-ylmethyl]-4-methanesulfonyl-benzenesulfonamide | 568 |

| | | |
|---|---|---|
| 225 | 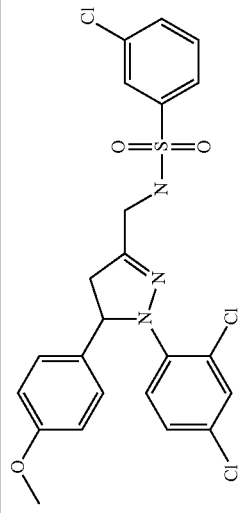 3-Chloro-N-[1-(2,4-dichloro-phenyl)-5-(4-methoxy-phenyl)-4,5-dihydro-1H-pyrazol-3-ylmethyl]-benzenesulfonamide | 524 |
| 226 | 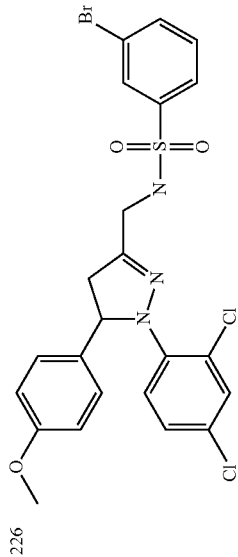 3-Bromo-N-[1-(2,4-dichloro-phenyl)-5-(4-methoxy-phenyl)-4,5-dihydro-1H-pyrazol-3-ylmethyl]-benzenesulfonamide | 569 |
| 227 | 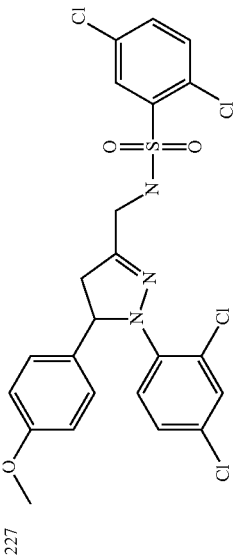 2,5-Dichloro-N-[1-(2,4-dichloro-phenyl)-5-(4-methoxy-phenyl)-4,5-dihydro-1H-pyrazol-3-ylmethyl]-benzenesulfonamide | 558 |
| 228 | 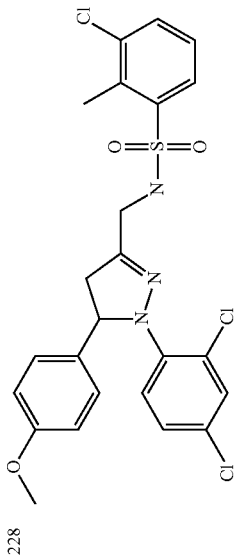 3-Chloro-N-[1-(2,4-dichloro-phenyl)-5-(4-methoxy-phenyl)-4,5-dihydro-1H-pyrazol-3-ylmethyl]-2-methyl-benzenesulfonamide | 538 |

| | -continued | | |
|---|---|---|---|
| 229 | Benzo[1,2,5]oxadiazole-4-sulfonic acid [1-(2,4-dichloro-phenyl)-5-(4-ethoxy-phenyl)-4,5-dihydro-1H-pyrazol-3-ylmethyl]-amide | | 546 |
| 230 | N-[1-(2,4-Dichloro-phenyl)-5-(4-ethoxy-phenyl)-4,5-dihydro-1H-pyrazol-3-ylmethyl]-4-methanesulfonyl-benzenesulfonamide | | 582 |
| 231 | 3-Chloro-N-[1-(2,4-dichloro-phenyl)-5-(4-ethoxy-phenyl)-4,5-dihydro-1H-pyrazol-3-ylmethyl]-benzenesulfonamide | | 538 |
| 232 | 3-Bromo-N-[1-(2,4-dichloro-phenyl)-5-(4-ethoxy-phenyl)-4,5-dihydro-1H-pyrazol-3-ylmethyl]-benzenesulfonamide | | 583 |

| | | | |
|---|---|---|---|
| 233 | 2,5-Dichloro-N-[1-(2,4-dichloro-phenyl)-5-(4-ethoxy-phenyl)-4,5-dihydro-1H-pyrazol-3-ylmethyl]-benzenesulfonamide | 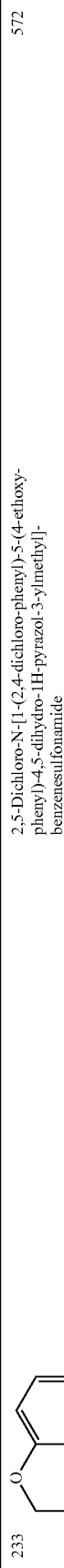 | 572 |
| 234 | 3-Chloro-N-[1-(2,4-dichloro-phenyl)-5-(4-ethoxy-phenyl)-4,5-dihydro-1H-pyrazol-3-ylmethyl]-2-methyl-benzenesulfonamide | 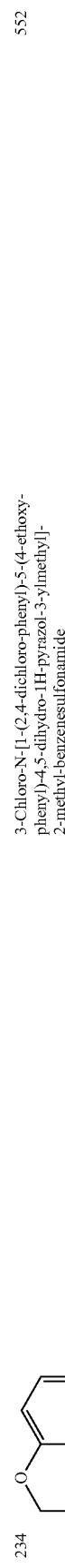 | 552 |
| 235 | (R)-Benzo[1,2,5]oxadiazole-4-sulfonic acid [5-(4-chloro-phenyl)-1-(2,4-dichloro-phenyl)-4,5-dihydro-1H-pyrazol-3-ylmethyl]-amide | 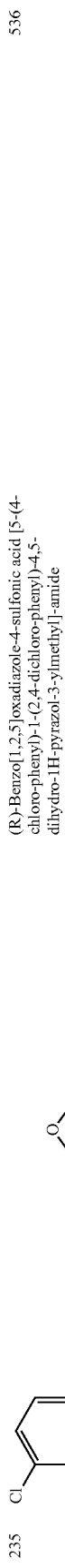 | 536 |
| 236 | (R)-N-[5-(4-Chloro-phenyl)-1-(2,4-dichloro-phenyl)-4,5-dihydro-1H-pyrazol-3-ylmethyl]-4-methanesulfonyl-benzenesulfonamide | 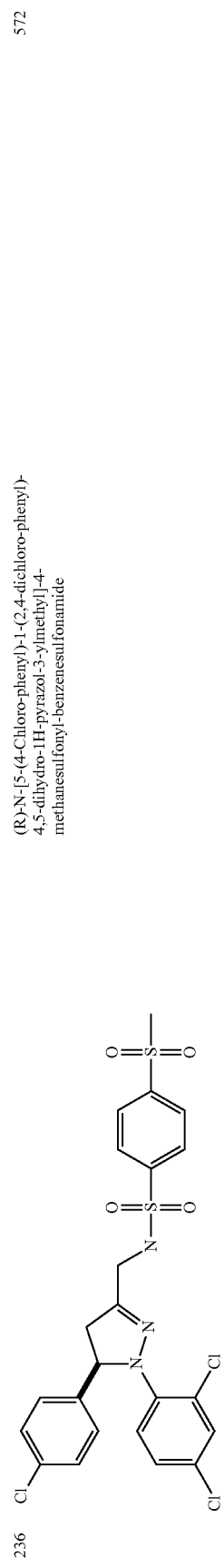 | 572 |

| | | | |
|---|---|---|---|
| 237 | 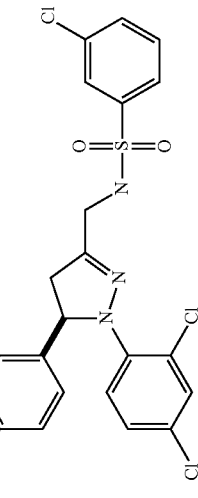 | (R)-3-Chloro-N-[5-(4-chloro-phenyl)-1-(2,4-dichloro-phenyl)-4,5-dihydro-1H-pyrazol-3-ylmethyl]-benzenesulfonamide | 528 |
| 238 | 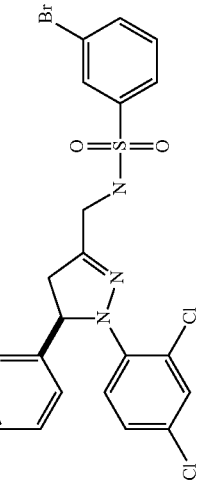 | (R)-3-Bromo-N-[5-(4-chloro-phenyl)-1-(2,4-dichloro-phenyl)-4,5-dihydro-1H-pyrazol-3-ylmethyl]-benzenesulfonamide | 573 |
| 239 | 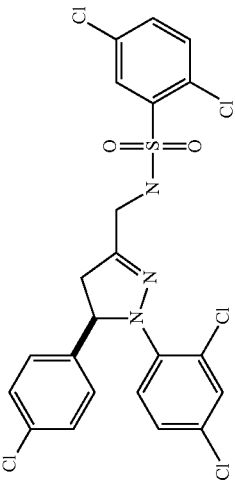 | (R)-2,5-Dichloro-N-[5-(4-chloro-phenyl)-1-(2,4-dichloro-phenyl)-4,5-dihydro-1H-pyrazol-3-ylmethyl]-benzenesulfonamide | 562 |
| 240 | 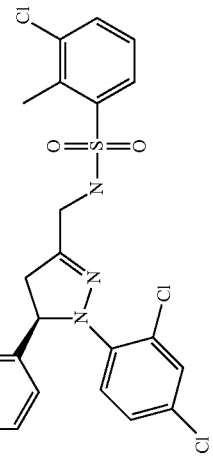 | 3-Chloro-N-[5-(4-chloro-phenyl)-1-(2,4-dichloro-phenyl)-4,5-dihydro-1H-pyrazol-3-ylmethyl]-2-methyl-benzenesulfonamide | 542 |

| 241 | 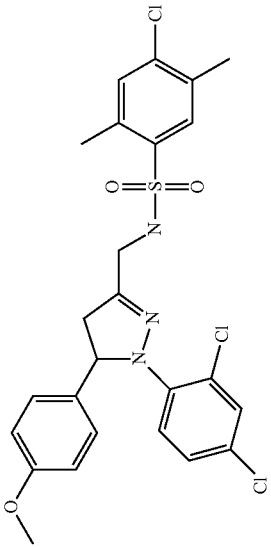 | 4-Chloro-N-[1-(2,4-dichloro-phenyl)-5-(4-methoxy-phenyl)-4,5-dihydro-1H-pyrazol-3-ylmethyl]-2,5-dimethyl-benzenesulfonamide | 552 |
| --- | --- | --- | --- |
| 242 | 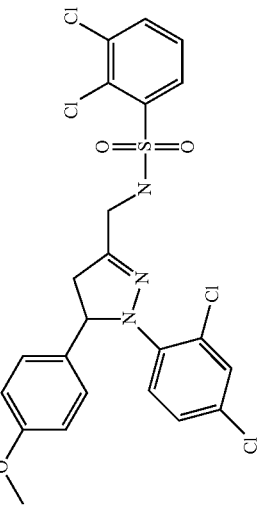 | 2,3-Dichloro-N-[1-(2,4-dichloro-phenyl)-5-(4-methoxy-phenyl)-4,5-dihydro-1H-pyrazol-3-ylmethyl]-benzenesulfonamide | 558 |
| 243 | 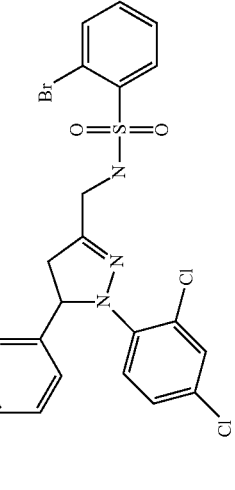 | 2-Bromo-N-[1-(2,4-dichloro-phenyl)-5-(4-methoxy-phenyl)-4,5-dihydro-1H-pyrazol-3-ylmethyl]-benzenesulfonamide | 569 |
| 244 | 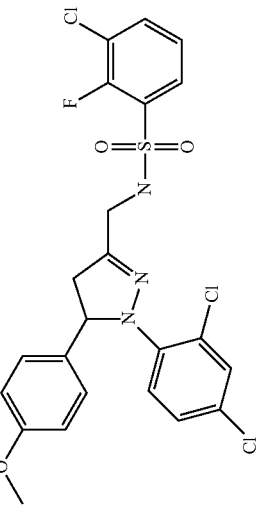 | 3-Chloro-N-[1-(2,4-dichloro-phenyl)-5-(4-methoxy-phenyl)-4,5-dihydro-1H-pyrazol-3-ylmethyl]-2-fluoro-benzenesulfonamide | 542 |

| | | |
|---|---|---|
| 245 | 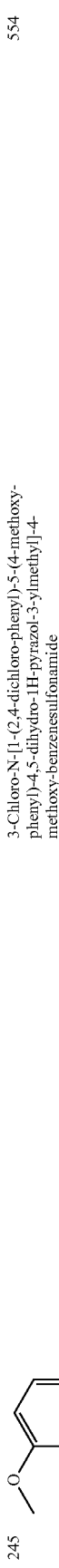 3-Chloro-N-[1-(2,4-dichloro-phenyl)-5-(4-methoxy-phenyl)-4,5-dihydro-1H-pyrazol-3-ylmethyl]-4-methoxy-benzenesulfonamide | 554 |
| 246 | 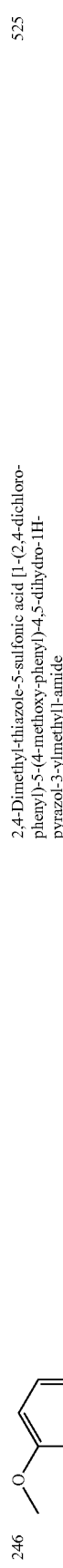 2,4-Dimethyl-thiazole-5-sulfonic acid [1-(2,4-dichloro-phenyl)-5-(4-methoxy-phenyl)-4,5-dihydro-1H-pyrazol-3-ylmethyl]-amide | 525 |
| 247 | 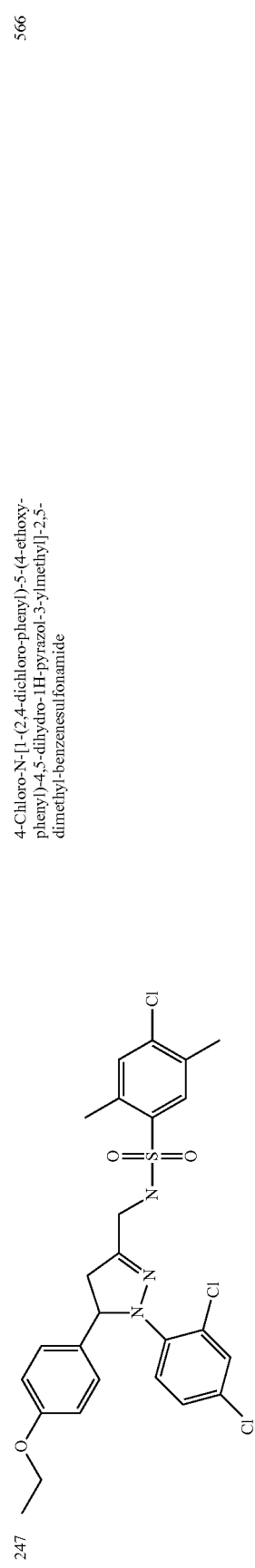 4-Chloro-N-[1-(2,4-dichloro-phenyl)-5-(4-ethoxy-phenyl)-4,5-dihydro-1H-pyrazol-3-ylmethyl]-2,5-dimethyl-benzenesulfonamide | 566 |

| | | -continued | |
|---|---|---|---|
| 248 | 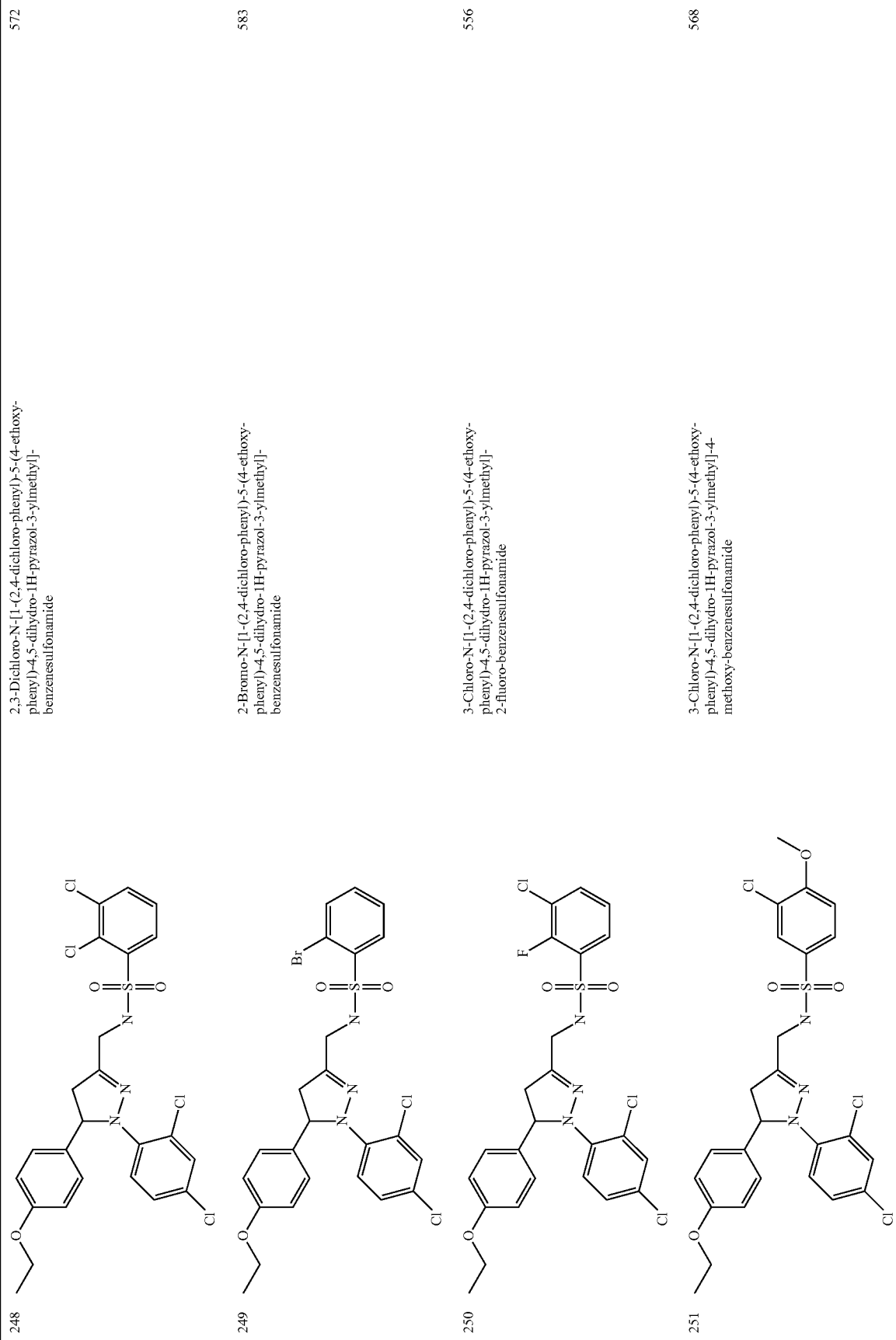 | 2,3-Dichloro-N-[1-(2,4-dichloro-phenyl)-5-(4-ethoxy-phenyl)-4,5-dihydro-1H-pyrazol-3-ylmethyl]-benzenesulfonamide | 572 |
| 249 | | 2-Bromo-N-[1-(2,4-dichloro-phenyl)-5-(4-ethoxy-phenyl)-4,5-dihydro-1H-pyrazol-3-ylmethyl]-benzenesulfonamide | 583 |
| 250 | | 3-Chloro-N-[1-(2,4-dichloro-phenyl)-5-(4-ethoxy-phenyl)-4,5-dihydro-1H-pyrazol-3-ylmethyl]-2-fluoro-benzenesulfonamide | 556 |
| 251 | | 3-Chloro-N-[1-(2,4-dichloro-phenyl)-5-(4-ethoxy-phenyl)-4,5-dihydro-1H-pyrazol-3-ylmethyl]-4-methoxy-benzenesulfonamide | 568 |

| | | |
|---|---|---|
| 252 | 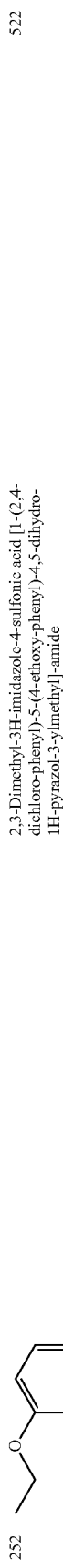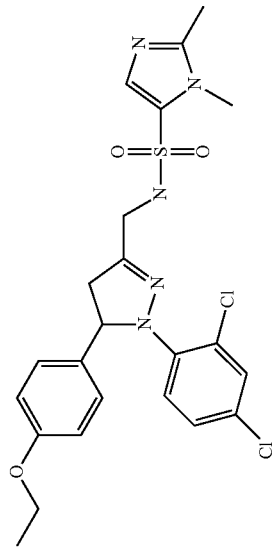 | 2,3-Dimethyl-3H-imidazole-4-sulfonic acid [1-(2,4-dichloro-phenyl)-5-(4-ethoxy-phenyl)-4,5-dihydro-1H-pyrazol-3-ylmethyl]-amide | 522 |
| 253 | 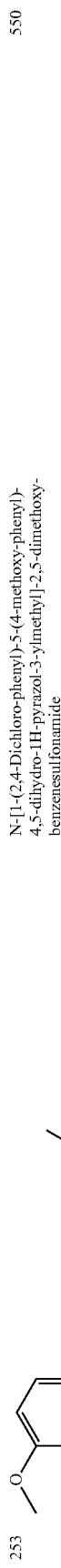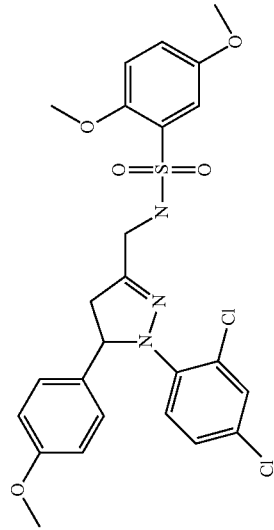 | N-[1-(2,4-Dichloro-phenyl)-5-(4-methoxy-phenyl)-4,5-dihydro-1H-pyrazol-3-ylmethyl]-2,5-dimethoxy-benzenesulfonamide | 550 |
| 254 | 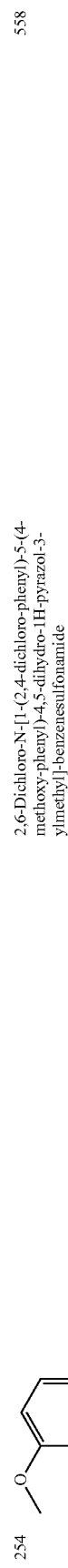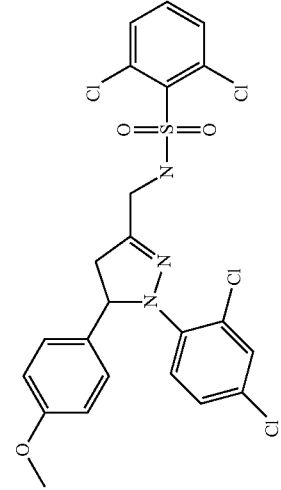 | 2,6-Dichloro-N-[1-(2,4-dichloro-phenyl)-5-(4-methoxy-phenyl)-4,5-dihydro-1H-pyrazol-3-ylmethyl]-benzenesulfonamide | 558 |

| | | |
|---|---|---|
| 255 | 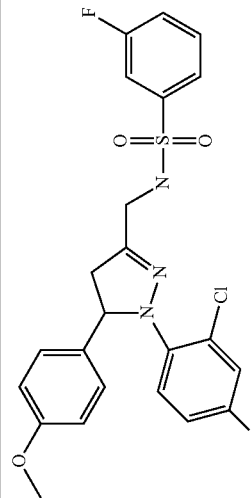 | N-[1-(2,4-Dichloro-phenyl)-5-(4-methoxy-phenyl)-4,5-dihydro-1H-pyrazol-3-ylmethyl]-3-fluoro-benzenesulfonamide | 508 |
| 256 | 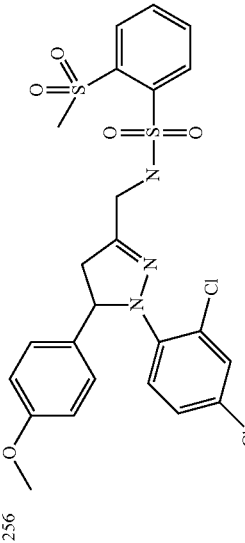 | N-[1-(2,4-Dichloro-phenyl)-5-(4-methoxy-phenyl)-4,5-dihydro-1H-pyrazol-3-ylmethyl]-2-methanesulfonyl-benzenesulfonamide | 568 |
| 257 | 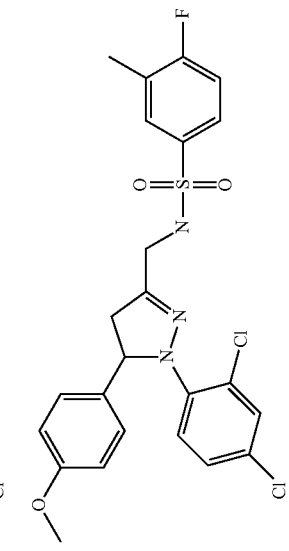 | N-[1-(2,4-Dichloro-phenyl)-5-(4-methoxy-phenyl)-4,5-dihydro-1H-pyrazol-3-ylmethyl]-4-fluoro-3-methyl-benzenesulfonamide | 522 |
| 258 | 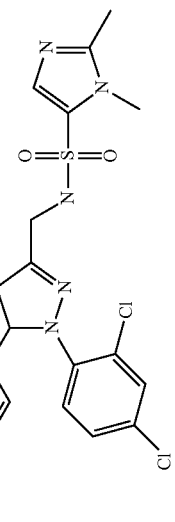 | 2,3-Dimethyl-3H-imidazole-4-sulfonic acid [1-(2,4-dichloro-phenyl)-5-(4-methoxy-phenyl)-4,5-dihydro-1H-pyrazol-3-ylmethyl]-amide | 508 |

| | -continued | | |
|---|---|---|---|
| 259 | 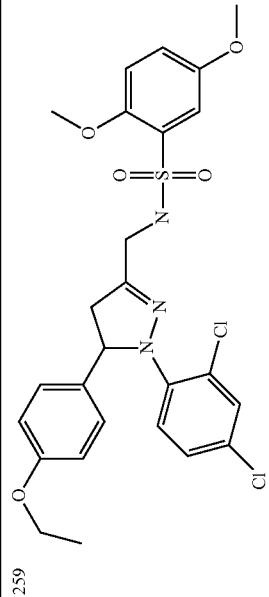 | N-[1-(2,4-Dichloro-phenyl)-5-(4-ethoxy-phenyl)-4,5-dihydro-1H-pyrazol-3-ylmethyl]-2,5-dimethoxy-benzenesulfonamide | 564 |
| 260 | 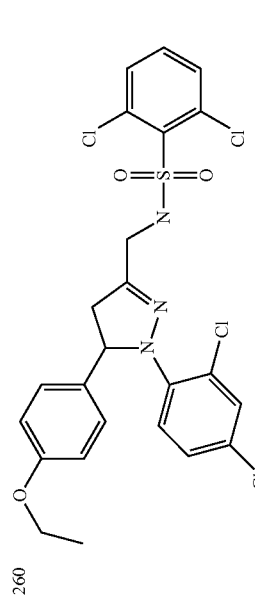 | 2,6-Dichloro-N-[1-(2,4-dichloro-phenyl)-5-(4-ethoxy-phenyl)-4,5-dihydro-1H-pyrazol-3-ylmethyl]-benzenesulfonamide | 572 |
| 261 | 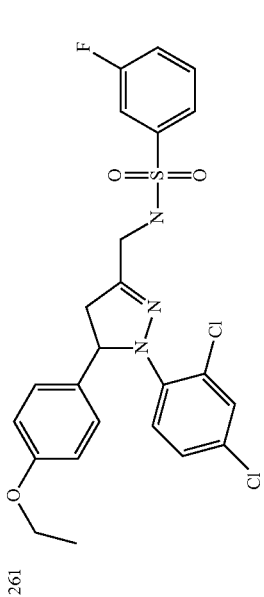 | N-[1-(2,4-Dichloro-phenyl)-5-(4-ethoxy-phenyl)-4,5-dihydro-1H-pyrazol-3-ylmethyl]-3-fluoro-benzenesulfonamide | 522 |
| 262 | 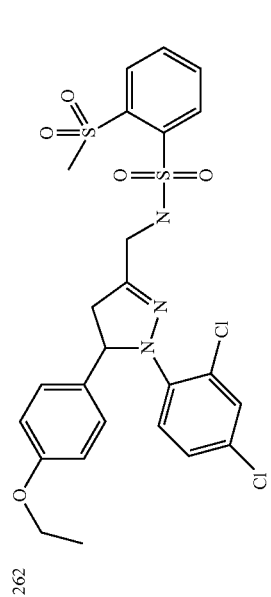 | N-[1-(2,4-Dichloro-phenyl)-5-(4-ethoxy-phenyl)-4,5-dihydro-1H-pyrazol-3-ylmethyl]-2-methanesulfonyl-benzenesulfonamide | 582 |

| | -continued | | |
|---|---|---|---|
| 263 |  | N-[1-(2,4-Dichloro-phenyl)-5-(4-ethoxy-phenyl)-4,5-dihydro-1H-pyrazol-3-ylmethyl]-4-fluoro-3-methyl-benzenesulfonamide | 536 |
| 264 | 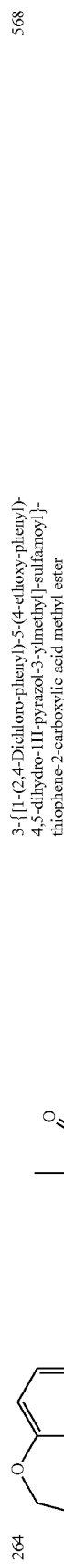 | 3-{[1-(2,4-Dichloro-phenyl)-5-(4-ethoxy-phenyl)-4,5-dihydro-1H-pyrazol-3-ylmethyl]-sulfamoyl}-thiophene-2-carboxylic acid methyl ester | 568 |
| 265 | 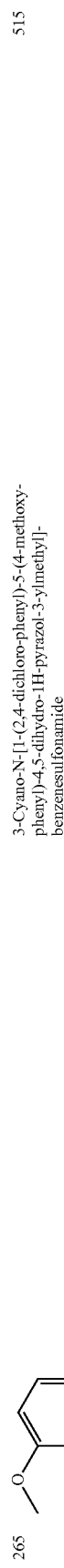 | 3-Cyano-N-[1-(2,4-dichloro-phenyl)-5-(4-methoxy-phenyl)-4,5-dihydro-1H-pyrazol-3-ylmethyl]-benzenesulfonamide | 515 |
| 266 | 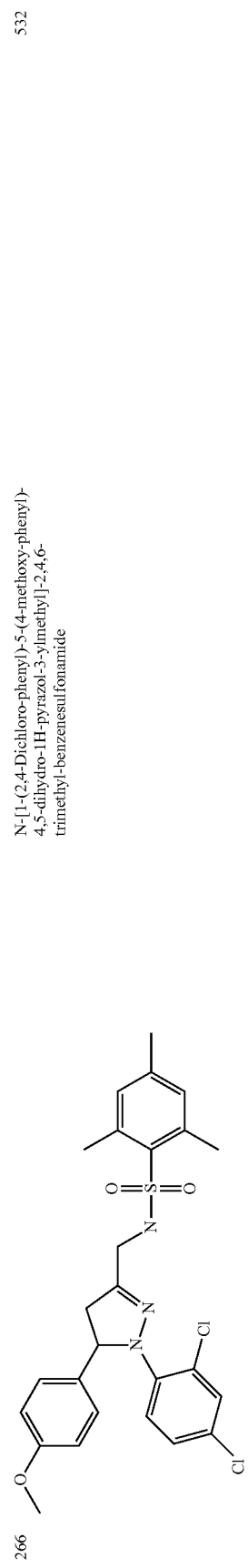 | N-[1-(2,4-Dichloro-phenyl)-5-(4-methoxy-phenyl)-4,5-dihydro-1H-pyrazol-3-ylmethyl]-2,4,6-trimethyl-benzenesulfonamide | 532 |

| | | -continued | |
|---|---|---|---|
| 267 | 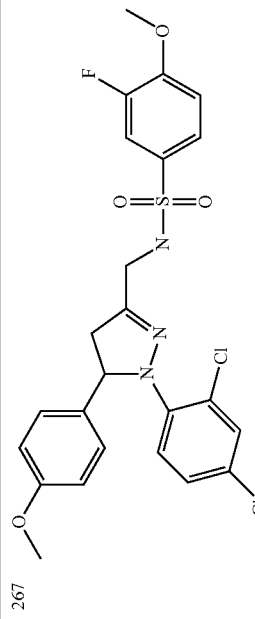 | N-[1-(2,4-Dichloro-phenyl)-5-(4-methoxy-phenyl)-4,5-dihydro-1H-pyrazol-3-ylmethyl]-3-fluoro-4-methoxy-benzenesulfonamide | 538 |
| 268 | 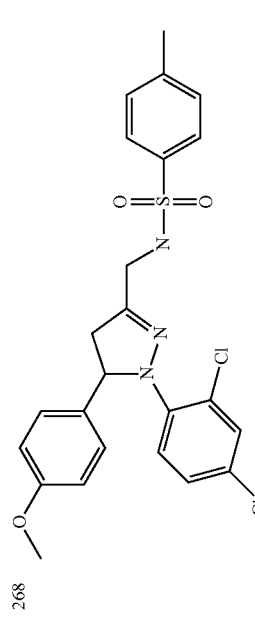 | N-[1-(2,4-Dichloro-phenyl)-5-(4-methoxy-phenyl)-4,5-dihydro-1H-pyrazol-3-ylmethyl]-4-methyl-benzenesulfonamide | 504 |
| 269 | 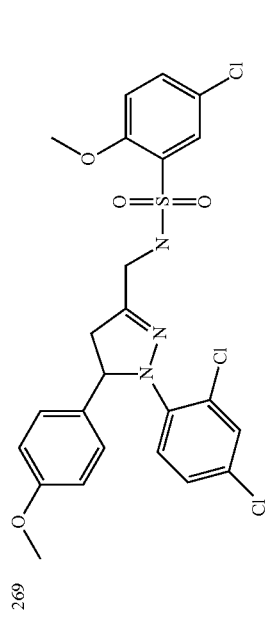 | 5-Chloro-N-[1-(2,4-dichloro-phenyl)-5-(4-methoxy-phenyl)-4,5-dihydro-1H-pyrazol-3-ylmethyl]-2-methoxy-benzenesulfonamide | 554 |
| 270 | 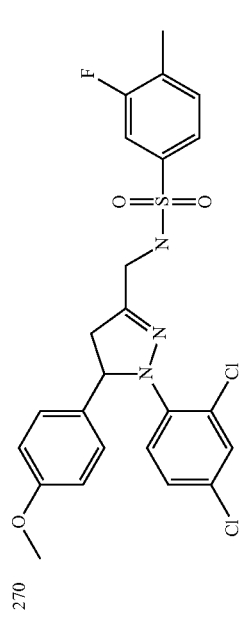 | N-[1-(2,4-Dichloro-phenyl)-5-(4-methoxy-phenyl)-4,5-dihydro-1H-pyrazol-3-ylmethyl]-3-fluoro-4-methyl-benzenesulfonamide | 522 |

| | | | |
|---|---|---|---|
| 271 | 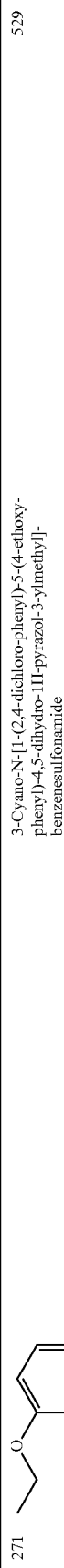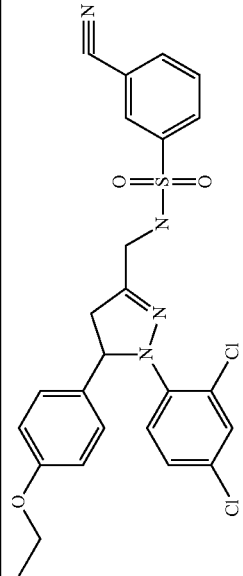 | 3-Cyano-N-[1-(2,4-dichloro-phenyl)-5-(4-ethoxy-phenyl)-4,5-dihydro-1H-pyrazol-3-ylmethyl]-benzenesulfonamide | 529 |
| 272 | | N-[1-(2,4-Dichloro-phenyl)-5-(4-ethoxy-phenyl)-4,5-dihydro-1H-pyrazol-3-ylmethyl]-2,4,6-trimethyl-benzenesulfonamide | 546 |
| 273 | 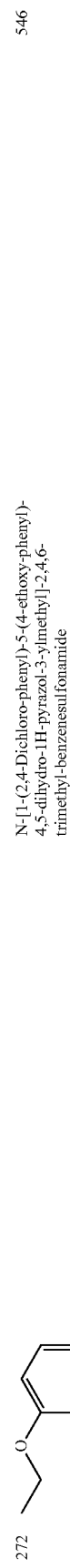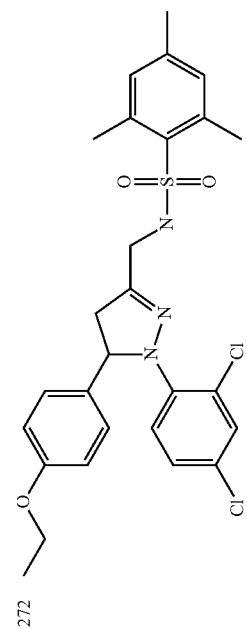 | N-[1-(2,4-Dichloro-phenyl)-5-(4-ethoxy-phenyl)-4,5-dihydro-1H-pyrazol-3-ylmethyl]-3-fluoro-4-methoxy-benzenesulfonamide | 552 |
| 274 | | N-[1-(2,4-Dichloro-phenyl)-5-(4-ethoxy-phenyl)-4,5-dihydro-1H-pyrazol-3-ylmethyl]-4-methyl-benzenesulfonamide | 518 |

| | | | |
|---|---|---|---|
| 275 |  | 5-Chloro-N-[1-(2,4-dichloro-phenyl)-5-(4-ethoxy-phenyl)-4,5-dihydro-1H-pyrazol-3-ylmethyl]-2-methoxy-benzenesulfonamide | 568 |
| 276 | | N-[1-(2,4-Dichloro-phenyl)-5-(4-ethoxy-phenyl)-4,5-dihydro-1H-pyrazol-3-ylmethyl]-3-fluoro-4-methyl-benzenesulfonamide | 536 |
| 277 | | N-[5-(4-Bromo-phenyl)-1-(2,4-dichloro-phenyl)-4,5-dihydro-1H-pyrazol-3-ylmethyl]-5-fluoro-2-methyl-benzenesulfonamide | 571 |
| 278 | | N-[5-(4-Bromo-phenyl)-1-(2,4-dichloro-phenyl)-4,5-dihydro-1H-pyrazol-3-ylmethyl]-2,5-difluoro-benzenesulfonamide | 575 |

| | | | |
|---|---|---|---|
| 279 | [structure] | N-[5-(4-Bromo-phenyl)-1-(2,4-dichloro-phenyl)-4,5-dihydro-1H-pyrazol-3-ylmethyl]-2-methyl-5-nitro-benzenesulfonamide | 598 |
| 280 | [structure] | N-[5-(4-Bromo-phenyl)-1-(2,4-dichloro-phenyl)-4,5-dihydro-1H-pyrazol-3-ylmethyl]-2,5-dimethyl-benzenesulfonamide | 567 |
| 281 | [structure] | N-[5-(4-Bromo-phenyl)-1-(2,4-dichloro-phenyl)-4,5-dihydro-1H-pyrazol-3-ylmethyl]-3-chloro-benzenesulfonamide | 573 |
| 282 | [structure] | N-[5-(4-Bromo-phenyl)-1-(2,4-dichloro-phenyl)-4,5-dihydro-1H-pyrazol-3-ylmethyl]-3-fluoro-benzenesulfonamide | 557 |

| | | | |
|---|---|---|---|
| 283 |  | N-[1-(2,4-Dichloro-phenyl)-5-(4-methoxy-phenyl)-4,5-dihydro-1H-pyrazol-3-ylmethyl]-2-methyl-5-nitro-benzenesulfonamide | 549 |
| 284 | 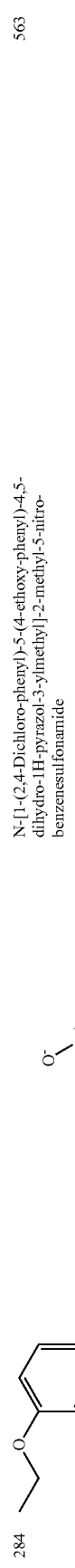 | N-[1-(2,4-Dichloro-phenyl)-5-(4-ethoxy-phenyl)-4,5-dihydro-1H-pyrazol-3-ylmethyl]-2-methyl-5-nitro-benzenesulfonamide | 563 |
| 285 | 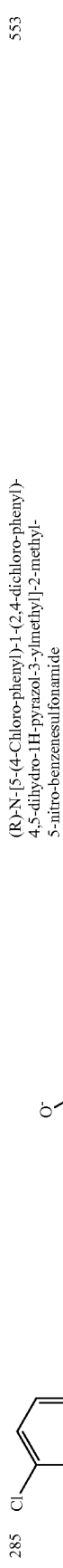 | (R)-N-[5-(4-Chloro-phenyl)-1-(2,4-dichloro-phenyl)-4,5-dihydro-1H-pyrazol-3-ylmethyl]-2-methyl-5-nitro-benzenesulfonamide | 553 |
| 286 | 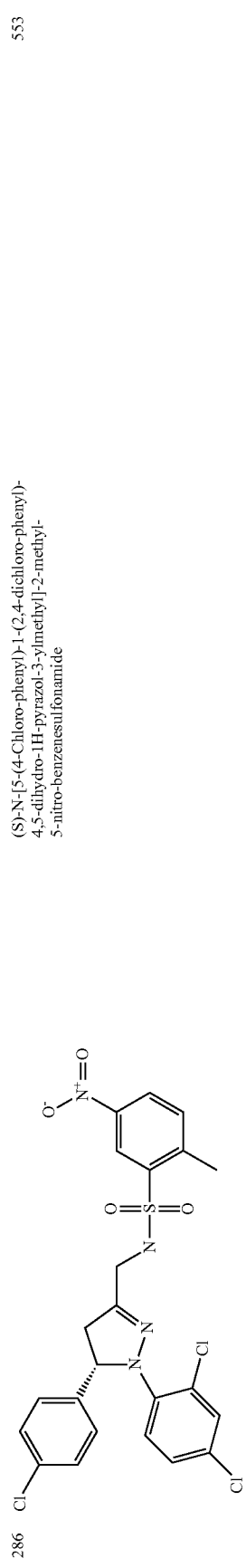 | (S)-N-[5-(4-Chloro-phenyl)-1-(2,4-dichloro-phenyl)-4,5-dihydro-1H-pyrazol-3-ylmethyl]-2-methyl-5-nitro-benzenesulfonamide | 553 |

| | | | |
|---|---|---|---|
| 287 |  | N-[5-(4-Bromo-phenyl)-1-(2,4-dichloro-phenyl)-4,5-dihydro-1H-pyrazol-3-ylmethyl]-3-cyano-benzenesulfonamide | 564 |
| 288 | 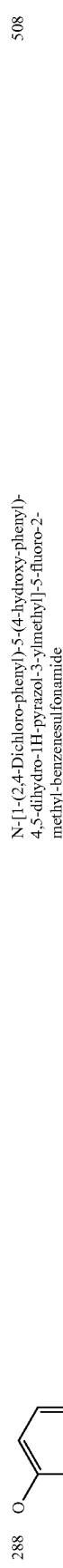 | N-[1-(2,4-Dichloro-phenyl)-5-(4-hydroxy-phenyl)-4,5-dihydro-1H-pyrazol-3-ylmethyl]-5-fluoro-2-methyl-benzenesulfonamide | 508 |
| 289 | 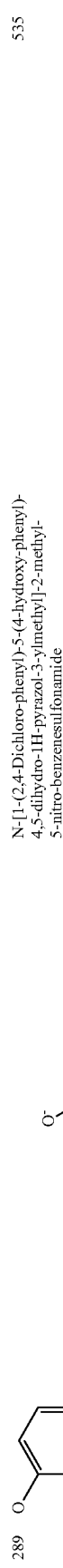 | N-[1-(2,4-Dichloro-phenyl)-5-(4-hydroxy-phenyl)-4,5-dihydro-1H-pyrazol-3-ylmethyl]-2-methyl-5-nitro-benzenesulfonamide | 535 |
| 290 | 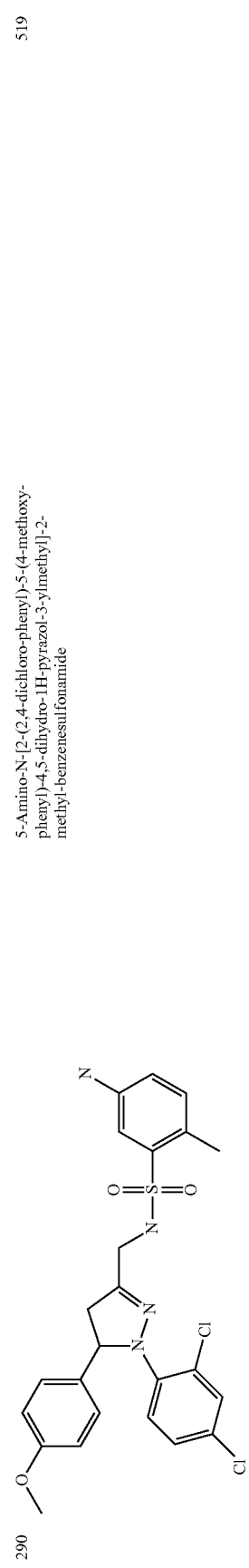 | 5-Amino-N-[2-(2,4-dichloro-phenyl)-5-(4-methoxy-phenyl)-4,5-dihydro-1H-pyrazol-3-ylmethyl]-2-methyl-benzenesulfonamide | 519 |

| | | |
|---|---|---|
| 291 | 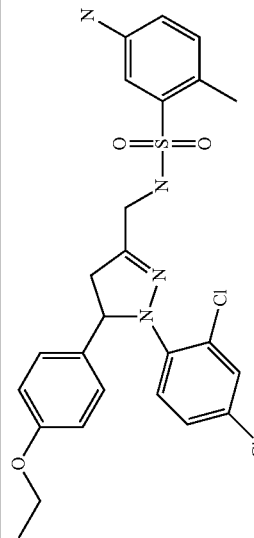 5-Amino-N-[1-(2,4-dichloro-phenyl)-5-(4-ethoxy-phenyl)-4,5-dihydro-1H-pyrazol-3-ylmethyl]-2-methyl-benzenesulfonamide | 533 |
| 292 | 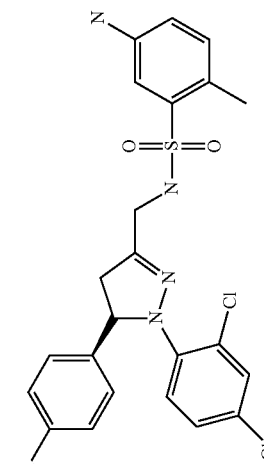 (R)-5-Amino-N-[5-(4-chloro-phenyl)-1-(2,4-dichloro-phenyl)-4,5-dihydro-1H-pyrazol-3-ylmethyl]-2-methyl-benzenesulfonamide | 523 |
| 293 | 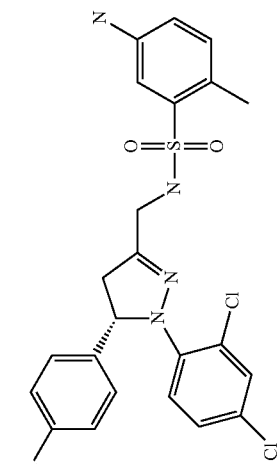 (S)-5-Amino-N-[5-(4-chloro-phenyl)-1-(2,4-dichloro-phenyl)-4,5-dihydro-1H-pyrazol-3-ylmethyl]-2-methyl-benzenesulfonamide | 523 |
| 294 | 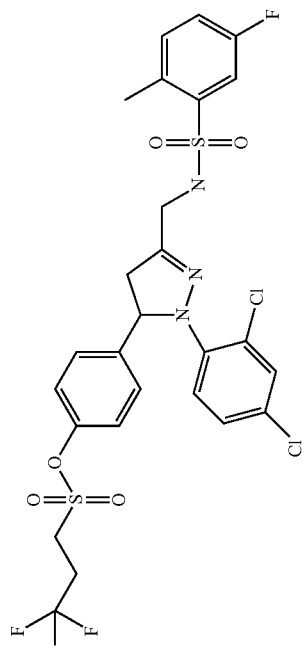 3,3,3-Trifluoro-propane-1-sulfonic acid 4-{2-(2,4-dichloro-phenyl)-5-[(5-fluoro-2-methyl-benzenesulfonyl)aminomethyl]-3,4-dihydro-2H-pyrazol-3-yl}-phenyl ester | 668 |

-continued

| | | | |
|---|---|---|---|
| 295 | 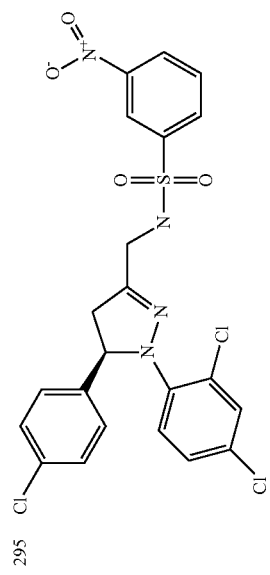 | (R)-N-[5-(4-Chloro-phenyl)-1-(2,4-dichloro-phenyl)-4,5-dihydro-1H-pyrazol-3-ylmethyl]-3-nitro-benzenesulfonamide | 539 |
| 296 | 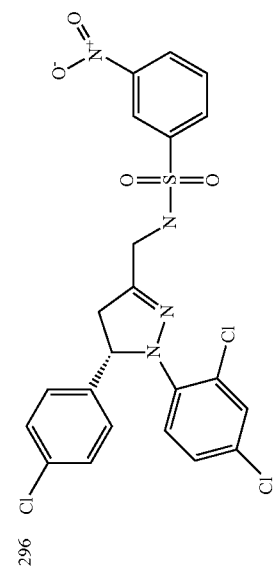 | (S)-N-[5-(4-Chloro-phenyl)-1-(2,4-dichloro-phenyl)-4,5-dihydro-1H-pyrazol-3-ylmethyl]-3-nitro-benzenesulfonamide | 539 |
| 297 | 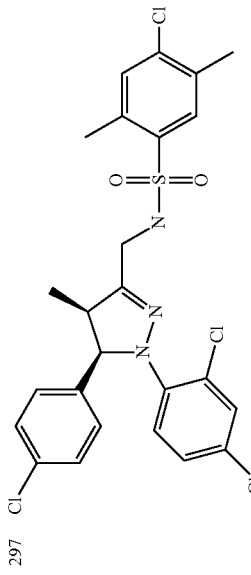 | cis(4RS-5RS)-4-Chloro-N-[5-(4-chloro-phenyl)-1-(2,4-dichloro-phenyl)-4-methyl-4,5-dihydro-1H-pyrazol-3-ylmethyl]-2,5-dimethyl-benzenesulfonamide | 1H NMR (300 MHz, METHANOL-$d_4$) δ ppm 0.75 (d, J=7.47 Hz, 3 H) 2.30 (s, 3 H) 2.63 (s, 3 H) 3.37 (br. s., 1 H) 3.96 (d, J=6.59 Hz, 2 H) 5.37 (d, J=10.40 Hz, 1 H) 7.01 (d, J=8.5 Hz, 2 H) 7.20 (d, J=8.35 Hz, 2 H0 7.08-7.25 (m, 2 H) 7.28 (d, J=1.61 Hz, 1 H) 7.41 (s, 1 H) 7.83 (s, 1 H) 570 |
| 298 | 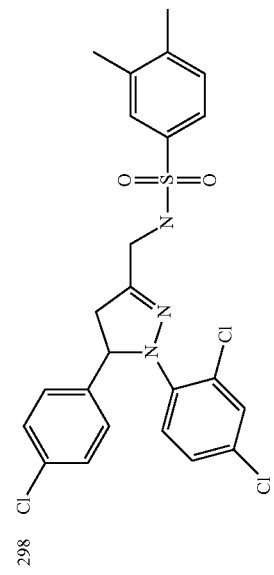 | N-[5-(4-Chloro-phenyl)-1-(2,4-dichloro-phenyl)-4,5-dihydro-1H-pyrazol-3-ylmethyl]-3,4-dimethyl-benzenesulfonamide | 522 |

| | | |
|---|---|---|
| 299 | N-[5-(4-Chloro-phenyl)-1-(2,4-dichloro-phenyl)-4,5-dihydro-1H-pyrazol-3-ylmethyl]-2-methoxy-5-methyl-benzenesulfonamide | 538 |
| 300 | (S)-N-[1-(2,4-Dichloro-phenyl)-5-(4-ethoxy-phenyl)-4,5-dihydro-1H-pyrazol-3-ylmethyl]-2-methoxy-5-methyl-benzenesulfonamide | 548 |
| 301 | (S)-N-[1-(2,4-Dichloro-phenyl)-5-(4-ethoxy-phenyl)-4,5-dihydro-1H-pyrazol-3-ylmethyl]-2-methoxy-5-methyl-benzenesulfonamide | 548 |

| | | -continued | | |
|---|---|---|---|---|
| 302 | 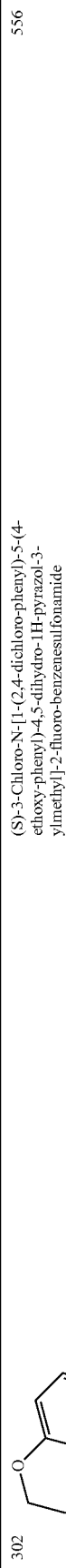 | (S)-3-Chloro-N-[1-(2,4-dichloro-phenyl)-5-(4-ethoxy-phenyl)-4,5-dihydro-1H-pyrazol-3-ylmethyl]-2-fluoro-benzenesulfonamide | 556 | |
| 303 | 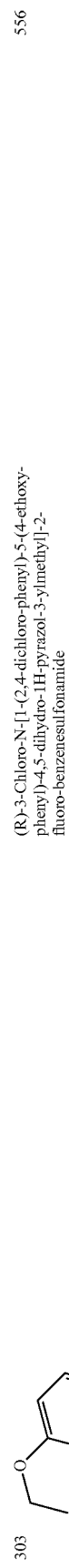 | (R)-3-Chloro-N-[1-(2,4-dichloro-phenyl)-5-(4-ethoxy-phenyl)-4,5-dihydro-1H-pyrazol-3-ylmethyl]-2-fluoro-benzenesulfonamide | 556 | |
| 304 |  | (R)-N-[1-(2,4-Dichloro-phenyl)-5-(4-ethoxy-phenyl)-4,5-dihydro-1H-pyrazol-3-ylmethyl]-2,5-difluoro-benzenesulfonamide | 540 | |

| | -continued | | |
|---|---|---|---|
| 305 | (S)-N-[1-(2,4-Dichloro-phenyl)-5-(4-ethoxy-phenyl)-4,5-dihydro-1H-pyrazol-3-ylmethyl]-2,5-difluoro-benzenesulfonamide | 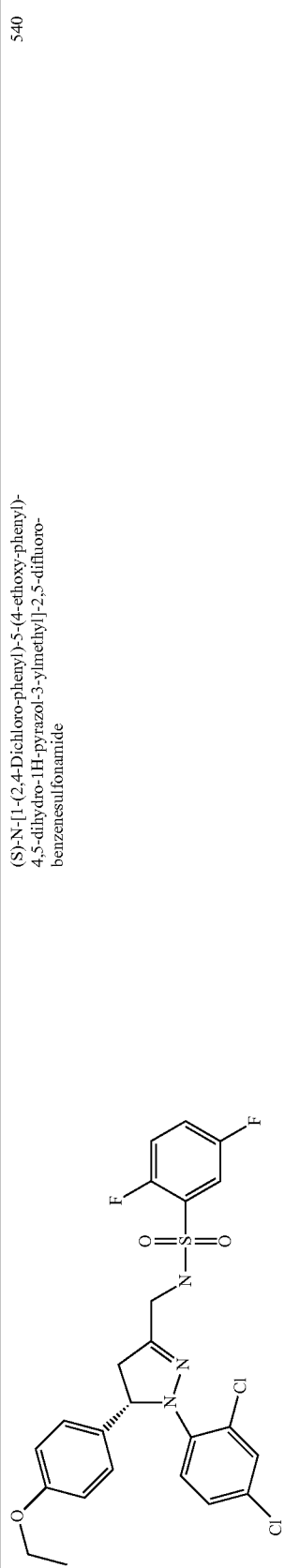 | 540 |
| 306 | Propane-1-sulfonic acid 4-{2-(2,4-dichloro-phenyl)-5-[(5-fluoro-2-methyl-benzenesulfonyl)amino)-methyl]-3,4-dihydro-2H-pyrazol-3-yl}-phenyl ester | 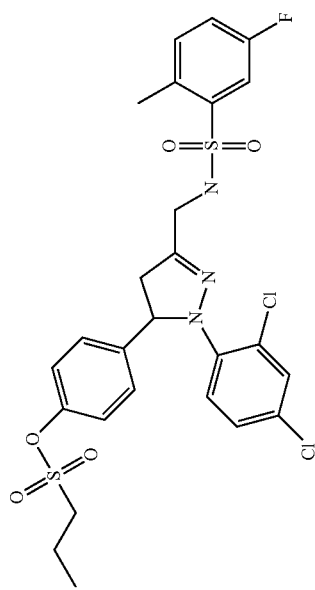 | 614 |
| 307 | Propane-2-sulfonic acid 4-{2-(2,4-dichloro-phenyl)-5-[(5-fluoro-2-methyl-benzenesulfonyl)amino)-methyl]-3,4-dihydro-2H-pyrazol-3-yl}-phenyl ester | 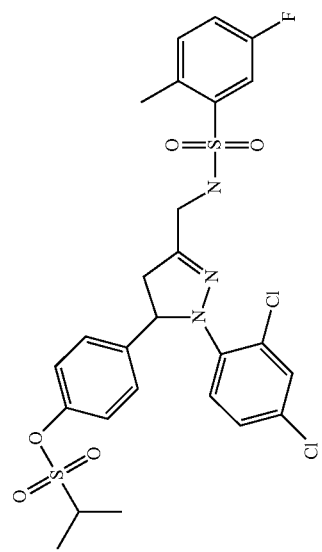 | 614 |

| | | |
|---|---|---|
| 308 | Ethanesulfonic acid 4-{2-(2,4-dichloro-phenyl)-5-[(5-fluoro-2-methyl-benzenesulfonyl)amino)-methyl]-3,4-dihydro-2H-pyrazol-3-yl}-phenyl ester | 600 |
| 309 | cis(4RS,5RS)-3,3,3-Trifluoro-propane-1-sulfonic acid 4-{2-(2,4-dichloro-phenyl)-5-[(5-fluoro-2-methyl-benzenesulfonyl)amino)-methyl]-4-methyl-3,4-dihydro-2H-pyrazol-3-yl}-phenyl ester | 682 |
| 310 | cis(4RS,5RS)-Propane-1-sulfonic acid 4-{2-(2,4-dichloro-phenyl)-5-[(5-fluoro-2-methyl-benzenesulfonyl)amino)-methyl]-4-methyl-3,4-dihydro-2H-pyrazol-3-yl}-phenyl ester | 628 |

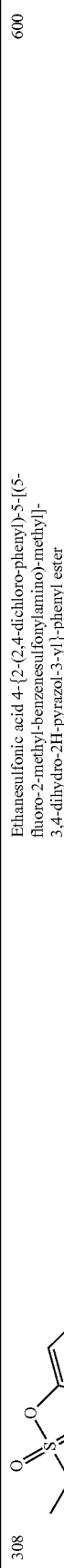
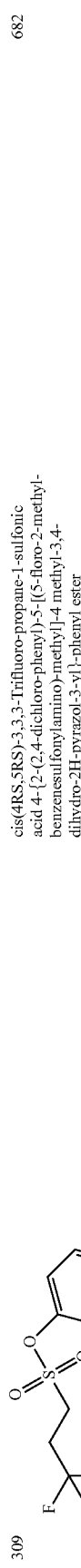
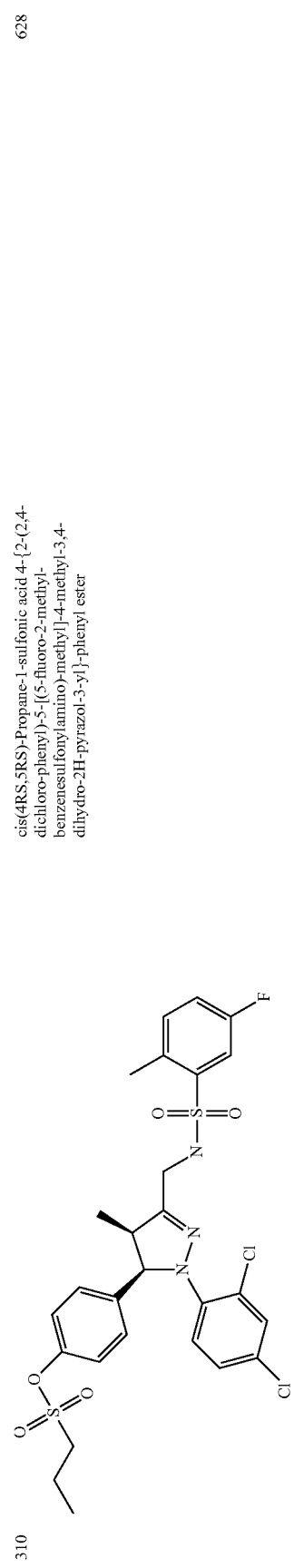

| | | |
|---|---|---|
| 311 | 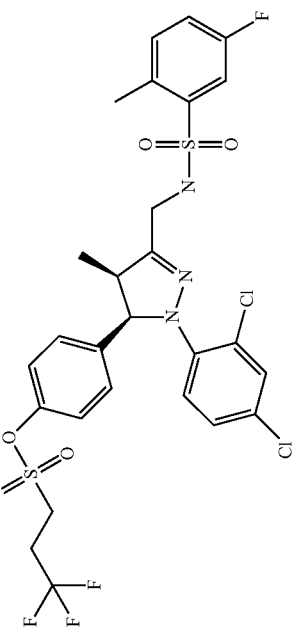 (4R,5R)-3,3,3-Trifluoro-propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester | 682 |
| 312 | 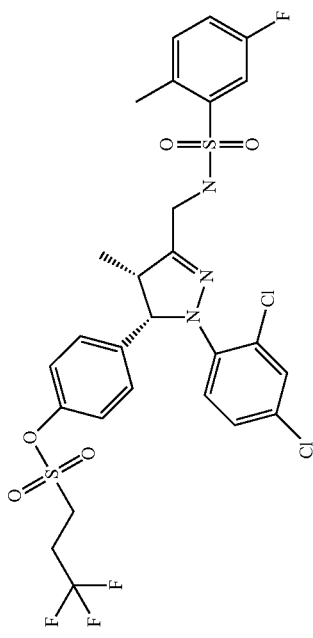 (4S,5S)-3,3,3-Trifluoro-propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester | 682 |
| 313 | 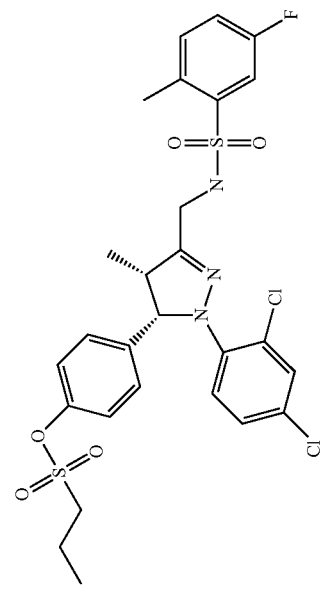 (4S,5S)-Propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester | 628 |

| | | |
|---|---|---|
| 314 | (4R,5R)-Propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester | 628 |
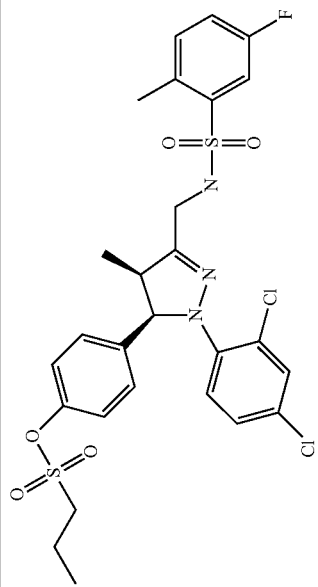

Pharmacological Data

The binding of the pyrazoline compounds of general formulae I, Ia and Ib to CB1-receptors was determined according to the method described in the section Pharmacological Methods, Part I.

The pyrazoline compounds of the present invention show a high affinity to the CB1-receptor (table 1.)

TABLE 1

| Compound according to example | $IC_{50}$.[nM] | $K_i$.[nM] | % inh. $10^{-7}$ M |
|---|---|---|---|
| 1 | 388 | — | 27.1 |
| 7 | 184 | — | 11.9 |
| 9 | 67.7 | 30.6 | 54.3 |
| 10 | 70 | — | 48.6 |
| 12 | 130 | — | 39.4 |
| 14 | 458 | — | 76.6 |
| 16 | — | — | 88.0 |
| 18 | 140 | — | 26.1 |
| 20 | — | — | 27.2 |
| 21 | 263 | — | 80.6 |
| 23 | 183 | — | 54.9 |
| 31 | — | — | 15.9 |
| 32 | 121.5 | — | 20.0 |
| 34 | 14.1 | — | 53.8 |
| 35 | — | — | 8.5 |
| 36 | — | — | 26.5 |
| 37 | — | — | 27.2 |
| 38 | 4.4 | — | 74.0 |
| 39 | 20.6 | — | 53.2 |
| 40 | 97 | 43.9 | 51.9 |
| 41 | — | — | 8.2 |
| 43 | — | — | 26.7 |
| 44 | 15 | 7.3 | 54.1 |
| 53 | 88.2 | 43.2 | — |
| 63 | 50.4 | 21 | — |
| 67 | 91 | 40.6 | — |
| 69 | 36.7 | 16.2 | — |
| 73 | 11.8 | 5.3 | — |
| 74 | 11 | 5.1 | — |
| 81 | 15.20 | 6.9 | — |
| 83 | 50.5 | 21.4 | — |
| 94 | 74 | 33 | — |
| 97 | 43.9 | 18.4 | — |
| 98 | 47.1 | 19.8 | — |
| 99 | 42.6 | 17.9 | — |
| 100 | 30.8 | 12.8 | — |
| 101 | 12.8 | 5.6 | — |
| 102 | 7.2 | 3 | — |
| 103 | 12.1 | 5.3 | — |
| 106 | 28.5 | 11.9 | — |
| 136 | 40 | 16.9 | — |
| 139 | 16.5 | 7 | — |
| 142 | 5.5 | 2.3 | — |
| 144 | 55 | 23.2 | — |
| 194 | 88.9 | 38.3 | — |
| 217 | 69 | 30.8 | — |
| 221 | 52.7 | 23.5 | — |
| 225 | 90.1 | 39.7 | — |
| 247 | 65.5 | 27.7 | — |
| 248 | 17.9 | 7.6 | — |
| 249 | 5.6 | 2.4 | — |
| 250 | 39.7 | 16.6 | — |
| 261 | 9.8 | 9.8 | — |
| 271 | 10.2 | 4.4 | — |
| 272 | 13.4 | 5.7 | — |
| 277 | 43 | 18.2 | — |
| 280 | 42 | 17.5 | — |

The invention claimed is:

1. A substituted pyrazoline compound of general formula I,

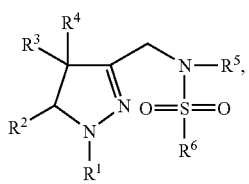

wherein $R^1$ represents unsubstituted or at least mono-substituted aryl which may be condensed with an unsubstituted or at least mono-substituted saturated or unsaturated, but not aromatic, mono- or bicyclic ring system; or unsubstituted or at least mono-substituted heteroaryl which may be condensed with an unsubstituted or at least mono-substituted saturated or unsaturated, but not aromatic, mono- or bicyclic ring system;

$R^2$ represents unsubstituted or at least mono-substituted aryl which may be condensed with an unsubstituted or at least mono-substituted saturated or unsaturated, but not aromatic, mono- or bicyclic ring system; or unsubstituted or at least mono-substituted heteroaryl which may be condensed with an unsubstituted or at least mono-substituted saturated or unsaturated, but not aromatic, mono- or bicyclic ring system;

$R^3$ and $R^4$, independent of one another, each represent H; F; Cl; Br; I; —CN; —$NO_2$; —NC; —OH; —$NH_2$; —SH; —C(=O)—H; —C(=O)—OH; —O—$R^7$; —S—$R^8$; —C(=O)—$OR^9$; —C(=O)—$R^{10}$;
unsubstituted or at least mono-substituted alkyl, alkenyl or alkynyl;
unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^5$ represents H or unsubstituted or at least mono-substituted alkyl, alkenyl or alkynyl; or —S(=O)$_2$—$R^6$;

$R^6$ represents —$NR^{6a}R^{6b}$; unsubstituted or at least mono-substituted alkyl, alkenyl or alkynyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^{6a}$ and $R^{6b}$, independent of one another, each represent H; unsubstituted or at least mono-substituted alkyl, alkenyl or alkynyl; or unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system;

$R^7$, $R^8$, $R^9$ and $R^{10}$, independent of one another, each represent
unsubstituted or at least mono-substituted alkyl, alkenyl or
alkynyl; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

optionally in a form of one of its stereoisomers, a racemate or in a form of a mixture of at least two of its stereoisomers, in any mixing ratio, or a physiologically acceptable salt thereof.

2. A compound according to claim 1, characterised in that
$R^1$ represents unsubstituted or at least mono-substituted aryl which may be condensed with an unsubstituted or at least mono-substituted saturated or unsaturated, but not aromatic, mono- or bicyclic ring system; or
unsubstituted or at least mono-substituted heteroaryl which may be condensed with an unsubstituted or at least mono-substituted saturated or unsaturated, but not aromatic, mono- or bicyclic ring system;

$R^2$ represents unsubstituted or at least mono-substituted aryl which may be condensed with an unsubstituted or at least mono-substituted saturated or unsaturated, but not aromatic, mono- or bicyclic ring system; or
unsubstituted or at least mono-substituted heteroaryl which may be condensed with an unsubstituted or at least mono-substituted saturated or unsaturated, but not aromatic, mono- or bicyclic ring system;

$R^3$ and $R^4$, independent of one another, each represent H; F; Cl; Br; I; —CN;
—NO$_2$; —NC; —OH; —NH$_2$; —SH; —C(=O)—H; —C(=O)—OH; —O—R$^7$; —S—R$^8$; —C(=O)—OR$^9$; —C(=O)—R$^{10}$; unsubstituted or at least mono-substituted alkyl, alkenyl or alkynyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^5$ represents H or unsubstituted or at least mono-substituted alkyl, alkenyl or alkynyl; or —S(=O)$_2$—R$^6$;

$R^6$ represents —NR$^{6a}$R$^{6b}$; unsubstituted or at least mono-substituted alkyl, alkenyl or alkynyl; unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

$R^{6a}$ and $R^{6b}$, independent of one another, each represent H; unsubstituted or at least mono-substituted alkyl, alkenyl or alkynyl; or unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system;

$R^7$, $R^8$, $R^9$ and $R^{10}$, independent of one another, each represent
unsubstituted or at least mono-substituted alkyl, alkenyl or
alkynyl; unsubstituted or at least mono-substituted aryl, -(alkylene)-aryl or -(alkenylene)-aryl which each may be condensed with an unsubstituted or at least mono-substituted saturated or unsaturated, but not aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

whereby
the aforementioned aryl groups are 6- or 10-membered;
the aforementioned heteroaryl groups are 5-, 6-, 7-, 8-, 9-, 10-, 11-, 12-, 13- or 14-membered and contain 1, 2, 3 or 4 heteroatom(s) independently selected from the group consisting of nitrogen, oxygen and sulfur as ring member(s);
the aforementioned mono- or bicyclic ring systems may contain 1, 2 or 3 heteroatom(s) as ring member(s), which may be identical or different and which can independently be selected from the group consisting of nitrogen, oxygen and sulfur and whereby the rings of the aforementioned mono- or bicyclic ring systems are, independent of one another, 5-, 6- or 7-membered;
the aforementioned alkyl groups are linear or branched and have 1, 2, 3, 4, 5, 6, 7, 8, 9, 10, 11, 12, 13, 14, 15 or 16 carbon atoms in the chain;

the aforementioned alkylene groups are linear or branched and have 1, 2, 3, 4, 5, 6, 7, 8, 9, 10, 11, 12, 13, 14, 15 or 16 carbon atoms in the chain;

the aforementioned alkenyl groups are linear or branched and have 2, 3, 4, 5, 6, 7, 8, 9, 10, 11, 12, 13, 14, 15 or 16 carbon atoms in the chain;

the aforementioned alkenylene groups are linear or branched and have 2, 3, 4, 5, 6, 7, 8, 9, 10, 11, 12, 13, 14, 15 or 16 carbon atoms in the chain;

the aforementioned alkynyl groups are linear or branched and have 2, 3, 4, 5, 6, 7, 8, 9, 10, 11, 12, 13, 14, 15 or 16 carbon atoms in the chain;

the aforementioned cycloalkyl groups have 3, 4, 5, 6, 7, 8, 9, 10, 11, 12, 13, 14, 15 or 16 carbon atoms in the ring;

the aforementioned cycloalkenyl groups have 5, 6, 7, 8, 9, 10, 11, 12, 13, 14, 15 or 16 carbon atoms in the ring;

the aforementioned heterocycloalkyl groups are 3-, 4-, 5-, 6-, 7-, 8-, 9-, 10-, 11-, 12-, 13-, 14-, 15- or 16-membered;

the aforementioned heterocycloalkenyl groups are 5-, 6-, 7-, 8-, 9-, 10-, 11-, 12-, 13-, 14-, 15- or 16-membered;

the aforementioned heterocycloalkyl groups and heterocycloalkenyl groups each contain 1, 2, 3 or 4 heteroatom(s) independently selected from the group consisting of nitrogen, oxygen and sulfur;

optionally in a form of one of its stereoisomers, a racemate or in a form of a mixture of at least two of its stereoisomers, in any mixing ratio, or a physiologically acceptable salt thereof.

3. A compound according to claim 1, characterised in that $R^1$ and $R^2$, independent of one another, each represent a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]-benzothiadiazolyl, [2.1.3]-benzoxadiazolyl, [1.2.3]-benzoxadiazolyl, benzoxazolyl, benzthiazolyl, benzisoxazolyl, benzisothiazolyl, imidazo[2,1-b]thiazolyl, 2H-chromenyl, pyranyl, indazolyl, quinazolinyl, benzotriazolyl, (2.3)-dihydrobenzothiazolyl, dihydrobenzofuranyl, [1.3]-benzodioxolyl, [1.4]-benzodioxanyl, [1.2.3.4]-tetrahydronaphthyl, [3.4]-dihydro-2H-benzo[1.4]oxazinyl, (2.3)-dihydro-1H-cyclopenta[b]indolyl, [1.2.3.4]-tetrahydroquinolinyl, [1.2.3.4]-tetrahydroisoquinolinyl and [1.2.3.4]-tetrahydroquinazolinyl, which in each case is bonded to the pyrazoline compound of general formula I via the aromatic or heteroaromatic part of the aforementioned radicals and which is in each case unsubstituted or which is in each case substituted with 1, 2, 3, 4 or 5 substituent(s) independently selected from the group consisting of —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —$OCH_3$, —)—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)—$CH_3$, —S(=O)—$C_2H_5$, —S(=O)—$C_3H_7$, —$S(=O)_2$—$CH_3$, —$S(=O)_2$—$C_2H_5$, —$S(=O)_2$—$C_3H_7$, —$S(=O)_2$-phenyl, —$NH_2$, —NH—$CH_3$, —NH—$C_2H_5$, —$N(CH_3)_2$, —$N(C_2H_5)_2$, —$CH_2$—$N(CH_3)_2$, —$(CH_2)$-morpholinyl, —$(CH_2)$-piperidinyl, —$(CH_2)$-piperazinyl, —$(CH_2)$—$N(C_2H_5)_2$, —$CH_2$—$N(C_3H_7)_2$, —$CH_2$—$N(C_4H_9)_2$, —$CH_2$—$N(CH_3)(C_2H_5)$, —O—$S(=O)_2$—$CH_3$, —O—$S(=O)_2$—$C_2H_5$, —O—$S(=O)_2$—$CH_2$—$CH_2$—$CH_3$, —O—$S(=O)_2$—$CH(CH_3)_2$, —O—$S(=O)_2$—$CF_3$, —O—$S(=O)_2$—$CH_2CF_3$, —O—$S(=O)_2$—$CH_2$—$CH_2$—$CF_3$, —S(=O)—$NH_2$, —$S(=O)_2$—NH—$CH_3$, —$S(=O)_2$—NH-phenyl, —NH—$S(=O)_2$—$CH_3$, cyclopropyl, cyclobutyl, cyclopentyl, cyclohexyl, pyrrolidinyl, piperidinyl, phenyl, thiophenyl, —O-phenyl and benzyl, whereby said phenyl radical and thiophenyl radical can be substituted with 1, 2 or 3 substituent(s) independently selected from the group consisting of F, Cl, Br, methyl, ethyl and n-propyl;

$R^3$ and $R^4$, independent of one another, each represent H; F; Cl; Br; I; —CN;

—$NO_2$; —NC; —OH; —$NH_2$; —SH; —C(=O)—H; —C(=O)—H; —O—$R^7$; —S—$R^8$; —C(=O)—$OR^9$; —C(=O)—$R^{10}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —$NH_2$, —NH—$CH_3$, —NH—$C_2H_5$, —$N(CH_3)_2$—$N(C_2H_5)_2$, —CN and —$NO_2$;

a radical selected from the group consisting of cyclopropyl, cyclobutyl, cyclopentyl, cyclohexyl, cycloheptyl, cyclooctyl, cyclononyl, cyclopentenyl, cyclohexenyl, cycloheptenyl, cyclononenyl, cyclooctenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1.3)-dioxolan-2-yl, isoxazolidinyl, isothioazolidinyl, pyrazolidinyl, oxazolidinyl, (1.2.4)-oxadiazolidinyl, (1.2.4)-thiadiazolidinyl, (1.2.4)-triazolidin-3-yl, (1.3.4)-thiadiazolidin-2-yl, (1.3.4)-triazolidin-1-yl, (1.3.4)-triazoldidin-2-yl, tetrahydropyridazinyl, tetrahydropyrimidinyl, tetrahydropyrazinyl, (1.3.5)-tetrahydrotriazinyl, (1.2.4)-tetrahydrotriazin-1-yl, (1.3)-dithian-2-yl, (1.3)-thiazolidinyl, (2.3)-dihydroimidazolyl, (4.5)-dihydroimidazolyl, (2.5)-dihydroimidazolyl, (3.4.5.6)-tetrahydropyridin-2-yl, (1.2.5.6)-tetrahydropyridin-1-yl, (1.2)-dihydropyridin-1-yl, (1.4)-dihydropyridin-1-yl, dihydropyranyl, (1.2.3.4)-tetrahydropyridin-1-yl, bicyclo[2.2.1]heptyl, bicyclo[3.1.1]heptyl, norbornenyl, 8-aza-bicyclo[3.2.1]octyl and 8-aza-spiro[4.5]decanyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of oxo (=O), thioxo (=S), —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)—$CH_3$, —S(=O)—$C_2H_5$, —S(=O)—$C_3H_7$, —$S(=O)_2$—$CH_3$, —$S(=O)_2$—$C_2H_5$, —$S(=O)_2$—$C_3H_7$, —$S(=O)_2$-phenyl, —$NH_2$, —NH—$CH_3$, —NH—$C_2H_5$, —$N(CH_3)_2$, —$N(C_2H_5)_2$, —$CH_2$—$N(CH_3)_2$, —($CH_2$)-morpholinyl, —($CH_2$)-piperidinyl, —($CH_2$)— piperazinyl, —($CH_2$)—$N(C_2H_5)_2$, —$CH_2$—$N(C_3H_7)_2$, —$CH_2$—$N(C_4H_9)_2$, —$CH_2$—$N(CH_3)(C_2H_5)$, —S(=O)—$NH_2$, —$S(=O)_2$—NH—$CH_3$, —$S(=O)_2$—NH-phenyl, —NH—$S(=O)_2$—$CH_3$, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

or a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]-benzothiadiazolyl, [2.1.3]-benzoxadiazolyl, [1.2.3]-benzoxadiazolyl, benzoxazolyl, benzthiazolyl, benzisoxazolyl, benzisothiazolyl, imidazo[2,1-b]thiazolyl, 2H-chromenyl, pyranyl, indazolyl, quinazolinyl, benzotriazolyl, (2.3)-dihydrobenzothiazolyl, dihydrobenzofuranyl, [1.3]-benzodioxolyl, [1.4]-benzodioxanyl, [1.2.3.4]-tetrahydronaphthyl, [3.4]-dihydro-2H-benzo[1.4]oxazinyl, (2.3)-dihydro-1H-cyclopenta[b]indolyl, [1.2.3.4]-tetrahydroquinolinyl, [1.2.3.4]-tetrahydroisoquinolinyl and [1.2.3.4]-tetrahydroquinazolinyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)—$CH_3$, —S(=O)—$C_2H_5$, —S(=O)—$C_3H_7$, —$S(=O)_2$—$H_3$, —$S(=O)_2$—$C_2H_5$, —$S(=O)_2$—$C_3H_7$, —$S(=O)_2$-phenyl, —$NH_2$, —NH—$CH_3$, —NH—$C_2H_5$, —$N(CH_3)_2$, —$N(C_2H_5)_2$, —$CH_2$—$N(CH_3)_2$, —($CH_2$)-morpholinyl, —($CH_2$)-piperidinyl, —($CH_2$)-piperazinyl, —($CH_2$)—$N(C_2H_5)_2$, —$CH_2$—$N(C_3H_7)_2$, —$CH_2$—$N(C_4H_9)_2$, —$CH_2$—$N(CH_3)(C_2H_5)$, —S(=O)—$NH_2$, —$S(=O)_2$—NH—$CH_3$, —$S(=O)_2$—NH-phenyl, —NH—$S(=O)_2$—$CH_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

$R^5$ represents H or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

$R^6$ represents —$NR^{6a}R^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —$NH_2$, —NH—$CH_3$, —NH—$C_2H_5$, —N($CH_3$)$_2$, —N($C_2H_5$)$_2$, —CN and —$NO_2$;

a radical selected from the group consisting of (1.2.3.4)-tetrahydrop-pyrimidinyl, 7,7a-dihydro-imidazo[2,1-b]thiazolyl, cyclopropyl, cyclobutyl, cyclopentyl, cyclohexyl, cycloheptyl, cyclooctyl, cyclononyl, cyclopentenyl, cyclohexenyl, cycloheptenyl, cyclononenyl, cyclooctenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1.3)-dioxolan-2-yl, isoxazolidinyl, isothioazolidinyl, pyrazolidinyl, oxazolidinyl, (1.2.4)-oxadiazolidinyl, (1.2.4)-thiadiazolidinyl, (1.2.4)-triazolidin-3-yl, (1.3.4)-thiadiazolidin-2-yl, (1.3.4)-triazolidin-1-yl, (1.3.4)-triazoldidin-2-yl, tetrahydropyridazinyl, tetrahydropyrimidinyl, tetrahydropyrazinyl, (1.3.5)-tetrahydrotriazinyl, (1.2.4)-tetrahydrotriazin-1-yl, (1.3)-dithian-2-yl, (1.3)-thiazolidinyl, (2.3)-dihydroimidazolyl, (4.5)-dihydroimidazolyl, (2.5)-dihydroimidazolyl, (3.4.5.6)-tetrahydropyridin-2-yl, (1.2.5.6)-tetrahydropyridin-1-yl, (1.2)-dihydropyridin-1-yl, (1.4)-dihydropyridin-1-yl, dihydropyranyl, (1.2.3.4)-tetrahydropyridin-1-yl, bicyclo[2.2.1]heptyl, bicyclo[3.1.1]heptyl, norbornenyl, 8-aza-bicyclo[3.2.1]octyl and 8-aza-spiro[4.5]decanyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of oxo (=O), thioxo (=S), —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —C(O$CH_3$)($C_2H_5$)$_2$, —C(O$CH_3$)($CH_3$)$_2$, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —S—$CH_3$, —S—$C_2H_5$, —S—$CH_2$—$CH_2$—$CH_3$, —S—CH($CH_3$)$_2$, —S—$CH_2$—$CH_2$—$CH_2$—$CH_3$, —S—C($CH_3$)$_3$, —C(=O)—OH, —C(=O)—O—$CH_3$, —C(=O)—O—$C_2H_5$, —C(=O)—O—$C_3H_7$, —C(=O)—O—C($CH_3$)$_3$, —O—C(=O)—$CH_3$, —O—C(=O)—$C_2H_5$, —O—C(=O)—CH($CH_3$)$_2$, —O—C(=O)—$CH_2$—$CH_2$—$CH_3$, —O—C(=O)—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—C($CH_3$)$_3$, —$NO_2$, —CHO, —C(=O)—$CH_3$, —C(=O)—$C_2H_5$, —C(=O)—C($CH_3$)$_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —S(=O)$_2$-phenyl, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)-morpholinyl, —($CH_2$)-piperidinyl, —($CH_2$)— piperazinyl, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —S(=O)—$NH_2$, —S(=O)$_2$—NH—$CH_3$, —S(=O)$_2$—NH-phenyl, —NH—S(=O)$_2$—$CH_3$, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

or a radical selected from the group consisting of 2-oxo-(1.2.3.4)-tetrahydroquinolinyl, phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]-benzothiadiazolyl, [2.1.3]-benzoxadiazolyl, [1.2.3]-benzoxadiazolyl, benzoxazolyl, benzo[1,4]-dioxine, quinoxaline, benzthiazolyl, benzisoxazolyl, benzisothiazolyl, imidazo[2,1-b]thiazolyl, 2H-chromenyl, pyranyl, indazolyl, quinazolinyl, benzotriazolyl, (2.3)-dihydrobenzothiazolyl, dihydrobenzofuranyl, 3H-benzothiazol-2-onyl, [1.3]-benzodioxolyl, [1.4]-benzodioxanyl, [1.2.3.4]-tetrahydronaphthyl, [3.4]-dihydro-2H-benzo[1.4]oxazinyl, (2.3)-dihydro-1H-cyclopenta[b]indolyl, [1.2.3.4]-tetrahydroquinolinyl, [1.2.3.4]-tetrahydroisoquinolinyl and [1.2.3.4]-tetrahydroquinazolinyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of —$CH_2$—$CH_2$—C(=O)—$OCH_3$, —$CH_2$—C(=O)—$OCH_3$, —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, —C($CH_3$)$_2$($C_2H_5$), n-pentyl, 2-pentyl, n-hexyl, —$CH_2$—OH, —$CH_2$—$CH_2$—OH, —$CH_2$—$CH_2$—$CH_2$—

OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)—piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

$R^{6a}$ and $R^{6b}$, independent of one another, each represent H; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —NH$_2$, —NH—CH$_3$, —NH—C$_2$H$_5$, —N(CH$_3$)$_2$, —N(C$_2$H$_5$)$_2$, —CN and —NO$_2$;

or a radical selected from the group consisting of cyclopropyl, cyclobutyl, cyclopentyl, cyclohexyl, cycloheptyl, cyclooctyl, cyclononyl, cyclopentenyl, cyclohexenyl, cycloheptenyl, cyclononenyl, cyclooctenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl and diazepanyl, which in each case may be bonded via a C$_{1-3}$-alkylene group or a C$_{2-3}$-alkenylene group and which is in each case unsubstituted or which is in each case substituted with 1, 2, 3, 4 or 5 substituent(s) independently selected from the group consisting of oxo (=O), thioxo (=S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$ and —O—C(CH$_3$);

$R^7$, $R^8$, $R^9$ and $R^{10}$, independent of one another, each represent
a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —NH$_2$, —NH—CH$_3$, —NH—C$_2$H$_5$, —N(CH$_3$)$_2$—N(C$_2$H$_5$)$_2$, —CN and —NO$_2$;

or a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, pyridazinyl, indolyl, isoindolyl, pyrimidinyl, pyrazinyl, quinolinyl, isoquinolinyl, benzo[b]furanyl, benzo[b]thiophenyl, benzoxazolyl, benzthiazolyl, benzisoxazolyl, benzisothiazolyl, imidazo[2,1-b]thiazolyl, 2H-chromenyl, pyranyl, indazolyl, quinazolinyl and benzotriazolyl, which in each case may be bonded via a C$_{1-3}$-alkylene group or a C$_{2-3}$-alkenylene group and which is in each case unsubstituted or which is in each case substituted with 1, 2, 3, 4 or 5 substituent(s) independently selected from the group consisting of —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

optionally in a form of one of its stereoisomers, a racemate or in a form of a mixture of at least two of its stereoisomers, in any mixing ratio, or a physiologically acceptable salt thereof.

4. A compound according to claim 1, characterised in that R$^1$ and R$^2$, independent of one another, each represent a radical selected from the group consisting of phenyl, naphthyl, pyridinyl, furyl (furanyl), thienyl (thiophenyl), [1.3]-benzodioxolyl and [1.4]-benzodioxanyl, which in each case is bonded to the pyrazoline compound of general formula I via the aromatic or heteroaromatic part of the aforementioned radicals and which is in each case unsubstituted or which is in each case substituted with 1, 2, 3, 4 or 5 substituent(s) independently selected from the group consisting of —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, —S(=O)—NH$_2$, —S(=O)$_2$—NH—CH$_3$ and —NH—S(=O)$_2$—CH$_3$;

R$^3$ represents H;

R$^4$ represents H; F; Cl; Br; I; —CN; —NO$_2$; —NC; —OH; —NH$_2$; —SH; —C(=O)—H; —C(=O)—OH; —O—R$^7$; —S—R$^8$; —C(=O)—OR$^9$; —C(=O)—R$^{10}$; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

R$^5$ represents H or a radical selected from the group consisting of methyl, ethyl, n-propyl, isopropyl, n-butyl, isobutyl, sec-butyl, tert-butyl, n-pentyl, and n-hexyl, which is in each case unsubstituted;

R$^6$ represents —NR$^{6a}$R$^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —NH$_2$, —NH—CH$_3$, —NH—C$_2$H$_5$, —N(CH$_3$)$_2$, —N(C$_2$H$_5$)$_2$, —CN and —NO$_2$;

a radical selected from the group consisting of (1.2.3.4)-tetrahydro-pyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, cyclononenyl, cyclooctenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1.3)-dioxolan-2-yl, isoxazolidinyl, isothioazolidinyl, pyrazolidinyl, oxazolidinyl, (1.2.4)-oxadiazolidinyl, (1.2.4)-thiadiazolidinyl, (1.2.4)-triazolidin-3-yl, (1.3.4)-thiadiazolidin-2-yl, (1.3.4)-triazolidin-1-yl, (1.3.4)-triazoldidin-2-yl, tetrahydropyridazinyl, tetrahydropyrimidinyl, tetrahydropyrazinyl, (1.3.5)-tetrahydrotriazinyl, (1.2.4)-tetrahydrotriazin-1-yl, (1.3)-dithian-2-yl, (1.3)-thiazolidinyl, (2.3)-dihydroimidazolyl, (4.5)-dihydroimidazolyl, (2.5)-dihydroimidazolyl, (3.4.5.6)-tetrahydropyridin-2-yl, (1.2.5.6)-tetrahydropyridin-1-yl, (1.2)-dihydropyridin-1-yl, (1.4)-dihydropyridin-1-yl, dihydropyranyl, (1.2.3.4)-tetrahydropyridin-1-yl, bicyclo[2.2.1]heptyl, bicyclo[3.1.1]heptyl, norbornenyl, 8-aza-bicyclo[3.2.1]octyl and 8-aza-spiro[4.5]decanyl, which in each case may be bonded via a C$_{1-3}$-alkylene group or a C$_{2-3}$-alkenylene group and which is in each case unsubstituted or which is in each case substituted with 1, 2, 3, 4 or 5 substituent(s) independently selected from the group consisting of oxo (=O), thioxo (=S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, —O-benzyl, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

or a radical selected from the group consisting of 2-oxo-(1.2.3.4)-tetrahydroquinolinyl, phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, [1.2.3]-oxadiazolyl, [1.2.4]-oxadiazolyl, [1.3.4]-oxadiazolyl, [1.2.5]-thiadiazolyl, [1.3.4]-thiadiazolyl, [1.2.4]-thiadiazolyl, [1.2.3]-triazolyl, pyridazinyl, indolyl, isoindolyl, pyrimidinyl, pyrazinyl, quinolinyl, isoquinolinyl, benzo[b]furanyl, benzo[b]thiophenyl, benzo[2.1.3]thiadiazolyl, [1.2.3]-benzothiadiazolyl, [2.1.3]-benzoxadiazolyl, [1.2.3]-benzoxadiazolyl, benzoxazolyl, benzthiazolyl, benzisoxazolyl, benzisothiazolyl, imidazo[2,1-b]thiazolyl, 2H-chromenyl, pyranyl, indazolyl, quinazolinyl, benzotriazolyl, (2.3)-dihydrobenzothiazolyl, 2,3-dihydro-benzo[1,4]-dioxine, 1,2,3,4-tetrahydro-quinoxaline, 2,3-dioxo-1,2,3,4-tetrahydro-quinoxaline, dihydrobenzofuranyl, 3H-benzothiazol-2-onyl, [1.3]-benzodioxolyl, [1.4]-benzodioxanyl, [1.2.3.4]-tetrahydronaphthyl, [3.4]-dihydro-2H-benzo[1.4]oxazinyl, (2.3)-dihydro-1H-cyclopenta[b]indolyl, [1.2.3.4]-tetrahydroquinolinyl, [1.2.3.4]-tetrahydroisoquinolinyl and [1.2.3.4]-tetrahydroquinazolinyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of —CH₂—CH₂—C(=O)—OCH₃, —CH₂—C(=O)—OCH₃, —CF₃, —C₂F₅, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, —C—(CH₃)₂(C₂H₅), n-pentyl, 2-pentyl, n-hexyl, —CH₂—OH, —CH₂—CH₂—OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)— piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, cyclopropyl, cyclobutyl, cyclopentyl, cyclohexyl, pyrrolidinyl, piperidinyl, phenyl, thiophenyl, —O-phenyl and benzyl, whereby said phenyl radical and said thiophenyl radical can be substituted with 1, 2 or 3 substituent(s) independently selected from the group consisting of F, Cl, Br, methyl, ethyl and n-propyl;

$R^{6a}$ and $R^{6b}$, independent of one another, each represent H or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted or which is in each case substituted with 1, 2, 3, 4 or 5 substituent(s) independently selected from the group consisting of —OH, F, Cl, Br, I, —O—CH₃ and —O—C₂H₅;

$R^7$, $R^8$, $R^9$ and $R^{10}$, independent of one another, each represent a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

or a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, pyridazinyl, indolyl, isoindolyl, pyrimidinyl, pyrazinyl, quinolinyl, isoquinolinyl, benzo[b]furanyl, benzo[b]thiophenyl, benzoxazolyl, benzthiazolyl, benzisoxazolyl, benzisothiazolyl, imidazo[2,1-b]thiazolyl, 2H-chromenyl, pyranyl, indazolyl, quinazolinyl and benzotriazolyl, which in each case may be bonded via a $C_{1-3}$-alkylene group or a $C_{2-3}$-alkenylene group and which is in each case unsubstituted or which is in each case substituted with 1, 2, 3, 4 or 5 substituent(s) independently selected from the group consisting of —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —S—$CH_3$, —S—$C_2H_5$, —S—$CH_2$—$CH_2$—$CH_3$, —S—CH($CH_3$)$_2$, —S—$CH_2$—$CH_2$—$CH_2$—$CH_3$, —S—C($CH_3$)$_3$, —C(=O)—OH, —C(=O)—O—$CH_3$, —C(=O)—O—$C_2H_5$, —C(=O)—O—$C_3H_7$, —C(=O)—O—C($CH_3$)$_3$, —O—C(=O)—$CH_3$, —O—C(=O)—$C_2H_5$, —O—C(=O)—CH($CH_3$)$_2$, —O—C(=O)—$CH_2$—$CH_2$—$CH_3$, —O—C(=O)—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—C($CH_3$)$_3$, —$NO_2$, —CHO, —C(=O)—$CH_3$, —C(=O)—$C_2H_5$, —C(=O)—C($CH_3$)$_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —S(=O)$_2$—$NH_2$, —S(=O)$_2$—NH—$CH_3$ and —NH—S(=O)$_2$—$CH_3$ optionally in a form of one of its stereoisomers, a racemate or in a form of a mixture of at least two of its stereoisomers, in any mixing ratio, or a physiologically acceptable salt thereof.

5. A compound according to claim 1, characterised in that $R^1$ and $R^2$, independent of one another, each represent a radical
selected from the group consisting of phenyl, naphthyl, pyridinyl, furyl (furanyl), thienyl (thiophenyl), [1.3]-benzodioxolyl and [1.4]-benzodioxanyl, which in each case is bonded to the pyrazoline compound of general formula I via the aromatic or heteroaromatic part of the aforementioned radicals and which is in each case unsubstituted or which is in each case substituted with 1, 2, 3, 4 or 5 substituent(s) independently selected from the group consisting of —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —S—$CH_3$, —S—$C_2H_5$, —S—$CH_2$—$CH_2$—$CH_3$, —S—CH($CH_3$)$_2$, —S—$CH_2$—$CH_2$—$CH_2$—$CH_3$, —S—C($CH_3$)$_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—C($CH_3$)$_3$, —$NO_2$, —CHO, —C(=O)—$CH_3$, —C(=O)—$C_2H_5$, —C(=O)—C($CH_3$)$_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —O—S(=O)$_2$—$CH_3$, —O—S(=O)$_2$—$C_2H_5$, —O—S(=O)$_2$—$CH_2$—$CH_2$—$CH_3$, —O—S(=O)$_2$—CH($CH_3$)$_2$, —O—S(=O)$_2$—$CF_3$, —O—S(=O)$_2$—$CH_2CF_3$, —O—S(=O)$_2$—$CH_2$—$CH_2$—$CF_3$, —S(=O)—$NH_2$, —S(=O)$_2$—NH—$CH_3$ and —NH—S(=O)$_2$—$CH_3$;

$R^3$ represents H;

$R^4$ represents H; F; Cl; Br; —C(=O)—OH; —C(=O)—$OR^9$; or a radical selected from the group consisting of methyl, ethyl, n-propyl, isopropyl, tert.-butyl and n-butyl, which is in each case unsubstituted;

$R^5$ represents H;

$R^6$ represents —$NR^{6a}R^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted; a radical selected from the group consisting of 2.4-dioxo-(1.2.3.4)-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —($CH_2$)-group and which is in each case unsubstituted or which is substituted with 1, 2 or 3 substituent(s) selected from the group consisting of methyl, ethyl, n-propyl, isopropyl, n-butyl, 2-butyl, tert-butyl, F, Cl and Br;

or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydroquinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —(CH₂)— or a —(CH₂)₂-group and which is in each case unsubstituted or which is in each case substituted with 1, 2, 3, 4 or 5 substituent(s) independently selected from the group consisting of —CH₂—CH₂—C(=O)—OCH₃, —CH₂—C(=O)—OCH₃, —CF₃, —C₂F₅, —C₃F₇, —C₄F₅, methyl, ethyl, n-propyl, isopropyl, n-butyl, isobutyl, 2-butyl, tert-butyl, —C—(CH₃)₂(C₂H₅), n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —C(=O)—O—CH₃, —C(=O)—O—C₂H₅, —C(=O)—O—CH₂—CH₂—CH₃, —C(=O)—O—CH(CH₃)₂, —C(=O)—O—CH₂—CH₂—CH₂—CH₃, —C(=O)—O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —O—C₂F₅, —O—C₃F₇, —O—C₄F₅, —SCF₃, —SCF₂H, —SCFH₂, —OH, —NH—C(=O)—CH₃, —NH—C(=O)—C₂H₅, —NH—C(=O)—C(CH₃)₃, —S(=O)—CH₃, —S(=O)—C₂H₅, —S(=O)—C₃H₇, —S(=O)₂CH₃, —S(=O)₂—C₂H₅, —S(=O)₂—C₃H₇, NO₂, —NH₂, —NH—CH₃, —NH—C₂H₅, —N(CH₃)₂, —N(C₂H₅)₂, cyclopropyl, cyclobutyl, cyclopentyl, cyclohexyl, phenyl, —O-phenyl and benzyl;

R⁶ᵃ and R⁶ᵇ, independent of one another, each represent H; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

R⁹ represents a radical selected from the group consisting of methyl, ethyl, n-propyl, isopropyl, n-butyl, isobutyl, sec-butyl, tert-butyl and n-pentyl, which is in each case unsubstituted;

optionally in a form of one of its stereoisomers, a racemate or in a form of a mixture of at least two of its stereoisomers, in any mixing ratio, or a physiologically acceptable salt thereof.

6. A compound of general formula Ia according to claim 4,

Ia wherein
D, E, F, G, J and K, independent of one another, each represent hydrogen,
methyl, ethyl, n-propyl, isopropyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —O—S(=O)₂—CH₃, —O—S(=O)₂—C₂H₅, —O—S(=O)₂—CH₂—CH₂—CH₃, —O—S(=O)₂—CH(CH₃)₂, —O—S(=O)₂—CF₃, —O—S(=O)₂—CH₂CF₃, —O—S(=O)₂—CH₂—CH₂—CF₃, F, Cl, Br, I, —CN, —OCF₃, —O—C₂F₅, —O—C₃F₇, —O—C₄F₉ and —OH;

and R⁴, R⁵ and R⁶ are each defined as in claim 4.

7. A compound according to claim 6, characterised in that D, E, F, G, J and K, independent of one another, each represent hydrogen,
methyl, ethyl, n-propyl, isopropyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —O—S(=O)₂—CH₃, —O—S(=O)₂—C₂H₅, —O—S(=O)₂—CH₂—CH₂—CH₃, —O—S(=O)₂—CH(CH₃)₂, —O—S(=O)₂CF₃, —O—S(=O)₂—CH₂CF₃, —O—S(=O)₂CH₂—CH₂—CF₃, F, Cl, Br, I, —CN, —OCF₃, —O—C₂F₅, —O—C₃F₇, —O—C₄F₉ and —OH;

R⁴ represents H; F; Cl; Br; —C(=O)—OH; —C(=O)—OR⁹; or a radical selected
from the group consisting of methyl, ethyl, n-propyl, isopropyl, tert.-butyl and n-butyl, which is in each case unsubstituted;

R⁵ represents H;

R⁶ represents —NR⁶ᵃR⁶ᵇ; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;
a radical selected from the group consisting of 2.4-dioxo-(1.2.3.4)-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —(CH₂)-group and which is in each case unsubstituted or which is substituted with 1, 2 or 3 substituent(s) selected from the group consisting of methyl, ethyl, n-propyl, isopropyl, n-butyl, 2-butyl, tert-butyl, F, Cl and Br;
or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —(CH₂)— or a —(CH₂)₂-group and which is in each case unsubstituted or which is in each case substituted with 1, 2, 3, 4 or 5 substituent(s) independently selected from the group consisting of —CH₂—CH₂—C(=O)—OCH₃, —CH₂—C(=O)—OCH₃, —CF₃, —C₂F₅, —C₃F₇, —C₄F₉, methyl, ethyl, n-propyl, isopropyl, n-butyl, isobutyl, 2-butyl, tert-butyl, —C—(CH₃)₂(C₂H₅), n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C (CH₃)₃, —C(=O)—O—CH₃, —C(=O)—O—C₂H₅, —C(=O)—O—CH₂—CH₂—CH₃, —C(=O)—O—CH(CH₃)₂, —C(=O)—O—CH₂—CH₂—CH₃, —C(=O)—O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —NH—C(=O)—CH₃, —NH—C(=O)—C₂H₅, —NH—C(=O)—C(CH₃)₃, —S(=O)—CH₃, —S(=O)—C₂H₅, —S(=O)—C₃H₇, —S(=O)—CH₃, —S(=O)—C₂H₅, —S(=O)₂—C₃H₇, NO₂, —NH₂, —NH—CH₃, —NH—C₂H₅, —N(CH₃)₂, —N(C₂H₅)₂, cyclopropyl, cyclobutyl, cyclopentyl, cyclohexyl, phenyl, —O-phenyl and benzyl; and R⁶ᵃ and R⁶ᵇ, independent of one another, each represent H; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted.

8. A compound of general formula Ib according to claim 4,

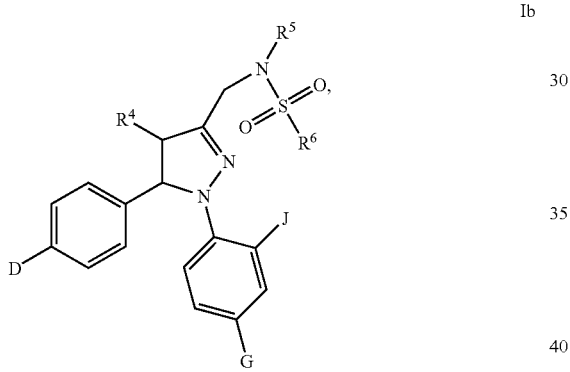

Ib

D, G and J, independent of one another, each represent hydrogen, —O—CH₃, —O—C₂H₅, —O—CH₂—CH₂—CH₃, —O—CH(CH₃)₂, —O—CH₂—CH₂—CH₂—CH₃, —O—C(CH₃)₃, —O—S(=O)₂—CH₃, —O—S(=O)₂—C₂H₅, —O—S(=O)₂—CH₂—CH₂—CH₃, —O—S(=O)₂—CH(CH₃)₂, —O—S(=O)₂—CF₃, —O—S(=O)₂—CH₂CF₃, —O—S(=O)₂—CH₂—CH₂—CF₃, F, Cl, Br, I, and —OH; and R⁴, R⁵ and R⁶ are each defined as in claim 4.

9. A compound according to claim 8, characterised in that D, G and J, independent of one another, each represent hydrogen, —O—CH₃, —O—C₂H₅, —O—CH₂—CH₂—CH₃, —O—CH(CH₃)₂, —O—CH₂—CH₂—CH₂—CH₃, —O—C(CH₃)₃, —O—S(=O)₂—CH₃, —O—S(=O)₂—C₂H₅, —O—S(=O)₂—CH₂—CH₂—CH₃, —O—S(=O)₂—CH(CH₃)₂, —O—S(=O)₂—CF₃, —O—S(=O)₂—CH₂CF₃, —O—S(=O)₂—CH₂—CH₂—CF₃, F, Cl, Br, I, and —OH;
R⁴ represents H; F; Cl; Br; —C(=O)—OH; —C(=O)—OR⁹; or a radical selected from the group consisting of methyl, ethyl, n-propyl, isopropyl, tert.-butyl and n-butyl, which is in each case unsubstituted;
R⁵ represents H;
R⁶ represents —NR⁶ᵃR⁶ᵇ; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;

a radical selected from the group consisting of 2.4-dioxo-(1.2.3.4)-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —(CH₂)-group and which is in each case unsubstituted or which is substituted with 1, 2 or 3 substituent(s) selected from the group consisting of methyl, ethyl, n-propyl, isopropyl, n-butyl, 2-butyl, tert-butyl, F, Cl and Br;

or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —(CH₂)— or a —(CH₂)₂-group and which is in each case unsubstituted or which is in each case substituted with 1, 2, 3, 4 or 5 substituent(s) independently selected from the group C₃F₇, —C₄F₉, methyl, ethyl, n-propyl, isopropyl, n-butyl, isobutyl, 2-butyl, tert-butyl, —C—(CH₃)₂(C₂H₅), n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —C(=O)—O—CH₃, —C(=O)—O—C₂H₅, —C(=O)—O—CH₂—CH₂—CH₃, —C(=O)—O—CH(CH₃)₂, —C(=O)—O—CH₂—CH₂—CH₂—CH₃, —C(=O)—O—C(CH₃)₃, —S—CH₃, —S—C₂H₅, —S—CH₂—CH₂—CH₃, —S—CH(CH₃)₂, S—CH₂—CH₂—CH₂—CH₃, —S—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —NH—C(=O)—CH₃, —NH—C(=O)—C₂H₅, —NH—C(=O)—C(CH₃)₃, —S(=O)—CH₃, —S(=O)—C₂H₅, —S(=O)—C₃H₇, —S(=O)₂—CH₃, —S(=O)₂—C₂H₅, —S(=O)₂—C₃H₇, NO₂, —NH₂, —NH—CH₃, —NH—C₂H₅, —N(CH₃)₂, —N(C₂H₅)₂, cyclopropyl, cyclobutyl, cyclopentyl, cyclohexyl, phenyl, —O-phenyl and benzyl; and R⁶ᵃ and R⁶ᵇ, independent of one another, each represent H; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted.

10. A compound according to claim 8, characterised in that D, G and J, each represent Cl,
R$^4$ represents hydrogen,
R$^5$ represents H;
R$^6$ represents —NR$^{6a}$R$^{6b}$; a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted;
a radical selected from the group consisting of 2.4-dioxo-(1.2.3.4)-tetrahydropyrimidinyl, 7,7a-dihydro-imidazo[2,1-b]thiazolyl, 7,7-dimethyl-2-oxo-bicyclo[2.2.1]heptyl, cyclopropyl, cyclobutyl, cyclopentyl, cyclohexyl, cycloheptyl, cyclooctyl, cyclononyl, cyclopentenyl, cyclohexenyl, cycloheptenyl, pyrrolidinyl, piperidinyl, morpholinyl, piperazinyl and thiomorpholinyl, which in each case may be bonded via a —(CH$_2$)-group and which is in each case unsubstituted or which is substituted with 1, 2 or 3 substituent(s) selected from the group consisting of methyl, ethyl, n-propyl, isopropyl, n-butyl, 2-butyl, tert-butyl, F, Cl and Br;
or a radical selected from the group consisting of isoxazolyl, pyridinyl, quinolinyl, 2-oxo-1.2.3.4-tetrahydroquinolinyl, phenyl, naphthyl, furyl (furanyl), thienyl (thiophenyl), imidazolyl, pyrazolyl, thiazolyl, benzo[b]furanyl, benzo[b]thiophenyl, imidazo[2,1-b]thiazolyl, benzoxazolyl, benzothiazolyl, 2,3-dihydro-benzoxazolyl, 2-oxo-2,3-dihydro-benzoxazolyl, 2,3-dihydro-benzo[1,4]-dioxine, 1,2,3,4-tetrahydro-quinoxaline, 2,3-dioxo-1,2,3,4-tetrahydro-quinoxaline, [1.2.3.4]-tetrahydroisoquinolinyl, benzo[2.1.3]thiadiazolyl, [2.1.3]-benzoxadiazolyl, 2-oxo-2H-chromenyl, [1.2.3.4]-tetrahydroisoquinolinyl, 3H-benzothiazol-2-onyl and dihydrobenzofuranyl, which in each case may be bonded via a —(CH$_2$)— or a —(CH$_2$)$_2$-group and which is in each case unsubstituted or which is in each case substituted with 1, 2, 3, 4 or 5 substituent(s) independently selected from the group consisting of —CH$_2$—CH$_2$—C(=O)—OCH$_3$, —CH$_2$—C(=O)—OCH$_3$, —CF$_3$, —C$_2$F$_5$, —C$_3$F$_7$, —C$_4$F$_9$, methyl, ethyl, n-propyl, isopropyl, n-butyl, isobutyl, 2-butyl, tert-butyl, —C—(CH$_3$)$_2$(C$_2$H$_5$), n-pentyl, 2-pentyl, n-hexyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —C(=O)—O—CH$_3$, —C(=O)—O—C$_2$H$_5$, —C(=O)—O—CH$_2$—CH$_2$—CH$_3$, —C(=O)—O—CH(CH$_3$)$_2$, —C(=O)—O—CH$_2$—CH$_2$—CH$_3$, —C(=O)—O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —NH—C(=O)—CH$_3$, —NH—C(=O)—C$_2$H$_5$, —NH—C(=)—C(CH$_3$)$_3$, —S(=O—)—CH$_3$, —S(=O)—C$_2$H$_5$, —S(=O)—C$_3$H$_7$, —S(=O)$_2$—CH$_3$, —S(=O)$_2$—C$_2$H$_5$, —S(=)$_2$—C$_3$H$_7$, NO$_2$, —NH$_2$, —NH—CH$_3$, —NH—C$_2$H$_5$, —N(CH$_3$)$_2$, —N(C$_2$H$_5$)$_2$, cyclopropyl, cyclobutyl, cyclopentyl, cyclohexyl, phenyl, —O-phenyl and benzyl; and R$^{6a}$ and R$^{6b}$, independent of one another, each represent H; or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl and 4-octyl, which is in each case unsubstituted.

11. A compound of general formula Ic according to claim 1,

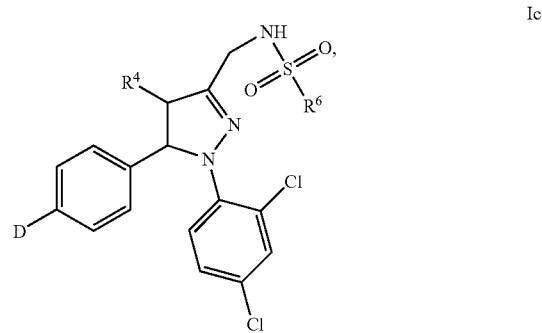

wherein
D represents —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, F, Cl, Br, I, or —OH;
R$^4$ represents hydrogen, —CH$_3$, —C$_2$H$_5$, —CH$_2$—CH$_2$—CH$_3$, —CH(CH$_3$)$_2$, —CH$_2$—CH$_2$—CH$_2$—CH$_3$, —CH$_2$—CH(CH$_3$)$_2$, or —CH(CH$_3$)$_3$;
and R$^6$ is defined as in claim 1.

12. A compound of general formula Ic according to claim 10, characterized in that
D represents —O—CH$_3$, —O—C$_2$H$_5$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CH$_2$—CH$_2$—CF$_3$, F, Cl, Br or —OH;
R$^4$ represents hydrogen, —CH$_3$, or —C$_2$H$_5$; and
R$^6$ represent —NR$^{6a}$R$^{6b}$, unsubstituted or at least monosubstituted alkyl, alkenyl or
alkynyl, unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl or -(alkylene)-heterocycloalkenyl which each may be condensed with an unsubstituted or at least mono-substituted saturated, unsaturated or aromatic mono- or bicyclic ring system; unsubstituted or at least mono-substituted aryl, -(alkylene)-aryl or -(alkenylene)-aryl which each may be condensed with an unsubstituted or at least mono-substituted saturated or unsaturated, but now aromatic, mono- or bicyclic ring system; or unsubstituted or at least mono-substituted heteroaryl, -(alkylene)-heteroaryl or -(alkenylene)-heteroaryl which each may be condensed with an unsubstituted or at least mono-substituted saturated or unsaturated, but not aromatic, mono- or bicyclic ring system;

R$^{6a}$ and R$^{6b}$, independent of one another, each represent H; unsubstituted or at least mono-substituted alkyl, alkenyl or alkynyl; or unsubstituted or at least mono-substituted cycloalkyl, -(alkylene)-cycloalkyl, cycloalkenyl, -(alkylene)-cycloalkenyl, heterocycloalkyl, -(alkylene)-heterocycloalkyl, heterocycloalkenyl, or -(alkylene)-heterocycloalkenyl which each may be condensed with an unsubstituted or at least mono-substituted saturated, unsaturated or aromatic mono- or bicyclic ring system.

13. A compound of general formula Id according to claim 1,

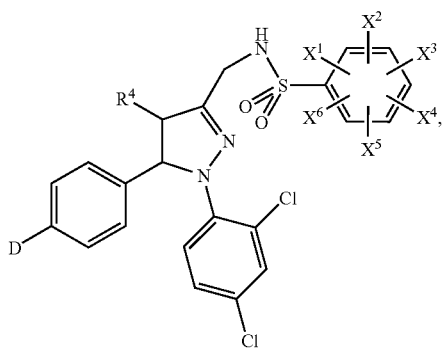

wherein

D represents —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—S(=O)$_2$—CH$_3$, —O—S(=O)$_2$—C$_2$H$_5$, —O—S(=O)$_2$—CH$_2$—CH$_2$—CH$_3$, —O—S(=O)$_2$—CH(CH$_3$)$_2$, —O—S(=O)$_2$—CF$_3$, —O—S(=O)$_2$—CH$_2$CF$_3$, —O—S(=O)$_2$—CH$_2$—CH$_2$—CF$_3$, F, Cl, Br, I, or —OH;

R$^4$ represents hydrogen, —CH$_3$, —C$_2$H$_5$, —CH$_2$—CH$_2$—CH$_3$, —CH(CH$_3$)$_2$, —CH$_2$—CH$_2$—CH$_2$—CH$_3$, —CH$_2$—CH(CH$_3$)$_2$, or —CH(CH$_3$)$_3$;

and X$^1$, X$^2$, X$^3$, X$^4$ and X$^5$ independently from one another represent hydrogen, —CH$_2$—CH$_2$—C(=O)—OCH$_3$, —CH$_2$—C(=O)—OCH$_3$, —CF$_3$, methyl, ethyl, n-propyl, isopropyl, n-butyl, isobutyl, 2-butyl, tert-butyl, —C—(CH$_3$)$_2$(C$_2$H$_5$), —O—CH$_3$, —O—C$_2$H$_5$, —O—CH$_2$—CH$_2$—CH$_3$, —O—CH(CH$_3$)$_2$, C(=O)—O—CH$_3$, C(=O)—O—C$_2$H$_5$, F, Cl, Br, I, —CN, —OCF$_3$, —OH, —NH—C(=O)—CH$_3$, —NH—C(=O)—C$_2$H$_5$, —S(=O)$_2$—CH$_3$, —S(=O)$_2$—C$_2$H$_5$, NO$_2$, —NH$_2$, —NH—CH$_3$, —NH—C$_2$H$_5$, —N(CH$_3$)$_2$, —N(C$_2$H$_5$)$_2$, cyclopropyl, cyclobutyl, cyclopentyl, cyclohexyl, phenyl, —O-phenyl and benzyl.

14. A compound according to claim 1 selected from the group consisting of 3-Chloro-N-[5-(4-chloro-phenyl)-1-(2,4-dichloro-phenyl)-4,5-dihydro-1H-pyrazol-3-ylmethyl]-benzenesulfonamide N-((5-(4-chlorophenyl)-1-(2,4-dichlorophenyl)-4,5-dihydro-1H-pyrazol-3-yl)methyl)dimethylaminosulfonamide N-[5-(4-Chloro-phenyl)-1-(2,4-dichloro-phenyl)-4,5-dihydro-1H-pyrazol-3-ylmethyl]-3-methoxy-benzenesulfonamide N-[5-(4-Chloro-phenyl)-1-(2,4-dichloro-phenyl)-4,5-dihydro-1H-pyrazol-3-ylmethyl]-2-methanesulfonyl-benzenesulfonamide N-[5-(4-Chloro-phenyl)-1-(2,4-dichloro-phenyl)-4,5-dihydro-1H-pyrazol-3-yl methyl]-4-cyclohexyl-benzenesulfonamide 3-Chloro-N-[5-(4-chloro-phenyl)-1-(2,4-dichloro-phenyl)-4,5-dihydro-1H-pyrazol-3-ylmethyl]-4-fluoro-benzenesulfonamide N-[5-(4-Chloro-phenyl)-1-(2,4-dichloro-phenyl)-4,5-dihydro-1H-pyrazol-3-ylmethyl]-C-(7,7-dimethyl-2-oxo-bicyclo[2.2.1]hept-1-yl)-methanesulfonamide 2H-Imidazole-4-sulfonic acid [5-(4-chloro-phenyl)-1-(2,4-dichloro-phenyl)-4,5-dihydro-1H-pyrazol-3-ylmethyl]-amide Thiophene-3-sulfonic acid [5-(4-chloro-phenyl)-1-(2,4-dichloro-phenyl)-4,5-dihydro-1H-pyrazol-3-ylmethyl]-amide N-((5-(4-chlorophenyl)-1-(2,4-dichlorophenyl)-4,5-dihydro-1H-pyrazol-3-yl)methyl)-3-cyanobenzenesulfonamide 4-tert-Butyl-N-[5-(4-chloro-phenyl)-1-(2,4-dichloro-phenyl)-4,5-dihydro-1H-pyrazol-3-ylmethyl]-benzenesulfonamide N-[5-(4-Chloro-phenyl)-1-(2,4-dichloro-phenyl)-4,5-dihydro-1H-pyrazol-3-ylmethyl]-C-phenyl-methanesulfonamide N-[5-(4-Chloro-phenyl)-1-(2,4-dichloro-phenyl)-4,5-dihydro-1H-pyrazol-3-ylmethyl]-2,5-dimethoxy-benzenesulfonamide Ethanesulfonic acid [5-(4-chloro-phenyl)-1-(2,4-dichloro-phenyl)-4,5-dihydro-1H-pyrazol-3-ylmethyl]-amide Propane-2-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-4-trifluoromethoxy-benzenesulfonamide N-[5-(4-Chloro-phenyl)-1-(2,4-dichloro-phenyl)-4,5-dihydro-1H-pyrazol-3-ylmethyl]-2-trifluoromethyl-benzenesulfonamide N-[5-(4-Chloro-phenyl)-1-(2,4-dichloro-phenyl)-4,5-dihydro-1H-pyrazol-3-ylmethyl]-3-trifluoromethyl-benzenesulfonamide 2-Oxo-2,3-dihydro-benzothiazole-6-sulfonic acid [5-(4-chloro-phenyl)-1-(2,4-dichloro-phenyl)-4,5-dihydro-1H-pyrazol-3-ylmethyl]-amide Butane-1-sulfonic acid [5-(4-chloro-phenyl)-1-(2,4-dichloro-phenyl)-4,5-dihydro-1H-pyrazol-3-ylmethyl]-amide Propane-1-sulfonic acid [5-(4-chloro-phenyl)-1-(2,4-dichloro-phenyl)-4,5-dihydro-1H-pyrazol-3-ylmethyl]-amide Cyclohexanesulfonic acid [5-(4-chloro-phenyl)-1-(2,4-dichloro-phenyl)-4,5-dihydro-1H-pyrazol-3-ylmethyl]-amide 2-Chloro-N-[5-(4-chloro-phenyl)-1-(2,4-dichloro-phenyl)-4,5-dihydro-1H-pyrazol-3-ylmethyl]-benzenesulfonamide N-[5-(4-Chloro-phenyl)-1-(2,4-dichloro-phenyl)-4,5-dihydro-1H-pyrazol-3-ylmethyl]-3-methyl-benzenesulfonamide N-[5-(4-Chloro-phenyl)-1-(2,4-dichloro-phenyl)-4,5-dihydro-1H-pyrazol-3-ylmethyl]-4-phenoxy-benzenesulfonamide Biphenyl-2-sulfonic acid [5-(4-chloro-phenyl)-1-(2,4-dichloro-phenyl)-4,5-dihydro-1H-pyrazol-3-ylmethyl]-amide 3-Chloro-N-[5-(4-chloro-phenyl)-1-(2,4-dichloro-phenyl)-4,5-dihydro-1H-pyrazol-3-ylmethyl]-2-fluoro-benzenesulfonamide N-[5-(4-Chloro-phenyl)-1-(2,4-dichloro-phenyl)-4,5-dihydro-1H-pyrazol-3-ylmethyl]-3-fluoro-benzenesulfonamide N-[5-(4-Chloro-phenyl)-1-(2,4-dichloro-phenyl)-4,5-dihydro-1H-pyrazol-3-ylmethyl]-4-methoxy-benzenesulfonamide 4-Bromo-N-[5-(4-chloro-phenyl)-1-(2,4-dichloro-phenyl)-4,5-dihydro-1H-pyrazol-3-ylmethyl]-benzenesulfonamide N-[5-(4-Chloro-phenyl)-1-(2,4-dichloro-phenyl)-4,5-dihydro-1H-pyrazol-3-ylmethyl]-C-cyclohexyl-methanesulfonamide 6-Chloro-7,7a-dihydro-imidazo[2,1-b]thiazole-5-sulfonic acid [5-(4-chloro-phenyl)-1-(2,4-dichloro-phenyl)-4,5-dihydro-1H-pyrazol-3-ylmethyl]-amide N-((5-(4-chlorophenyl)-1-(2,4-dichlorophenyl)-4,5-dihydro-1H-pyrazol-3-yl)methyl)-2-cyanobenzenesulfonamide 2-Chloro-N-[5-(4-chloro-phenyl)-1-(2,4-dichloro-phenyl)-4,5-dihydro-1H-pyrazol-3-ylmethyl]-6-methyl-benzenesulfonamide 3-(4-{[5-(4-Chloro-phenyl)-1-(2,4-dichloro-phenyl)-4,5-dihydro-1H-pyrazol-3-ylmethyl]-sulfamoyl}-phenyl)-propionic acid methyl ester N-[5-(4-Chloro-phenyl)-1-(2,4-dichloro-phenyl)-4,5-dihydro-1H-pyrazol-3-ylmethyl]-2-methoxy-4-methyl-benzenesulfonamide Benzo[b]thiophene-3-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-5-fluoro-2-methyl-benzenesulfonamide 4-Chloro-N-[5-(4-chloro-phenyl)-1-(2,4-dichloro-phenyl)-4,5-dihydro-1H-pyrazol-3-ylmethyl]-2,5-dimethyl-benzenesulfonamide N-[5-(4-Chloro-phenyl)-1-(2,4-dichloro-phenyl)-4,5-dihydro-1H-pyrazol-3-ylmethyl]-2,4,6-trimethyl-benzenesulfonamide N-(2-Chloro-4-{[5-(4-chloro-phenyl)-1-(2,4-dichloro-phenyl)-4,5-dihydro-1H-pyrazol-3-ylmethyl]-sulfamoyl}-phenyl)-acetamide 2,3-Dihydro-benzofuran-5-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-4-ethyl-benzenesulfonamide N-[5-(4-Chloro-phenyl)-1-(2,4-dichloro-phenyl)-4,5-dihydro-1H-pyrazol-3-ylmethyl]-2,5-dimethyl-benzenesulfonamide N-[5-(4-Chloro-phenyl)-1-(2,4-dichloro-phenyl)-4,5-dihydro-1H-pyrazol-3-ylmethyl]-2-methoxy-4-methyl-benzenesulfonamide N-[5-(4-Chloro-phenyl)-1-(2,4-dichloro-phenyl)-4,5-dihydro-1H-pyrazol-3-ylmethyl]-2,4-dimethoxy-benzenesulfonamide N-[5-(4-Chloro-phenyl)-1-(2,4-dichloro-phenyl)-4,5-dihydro-1H-pyrazol-3-ylmethyl]-4-propyl-benzenesulfonamide 3,5-Dimethyl-isoxazole-4-sulfonic acid [5-(4-chloro-phenyl)-1-(2,4-dichloro-phenyl)-4,5-dihydro-1H-pyrazol-3-ylmethyl]-amide 1,2-Dimethyl-1H-imidazole-4-sulfonic acid [5-(4-chloro-phenyl)-1-(2,4-dichloro-phenyl)-4,5-dihydro-1H-pyrazol-3-ylmethyl]-amide 5-Methyl-isoxazole-4-sulfonic acid [5-(4-chloro-phenyl)-1-(2,4-dichloro-phenyl)-4,5-dihydro-1H-pyrazol-3-ylmethyl]-amide 1-Methyl-1H-imidazole-4-sulfonic acid [5-(4-chloro-phenyl)-1-(2,4-dichloro-phenyl)-4,5-dihydro-1H-pyrazol-3-ylmethyl]-amide 6-Methyl-2,4-dioxo-1,2,3,4-tetrahydro-pyrimidine-5-sulfonic acid [5-(4-chloro-phenyl)-1-(2,4-dichloro-phenyl)-4,5-dihydro-1H-pyrazol-3-ylmethyl]-amide Pyridine-3-sulfonic acid [5-(4-chloro-phenyl)-1-(2,4-dichloro-phenyl)-4,5-dihydro-1H-pyrazol-3-ylmethyl]-amide hydrochloride Quinoline-8-sulfonic acid [5-(4-chloro-phenyl)-1-(2,4-dichloro-phenyl)-4,5-dihydro-1H-pyrazol-3-ylmethyl]-amide 5-Amino-naphthalene-1-sulfonic acid [5-(4-chloro-phenyl)-1-(2,4-dichloro-phenyl)-4,5-dihydro-1H-pyrazol-3-ylmethyl]-amide 3-Methyl-quinoline-8-sulfonic acid [5-(4-chloro-phenyl)-1-(2,4-dichloro-phenyl)-4,5-dihydro-1H-pyrazol-3-ylmethyl]-amide N-(5-{[5-(4-Chloro-phenyl)-1-(2,4-dichloro-phenyl)-4,5-dihydro-1H-pyrazol-3-ylmethyl]-sulfamoyl}-naphthalen-1-yl)-acetamide 5-Dimethylamino-naphthalene-1-sulfonic acid [5-(4-chloro-phenyl)-1-(2,4-dichloro-phenyl)-4,5-dihydro-1H-pyrazol-3-ylmethyl]-amide 2-Oxo-1,2,3,4-tetrahydro-quinoline-6-sulfonic acid [5-(4-chloro-phenyl)-1-(2,4-dichloro-phenyl)-4,5-dihydro-1H-pyrazol-3-ylmethyl]-amide 5-Amino-naphthalene-1-sulfonic acid [5-(4-chloro-phenyl)-1-(2,4-dichloro-phenyl)-4,5-dihydro-1H-pyrazol-3-ylmethyl]-amide hydrochloride Quinoline-8-sulfonic acid [5-(4-chloro-phenyl)-1-(2,4-dichloro-phenyl)-4,5-dihydro-1H-pyrazol-3-ylmethyl]-amide hydrochloride 3-Methyl-quinoline-8-sulfonic acid [5-(4-chloro-phenyl)-1-(2,4-dichloro-phenyl)-4,5-dihydro-1H-pyrazol-3-ylmethyl]-amide hydrochloride (R)—N-[5-(4-Chloro-phenyl)-1-(2,4-dichloro-phenyl)-4,5-dihydro-1H-pyrazol-3-ylmethyl]-5-fluoro-2-methyl-benzenesulfonamide (S)—N-[5-(4-Chloro-phenyl)-1-(2,4-dichloro-phenyl)-4,5-dihydro-1H-pyrazol-3-ylmethyl]-5-fluoro-2-methyl-benzenesulfonamide (R)-2-Chloro-N-[5-(4-chloro-phenyl)-1-(2,4-dichloro-phenyl)-4,5-dihydro-1H-pyrazol-3-ylmethyl]-6-methyl-benzenesulfonamide (S)-2-Chloro-N-[5-(4-chloro-phenyl)-1-(2,4-dichloro-phenyl)-4,5-dihydro-1H-pyrazol-3-ylmethyl]-6-methyl-benzenesulfonamide (R)-4-Chloro-N-[5-(4-chloro-phenyl)-1-(2,4-dichloro-phenyl)-4,5-dihydro-1H-pyrazol-3-ylmethyl]-2,5-dimethyl-benzenesulfonamide (S)-4-Chloro-N-[5-(4-chloro-phenyl)-1-(2,4-dichloro-phenyl)-4,5-dihydro-1H-pyrazol-3-ylmethyl]-2,5-dimethyl-benzenesulfonamide (R)—N-[5-(4-Chloro-phenyl)-1-(2,4-dichloro-phenyl)-4,5-dihydro-1H-pyrazol-3-ylmethyl]-2,5-dimethyl-benzenesulfonamide (S)—N-[5-(4-Chloro-phenyl)-1-(2,4-dichloro-phenyl)-4,5-dihydro-1H-pyrazol-3-ylmethyl]-2,5-dimethyl-benzenesulfonamide N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide trans(4SR,5RS)—N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide
cis-(4RS,5RS)—N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide
(4R,5R)—N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide
(4S,5S)—N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide
(4R,5S)—N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide
(4S,5R)—N-[5-(4-Chloro-phenyl)-1-(2,4-dichloro-phenyl)-4-methyl-4,5-dihydro-1H-pyrazol-3-ylmethyl]-5-fluoro-2-methyl-benzenesulfonamide
N-[5-(4-Chloro-phenyl)-1-(2,4-dichloro-phenyl)-4,5-dihydro-1H-pyrazol-3-ylmethyl]-2-fluoro-benzenesulfonamide
N-[5-(4-Chloro-phenyl)-1-(2,4-dichloro-phenyl)-4,5-dihydro-1H-pyrazol-3-ylmethyl]-2,5-difluoro-benzenesulfonamide
5-Chloro-N-[5-(4-chloro-phenyl)-1-(2,4-dichloro-phenyl)-4,5-dihydro-1H-pyrazol-3-ylmethyl]-2-fluoro-benzenesulfonamide
2-Chloro-N-[5-(4-chloro-phenyl)-1-(2,4-dichloro-phenyl)-4,5-dihydro-1H-pyrazol-3-ylmethyl]-5-trifluoromethyl-benzenesulfonamide
3,5-Dichloro-N-[5-(4-chloro-phenyl)-1-(2,4-dichloro-phenyl)-4,5-dihydro-1H-pyrazol-3-ylmethyl]-2-hydroxy-benzenesulfonamide
cis-(4RS,5RS)—N-[5-(4-Chloro-phenyl)-1-(2,4-dichloro-phenyl)-4-methyl-4,5-dihydro-1H-pyrazol-3-ylmethyl]-2,5-dimethyl-benzenesulfonamide
3,5-dichloro-N-((5-(4-chlorophenyl)-1-(2,4-dichlorophenyl)-4,5-dihydro-1H-pyrazol-3-yl)methyl)-N-(3,5-dichloro-2-hydroxyphenylsulfonyl)-2-hydroxybenzenesulfonamide
N-[5-(4-Chloro-phenyl)-1-(2,4-dichloro-phenyl)-4,5-dihydro-1H-pyrazol-3-ylmethyl]-4-fluoro-2-methyl-benzenesulfonamide
N-[5-(4-Chloro-phenyl)-1-(2,4-dichloro-phenyl)-4,5-dihydro-1H-pyrazol-3-ylmethyl]-3-fluoro-4-methyl-benzenesulfonamide
5-Bromo-6-chloro-pyridine-3-sulfonic acid [5-(4-chloro-phenyl)-1-(2,4-dichloro-phenyl)-4,5-dihydro-1H-pyrazol-3-ylmethyl]-amide
3,5-Dichloro-N-[5-(4-chloro-phenyl)-1-(2,4-dichloro-phenyl)-4,5-dihydro-1H-pyrazol-3-ylmethyl]-4-hydroxy-benzenesulfonamide
N-[5-(4-Chloro-phenyl)-1-(2,4-dichloro-phenyl)-4,5-dihydro-1H-pyrazol-3-ylmethyl]-benzenesulfonamide
3-{[5-(4-Chloro-phenyl)-1-(2,4-dichloro-phenyl)-4,5-dihydro-1H-pyrazol-3-ylmethyl]-sulfamoyl}-thiophene-2-carboxylic acid methyl ester
5-Bromo-6-chloro-pyridine-3-sulfonic acid [5-(4-chloro-phenyl)-1-(2,4-dichloro-phenyl)-4,5-dihydro-1H-pyrazol-3-ylmethyl]-amide hydrochloride
N-[1-(2,4-Dichloro-phenyl)-5-(4-methoxy-phenyl)-4,5-dihydro-1H-pyrazol-3-ylmethyl]-2-fluoro-benzenesulfonamide
N-[1-(2,4-Dichloro-phenyl)-5-(4-methoxy-phenyl)-4,5-dihydro-1H-pyrazol-3-ylmethyl]-2,5-difluoro-benzenesulfonamide
5-Chloro-N-[1-(2,4-dichloro-phenyl)-5-(4-methoxy-phenyl)-4,5-dihydro-1-pyrazol-3-ylmethyl]-2-fluoro-benzenesulfonamide
2-Chloro-N-[1-(2,4-dichloro-phenyl)-5-(4-methoxy-phenyl)-4,5-dihydro-1H-pyrazol-3-ylmethyl]-5-trifluoromethyl-benzenesulfonamide
N-[1-(2,4-Dichloro-phenyl)-5-(4-methoxy-phenyl)-4,5-dihydro-1H-pyrazol-3-ylmethyl]-5-fluoro-2-methyl-benzene sulfonamide
N-[1-(2,4-Dichloro-phenyl)-5-(4-methoxy-phenyl)-4,5-dihydro-1H-pyrazol-3-ylmethyl]-2,5-dimethyl-benzenesulfonamide
N-[1-(2,4-Dichloro-phenyl)-5-(4-ethoxy-phenyl)-4,5-dihydro-1H-pyrazol-3-ylmethyl]-2-fluoro-benzenesulfonamide
N-[1-(2,4-Dichloro-phenyl)-5-(4-ethoxy-phenyl)-4,5-dihydro-1H-pyrazol-3-ylmethyl]-2,5-difluoro-benzenesulfonamide
5-Chloro-N-[1-(2,4-dichloro-phenyl)-5-(4-ethoxy-phenyl)-4,5-dihydro-1H-pyrazol-3-ylmethyl]-2-fluoro-benzenesulfonamide
2-Chloro-N-[1-(2,4-dichloro-phenyl)-5-(4-ethoxy-phenyl)-4,5-dihydro-1H-pyrazol-3-ylmethyl]-5-trifluoromethyl-benzenesulfonamide
N-[1-(2,4-Dichloro-phenyl)-5-(4-ethoxy-phenyl)-4,5-dihydro-1H-pyrazol-3-ylmethyl]-5-fluoro-2-methyl-benzenesulfonamide
N-[1-(2,4-Dichloro-phenyl)-5-(4-ethoxy-phenyl)-4,5-dihydro-1H-pyrazol-3-ylmethyl]-2,5-dimethyl-benzenesulfonamide
(R)—N-[5-(4-Chloro-phenyl)-1-(2,4-dichloro-phenyl)-4,5-dihydro-1H-pyrazol-3-ylmethyl]-2-fluoro-benzenesulfonamide
(R)—N-[5-(4-Chloro-phenyl)-1-(2,4-dichloro-phenyl)-4,5-dihydro-1H-pyrazol-3-ylmethyl]-2,5-difluoro-benzenesulfonamide
(R)-5-Chloro-N-[5-(4-chloro-phenyl)-1-(2,4-dichloro-phenyl)-4,5-dihydro-1H-pyrazol-3-ylmethyl]-2-fluoro-benzenesulfonamide
(R)—N-[5-(4-Chloro-phenyl)-1-(2,4-dichloro-phenyl)-4,5-dihydro-1H-pyrazol-3-ylmethyl]-2,4,6-trimethyl-benzenesulfonamide
(S)—N-[5-(4-Chloro-phenyl)-1-(2,4-dichloro-phenyl)-4,5-dihydro-1H-pyrazol-3-ylmethyl]-2-fluoro-benzenesulfonamide
(S)—N-[5-(4-Chloro-phenyl)-1-(2,4-dichloro-phenyl)-4,5-dihydro-1H-pyrazol-3-ylmethyl]-2,5-difluoro-benzenesulfonamide
(S)-5-Chloro-N-[5-(4-chloro-phenyl)-1-(2,4-dichloro-phenyl)-4,5-dihydro-1H-pyrazol-3-ylmethyl]-2-fluoro-benzenesulfonamide
(S)—N-[5-(4-Chloro-phenyl)-1-(2,4-dichloro-phenyl)-4,5-dihydro-1H-pyrazol-3-ylmethyl]-2,4,6-trimethyl-benzenesulfonamide
2-Oxo-2H-chromene-5-sulfonic acid [5-(4-chloro-phenyl)-1-(2,4-dichloro-phenyl)-4,5-dihydro-1H-pyrazol-3-ylmethyl]-amide
N-[5-(4-Chloro-phenyl)-1-(2,4-dichloro-phenyl)-4,5-dihydro-1H-pyrazol-3-ylmethyl]-2,6-difluoro-benzenesulfonamide
Biphenyl-4-sulfonic acid [5-(4-chloro-phenyl)-1-(2,4-dichloro-phenyl)-4,5-dihydro-1H-pyrazol-3-ylmethyl]-amide
Benzo[1,2,5]oxadiazole-4-sulfonic acid [5-(4-chloro-phenyl)-1-(2,4-dichloro-phenyl)-4,5-dihydro-1H-pyrazol-3-ylmethyl]-amide Benzo[1,2,5]thiadiazole-4-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-4-isopropyl-benzenesulfonamide N-[5-(4-Chloro-phenyl)-1-(2,4-dichloro-phenyl)-4,5-dihydro-1H-pyrazol-3-ylmethyl]-3,4-difluoro-benzenesulfonamide 3,4-Dichloro-N-[5-(4-chloro-phenyl)-1-(2,4-dichloro-phenyl)-4,5-dihydro-1H-pyrazol-3-ylmethyl]-benzenesulfonamide 7-Chloro-benzo[1,2,5]oxadiazole-4-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-4-isopropoxy-benzenesulfonamide 3-Chloro-N-[5-(4-chloro-phenyl)-1-(2,4-dichloro-phenyl)-4,5-dihydro-1H-pyrazol-3-ylmethyl]-4-methoxy-benzenesulfonamide 2,4-Dimethyl-thiazole-5-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-2,4-difluoro-benzenesulfonamide Benzo[b]thiophene-2-sulfonic acid [5-(4-chloro-phenyl)-1-(2,4-dichloro-phenyl)-4,5-dihydro-1H-pyrazol-3-ylmethyl]-amide 3-Bromo-N-[5-(4-chloro-phenyl)-1-(2,4-dichloro-phenyl)-4,5-dihydro-1H-pyrazol-3-ylmethyl]-benzenesulfonamide N-[5-(4-Chloro-phenyl)-1-(2,4-dichloro-phenyl)-4,5-dihydro-1H-pyrazol-3-ylmethyl]-2,3,5,6-tetramethyl-benzenesulfonamide 3-Chloro-N-[5-(4-chloro-phenyl)-1-(2,4-dichloro-phenyl)-4,5-dihydro-1H-pyrazol-3-ylmethyl]-2-methyl-benzenesulfonamide N-[5-(4-Chloro-phenyl)-1-(2,4-dichloro-phenyl)-4,5-dihydro-1H-pyrazol-3-ylmethyl]-4-fluoro-3-methyl-benzenesulfonamide 5-Bromo-N-[5-(4-chloro-phenyl)-1-(2,4-dichloro-phenyl)-4,5-dihydro-1H-pyrazol-3-ylmethyl]-2-methoxy-benzenesulfonamide 2-(2,2,2-Trifluoro-acetyl)-1,2,3,4-tetrahydro-isoquinoline-7-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-2,3,4,5,6-pentamethyl-benzenesulfonamide 2,4-Dichloro-N-[5-(4-chloro-phenyl)-1-(2,4-dichloro-phenyl)-4,5-dihydro-1H-pyrazol-3-ylmethyl]-benzenesulfonamide N-[5-(4-Chloro-phenyl)-1-(2,4-dichloro-phenyl)-4,5-dihydro-1H-pyrazol-3-ylmethyl]-4-methanesulfonyl-benzenesulfonamide 4-Chloro-N-[5-(4-chloro-phenyl)-1-(2,4-dichloro-phenyl)-4,5-dihydro-1H-pyrazol-3-ylmethyl]-benzenesulfonamide 2-Bromo-N-[5-(4-chloro-phenyl)-1-(2,4-dichloro-phenyl)-4,5-dihydro-1H-pyrazol-3-ylmethyl]-benzenesulfonamide 2,3-Dihydro-benzo[1,4]dioxine-6-sulfonic acid [5-(4-chloro-phenyl)-1-(2,4-dichloro-phenyl)-4,5-dihydro-1H-pyrazol-3-ylmethyl]-amide 4-Butyl-N-[5-(4-chloro-phenyl)-1-(2,4-dichloro-phenyl)-4,5-dihydro-1H-pyrazol-3-ylmethyl]-benzenesulfonamide 2,5-Dichloro-N-[5-(4-chloro-phenyl)-1-(2,4-dichloro-phenyl)-4,5-dihydro-1H-pyrazol-3-ylmethyl]-benzenesulfonamide 4-Bromo-N-[5-(4-chloro-phenyl)-1-(2,4-dichloro-phenyl)-4,5-dihydro-1H-pyrazol-3-ylmethyl]-3-methyl-benzenesulfonamide N-[5-(4-Chloro-phenyl)-1-(2,4-dichloro-phenyl)-4,5-dihydro-1H-pyrazol-3-ylmethyl]-4-(1,1-dimethyl-propyl)-benzenesulfonamide N-[5-(4-Chloro-phenyl)-1-(2,4-dichloro-phenyl)-4,5-dihydro-1H-pyrazol-3-ylmethyl]-2-methyl-5-nitro-benzenesulfonamide 2,3-Dichloro-N-[5-(4-chloro-phenyl)-1-(2,4-dichloro-phenyl)-4,5-dihydro-1H-pyrazol-3-ylmethyl]-benzenesulfonamide N-[5-(4-Chloro-phenyl)-1-(2,4-dichloro-phenyl)-4,5-dihydro-1H-pyrazol-3-ylmethyl]-3-nitro-benzenesulfonamide 2-Bromo-N-[5-(4-chloro-phenyl)-1-(2,4-dichloro-phenyl)-4,5-dihydro-1H-pyrazol-3-ylmethyl]-4-fluoro-benzenesulfonamide 4-Bromo-N-[5-(4-chloro-phenyl)-1-(2,4-dichloro-phenyl)-4,5-dihydro-1H-pyrazol-3-ylmethyl]-3-trifluoromethyl-benzenesulfonamide 5-Methyl-benzo[1,2,5]thiadiazole-4-sulfonic acid [5-(4-chloro-phenyl)-1-(2,4-dichloro-phenyl)-4,5-dihydro-1H-pyrazol-3-ylmethyl]-amide 2,2,4,6,7-Pentamethyl-2,3-dihydro-benzofuran-5-sulfonic acid [5-(4-chloro-phenyl)-1-(2,4-dichloro-phenyl)-4,5-dihydro-1H-pyrazol-3-ylmethyl]-amide 2,6-Dichloro-N-[5-(4-chloro-phenyl)-1-(2,4-dichloro-phenyl)-4,5-dihydro-1H-pyrazol-3-ylmethyl]-benzenesulfonamide 4-{[5-(4-Chloro-phenyl)-1-(2,4-dichloro-phenyl)-4,5-dihydro-1H-pyrazol-3-ylmethyl]-sulfamoyl}-2,5-dimethyl-furan-3-carboxylic acid methyl ester 2-Oxo-2,3-dihydro-benzooxazole-6-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-3-fluoro-4-methoxy-benzenesulfonamide Pyridine-2-sulfonic acid [5-(4-chloro-phenyl)-1-(2,4-dichloro-phenyl)-4,5-dihydro-1H-pyrazol-3-ylmethyl]-amide N-[5-(4-Chloro-phenyl)-1-(2,4-dichloro-phenyl)-4,5-dihydro-1H-pyrazol-3-ylmethyl]-4-methoxy-2,3,6-trimethyl-benzenesulfonamide 5-Chloro-N-[5-(4-chloro-phenyl)-1-(2,4-dichloro-phenyl)-4,5-dihydro-1H-pyrazol-3-ylmethyl]-2-methoxy-benzenesulfonamide N-[5-(4-Chloro-phenyl)-1-(2,4-dichloro-phenyl)-4,5-dihydro-1H-pyrazol-3-ylmethyl]-2-fluoro-5-methyl-benzenesulfonamide N-[5-(4-Chloro-phenyl)-1-(2,4-dichloro-phenyl)-4,5-dihydro-1H-pyrazol-3-ylmethyl]-3,4-dimethoxy-benzenesulfonamide N-[5-(4-Chloro-phenyl)-1-(2,4-dichloro-phenyl)-4,5-dihydro-1H-pyrazol-3-ylmethyl]-4-methyl-benzenesulfonamide 3-{[5-(4-Chloro-phenyl)-1-(2,4-dichloro-phenyl)-4,5-dihydro-1H-pyrazol-3-ylmethyl]-sulfamoyl}-4-methoxy-benzoic acid methyl ester N-[5-(4-Chloro-phenyl)-1-(2,4-dichloro-phenyl)-4,5-dihydro-1H-pyrazol-3-ylmethyl]-2-nitro-benzenesulfonamide
Naphthalene-2-sulfonic acid [5-(4-chloro-phenyl)-1-(2,4-dichloro-phenyl)-4,5-dihydro-1H-pyrazol-3-ylmethyl]-amide
N-(3-{[5-(4-Chloro-phenyl)-1-(2,4-dichloro-phenyl)-4,5-dihydro-1H-pyrazol-3-ylmethyl-sulfamoyl}-4-ethoxy-phenyl)-acetamide
N-[5-(4-Chloro-phenyl)-1-(2,4-dichloro-phenyl)-4,5-dihydro-1H-pyrazol-3-ylmethyl]-5-ethyl-2-methoxy-benzenesulfonamide
5-Chloro-3-methyl-benzo[b]thiophene-2-sulfonic acid [5-(4-chloro-phenyl)-1-(2,4-dichloro-phenyl)-4,5-dihydro-1H-pyrazol-3-ylmethyl]-amide
3,5-Dichloro-N-[5-(4-chloro-phenyl)-1-(2,4-dichloro-phenyl)-4,5-dihydro-1H-pyrazol-3-ylmethyl]-benzenesulfonamide
3-Methyl-2-oxo-2,3-dihydro-benzooxazole-6-sulfonic acid [5-(4-chloro-phenyl)-1-(2,4-dichloro-phenyl)-4,5-dihydro-1H-pyrazol-3-ylmethyl]-amide
1,4-Dimethyl-2,3-dioxo-1,2,3,4-tetrahydro-quinoxaline-6-sulfonic acid [5-(4-chloro-phenyl)-1-(2,4-dichloro-phenyl)-4,5-dihydro-1H-pyrazol-3-ylmethyl]-amide
1,3,5-Trimethyl-1H-pyrazole-4-sulfonic acid [5-(4-chloro-phenyl)-1-(2,4-dichloro-phenyl)-4,5-dihydro-1H-pyrazol-3-ylmethyl]-amide
N-[5-(4-Chloro-phenyl)-1-(2,4-dichloro-phenyl)-4,5-dihydro-1H-pyrazol-3-ylmethyl]-2,5-bis-trifluoromethyl-benzenesulfonamide
2-Methyl-benzothiazole-6-sulfonic acid [5-(4-chloro-phenyl)-1-(2,4-dichloro-phenyl)-4,5-dihydro-1H-pyrazol-3-ylmethyl]-amide
4-Chloro-N-[5-(4-chloro-phenyl)-1-(2,4-dichloro-phenyl)-4,5-dihydro-1H-pyrazol-3-ylmethyl]-2,5-difluoro-benzenesulfonamide
N-[5-(4-Chloro-phenyl)-1-(2,4-dichloro-phenyl)-4,5-dihydro-1H-pyrazol-3-ylmethyl]-2,4,5-trifluoro-benzenesulfonamide
5-Bromo-N-[5-(4-chloro-phenyl)-1-(2,4-dichloro-phenyl)-4,5-dihydro-1H-pyrazol-3-ylmethyl]-2,4-difluoro-benzenesulfonamide
N-[5-(4-Chloro-phenyl)-1-(2,4-dichloro-phenyl)-4,5-dihydro-1H-pyrazol-3-ylmethyl]-2-nitro-4-trifluoromethyl-benzenesulfonamide
N-[5-(4-Chloro-phenyl)-1-(2,4-dichloro-phenyl)-4,5-dihydro-1H-pyrazol-3-ylmethyl]-2,3,4,5,6-pentafluoro-benzenesulfonamide
4-Bromo-N-[5-(4-chloro-phenyl)-1-(2,4-dichloro-phenyl)-4,5-dihydro-1H-pyrazol-3-ylmethyl]-2-trifluoromethoxy-benzenesulfonamide
5-Chloro-N-[5-(4-chloro-phenyl)-1-(2,4-dichloro-phenyl)-4,5-dihydro-1H-pyrazol-3-ylmethyl]-2,4-difluoro-benzenesulfonamide
N-[5-(4-Chloro-phenyl)-1-(2,4-dichloro-phenyl)-4,5-dihydro-1H-pyrazol-3-ylmethyl]-2,3,4-trifluoro-benzenesulfonamide
2-Bromo-N-[5-(4-chloro-phenyl)-1-(2,4-dichloro-phenyl)-4,5-dihydro-1H-pyrazol-3-ylmethyl]-4,6-difluoro-benzenesulfonamide
2,3,4-Trichloro-N-[5-(4-chloro-phenyl)-1-(2,4-dichloro-phenyl)-4,5-dihydro-1H-pyrazol-3-ylmethyl]-benzenesulfonamide
4-Methyl-naphthalene-1-sulfonic acid [5-(4-chloro-phenyl)-1-(2,4-dichloro-phenyl)-4,5-dihydro-1H-pyrazol-3-ylmethyl]-amide
2-Chloro-N-[5-(4-chloro-phenyl)-1-(2,4-dichloro-phenyl)-4,5-dihydro-1H-pyrazol-3-ylmethyl]-4,5-difluoro-benzenesulfonamide
2,4,6-Trichloro-N-[5-(4-chloro-phenyl)-1-(2,4-dichloro-phenyl)-4,5-dihydro-1H-pyrazol-3-ylmethyl]-benzenesulfonamide
4-Bromo-N-[5-(4-chloro-phenyl)-1-(2,4-dichloro-phenyl)-4,5-dihydro-1H-pyrazol-3-ylmethyl]-2,5-difluoro-benzenesulfonamide
N-[5-(4-Chloro-phenyl)-1-(2,4-dichloro-phenyl)-4,5-dihydro-1H-pyrazol-3-ylmethyl]-4-nitro-benzenesulfonamide
2,4-Dichloro-N-[5-(4-chloro-phenyl)-1-(2,4-dichloro-phenyl)-4,5-dihydro-1H-pyrazol-3-ylmethyl]-5-methyl-benzenesulfonamide
Naphthalene-1-sulfonic acid [5-(4-chloro-phenyl)-1-(2,4-dichloro-phenyl)-4,5-dihydro-1H-pyrazol-3-ylmethyl]-amide
N-[5-(4-Chloro-phenyl)-1-(2,4-dichloro-phenyl)-4,5-dihydro-1H-pyrazol-3-ylmethyl]-4-fluoro-2-methyl-benzenesulfonamide
(S)—N-[5-(4-Chloro-phenyl)-1-(2,4-dichloro-phenyl)-4,5-dihydro-1H-pyrazol-3-ylmethyl]-benzenesulfonamide
(S)-Pyridine-3-sulfonic acid [5-(4-chloro-phenyl)-1-(2,4-dichloro-phenyl)-4,5-dihydro-1H-pyrazol-3-ylmethyl]-amide hydrochloride
(S)-6-Chloro-imidazo[2,1-b]thiazole-5-sulfonic acid [5-(4-chloro-phenyl)-1-(2,4-dichloro-phenyl)-4,5-dihydro-1H-pyrazol-3-ylmethyl]-amide
(S)-2-Chloro-N-[5-(4-chloro-phenyl)-1-(2,4-dichloro-phenyl)-4,5-dihydro-1H-pyrazol-3-ylmethyl]-5-trifluoromethyl-benzenesulfonamide
(R)—N-[5-(4-Chloro-phenyl)-1-(2,4-dichloro-phenyl)-4,5-dihydro-1H-pyrazol-3-ylmethyl]-4-fluoro-2-methyl-benzenesulfonamide
(R)—N-[5-(4-Chloro-phenyl)-1-(2,4-dichloro-phenyl)-4,5-dihydro-1H-pyrazol-3-ylmethyl]-benzenesulfonamide
(R)-Pyridine-3-sulfonic acid [5-(4-chloro-phenyl)-1-(2,4-dichloro-phenyl)-4,5-dihydro-1H-pyrazol-3-ylmethyl]-amide
(R)-6-Chloro-imidazo[2,1-b]thiazole-5-sulfonic acid [5-(4-chloro-phenyl)-1-(2,4-dichloro-phenyl)-4,5-dihydro-1H-pyrazol-3-ylmethyl]-amide
(R)-2-Chloro-N-[5-(4-chloro-phenyl)-1-(2,4-dichloro-phenyl)-4,5-dihydro-1H-pyrazol-3-ylmethyl]-5-trifluoromethyl-benzenesulfonamide
N-[1-(2,4-Dichloro-phenyl)-5-(4-methoxy-phenyl)-4,5-dihydro-1H-pyrazol-3-ylmethyl]-2-fluoro-5-methyl-benzenesulfonamide
N-[1-(2,4-Dichloro-phenyl)-5-(4-methoxy-phenyl)-4,5-dihydro-1H-pyrazol-3-ylmethyl]-4-fluoro-2-methyl-benzenesulfonamide
N-[1-(2,4-Dichloro-phenyl)-5-(4-methoxy-phenyl)-4,5-dihydro-1H-pyrazol-3-ylmethyl]-benzenesulfonamide
Pyridine-3-sulfonic acid [1-(2,4-dichloro-phenyl)-5-(4-methoxy-phenyl)-4,5-dihydro-1H-pyrazol-3-ylmethyl]-amide hydrochloride
6-Chloro-imidazo[2,1-b]thiazole-5-sulfonic acid [1-(2,4-dichloro-phenyl)-5-(4-methoxy-phenyl)-4,5-dihydro-1H-pyrazol-3-ylmethyl]-amide
N-[1-(2,4-Dichloro-phenyl)-5-(4-methoxy-phenyl)-4,5-dihydro-1H-pyrazol-3-ylmethyl]-2-methoxy-5-methyl-benzenesulfonamide N-[1-(2,4-Dichloro-phenyl)-5-(4-ethoxy-phenyl)-4,5-dihydro-1H-pyrazol-3-ylmethyl]-2-fluoro-5-methyl-benzenesulfonamide N-[1-(2,4-Dichloro-phenyl)-5-(4-ethoxy-phenyl)-4,5-dihydro-1H-pyrazol-3-ylmethyl]-4-fluoro-2-methyl-benzenesulfonamide N-[1-(2,4-Dichloro-phenyl)-5-(4-ethoxy-phenyl)-4,5-dihydro-1H-pyrazol-3-ylmethyl]-benzenesulfonamide Pyridine-3-sulfonic acid [1-(2,4-dichloro-phenyl)-5-(4-ethoxy-phenyl)-4,5-dihydro-1H-pyrazol-3-ylmethyl]-amide 6-Chloro-imidazo[2,1-b]thiazole-5-sulfonic acid [1-(2,4-dichloro-phenyl)-5-(4-ethoxy-phenyl)-4,5-dihydro-1H-pyrazol-3-ylmethyl]-amide N-[1-(2,4-Dichloro-phenyl)-5-(4-ethoxy-phenyl)-4,5-dihydro-1H-pyrazol-3-ylmethyl]-2-methoxy-5-methyl-benzenesulfonamide N-[1-(2,4-Dichloro-phenyl)-5-(4-ethoxy-phenyl)-4,5-dihydro-1H-pyrazol-3-ylmethyl]-2,6-difluoro-benzenesulfonamide 2-Chloro-N-[1-(2,4-dichloro-phenyl)-5-(4-ethoxy-phenyl)-4,5-dihydro-1H-pyrazol-3-ylmethyl]-benzenesulfonamide N-[1-(2,4-Dichloro-phenyl)-5-(4-ethoxy-phenyl)-4,5-dihydro-1H-pyrazol-3-ylmethyl]-2,4-difluoro-benzenesulfonamide 2-Chloro-N-[1-(2,4-dichloro-phenyl)-5-(4-ethoxy-phenyl)-4,5-dihydro-1H-pyrazol-3-ylmethyl]-6-methyl-benzenesulfonamide N-[1-(2,4-Dichloro-phenyl)-5-(4-ethoxy-phenyl)-4,5-dihydro-1H-pyrazol-3-ylmethyl]-3-methyl-benzenesulfonamide N-[1-(2,4-Dichloro-phenyl)-5-(4-ethoxy-phenyl)-4,5-dihydro-1H-pyrazol-3-ylmethyl]-3-methoxy-benzenesulfonamide N-[1-(2,4-Dichloro-phenyl)-5-(4-methoxy-phenyl)-4,5-dihydro-1H-pyrazol-3-ylmethyl]-2,6-difluoro-benzenesulfonamide 2-Chloro-N-[1-(2,4-dichloro-phenyl)-5-(4-methoxy-phenyl)-4,5-dihydro-1H-pyrazol-3-ylmethyl]-benzenesulfonamide N-[1-(2,4-Dichloro-phenyl)-5-(4-methoxy-phenyl)-4,5-dihydro-1H-pyrazol-3-ylmethyl]-2,4-difluoro-benzenesulfonamide 2-Chloro-N-[1-(2,4-dichloro-phenyl)-5-(4-methoxy-phenyl)-4,5-dihydro-1H-pyrazol-3-ylmethyl]-6-methyl-benzenesulfonamide N-[1-(2,4-Dichloro-phenyl)-5-(4-methoxy-phenyl)-4,5-dihydro-1H-pyrazol-3-ylmethyl]-3-methyl-benzenesulfonamide N-[1-(2,4-Dichloro-phenyl)-5-(4-methoxy-phenyl)-4,5-dihydro-1H-pyrazol-3-ylmethyl]-3-methoxy-benzenesulfonamide 1,2,3,4-Tetrahydro-isoquinoline-7-sulfonic acid [5-(4-chloro-phenyl)-1-(2,4-dichloro-phenyl)-4,5-dihydro-1H-pyrazol-3-ylmethyl]-amide Benzo[1,2,5]oxadiazole-4-sulfonic acid [1-(2,4-dichloro-phenyl)-5-(4-methoxy-phenyl)-4,5-dihydro-1H-pyrazol-3-ylmethyl]-amide N-[1-(2,4-Dichloro-phenyl)-5-(4-methoxy-phenyl)-4,5-dihydro-1H-pyrazol-3-ylmethyl]-4-methanesulfonyl-benzenesulfonamide 3-Chloro-N-[1-(2,4-dichloro-phenyl)-5-(4-methoxy-phenyl)-4,5-dihydro-1H-pyrazol-3-ylmethyl]-benzenesulfonamide 3-Bromo-N-[1-(2,4-dichloro-phenyl)-5-(4-methoxy-phenyl)-4,5-dihydro-1H-pyrazol-3-ylmethyl]-benzenesulfonamide 2,5-Dichloro-N-[1-(2,4-dichloro-phenyl)-5-(4-methoxy-phenyl)-4,5-dihydro-1H-pyrazol-3-ylmethyl]-benzenesulfonamide 3-Chloro-N-[1-(2,4-dichloro-phenyl)-5-(4-methoxy-phenyl)-4,5-dihydro-1H-pyrazol-3-ylmethyl]-2-methyl-benzenesulfonamide Benzo[1,2,5]oxadiazole-4-sulfonic acid [1-(2,4-dichloro-phenyl)-5-(4-ethoxy-phenyl)-4,5-dihydro-1H-pyrazol-3-ylmethyl]-amide N-[1-(2,4-Dichloro-phenyl)-5-(4-ethoxy-phenyl)-4,5-dihydro-1H-pyrazol-3-ylmethyl]-4-methanesulfonyl-benzenesulfonamide 3-Chloro-N-[1-(2,4-dichloro-phenyl)-5-(4-ethoxy-phenyl)-4,5-dihydro-1H-pyrazol-3-ylmethyl]-benzenesulfonamide 3-Bromo-N-[1-(2,4-dichloro-phenyl)-5-(4-ethoxy-phenyl)-4,5-dihydro-1H-pyrazol-3-ylmethyl]-benzenesulfonamide 2,5-Dichloro-N-[1-(2,4-dichloro-phenyl)-5-(4-ethoxy-phenyl)-4,5-dihydro-1H-pyrazol-3-ylmethyl]-benzenesulfonamide 3-Chloro-N-[1-(2,4-dichloro-phenyl)-5-(4-ethoxy-phenyl)-4,5-dihydro-1H-pyrazol-3-ylmethyl]-2-methyl-benzenesulfonamide (R)-Benzo[1,2,5]oxadiazole-4-sulfonic acid [5-(4-chloro-phenyl)-1-(2,4-dichloro-phenyl)-4,5-dihydro-1H-pyrazol-3-ylmethyl]-amide (R)—N-[5-(4-Chloro-phenyl)-1-(2,4-dichloro-phenyl)-4,5-dihydro-1H-pyrazol-3-ylmethyl]-4-methanesulfonyl-benzenesulfonamide (R)-3-Chloro-N-[5-(4-chloro-phenyl)-1-(2,4-dichloro-phenyl)-4,5-dihydro-1H-pyrazol-3-ylmethyl]-benzenesulfonamide (R)-3-Bromo-N-[5-(4-chloro-phenyl)-1-(2,4-dichloro-phenyl)-4,5-dihydro-1H-pyrazol-3-ylmethyl]-benzenesulfonamide (R)-2,5-Dichloro-N-[5-(4-chloro-phenyl)-1-(2,4-dichloro-phenyl)-4,5-dihydro-1H-pyrazol-3-ylmethyl]-benzenesulfonamide 3-Chloro-N-[5-(4-chloro-phenyl)-1-(2,4-dichloro-phenyl)-4,5-dihydro-1H-pyrazol-3-ylmethyl]-2-methyl-benzenesulfonamide 4-Chloro-N-[1-(2,4-dichloro-phenyl)-5-(4-methoxy-phenyl)-4,5-dihydro-1H-pyrazol-3-ylmethyl]-2,5-dimethyl-benzenesulfonamide 2,3-Dichloro-N-[1-(2,4-dichloro-phenyl)-5-(4-methoxy-phenyl)-4,5-dihydro-1H-pyrazol-3-ylmethyl]-benzenesulfonamide 2-Bromo-N-[1-(2,4-dichloro-phenyl)-5-(4-methoxy-phenyl)-4,5-dihydro-1H-pyrazol-3-ylmethyl]-benzenesulfonamide 3-Chloro-N-[1-(2,4-dichloro-phenyl)-5-(4-methoxy-phenyl)-4,5-dihydro-1H-pyrazol-3-ylmethyl]-2-fluoro-benzenesulfonamide 3-Chloro-N-[1-(2,4-dichloro-phenyl)-5-(4-methoxy-phenyl)-4,5-dihydro-1H-pyrazol-3-ylmethyl]-4-methoxy-benzenesulfonamide 2,4-Dimethyl-thiazole-5-sulfonic acid [1-(2,4-dichloro-phenyl)-5-(4-methoxy-phenyl)-4,5-dihydro-1H-pyrazol-3-ylmethyl]-amide 4-Chloro-N-[1-(2,4-dichloro-phenyl)-5-(4-ethoxy-phenyl)-4,5-dihydro-1H-pyrazol-3-ylmethyl]-2,5-dimethyl-benzenesulfonamide 2,3-Dichloro-N-[1-(2,4-dichloro-phenyl)-5-(4-ethoxy-phenyl)-4,5-dihydro-1H-pyrazol-3-ylmethyl]-benzenesulfonamide
2-Bromo-N-[1-(2,4-dichloro-phenyl)-5-(4-ethoxy-phenyl)-4,5-dihydro-1H-pyrazol-3-ylmethyl]-benzenesulfonamide
3-Chloro-N-[1-(2,4-dichloro-phenyl)-5-(4-ethoxy-phenyl)-4,5-dihydro-1H-pyrazol-3-ylmethyl]-2-fluoro-benzenesulfonamide
3-Chloro-N-[1-(2,4-dichloro-phenyl)-5-(4-ethoxy-phenyl)-4,5-dihydro-1H-pyrazol-3-ylmethyl]-4-methoxy-benzenesulfonamide
2,3-Dimethyl-3H-imidazole-4-sulfonic acid [1-(2,4-dichloro-phenyl)-5-(4-ethoxy-phenyl)-4,5-dihydro-1H-pyrazol-3-ylmethyl]-amide
N-[1-(2,4-Dichloro-phenyl)-5-(4-methoxy-phenyl)-4,5-dihydro-1H-pyrazol-3-ylmethyl]-2,5-dimethoxy-benzenesulfonamide
2,6-Dichloro-N-[1-(2,4-dichloro-phenyl)-5-(4-methoxy-phenyl)-4,5-dihydro-1H-pyrazol-3-ylmethyl]-benzenesulfonamide
N-[1-(2,4-Dichloro-phenyl)-5-(4-methoxy-phenyl)-4,5-dihydro-1H-pyrazol-3-ylmethyl]-3-fluoro-benzenesulfonamide
N-[1-(2,4-Dichloro-phenyl)-5-(4-methoxy-phenyl)-4,5-dihydro-1H-pyrazol-3-ylmethyl]-2-methanesulfonyl-benzenesulfonamide
N-[1-(2,4-Dichloro-phenyl)-5-(4-methoxy-phenyl)-4,5-dihydro-1H-pyrazol-3-ylmethyl]-4-fluoro-3-methyl-benzenesulfonamide
2,3-Dimethyl-3H-imidazole-4-sulfonic acid [1-(2,4-dichloro-phenyl)-5-(4-methoxy-phenyl)-4,5-dihydro-1H-pyrazol-3-ylmethyl]-amide
N-[1-(2,4-Dichloro-phenyl)-5-(4-ethoxy-phenyl)-4,5-dihydro-1H-pyrazol-3-ylmethyl]-2,5-dimethoxy-benzenesulfonamide
2,6-Dichloro-N-[1-(2,4-dichloro-phenyl)-5-(4-ethoxy-phenyl)-4,5-dihydro-1H-pyrazol-3-ylmethyl]-benzenesulfonamide
N-[1-(2,4-Dichloro-phenyl)-5-(4-ethoxy-phenyl)-4,5-dihydro-1H-pyrazol-3-ylmethyl]-3-fluoro-benzenesulfonamide
N-[1-(2,4-Dichloro-phenyl)-5-(4-ethoxy-phenyl)-4,5-dihydro-1H-pyrazol-3-ylmethyl]-2-methanesulfonyl-benzenesulfonamide
N-[1-(2,4-Dichloro-phenyl)-5-(4-ethoxy-phenyl)-4,5-dihydro-1H-pyrazol-3-ylmethyl]-4-fluoro-3-methyl-benzenesulfonamide
3-{[1-(2,4-Dichloro-phenyl)-5-(4-ethoxy-phenyl)-4,5-dihydro-1H-pyrazol-3-ylmethyl]-sulfamoyl}-thiophene-2-carboxylic acid methyl ester
3-Cyano-N-[1-(2,4-dichloro-phenyl)-5-(4-methoxy-phenyl)-4,5-dihydro-1H-pyrazol-3-ylmethyl]-benzenesulfonamide
N-[1-(2,4-Dichloro-phenyl)-5-(4-methoxy-phenyl)-4,5-dihydro-1H-pyrazol-3-ylmethyl]-2,4,6-trimethyl-benzenesulfonamide
N-[1-(2,4-Dichloro-phenyl)-5-(4-methoxy-phenyl)-4,5-dihydro-1H-pyrazol-3-ylmethyl]-3-fluoro-4-methoxy-benzenesulfonamide
N-[1-(2,4-Dichloro-phenyl)-5-(4-methoxy-phenyl)-4,5-dihydro-1H-pyrazol-3-ylmethyl]-4-methyl-benzenesulfonamide
5-Chloro-N-[1-(2,4-dichloro-phenyl)-5-(4-methoxy-phenyl)-4,5-dihydro-1H-pyrazol-3-ylmethyl]-2-methoxy-benzenesulfonamide
N-[1-(2,4-Dichloro-phenyl)-5-(4-methoxy-phenyl)-4,5-dihydro-1H-pyrazol-3-ylmethyl]-3-fluoro-4-methyl-benzenesulfonamide
3-Cyano-N-[1-(2,4-dichloro-phenyl)-5-(4-ethoxy-phenyl)-4,5-dihydro-1H-pyrazol-3-ylmethyl]-benzenesulfonamide
N-[1-(2,4-Dichloro-phenyl)-5-(4-ethoxy-phenyl)-4,5-dihydro-1H-pyrazol-3-ylmethyl]-2,4,6-trimethyl-benzenesulfonamide
N-[1-(2,4-Dichloro-phenyl)-5-(4-ethoxy-phenyl)-4,5-dihydro-1H-pyrazol-3-ylmethyl]-3-fluoro-4-methoxy-benzenesulfonamide
N-[1-(2,4-Dichloro-phenyl)-5-(4-ethoxy-phenyl)-4,5-dihydro-1H-pyrazol-3-ylmethyl]-4-methyl-benzenesulfonamide
5-Chloro-N-[1-(2,4-dichloro-phenyl)-5-(4-ethoxy-phenyl)-4,5-dihydro-1H-pyrazol-3-ylmethyl]-2-methoxy-benzenesulfonamide
N-[1-(2,4-Dichloro-phenyl)-5-(4-ethoxy-phenyl)-4,5-dihydro-1H-pyrazol-3-ylmethyl]-3-fluoro-4-methyl-benzenesulfonamide
N-[5-(4-Bromo-phenyl)-1-(2,4-dichloro-phenyl)-4,5-dihydro-1H-pyrazol-3-ylmethyl]-5-fluoro-2-methyl-benzenesulfonamide
N-[5-(4-Bromo-phenyl)-1-(2,4-dichloro-phenyl)-4,5-dihydro-1H-pyrazol-3-ylmethyl]-2,5-difluoro-benzenesulfonamide
N-[5-(4-Bromo-phenyl)-1-(2,4-dichloro-phenyl)-4,5-dihydro-1H-pyrazol-3-ylmethyl]-2-methyl-5-nitro-benzenesulfonamide
N-[5-(4-Bromo-phenyl)-1-(2,4-dichloro-phenyl)-4,5-dihydro-1H-pyrazol-3-ylmethyl]-2,5-dimethyl-benzenesulfonamide
N-[5-(4-Bromo-phenyl)-1-(2,4-dichloro-phenyl)-4,5-dihydro-1H-pyrazol-3-ylmethyl]-3-chloro-benzenesulfonamide
N-[5-(4-Bromo-phenyl)-1-(2,4-dichloro-phenyl)-4,5-dihydro-1H-pyrazol-3-ylmethyl]-3-fluoro-benzenesulfonamide
N-[1-(2,4-Dichloro-phenyl)-5-(4-methoxy-phenyl)-4,5-dihydro-1H-pyrazol-3-ylmethyl]-2-methyl-5-nitro-benzenesulfonamide
N-[1-(2,4-Dichloro-phenyl)-5-(4-ethoxy-phenyl)-4,5-dihydro-1H-pyrazol-3-ylmethyl]-2-methyl-5-nitro-benzenesulfonamide
(R)—N-[5-(4-Chloro-phenyl)-1-(2,4-dichloro-phenyl)-4,5-dihydro-1H-pyrazol-3-ylmethyl]-2-methyl-5-nitro-benzenesulfonamide
(S)—N-[5-(4-Chloro-phenyl)-1-(2,4-dichloro-phenyl)-4,5-dihydro-1H-pyrazol-3-ylmethyl]-2-methyl-5-nitro-benzenesulfonamide
N-[5-(4-Bromo-phenyl)-1-(2,4-dichloro-phenyl)-4,5-dihydro-1H-pyrazol-3-ylmethyl]-3-cyano-benzenesulfonamide
N-[1-(2,4-Dichloro-phenyl)-5-(4-hydroxy-phenyl)-4,5-dihydro-1H-pyrazol-3-ylmethyl]-5-fluoro-2-methyl-benzenesulfonamide
N-[1-(2,4-Dichloro-phenyl)-5-(4-hydroxy-phenyl)-4,5-dihydro-1H-pyrazol-3-ylmethyl]-2-methyl-5-nitro-benzenesulfonamide
5-Amino-N-[1-(2,4-dichloro-phenyl)-5-(4-methoxy-phenyl)-4,5-dihydro-1H-pyrazol-3-ylmethyl]-2-methyl-benzenesulfonamide
5-Amino-N-[1-(2,4-dichloro-phenyl)-5-(4-ethoxy-phenyl)-4,5-dihydro-1H-pyrazol-3-ylmethyl]-2-methyl-benzenesulfonamide (R)-5-Amino-N-[5-(4-chloro-phenyl)-1-(2,4-dichloro-phenyl)-4,5-dihydro-1H-pyrazol-3-ylmethyl]-2-methyl-benzenesulfonamide (S)-5-Amino-N-[5-(4-chloro-phenyl)-1-(2,4-dichloro-phenyl)-4,5-dihydro-1H-pyrazol-3-ylmethyl]-2-methyl-benzenesulfonamide 3,3,3-Trifluoro-propane-1-sulfonic acid 4-{2-(2,4-dichloro-phenyl)-5-[(5-fluoro-2-methyl-benzenesulfonylamino)-methyl]-3,4-dihydro-2H-pyrazol-3-yl}-phenyl ester (R)—N-[5-(4-Chloro-phenyl)-1-(2,4-dichloro-phenyl)-4,5-dihydro-1H-pyrazol-3-ylmethyl]-3-nitro-benzenesulfonamide (S)—N-[5-(4-Chloro-phenyl)-1-(2,4-dichloro-phenyl)-4,5-dihydro-1H-pyrazol-3-ylmethyl]-3-nitro-benzenesulfonamide cis(4RS-5RS)-4-Chloro-N-[5-(4-chloro-phenyl)-1-(2,4-dichloro-phenyl)-4-methyl-4,5-dihydro-1H-pyrazol-3-ylmethyl]-2,5-dimethyl-benzenesulfonamide N-[5-(4-Chloro-phenyl)-1-(2,4-dichloro-phenyl)-4,5-dihydro-1H-pyrazol-3-ylmethyl]-3,4-dimethyl-benzenesulfonamide N-[5-(4-Chloro-phenyl)-1-(2,4-dichloro-phenyl)-4,5-dihydro-1H-pyrazol-3-ylmethyl]-2-methoxy-5-methyl-benzenesulfonamide (S)—N-[1-(2,4-Dichloro-phenyl)-5-(4-ethoxy-phenyl)-4,5-dihydro-1H-pyrazol-3-ylmethyl]-2-methoxy-5-methyl-benzenesulfonamide (S)—N-[1-(2,4-Dichloro-phenyl)-5-(4-ethoxy-phenyl)-4,5-dihydro-1H-pyrazol-3-ylmethyl]-2-methoxy-5-methyl-benzenesulfonamide (S)-3-Chloro-N-[1-(2,4-dichloro-phenyl)-5-(4-ethoxy-phenyl)-4,5-dihydro-1H-pyrazol-3-ylmethyl]-2-fluoro-benzenesulfonamide (R)-3-Chloro-N-[1-(2,4-dichloro-phenyl)-5-(4-ethoxy-phenyl)-4,5-dihydro-1H-pyrazol-3-ylmethyl]-2-fluoro-benzenesulfonamide (R)—N-[1-(2,4-Dichloro-phenyl)-5-(4-ethoxy-phenyl)-4,5-dihydro-1H-pyrazol-3-ylmethyl]-2,5-difluoro-benzenesulfonamide (S)—N-[1-(2,4-Dichloro-phenyl)-5-(4-ethoxy-phenyl)-4,5-dihydro-1H-pyrazol-3-ylmethyl]-2,5-difluoro-benzenesulfonamide Propane-1-sulfonic acid 4-{2-(2,4-dichloro-phenyl)-5-[(5-fluoro-2-methyl-benzenesulfonylamino)-methyl]-3,4-dihydro-2H-pyrazol-3-yl}-phenyl ester Propane-2-sulfonic acid 4-{2-(2,4-dichloro-phenyl)-5-[(5-fluoro-2-methyl-benzenesulfonylamino)-methyl]-3,4-dihydro-2H-pyrazol-3-yl}-phenyl ester Ethanesulfonic acid 4-{2-(2,4-dichloro-phenyl)-5-[(5-fluoro-2-methyl-benzenesulfonylamino)-methyl]-3,4-dihydro-2H-pyrazol-3-yl}-phenyl ester cis(4RS,5RS)-3,3,3-Trifluoro-propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester cis(4RS,5RS)-Propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester (4R,5R)-3,3,3-Trifluoro-propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester (4S,5S)-3,3,3-Trifluoro-propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester (4S,5S)-Propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester, and (4R,5R)-Propane-1-sulfonic acid 4-{2-(2,4-dichloro-phenyl)-5-[(5-fluoro-2-methyl-benzenesulfonylamino)-methyl]-4-methyl-3,4-dihydro-2H-pyrazol-3-yl}-phenyl ester optionally in a form of one of its stereoisomers, a racemate or in a form of a mixture of at least two of its stereoisomers, in any mixing ratio, or a physiologically acceptable salt thereof.

15. A compound according to claim 1 selected from the group consisting of

N-[1-(2,4-Dichloro-phenyl)-5-(4-ethoxy-phenyl)-4,5-dihydro-1H-pyrazol-3-ylmethyl]-2,5-difluoro-benzenesulfonamide, N-[5-(4-Chloro-phenyl)-1-(2,4-dichloro-phenyl)-4,5-dihydro-1H-pyrazol-3-ylmethyl]-2-methyl-5-nitro-benzenesulfonamide, and N-[5-(4-Chloro-phenyl)-1-(2,4-dichloro-phenyl)-4,5-dihydro-1H-pyrazol-3-ylmethyl]-3-nitro-benzenesulfonamide;

optionally in a form of one of its stereoisomers, a racemate or in a form of a mixture of at least two of its stereoisomers, in any mixing ratio, or a physiologically acceptable salt thereof.

16. A process for the preparation of a compound of general formula I according to claim 1, characterised in that at least one compound of general formula II,

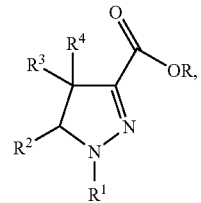

wherein $R^1$, $R^2$, $R^3$ and $R^4$ have the meaning according to claim 1 and R denotes hydrogen or a $C_{1-6}$alkyl group, is reacted in a reaction medium, in the presence of a reducing agent, to yield at least one compound of general formula III,

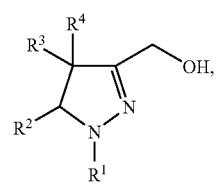

wherein $R^1$, $R^2$, $R^3$ and $R^4$ have the meaning according to claim 1, which is optionally isolated or purified;

and at least one compound of general formula III is reacted in a reaction medium with at least one halogenation agent or with at least one compound of general formula X—S(=O)$_2$—Cl, wherein X denotes methyl, phenyl, p-methylphenyl or trifluoromethyl, to yield at least one compound of general formula IV,

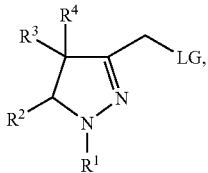

IV wherein $R^1$, $R^2$, $R^3$ and $R^4$ have the meaning according to claim 1 and LG denotes Cl, Br, methansulfonate, benzenesulfonate, toluenesulfonate or trifluoromethansulfonate, which is optionally isolated or purified;

and at least one compound of general formula IV is reacted in a reaction medium, with at least one compound of general formula $H_2NR^5$, wherein $R^5$ has the meaning according to claim 1, optionally in the presence of at least one base, and optionally treatment with a solution of hydrogen chloride, to yield at least one compound of general formula V, optionally in form of the respective hydrogen chloride,

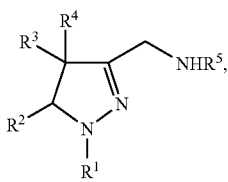

V wherein $R^1$, $R^2$, $R^3$, $R^4$ and $R^5$ have the meaning according to claim 1, which is optionally isolated or purified;

or at least one compound of general formula II, wherein R denotes hydrogen, is reacted in a reaction medium with thionyl chloride or thionyl bromide to yield at least one compound of general formula VI,

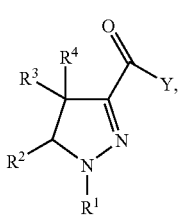

VI wherein $R^1$, $R^2$, $R^3$ and $R^4$ have the meaning according to claim 1 and Y denotes chlorine or bromine, which is optionally purified or isolated;

and at least one compound of general formula VI is reacted in a reaction medium, with at least one compound of general formula $H_2NR^5$, wherein $R^5$ has the meaning according to claim 1, optionally in the presence of at least one base, to yield at least one compound of general formula VII,

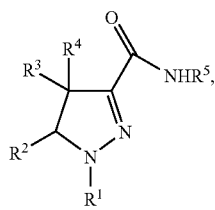

VII wherein $R^1$, $R^2$, $R^3$, $R^4$ and $R^5$ have the meaning according to claim 1, which is optionally purified or isolated;

and at least one compound of general formula VII is reacted in a reaction medium with at least one reducing agent, or is reacted in a reaction medium via catalytic hydrogenation, to yield at least one compound of general formula V, which is optionally purified or isolated;

and at least one compound of general formula V is reacted in a reaction medium, optionally in an inert atmosphere, optionally in the presence of at least one base, with at least one compound of general formula $R^6$—S(=O)$_2$-Hal, wherein $R^6$ has the meaning according to claim 1 and Hal denotes a halogen atom, to yield at least one compound of general formula I,

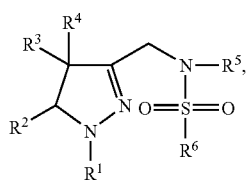

I wherein $R^1$, $R^2$, $R^3$, $R^4$, $R^5$ and $R^6$ have the meaning according to claim 1, which is optionally isolated or purified.

17. A medicament comprising at least one compound according to claim 1 and optionally at least one physiologically acceptable auxiliary agent.

18. A method for the treatment of obesity and metabolic syndrome the method comprising administering to a patient the medicament of claim 17.

* * * * *